US012577227B2

(12) United States Patent
Lee et al.

(10) Patent No.: US 12,577,227 B2
(45) Date of Patent: Mar. 17, 2026

(54) WDR5 INHIBITORS AND MODULATORS

(71) Applicant: Vanderbilt University, Nashville, TN (US)

(72) Inventors: Taekyu Lee, Brentwood, TN (US); Changho Han, Nashville, TN (US); Jonathan J. Mills, Nashville, TN (US); Kevin B. Teuscher, Nashville, TN (US); Jianhua Tian, Montgomery, MD (US); Kenneth M. Meyers, Nashville, TN (US); Somenath Chowdhury, Nashville, TN (US); Stephen W. Fesik, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 1095 days.

(21) Appl. No.: 17/613,717

(22) PCT Filed: Jun. 4, 2020

(86) PCT No.: PCT/US2020/036188
§ 371 (c)(1),
(2) Date: Nov. 23, 2021

(87) PCT Pub. No.: WO2020/247679
PCT Pub. Date: Dec. 10, 2020

(65) Prior Publication Data

US 2022/0242849 A1 Aug. 4, 2022

Related U.S. Application Data

(60) Provisional application No. 62/856,873, filed on Jun. 4, 2019.

(51) Int. Cl.

| | |
|---|---|
| ***C07D 401/14*** | (2006.01) |
| ***C07D 403/06*** | (2006.01) |
| ***C07D 403/12*** | (2006.01) |
| ***C07D 403/14*** | (2006.01) |
| ***C07D 413/06*** | (2006.01) |
| ***C07D 413/12*** | (2006.01) |
| ***C07D 413/14*** | (2006.01) |
| ***C07D 417/14*** | (2006.01) |

(52) U.S. Cl.
CPC ......... *C07D 401/14* (2013.01); *C07D 403/06* (2013.01); *C07D 403/12* (2013.01); *C07D 403/14* (2013.01); *C07D 413/06* (2013.01); *C07D 413/12* (2013.01); *C07D 413/14* (2013.01); *C07D 417/14* (2013.01)

(58) Field of Classification Search
CPC ................ C07D 401/14; C07D 403/06; C07D 403/12; C07D 403/14; C07D 413/06; C07D 413/12; C07D 413/14; C07D 417/14; C07D 471/04; A61P 35/00
See application file for complete search history.

(56) References Cited

U.S. PATENT DOCUMENTS

| | | | | |
|---|---|---|---|---|
| 6,255,314 | B1 * | 7/2001 | Miyadera | A61K 31/505 514/274 |
| 9,878,989 | B2 * | 1/2018 | Sugimoto | C07D 471/04 |
| 10,246,433 | B2 | 4/2019 | Edwards et al. | |
| 10,807,959 | B2 | 10/2020 | Gogliotti et al. | |
| 10,844,044 | B2 | 11/2020 | Alvarado et al. | |
| 2003/0195211 | A1 | 10/2003 | Sadhu et al. | |
| 2005/0124614 | A1 | 6/2005 | Gangloff et al. | |
| 2008/0085890 | A1 | 4/2008 | Tsou et al. | |
| 2011/0046114 | A1 | 2/2011 | Molino et al. | |
| 2015/0361067 | A1 | 12/2015 | Collins et al. | |
| 2016/0347744 | A1 | 12/2016 | Corkey et al. | |
| 2018/0086767 | A1 | 3/2018 | Fesik et al. | |
| 2018/0265517 | A1 | 9/2018 | Marx et al. | |
| 2018/0362516 | A1 | 12/2018 | Sugimoto et al. | |
| 2020/0055824 | A1 | 2/2020 | Gogliotti et al. | |
| 2020/0102288 | A1 | 4/2020 | Alvarado et al. | |
| 2023/0012362 | A1 | 1/2023 | Lee et al. | |

FOREIGN PATENT DOCUMENTS

| | | | | |
|---|---|---|---|---|
| AR | 107646 | A1 * | 5/2018 | A01N 1/00 |
| CN | 109503556 | A * | 3/2019 | A01N 43/713 |
| WO | 200181346 | A2 | 11/2001 | |
| WO | 2007122482 | A1 | 11/2007 | |
| WO | 2017040449 | A1 | 3/2017 | |
| WO | 2018068017 | A1 | 4/2018 | |
| WO | WO-2018146313 | A1 * | 8/2018 | A61K 31/553 |
| WO | 2020086857 | A1 | 4/2020 | |

(Continued)

OTHER PUBLICATIONS

Machine Translation of AR107647A1 (Year: 2018).*
Brown, N. Bioisosteres in medicinal chemistry. Wiley-Vch, Cop. (Year: 2012).*
Brameld, K. A., Kuhn, B., Reuter, D. C., & Stahl, M. Small Molecule Conformational Preferences Derived from Crystal Structure Data. A Medicinal Chemistry Focused Analysis. Journal of Chemical Information and Modeling, 48(1), 1-24. https://doi.org/10.1021/ci7002494 (Year: 2008).*
Machine Translation of CN109503556A (Year: 2019).*
Balgobind et al., "The heterogeneity of pediatric MLL-rearranged acute myeloid leukemia", Leukemia, 2011, vol. 25, pp. 1239-1248.
Cao et al., "Targeting MLL1 H3K4 Methyltransferase Activity in Mixed-Lineage Leukemia", Molecular Cell, 2014, vol. 53, pp. 247-261.
Carugo et al., "In Vivo Funcitonal Platform Targeting Patient-Derived Xenografts Identifies WDR5-Myc Association as a Critical Determinant of Pancreatic Cancer", Cell Reports, 2016, vol. 16, pp. 133-147.

(Continued)

*Primary Examiner* — Scarlett Y Goon
*Assistant Examiner* — Hoi Yan Lee
(74) *Attorney, Agent, or Firm* — Michael Best & Friedrich LLP

(57) ABSTRACT

Quinazolin-4(3H)-one, 2,3-dihydroquinazolin-4(1H)-one, 3,4-dihydrobenzo[f][1,4]oxazepin-5(2H)-one, and 3,4-dihydro-1H-benzo[e][1,4]diazepine-2,5-dione compounds and derivatives inhibit WDR5 and associated protein-protein interactions, and the compounds and their pharmaceutical compositions are useful for treating disorders and conditions in a subject, such as cancer cell proliferation.

18 Claims, No Drawings

(56) References Cited

FOREIGN PATENT DOCUMENTS

WO 2021026672 A1 2/2021
WO 2021028806 A1 2/2021

OTHER PUBLICATIONS

Caslini et al., "Interaction of MLL Amino Terminal Sequences with Menin Is Required for Transformation", Cancer Res., 2007, vol. 67, pp. 7275-7283.
Chen et al., "Upregulated WDR5 promotes proliferation, self-renewal and chemoresistance in bladder cancer via mediating H3K4 trimethylation", Scientific Reports, 2015, vol. 5, pp. 8293.
Dai et al, "WDR5 Expression Is Prognostic of Breast Cancer Outcome", PLOSOne, 2015, vol. 10, PMC4565643.
Dess et al., "Readily Accessible 12-I-5 oxidant for the conversion of primary and secondary alcohols to aldehydes and ketones", J. Org. Chem., 1983, vol. 48, p. 4155-4156.
Dias et al., "Structural analysis of the KANSL1/WDR5/KANSL2 complex reveals that WDR5 is required for efficient assembly and chromatin targeting of the NSL complex", Genes and Development, 2014, vol. 28, pp. 929-942.
Dimartino et al., "Review: MLL Rearrangements in Haematological Malignancies: Lessons from Clinical and Biological Studies", British Journal of Haematol., 1999, vol. 106, pp. 614-626.
Ee et al., "An Embryonic Stem Cell-Specific NuRD Complex Functions through Interaction with WDR5", Stem Cell Reports, 2017, vol. 8, pp. 1488-1496.
Karatas et al., "Discovery of a Highly Potent, Cell-Permeable Macrocyclic Peptidomimetic (MM-589) Targeting the WD Repeat Doman 5 Protein (WDR5)-Mixed Lineage Leukemia (MLL) Protein-Protein Interaction", J. Med. Chem., 2017, vol. 60, pp. 4818-4839.
Li et al., "MOF and H4 K16 Acetylation Play Important Roles in DNA Damage Repar by Modulating Recruitment of DNA Damanage Repair Protein Mdc1", Molecular and Cellular Biology, 2010, vol. 30, pp. 5335-5347.
Littke, Fu, "Palladium-Catalyzed Coupling Reactions of Aryl Chlorides", Angew. Chem., Int. Ed., 2002, vol. 41, pp. 4176-4211.
Marschalek, "Mechanisms of leukemogenesis by MLL fusion proteins", British Journal of Haematol., 2010, vol. 152, pp. 141-154.
Milne et al., "Leukemogenic MLL Fusion Proteins Bind across a Broad Region of the Hox a9 Locus, Promoting Transcription and Multiple Histone Modifications", Cancer Res., 2005, vol. 65, pp. 11367-11374.
Milne et al., "MLL Targets SET Domain Methyltransferase Activity to Hox Gene Promoters", Mol. Cell, 2002, vol. 10, pp. 1107-1117.
Miyaura et al., "Palladium Catalyzed Cross-Coupling Reactions of Organoboron Compounds", Chem. Rev., 1995, p. 2457-2483.
Nakamura et al., "ALL-1 Is a Histone Methyltransferase that Assemblesl a Supercomplex of Proteins Involved in Transcriptional Regulation", Mol. Cell., 2002, vol. 10, pp. 1119-1128.
Patel et al., "On the Mechanism of Multiple Lysine Methylation by the Human Mixed Lineage Luekemia Protein-1 (MLL1) Core Complex", J. Biol. Chem., 2009, vol. 284, pp. 24242-24256.
Pigazzi et al., "MLL Partner genes drive distinct gene expression profiles and genomic alterations in pediatric actute myeloid leukemia: an AIEOP study", Leukemia, 2011, vol. 25, pp. 560-563.
Pui et al., "Clinical heterogeneity in childhood acute lymphoblastic leukemia with 11q23 rearrangements", Leukemia, 2003, vol. 17, pp. 700-706.
Senisterra et al., "Small-molecule inhibition of MLL activity by disruption of its interaction with WDR5", Biochem J., 2013, vol. 449, pp. 151-159.
Slany, "The molecular biology of mixed lineage leukemia", Haematologica, 2009, vol. 94, pp. 984-993.
Song et al., "WDR5 Interacts with Mixed Lineage Leukemia (MLL) Protein via the Histone H3-binding Pocket", J. Biol. Chem., 2008, vol. 283, pp. 35258-35264.
Sun et al., "WDR5 Supports an N-Myc Transcriptional Complex That Drives a Protumorigenic Gene Expression Signature in Neuroblastoma", Cancer Research, 2015, vol. 75, pp. 5143-5154.
Tamai et al., "11q23/MLL Acute Leukemia: Update of Clinical Aspects", J. Clin. Exp. Hematopathol., 2010, vol. 50, pp. 91-98.
Tan et al., "PI3K/AKT-mediated upregulation of WDR5 promotes colorectal cancer metastasis by directly targeting ZNF407", Cell Death & Disease, 2017, vol. 8, e2686, 12 pages.
Thachuk et al., "Involvement of a Homolog of *Drosophila* Trithorax by 11q23 Chromosomal Translocations in Acute Leukemias", Cell, 1992, vol. 71, pp. 691-700.
Thomas et al., "Interaction with WDR5 Promotes Target Gene Recognition and Tumorigenesis by MYC", Molecular Cell, 2015, vol. 58, pp. 440-452.
Tian et al.., "Discovery and Structure Based Optimization of Potent and Selective WD Repeat Domain 5 (WDR5) Inhibitors Containing a Dihydroisoquinolinone Bicyclic Core", J. Med. Chem., 2020, vol. 63, pp. 656-675.
Tomizawa et al., "Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group", Leukemia, 2007, vol. 21, pp. 2258-2263.
Wolff, "The Schmidt Reaction", Organic Reactions, 2011, pp. 307-336.
Yokoyama et al., "Leukemia Proto-Oncoprotein MLL Forms a SET1-Like Histone Methyltransferase Complex with Menin to Regulate Hox Gene Expression", Mol. Cell Biol., 2004, vol. 24, pp. 5639-5649.
Yokoyama et al., "The Menin Tumor Suppressor Protein Is an Essential Oncogenic Cofactor for MLL-Associated Leukemogenesis", Cell, 2005, vol. 123, pp. 207-218.
Yu et al., "MLL, a mammalian trithorax-group gene, functions as a transcriptional maintenance factor in morphogenesis", Proc. Natl. Acad. Sci., 1998, vol. 95, pp. 10632-10636.
International Search Report and Written Opinion for Application No. PCT/US20/36188 dated Oct. 26, 2020 (10 pages).
International Preliminary Report on Patentability for Application No. PCT/US20/036188 dated Dec. 7, 2021 (7 pages).
Aho et al., "Displacement of WDR5 from Chromatin by a WIN Site Inhibitor with Picomolar Affinity", Cell Reports, vol. 26, No. 11, 2019, pp. 2916-2928.

* cited by examiner

WDR5 INHIBITORS AND MODULATORS

RELATED APPLICATIONS

This patent application is the U.S. national stage entry, under 35 U.S.C. § 371, of International Application Number PCT/US2020/036188, filed Jun. 4, 2020, which claims priority to U.S. Provisional Application No. 62/856,873, filed Jun. 4, 2019, the entire contents of each of which are hereby incorporated by reference.

STATEMENT OF GOVERNMENT INTEREST

This invention was made with government support under Contract No. HHSN261200800001E, awarded by the National Institutes of Health. The government has certain rights in the invention.

TECHNICAL FIELD

The present invention relates generally to compounds that inhibit the binding of transcription factors, regulatory regulators, and chromatin to WDR5 and methods of use thereof. In particular embodiments, the present invention provides compositions comprising imino-azacycle-benzamide compounds and methods of use thereof to inhibit or modulate the interaction of WDR5 with chromatin, cognate transcription and other regulatory factors, including for example the histone methyltransferase MLL1, for the treatment of leukemia, solid cancers and other diseases dependent on activity of WDR5.

BACKGROUND

Mixed lineage leukemia (MLL) presents a heterogeneous group of acute myeloid leukemia and acute lymphoblastic leukemia bearing features of more than one hematopoietic cell lineage. MLL accounts for about 80% of infant acute leukemia cases (Tomizawa, D.; et. al. *Leukemia,* 2007, 21, 2258-63) and 10% of all acute leukemia cases (Marschalek, R. *Br. J. Haematol.* 2011, 152, 141-54). MLL leukemia patients have a poor prognosis with overall 5-year survival ratio around 35% (Dimartino, J. F.; Cleary, M. L., *Br. J. Haematol.* 1999, 106, 614-626; Pui, C., et al. *Leukemia,* 2003, 4, 700-706; Tomizawa, D.; et. al. *Leukemia,* 2007, 21, 2258-63).

MLL is composed of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila trithorax* (Trx) (Thachuk, D. C.; et al. *Cell,* 1992, 71, 691-700). Wild type MLL binds to regulatory regions of homeox (HOX) genes (Milne, T. A.; et al. *Cancer Res.,* 2005, 65, 11367-74) through the amino terminal fragment while the catalytic C-terminal domain catalyzes the Histone 3 lysine 4 (H3K4) methylation via interaction with WDR5 and up regulates target gene transcription (Nakamura, T.; et al. *Mol. Cell,* 2002, 10, 1119-28; Yokoyama, A. et al. *Mol. Cell Biol.,* 2004, 24, 5639-49; Milne, T. A.; et al. *Mol. Cell,* 2002, 10, 1107-17). Wild type MLL in conjunction with WDR5 is required for maintenance HOX genes expression and is widely expressed not only during embryo development but also in adult tissues including myeloid and lymphoid cells (Yu, B. D.; et al. *Proc. Natl. Acad. Sci.,* 1998, 95, 10632-10636). Reciprocal translocations of MLL gene result in-frame fusion of the 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, C., et al. *Leukemia,* 2003, 4, 700-706; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, C.; et al. *Cancer Res.,* 2007, 67, 7275-83; Yokoyama, A.; et al. *Cell,* 2005, 123, 207-18). The numerous chromosomal translocations of MLL gene and partner genes add to the complexity of MLL leukemia treatment. Although HOX9 and MEIS1 overexpression are commonly observed among MLL leukemia patients, each rearrangement leads to distinct dysregulated target gene expression patterns and downstream events (Slany, R. K., Haematologica, 2009, 94, 984-993). Clinical studies reveal that MLL of different chromosomal translocations are associated with different prognosis and are treated differently under current protocols (Tamai, H., et al. *J. Clin. Exp. Hematop.,* 2010, 50, 91-98; Balgobind, B. V., et al. *Leukemia,* 2011, 8, 1239-1248; Pigazzi, M.; et al. Leukemia, 2011, 25, 560-563).

Intrinsic histone methyltransferase (HMT) activity of MLL1 is extremely low and requires a complex assembly of WDR5, RbBP5, ASH2L, and DPY30 protein partners for effective H3K4 trimethylation, the so-called WRAD complex (Patel, A.; et al. *J. Biol. Chem.,* 2009, 284, 24242-56). The binding of MLL1 to WDR5 (WD40 repeat protein 5) is particularly critical for HMT activity and occurs through a conserved arginine containing motif on MLL1 called the "Win" or WDR5 interaction motif Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, F.; et al. *Molecular Cell,* 2014, 53, 247-61, Karatas, H.; et al. *J. Med. Chem.,* 2017, 60, 4818-4839). In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. In addition to the highly characterized WDR5-MLL1 interaction, disruption of WDR5 with other transcription factors/epigenetic writers or displacement from chromatin itself could have a desirable benefit as a cancer treatment strategy. For example, WDR5 acts as a scaffold protein with the following chromatin complexes/structures, including histone H3 (via R2 residues, e.g. see Song, J.-J., et al. *J. Biol. Chem.* 2008, 283, 35258-64), NSL/MOF (Li, X., et al. Molecular and Cellular Biology, 2010, 30, 5335-47, Dias, J., et al. *Genes & Development,* 2014, 28, 929-942), C/EBPα p30 (Senisterra, G., et al. *Biochem. J,* 2013, 449, 151-159), c-MYC (Thomas, L. R.; et al. *Molecular Cell,* 2015, 58, 440-52, herein incorporated by reference in its entirety), and the NuRD complex (Ee, L.-S., et al. Stem Cell Reports, 2017, 8, 1488-96). In addition, WDR5 expression levels have been reported to be correlative and connected to patient prognosis in several other cancer types, including neuroblastoma (Sun, Y. et al. *Cancer Research,* 2015, 75, 5143-

54), breast cancer (Dai, X. et al. *PLoSOne,* 2015, 10, PMC4565643), bladder cancer (Chen, X. et al. *Scientific Reports,* 2015, 5, 8293), and colorectal cancer (Tan, X. et al. *Cell Death & Disease,* 2017, 8, PMC5386518). In addition, in an unbiased shRNA screen in human xenografts, WDR5 was identified as an important target in pancreatic cancer (Carugo, A. et al. *Cell Reports,* 2016, 16, 133-147). Based on the growing number of complexes identified which utilize WDR5 to maintain tumor fitness and growth, the emerging importance of WDR5 in several cancer types is not unexpected. In the case of the c-MYC-WDR5 interaction, the MYC oncoprotein utilizes a molecularly defined interaction with WDR5 to bind to its target genes on chromatin. MYC is overexpressed in a majority of malignancies and contributes to an estimated 70,000-100,000 cancer deaths per year in the United States. Thus, disruption of WDR5 from chromatin as a strategy to displace MYC from its target genes may provide a beneficial strategy to treat MYC-driven tumors.

SUMMARY

The molecules described herein can inhibit or modulate the interaction of WDR5 with chromatin, cognate transcription and other regulatory factors, including for example the histone methyltransferase MLL1, and can provide a therapeutic approach to treat cancers associated with such interactions (e.g., the MLL1-WDR5 interaction).

In one aspect, the invention provides compounds of formula (I), (I)

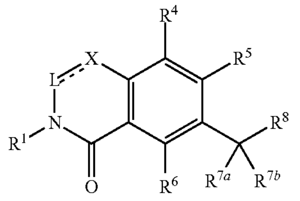

or a pharmaceutically acceptable salt thereof, wherein:

$R^1$ is $G^1$ or —$(CR^aR^b)_p$-$G^1$;

p is 1, 2, or 3;

$G^1$ is a 6- to 12-membered aryl, a 5- to 12-membered heteroaryl, a 4- to 12-membered heterocyclyl, or a $C_{3-10}$carbocycle optionally fused to a phenyl or to a 5- to 6-membered heteroaryl, wherein $G^1$ is optionally substituted with 1-5 substituents independently selected from the group consisting of halogen, $C_{1-6}$alkyl, $C_{1-6}$haloalkyl, oxo, —$OR^{1a}$, —$N(R^{1a})$, —$SR^{1a}$, cyano, —$C(O)OR^{1a}$, —$C(O)N(R^{1a})_2$, —$C(O)R^{1a}$, —$SOR^{1b}$, —$SO_2R^{1b}$, —$SO_2N(R^{1a})_2$, —$NR^{1a}C(O)R^{1a}$, —$NR^{1a}C(O)OR^{1b}$, —$NR^{1a}C(O)N(R^{1a})_2$, —$NR^{1a}S(O)_2R^{1b}$, —$NR^{1a}S(O)_2N(R^{1a})_2$, and -$L^1$-$G^{1a}$;

L is —$(CR^{2a}R^{2b})_n$—, wherein ------ is a single bond and X is O, $NR^3$, or S; or L is —$C(R^{2c})$, wherein ------ is a double bond and X is N;

n is 1, 2, or 3;

$R^{1a}$, at each occurrence, is independently hydrogen, $C_{1-6}$alkyl, $C_{1-6}$haloalkyl, —$C_{2-4}$alkylene-Y, $G^{1a}$, or —$C_{1-6}$alkylene-$G^{1a}$, wherein two $R^{1a}$, together with a common nitrogen atom to which the $R^{1a}$ attach optionally form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

Y, at each occurrence, is independently —OH, —$OC_{1-4}$ alkyl, —$NH_2$, —$NHC_{1-4}$alkyl, or —$N(C_{1-4}alkyl)_2$;

$R^{1b}$, at each occurrence, is independently $C_{1-6}$alkyl, $C_{1-6}$haloalkyl, $G^{1a}$, or —$C_{1-6}$alkylene-$G^{1a}$;

$L^1$ is a bond or $C_{1-3}$alkylene;

$G^{1a}$, at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}C(O)R^{1c}$, —$NR^{1c}C(O)OR^{1d}$, —$NR^{1c}C(O)N(R^{1c})_2$, —$NR^{1c}S(O)_2R^{1d}$, and —$NR^{1c}S(O)_2N(R^{1d})_2$;

$R^a$, at each occurrence, is independently hydrogen, $C_{1-4}$alkyl, $C_{1-4}$haloalkyl, —$C_{1-6}$alkylene-$R^{aa}$, $G^{1b}$, or —$C_{1-6}$alkylene-$G^{1b}$, wherein each $C_{1-6}$alkylene is optionally substituted with 1-4 halogen;

$R^{aa}$, at each occurrence, is independently —$OR^{1e}$, —$N(R^{1e})_2$, —$SR^{1e}$, cyano, —$C(O)OR^{1e}$, —$C(O)N(R^{1e})_2$, —$C(O)R^{1e}$, —$SOR^{1f}$, —$SO_2R^{1f}$, —$SO_2N(R^{1e})_2$, —$NR^{1e}C(O)R^{1e}$, —$NR^{1e}C(O)OR^{1f}$, —$NR^{1e}C(O)N(R^{1e})_2$, —$NR^{1e}S(O)_2R^{1f}$, or —$NR^{1e}S(O)_2N(R^{1e})_2$;

$G^{1b}$, at each occurrence, is independently a $C_{3-6}$carbocycle or a 4- to 10-membered heterocyclyl, wherein the $C_{3-6}$carbocycle and 4- to 10-membered heterocyclyl are optionally substituted with 1-4 substituents independently selected from the group consisting of halogen, $C_{1-4}$alkyl, $C_{1-4}$haloalkyl, oxo, —$OR^{1e}$, —$N(R^{1e})_2$, —$SR^{1e}$, cyano, —$C(O)OR^{1e}$, —$C(O)N(R^{1e})_2$, —$C(O)R^{1e}$, —$SOR^{1f}$, —$SO_2R^{1f}$, —$SO_2N(R^{1e})_2$, —$NR^{1e}C(O)R^{1e}$, —$NR^{1e}C(O)OR^{1f}$, —$NR^{1e}C(O)N(R^{1e})_2$—$NR^{1e}S(O)_2R^{1f}$ and —$NR^{1e}S(O)_2N(R^{1e})_2$;

$R^b$ is hydrogen or $C_{1-4}$alkyl;

or alternatively one $R^a$ and one $R^b$ together with the carbon atom to which they are attached form a 3-8 membered saturated or partially unsaturated carbocyclic or heterocyclic ring;

or alternatively one $R^a$ and one $R^b$ are taken together to form an oxo group;

$R^{2a}$ and $R^{2b}$, at each occurrence, are independently hydrogen, halogen, $C_{1-4}$alkyl, $C_{1-4}$haloalkyl, $C_{3-6}$cycloalkyl, or —$C_{1-3}$alkylene-$C_{3-6}$cycloalkyl; or alternatively one $R^{2a}$ and one $R^{2b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$ haloalkyl, and —$OC_{1-4}$alkyl; or alternatively one $R^{2a}$ and one $R^{2b}$ are taken together to form an oxo group;

$R^{2c}$ is hydrogen, $C_{1-4}$alkyl, $C_{1-4}$haloalkyl, $C_{3-6}$cycloalkyl, or —$C_{1-3}$alkylene-$C_{3-6}$cycloalkyl;

$R^3$ is hydrogen or $C_{1-6}$alkyl;

$R^4$ is halogen, $C_{1-6}$haloalkyl, $C_{1-6}$haloalkenyl, —$OR^{4a}$, —$SR^{4a}$, —$N(R^{4a})_2$, —$S(O)R^{4b}$, —$S(O)_2R^{4b}$, —$S(O)_2N(R^{4a})_2$, —$C(O)N(R^{4a})_2$, —$C(O)R^{4a}$, —$NR^{4a}C(O)R^{4a}$—$NR^{4a}C(O)OR^{4b}$, —$NR^{4a}C(O)N(R^{4a})_2$, —$NR^{4a}S(O)_2R^{4b}$, $NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or —$C_{1-3}$ alkylene-$G^2$;

$R^{4b}$ is $C_{1-6}$alkyl, $C_{1-6}$haloalkyl, $G^2$, or —$C_{1-3}$alkylene-$G^2$;

$G^2$, at each occurrence, is independently a $C_{3-10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of halogen, $C_{1-6}$alkyl, $C_{1-6}$haloalkyl, oxo, $—OR^{4c}$, $—N(R^{4c})_2$, $—SR^{4c}$, cyano, $—C(O)OR^{4c}$, $—C(O)N(R^{4c})_2$, $—C(O)R^{4c}$, $—SOR^{4d}$, $—SO_2R^{4d}$, $—SO_2N(R^{4c})_2$, $—NR^{4c}C(O)R^{4c}$, $—NR^{4c}C(O)OR^{4d}$, $—NR^{4c}C(O)N(R^{4c})_2$, $—NR^{4c}S(O)_2R^{4d}$, $—NR^{4c}S(O)_2N(R^{4c})_2$, $C_{3-8}$cycloalkyl, and $—C_{1-3}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^{1c}$, $R^{1e}$, and $R^{4c}$, at each occurrence, are independently hydrogen, $C_{1-6}$alkyl, $C_{1-6}$haloalkyl, $C_{3-8}$ cycloalkyl, or $—C_{1-6}$alkylene-$C_{3-8}$cycloalkyl, wherein each $C_{3-8}$cycloalkyl is optionally substituted with 1-4 substituents independently selected from the group consisting of $C_{1-4}$ alkyl and halogen, wherein alternatively two $R^{1c}$, two $R^{1e}$, and/or two $R^{4c}$, together with a common nitrogen atom to which the $R^{1c}$, $R^{1e}$, and/or $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and $—OC_{1-4}$alkyl;

$R^{1d}$, $R^{1f}$, and $R^{4d}$, at each occurrence, are independently $C_{1-6}$alkyl, $C_{1-6}$haloalkyl, $C_{3-8}$cycloalkyl, or $—C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or $—OC_{1-4}$alkyl;

$R^{7a}$ and $R^{7b}$ are independently selected from the group consisting of hydrogen, halogen, $C_{1-4}$ alkyl, and $C_{1-4}$haloalkyl, or $R^{7a}$ and $R^{7b}$ are taken together to form an oxo group;

$R^8$ is

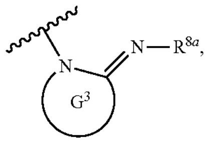,
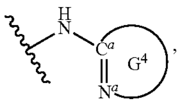, indolyl, pyrrolopyridinyl, or imidazolyl, wherein the indolyl, pyrrolopyridinyl, and imidazolyl are optionally substituted with 1-3 substituents independently selected from the group consisting of $C_{1-4}$alkyl, $C_{1-4}$haloalkyl, $C_{3-8}$cycloalkyl, and $—C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$ haloalkyl, OH, and $—OC_{1-4}$alkyl;

$G^3$ is a 5- to 12-membered heterocyclic ring system containing a first nitrogen at the point of attachment and optionally 1-4 additional heteroatoms selected from the group consisting of oxygen, nitrogen, and sulfur, $G^3$ having the imine substituent $=NR^{8a}$ adjacent to the first nitrogen and being optionally substituted with 1-4 substituents independently selected from the group consisting of halogen, oxo, $C_{1-6}$alkyl, $C_{1-6}$haloalkyl, $G^{3a}$ and $—C_{1-3}$alkylene-$G^{3a}$; $G^4$ is a 5- to 7-membered heterocyclic or 5- to 6-membered heteroaryl ring system, $G^4$ being attached at a first carbon atom $C^a$ and containing a first nitrogen Na double bonded to $C^a$, $G^4$ being optionally substituted with 1-4 substituents independently selected from the group consisting of halogen, oxo, $C_{1-6}$alkyl, $C_{1-6}$haloalkyl, and $C_{3-6}$cycloalkyl;

$R^{8a}$ is hydrogen, $C_{1-4}$alkyl, $C_{3-6}$cycloalkyl, $C(O)C_{1-4}$alkyl, or $C(O)OC_{1-4}$alkyl; and $G^{3a}$ is $C_{3-10}$carbocycle or a 6- to 12 membered aryl, wherein $G^{3a}$ is optionally substituted with 1-4 substituents independently selected from the group consisting of halogen, $C_{1-4}$alkyl, $C_{1-4}$ haloalkyl, OH, and $—OC_{1-4}$ alkyl.

In another aspect, the invention provides a pharmaceutical composition comprising a compound of formula (I), or a pharmaceutically acceptable salt thereof, and a pharmaceutically acceptable carrier.

In another aspect, the invention provides a method for the treatment of cancer, comprising administering to a subject in need thereof a therapeutically effective amount of a compound of formula (I), or a pharmaceutically acceptable salt or composition thereof.

In another aspect, the invention provides a method for inhibiting the binding of MLL1 to WDR5, comprising administering to a subject in need thereof a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of cancer.

In another aspect, the invention provides a compound of formula (I), or a pharmaceutically acceptable salt or composition thereof, for use in the inhibition of binding of MLL1 to WDR5.

In another aspect, the invention provides the use of a compound of formula (I), or a pharmaceutically acceptable salt or composition thereof, in the manufacture of a medicament for the treatment of cancer.

In another aspect, the invention provides the use of a compound of formula (I), or a pharmaceutically acceptable salt or composition thereof, in the manufacture of a medicament for the inhibition of binding of MLL1 to WDR5.

In another aspect, the invention provides a kit comprising a compound of formula (I), or a pharmaceutically acceptable salt or composition thereof, and instructions for use.

DETAILED DESCRIPTION

Disclosed herein are inhibitors of WDR5 which bind at the WDR5 interaction or WIN-site. The inhibitors can be compounds of formula (I). Compounds of formula (I) can be used to treat cancers associated with the MLL1-WDR5 interaction. In one aspect, disclosed are compounds of formula (I) as WDR5-WIN-site inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched chain saturated hydrocarbon, for example, of 2 to 5 carbon atoms. Representative examples of alkylene include, but are not limited to, $—CH_2CH_2—$, $—CH_2CH_2CH_2—$, $—CH_2CH_2CH_2CH_2—$, and $—CH_2CH_2CH_2CH_2CH_2—$.

The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cycloalkyl," as used herein, refers to a saturated ring system containing all carbon atoms as ring members and zero double bonds. A cycloalkyl may be a monocyclic cycloalkyl (e.g., cyclopropyl), a fused bicyclic cycloalkyl (e.g., decahydronaphthalenyl), a bridged cycloalkyl in which two non-adjacent atoms of a ring are linked by an alkylene bridge of 1, 2, 3, or 4 carbon atoms (e.g., bicyclo[2.2.1]heptanyl), or a spirocycle. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl," as used herein, means a non-aromatic monocyclic or multicyclic ring system containing all carbon atoms as ring members and at least one carbon-carbon double bond and preferably having from 5-10 carbon atoms per ring. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl.

The term "carbocyclyl" or "carbocycle" means a "cycloalkyl" or a "cycloalkenyl."

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a phenyl, a monocyclic carbocyclic ring, a monocyclic heteroaryl, or a monocyclic heterocycle. The bicyclic heteroaryl group is attached to the parent molecular moiety at an aromatic ring atom. The bicyclic heteroaryl group includes a 9-membered fused bicyclic aromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term “heterocycle” or “heterocyclic,” as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a monocyclic heterocycle fused to a monocyclic heteroaryl, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a non-aromatic ring atom (e.g., 2-oxaspiro[3.3]heptan-6-yl, indolin-1-yl, hexahydrocyclopenta[b]pyrrol-1(2H)-yl). Representative examples of bicyclic heterocycles include, but are not limited to, chroman-4-yl, 2,3-dihydrobenzofuran-3-yl, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and 1,2,3,4-tetrahydroisoquinolin-2-yl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety at a non-aromatic ring atom.

The term “hydrocarbylene,” as used herein, refers to a straight, unbranched hydrocarbon chain, bonded on each end to flanking atoms of the parent molecule, wherein the carbons of the hydrocarbylene may be saturated or unsaturated and may bond to the flanking atoms by single or double bonds. The term hydrocarbylene encompasses “alkylene” and alkylene containing unsaturated carbon atoms, including an unsaturated terminal carbon atom of the hydrocarbylene. Unsaturated carbon atoms may be part of a carbonyl or imine moiety. For example, of a $C_2$hydrocarbylene includes $—CH_2CH_2—$. A $C_2$hydrocarbylene substituted with oxo includes $—CH_2C(O)—$. A $C_1$hydrocarbylene includes $—CH_2—$ and

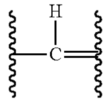

.

Terms such as “alkyl,” “cycloalkyl,” “alkylene,” etc. may be preceded by a designation indicating the number of atoms present in the group in a particular instance (e.g., “$C_{1-4}$ alkyl,” “$C_{3-6}$cycloalkyl,” “$C_{1-4}$alkylene”). These designations are used as generally understood by those skilled in the art. For example, the representation “C” followed by a subscripted number indicates the number of carbon atoms present in the group that follows. Thus, “$C_3$alkyl” is an alkyl group with three carbon atoms (i.e., n-propyl, isopropyl). Where a range is given, as in “$C_{1-4}$,” the members of the group that follows may have any number of carbon atoms falling within the recited range. A “$C_{1-4}$alkyl,” for example, is an alkyl group having from 1 to 4 carbon atoms, however arranged (i.e., straight chain or branched).

The term “substituted” refers to a group that may be further substituted with one or more non-hydrogen substituent groups. Substituent groups may include, for example, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term “allosteric site” as used herein refers to a ligand binding site that is topographically distinct from the orthosteric binding site.

The term “modulator” as used herein refers to a molecular entity (e.g., but not limited to, a ligand and a disclosed compound) that modulates the activity of the target receptor protein.

The term “ligand” as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed are compounds of formula (I), wherein $R^1$, $R^4$, $R^5$, $R^6$, $R^7$, $R^{7b}$, $R^8$, L, and X are as defined herein. Embodiments of formula (I) include the following descriptions of $R^1$, $R^4$, $R^5$, $R^6$, $R^{7a}$, $R^{7b}$, $R^8$, L, and X, and any combinations thereof.

In some embodiments, $R^8$ is

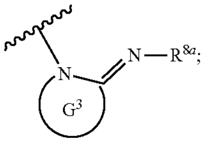

$G^3$ is a 5- to 12-membered heterocyclic ring system containing a first nitrogen at the point of attachment and optionally 1-4 additional heteroatoms selected from the group consisting of oxygen, nitrogen, and sulfur, $G^3$ having the imine substituent $=NR^{8a}$ adjacent to the first nitrogen and being optionally substituted with 1-4 substituents independently selected from the group consisting of halogen, oxo, $C_{1-6}$alkyl, $C_{1-6}$haloalkyl, $G^{3a}$ and —$C_{1-3}$alkylene-$G^{3a}$; $R^{8a}$ is hydrogen, $C_{1-4}$alkyl, $C_{3-6}$cycloalkyl, $C(O)C_{1-4}$alkyl, or $C(O)OC_{1-4}$alkyl; and $G^{3a}$ is $C_{3-10}$carbocycle or a 6- to 12 membered aryl, wherein $G^{3a}$ is optionally substituted with 1-4 substituents independently selected from the group consisting of halogen, $C_{1-4}$alkyl, $C_{1-4}$haloalkyl, OH, and —$OC_{1-4}$alkyl. In some embodiments, the 5- to 12-membered heterocyclic ring system at $G^3$ is a 5- to 8-membered monocyclic heterocycle, optionally substituted as described herein. In some embodiments, the optional substituents of $G^3$ are selected from the group consisting of halogen (e.g., fluoro), $C_{1-4}$alkyl (e.g., methyl), $C_{1-4}$ haloalkyl (e.g., difluoromethyl), $C_{3-8}$cycloalkyl (e.g., cyclopropyl), and $C_{1-3}$alkylene-$C_{3-8}$ cycloalkyl. In the compounds described herein, $R^{8a}$ may be hydrogen.

In some embodiments, $R^8$ is

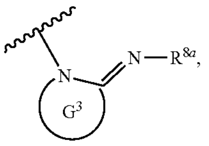

and is selected from the group consisting

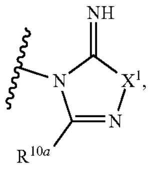

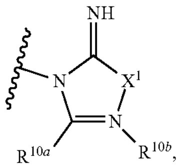

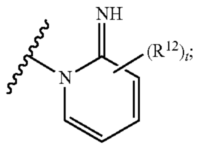

$X^1$ is $NR^{13}$, O, or S; $R^{10a}$ and $R^{10b}$ are independently hydrogen, halogen, $C_{1-4}$alkyl, $C_{1-4}$haloalkyl, $C_{3-8}$cycloalkyl, or —$C_{1-3}$ alkylene-$C_{3-8}$cycloalkyl; $R^{12}$, at each occurrence, is independently halogen, $C_{1-4}$alkyl, $C_{1-4}$ haloalkyl, $C_{3-8}$cycloalkyl, or —$C_{1-3}$alkylene-$C_{3-8}$cycloalkyl; $R^{13}$ is hydrogen, $C_{1-4}$alkyl, $C_{1-4}$ haloalkyl, $C_{3-8}$cycloalkyl, or —$C_{1-3}$alkylene-$C_{3-8}$cycloalkyl; wherein each cycloalkyl in $R^{10a}$, $R^{10b}$, $R^{12}$, and $R^{13}$ is further optionally substituted with 1-4 substituents independently selected from the group consisting of halogen, $C_{1-4}$alkyl, $C_{1-4}$haloalkyl, OH, and —$OC_{1-4}$alkyl; and t is 0, 1, 2, 3, or 4.

$R^8$ may be

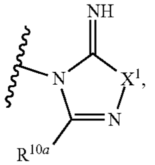

wherein $X^1$ and $R^{10a}$ are as defined herein. $X^1$ may be $NR^{13}$; and $R^{10a}$ and $R^{13}$ are as defined herein. In some embodiments, $R^{10a}$ is hydrogen and $R^{13}$ is $C_{1-4}$alkyl.

$R^8$ may be

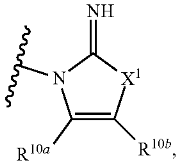

wherein $X^1$, $R^{10a}$, and $R^{10b}$ are as defined herein. $X^1$ may be $NR^{13}$ or O; and $R^{10a}$, $R^{10b}$, and $R^{13}$ are as defined herein. In some embodiments, $R^{10a}$ and $R^{10b}$ are hydrogen; and $R^{13}$ is $C_{1-4}$alkyl (e.g., methyl).

$R^8$ may be

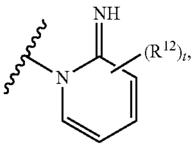

wherein $R^{12}$ and t are as defined herein. In some embodiments, t is 0.

$R^8$ may be

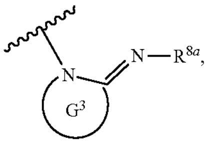

for example,

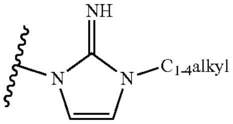

(e.g., 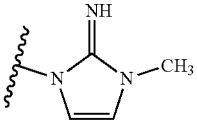 ),

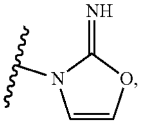

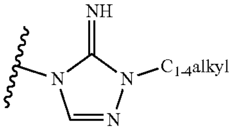

(e.g., 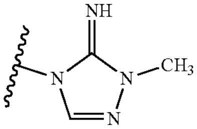 ), or

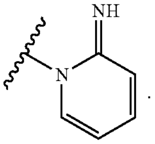

In some embodiments, $R^8$ is the imidazolyl, indolyl, or pyrrolopyridinyl as defined herein. The imidazolyl may be

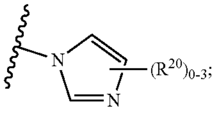

the indolyl may be

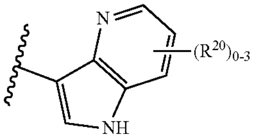

or

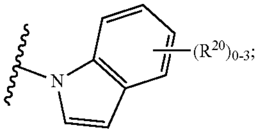

and the pyrrolopyridinyl may be

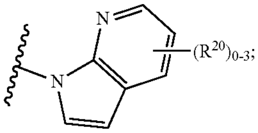

wherein $R^{20}$, at each occurrence, is independently $C_{1-4}$alkyl, $C_{1-4}$ haloalkyl, $C_{3-8}$cycloalkyl, or —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl. The imidazolyl may be

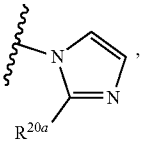

wherein $R^{20a}$ is hydrogen, $C_{1-4}$alkyl, or $C_{3-8}$cycloalkyl; the indolyl may be

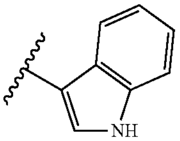 or 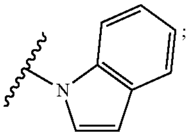;

and the pyrrolopyridinyl may be

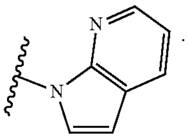 [SMILES: *n1ccc2cccnc21].

For example, the imidazolyl may be

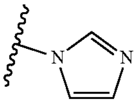 or 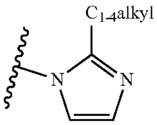

-continued (e.g., 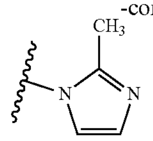, 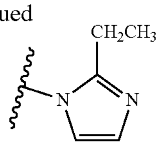).

In some embodiments, $R^8$ is

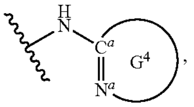

$G^4$ is as defined herein. Exemplary heteroaryl $G^4$ rings include isoxazole (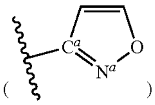)

and pyridine (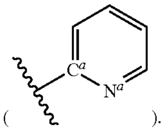).

Exemplary heterocyclic $G^4$ rings include imidazoline (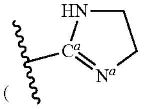).

Accordingly, $R^8$ may be

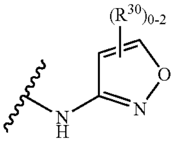

(e.g., 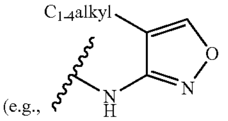 such as

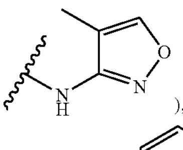), 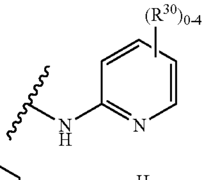

(e.g., 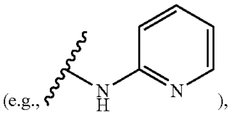), or 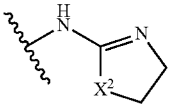

(e.g., 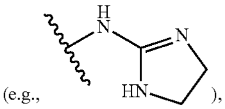), wherein $R^{30}$, at each occurrence, is independently halogen, $C_{1-4}$alkyl, $C_{1-4}$haloalkyl, or $C_{3-6}$cycloalkyl; and $X^2$ is $CH_2$, O, or NH.

$R^1$ may be $G^1$ or —$(CR^aR^b)_p$-$G^1$, wherein $R^a$, $R^b$, $G^1$, and p are as defined herein. The optional substituents of $G^1$ are independently selected from the group consisting of halogen, $C^{1-6}$alkyl (e.g., methyl), $C_{1-6}$haloalkyl (trifluoromethyl), oxo, —$OR^{1a}$, —$N(R^{1a})_2$, —$SR^{1a}$, cyano, —$C(O)OR^{1a}$, —$C(O)N(R^{1a})_2$, —$C(O)R^{1a}$, —$SOR^{1b}$, —$SO_2R^{1b}$, —$SO_2N(R^{1a})_2$, —$NR^{1a}C(O)R^{1a}$, —$NR^{1a}C(O)OR^{1b}$, —$NR^{1a}C(O)N(R^{1a})_2$, —$NR^{1a}S(O)_2R^{1b}$, —$NR^{1a}S(O)_2N(R^{1a})_2$, and -$L^1$-$G^{1a}$.

$R^{1a}$, at each occurrence, is independently hydrogen, $C_{1-6}$alkyl (e.g., methyl), $C_{1-6}$haloalkyl, —$C_{2-4}$alkylene-Y (e.g., —$CH_2CH_2$—Y), $G^{1a}$, or —$C_{1-6}$alkylene-$G^{1a}$, wherein two $R^{1a}$, together with a common nitrogen atom to which the $R^{1a}$ attach optionally form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl. Y, at each occurrence, is independently —OH, —$OC_{1-4}$alkyl (e.g., $OCH_3$), —$NH_2$, —$NHC_{1-4}$alkyl, or —$N(C_{1-4}alkyl)_2$ (e.g., $N(CH_3)_2$).

$R^{1b}$, at each occurrence, is independently $C_{1-6}$alkyl, $C_{1-6}$haloalkyl, $G^{1a}$, or —$C_{1-6}$alkylene-$G^{1a}$.

$G^1$ may be substituted with 1-3 substituents independently selected from the group consisting of $C_{1-4}$alkyl, —$OC_{1-4}$alkyl, —C(O)OH, —$C(O)OC_{1-4}$alkyl, —$C(O)NHC_{1-4}$alkyl, —C(O)NH—$C_{2-4}$alkylene-$OC_{1-4}$alkyl, or —C(O)NH—$C_{2-4}$alkylene-$N(C_{1-4}alkyl)_2$. $G^1$ may be substituted with 1-3 substituents independently selected from the group consisting of $CH_3$, —O $CH_3$, —C(O)OH, —$C(O)OCH_2CH_3$, —$C(O)NHCH_3$, —C(O)NH—$CH_2CH_2$—$OCH_3$, or —C(O)NH—$CH_2CH_2$—$N(CH_3)_2$.

$R^1$ may be —$(CR^aR^b)_p$-$G^1$; and $R^a$, $R^b$, $G^{1a}$, and p are as defined herein. In the embodiments described herein, p may be 1. $G^1$ may be a phenyl or a 5- to 6-membered heteroaryl, wherein $G^1$ is optionally substituted as defined herein. For example, $G^1$ may be substituted with 1-3 substituents independently selected from the group consisting of $C_{1-4}$alkyl and —$OC_{1-4}$alkyl. $G^1$ may be substituted with 1-3 substituents independently selected from the group consisting of $CH_3$ and —$OCH_3$. The 5- to 6-membered heteroaryl of $G^1$ may contain 1-3 nitrogen atoms. $G^1$ may be a phenyl or pyridinyl, where $G^1$ is optionally substituted as defined herein. $G^1$ may be

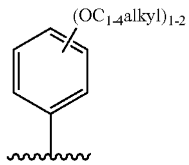 (e.g., 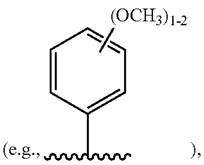),

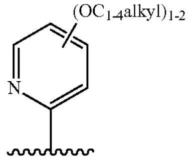 (e.g., 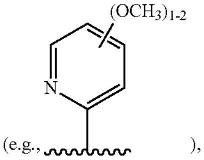), or

-continued
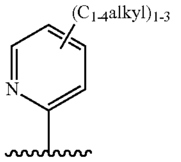
(e.g.,
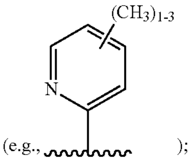
);
$G^1$ may be
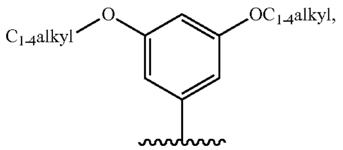
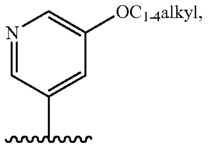
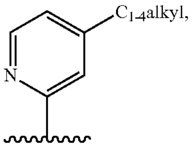
or
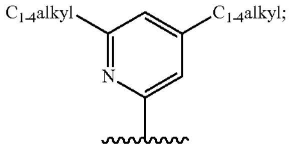
$G^1$ may be
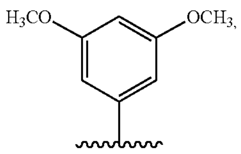
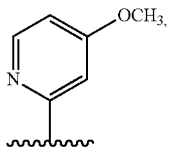
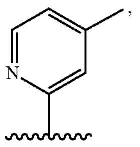
or
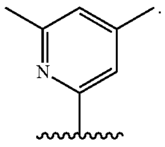
Included in the invention are compounds wherein $R^1$ is
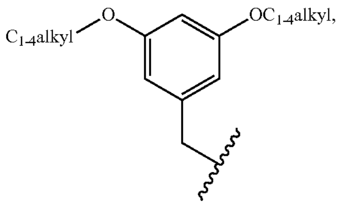
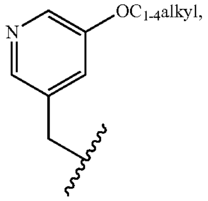
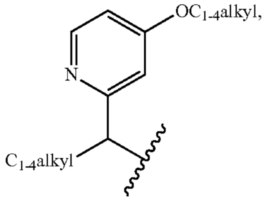
-continued
(e.g.,
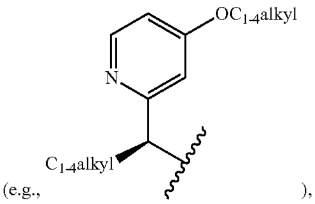
),
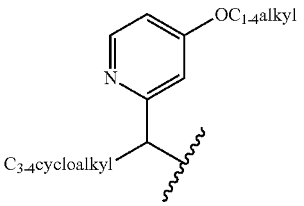
(e.g.,
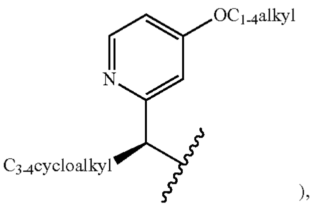
),
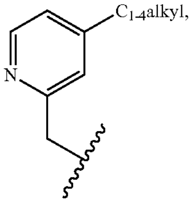
or
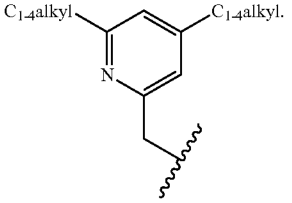
Still further included are compounds wherein $R^1$ is
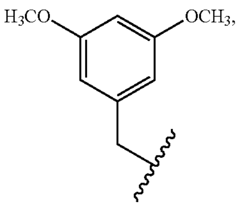
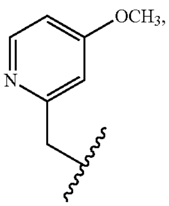
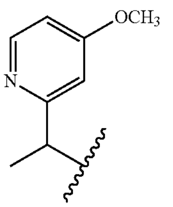
(e.g.,
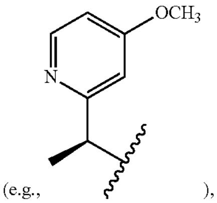
),
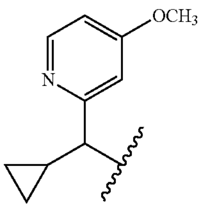
(e.g.,
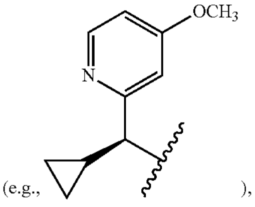
), -continued

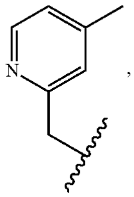

, or

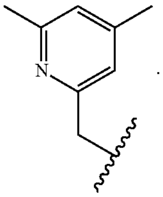

.

R[1] may be G[1]; wherein G[1] is as defined herein. G[1] may be a 6- to 12-membered aryl, an 8- to 10-membered heteroaryl, an 8- to 11-membered heterocycle, or a $C_{5-7}$carbocycle fused to a phenyl or to a 5- to 6-membered heteroaryl, wherein the 8- to 11-membered heterocycle is a 5- to 7-membered monocyclic heterocycle fused to a phenyl or to a 5- to 6-membered heteroaryl, and wherein G[1] is optionally substituted as defined herein. G[1] may be a phenyl substituted with $G^{1a}$. $G^{1a}$ may be a phenyl. For example, G[1] may be

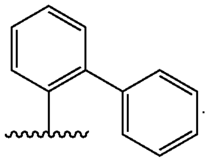 [SMILES: *c1ccccc1-c1ccccc1]

$G^1$ may be the optionally substituted 8- to 10-membered heteroaryl, such as an optionally substituted quinolinyl, e.g., quinolin-4-yl or quinolin-5-yl. The 8- to 10-membered heteroaryl may be substituted with 1-3 substituents independently selected from the group consisting of $C_{1-4}$alkyl, —$OC_{1-4}$alkyl, —C(O)OH, —C(O)$OC_{1-4}$alkyl, —C(O)$NHC_{1-4}$alkyl, —C(O)NH—$C_{2-4}$alkylene-$OC_{1-4}$alkyl, and —C(O)NH—$C_{2-4}$alkylene-N($C_{1-4}$alkyl)$_2$. The 8- to 10-membered heteroaryl may be substituted with 1-3 substituents independently selected from the group consisting of $CH_3$, —O $CH_3$, —C(O)OH, —C(O)$OCH_2CH_3$, —C(O)$NHCH_3$, —C(O)NH—$CH_2CH_2$—$OCH_3$, and —C(O)NH—$CH_2CH_2$—N$(CH_3)_2$. For example, $G^1$ may be

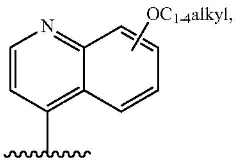

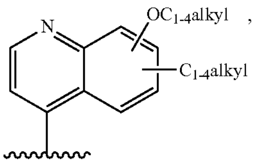

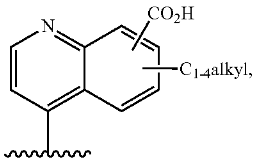

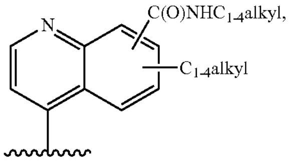

-continued

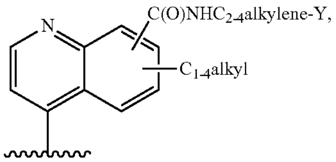

(e. g.,

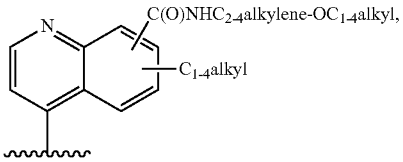

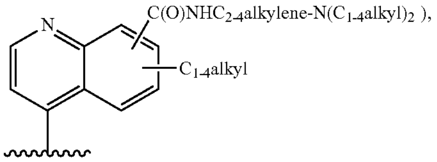

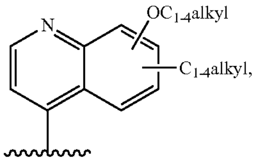

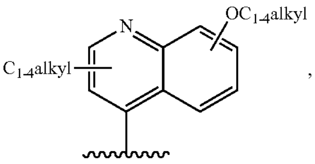

,

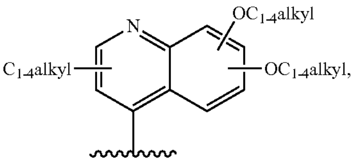

or

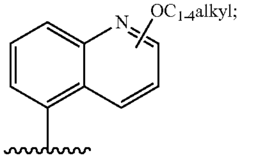

$G^1$ may be

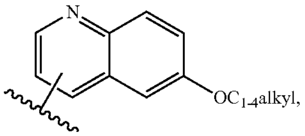

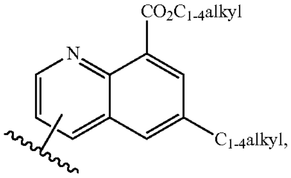

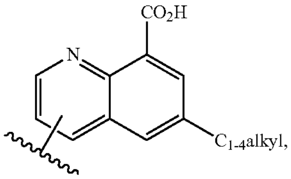

-continued
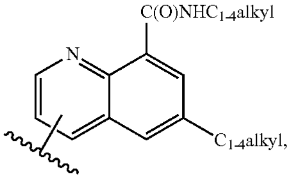
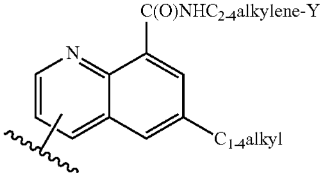
(e. g.,
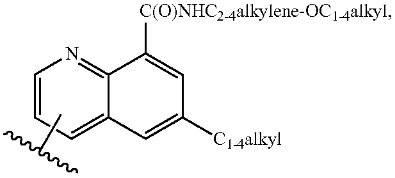
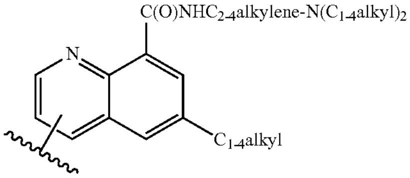
),
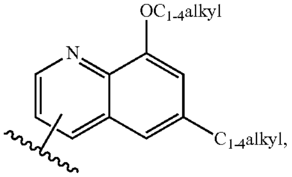
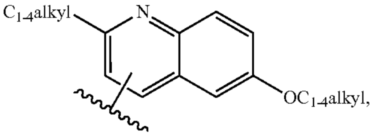
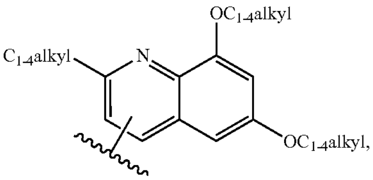
or
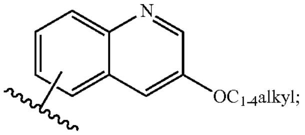
G[1] may be
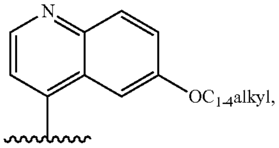
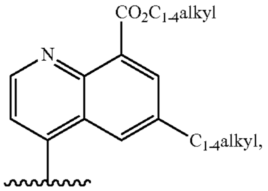
-continued
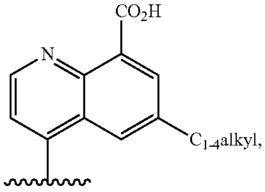
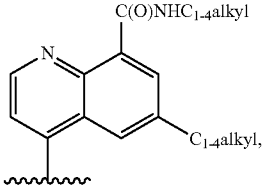
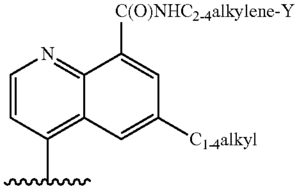
(e. g.,
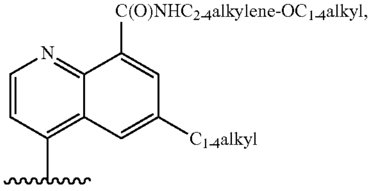
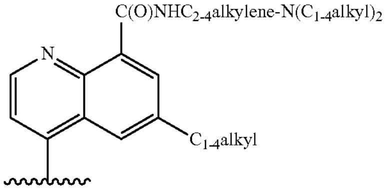
),
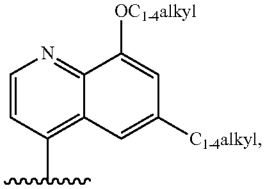
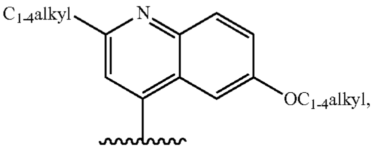
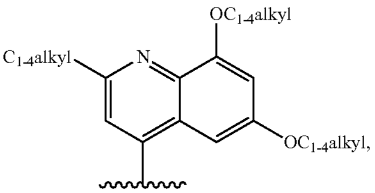
or
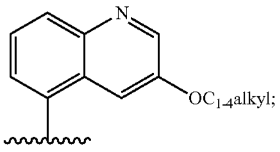

-continued and $G^1$ may be

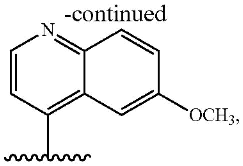

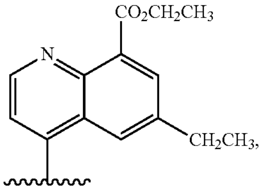

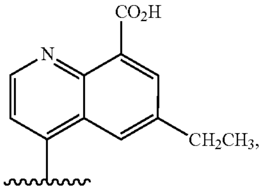

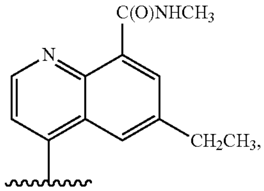

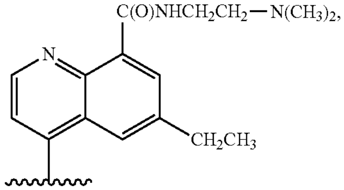

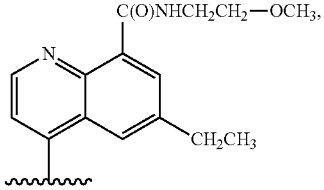

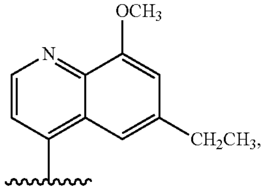

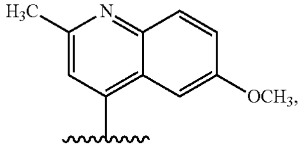

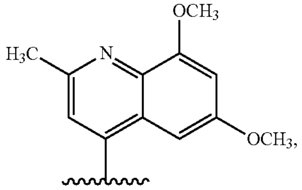

or

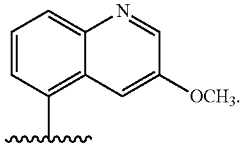

$G^1$ may be the optionally substituted $C_{5-7}$carbocycle fused to a phenyl or to a 5- to 6-membered heteroaryl. In the $C_{5-7}$carbocycle fused to the phenyl or to the 5- to 6-membered heteroaryl, the $C_{5-7}$carbocyclic ring is attached to the parent molecular moiety, such as an optionally substituted 1,2,3,4-tetrahydronaphthalen-1-yl. For example, $G^1$ may be

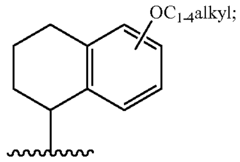

$G^1$ may be

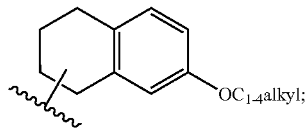

$G^1$ may be

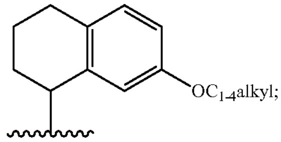

and $G^1$ may be

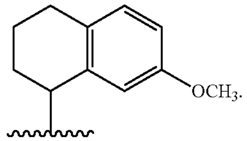 [SMILES: *C1CCCc2ccc(OC)cc21]

$G^1$ may be the optionally substituted 8- to 11-membered heterocycle, wherein the 8- to 11-membered heterocycle is a 5- to 7-membered monocyclic heterocycle fused to a phenyl or to a 5- to 6-membered heteroaryl. In the 5- to 7-membered monocyclic heterocycle fused to the phenyl or to the 5- to 6-membered heteroaryl, the 5- to 7-membered heterocyclic ring is attached to the parent molecular moiety, such as an optionally substituted chroman-4-yl. For example, $G^1$ may be

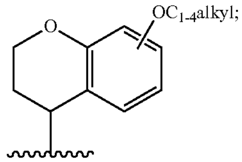

$G^1$ may be

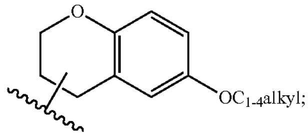

$G^1$ may be

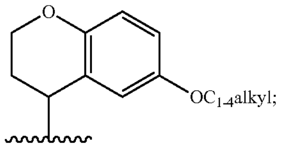

and $G^1$ may be

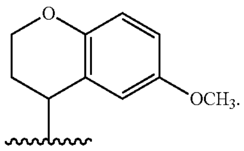 [SMILES: *C1CCOc2ccc(OC)cc21]

Any $G^1$, as defined herein, may be substituted with 1-3 substituents independently selected from the group consisting of halogen (e.g., fluoro, chloro), $C_{1-6}$alkyl (e.g., methyl, ethyl), $C_{1-6}$haloalkyl, —$OR^{1a}$ (e.g., $OCH_3$), —$N(R^{1a})_2$, —$SR^{1a}$, cyano, —$C(O)OR^{1a}$, —$C(O)N(R^{1a})$, —$C(O)R^{1a}$, —$SO_2R^{1b}$, —$NR^{1a}C(O)R^{1a}$, $C_{3-8}$cycloalkyl (e.g., cyclopropyl), and —$C_{1-3}$alkylene-$C_{3-8}$ cycloalkyl, wherein each $C_{3-8}$cycloalkyl is optionally substituted with 1-4 substituents independently selected from the group consisting of $C_{1-4}$alkyl and halogen, wherein $R^{1a}$ and $R^{1b}$ are as defined herein. $G^1$, as defined herein, may be substituted with 1-3 substituents independently selected from the group consisting of halogen (e.g., fluoro, chloro), $C_{1-6}$alkyl (e.g., methyl, ethyl), —$OC_{1-6}$alkyl (e.g., $OCH_3$), and $C_{3-8}$cycloalkyl (e.g., cyclopropyl).

In the embodiments described herein, $R^a$ may be hydrogen, $C_{1-4}$alkyl (e.g., methyl), or $G^{1b}$, wherein $G^{1b}$ is as defined herein (e.g., $C_{3-6}$carbocycle such as cyclopropyl).

In the embodiments described herein are further embodiments, wherein $R^b$ is hydrogen.

The carbon atom to which $R^a$ and $R^b$ attach may have either R or S stereochemistry.

In some embodiments, $R^4$ is $G^2$; wherein $G^2$ is as defined herein. $G^2$ may be a 6- to 12-membered aryl or a 5- to 12-membered heteroaryl, and optionally substituted as defined herein. $R^4$ may be $G^2$, wherein $G^2$ may be a phenyl or a 5- to 6-membered heteroaryl, and optionally substituted as defined herein. The 5- to 6-membered heteroaryl of $G^2$ may contain 1-3 heteroatoms independently selected from the group consisting of sulfur and nitrogen. $R^4$ may be $G^2$, wherein $G^2$ may be phenyl, pyridinyl, pyrazolyl, or thiazolyl, and $G^2$ is optionally substituted as defined herein. For example, $G^2$ is optionally substituted with 1-4 substituents independently selected from the group consisting of halogen, $C_{1-6}$alkyl, and $C_{1-6}$haloalkyl. $R^4$ may be

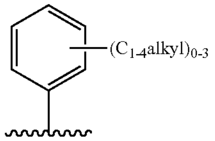 (e. g., 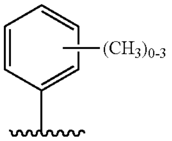),

-continued

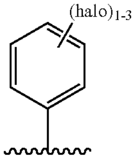 (e. g., 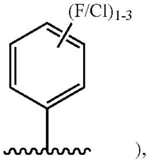),

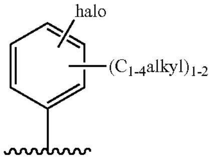 (e. g., 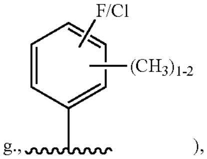),

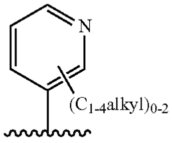 (e. g., 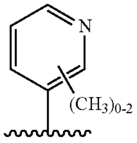),

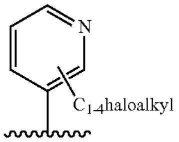 (e. g., 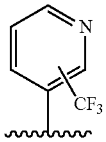),

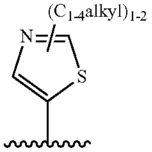 (e. g., 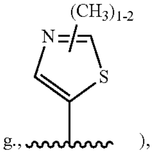), or

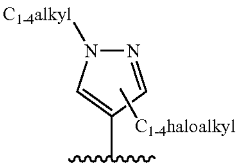 (e. g., 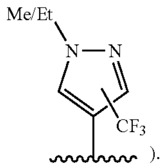).

$R^4$ may be 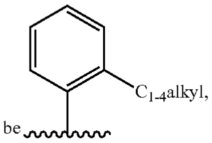 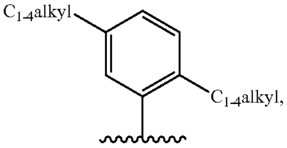

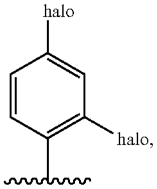 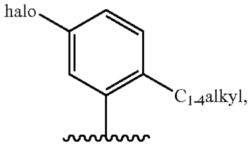

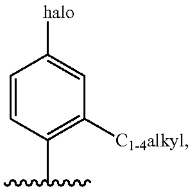 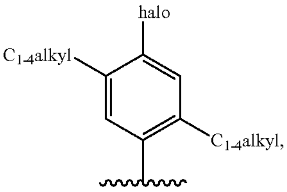

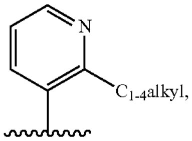 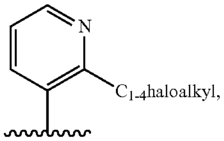

-continued

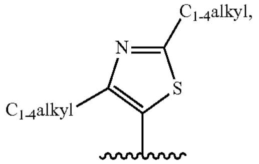 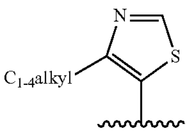, or 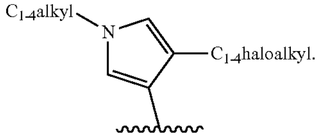

$R^4$ may be 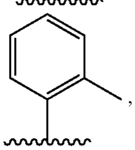, 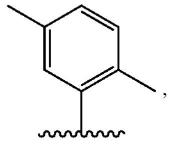,

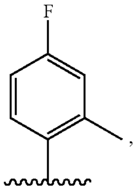, 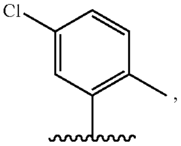, 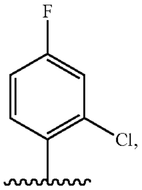

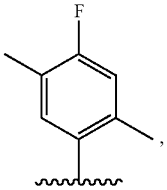, 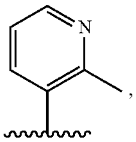, 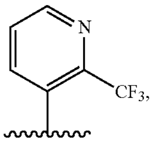

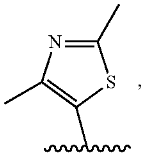, 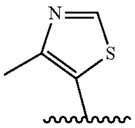, 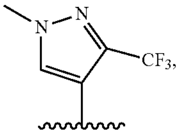 or

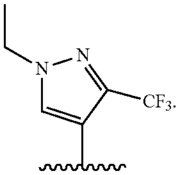

$R^{1a}$, $R^{1c}$, $R^{1e}$, $R^{4a}$, and $R^{4c}$ may independently be hydrogen, $C_{1-6}$alkyl, or $C_{1-6}$haloalkyl.

$R^{1b}$, $R^{1d}$, $R^{1f}$, $R^{4b}$, and $R^{4d}$ may independently be $C_{1-6}$alkyl or $C_{1-6}$haloalkyl.

In the compounds described herein $R^{2a}$ and $R^{2b}$ may be independently hydrogen or $C_{1-4}$ alkyl. For example $R^{2a}$ may be hydrogen and $R^{2b}$ methyl. When the carbon to which $R^{2a}$ and $R^{2b}$ attach is assymetrically substituted, it may have either (R) or (S) stereochemistry.

In the compounds described herein, $R^3$ may be hydrogen or $C_{1-6}$alkyl.

In one aspect of the invention, L is —$(CR^{2a}R^{2b})_n$—, wherein ------ is a single bond and X is O, $NR^3$, or S; or L is —$C(R^{2c})$, wherein ------ is a double bond and X is N. In the group L of formula (I), —$C(R^{2c})$: refers to a carbon atom with substituent $R^{2c}$, where the carbon atom is bonded to X by a double bond and on the other side to the adjacent nitrogen ring atom by a single bond. The group —$C(R^{2c})$: may alternately be written as

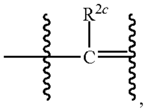, as shown below in formula (I-A).

In the compounds described herein n may be 1 (e.g., formula (I-A)); n may be 2 (e.g., formula (I-B1).

In another aspect of the invention, L is a $C_{2-1}$hydrocarbylene optionally substituted with 1-2 $C_{1-4}$alkyl or oxo. For example, L may be a $C_2$hydrocarbylene optionally substituted with $C_{1-4}$alkyl or oxo, e.g., —$CH_2CH_2$—, —$CH_2C(O)$—, or —$CH_2CH(CH_3)$—. L may be a $C_1$hydrocarbylene optionally substituted with $C_{1-4}$alkyl, e.g., —$CH_2$—,

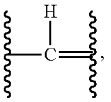, or 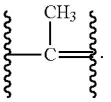.

In the compounds described herein, formula (I) may have formula (I-A)

(I-A)

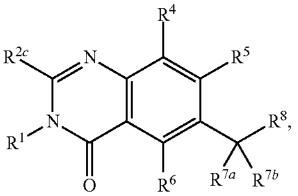

wherein $R^1$, $R^{2c}$, $R^4$, $R^5$, $R^6$, $R^{7a}$, $R^{7b}$, and $R^8$ are as defined herein. In the compounds described herein, $R^{2c}$ may be hydrogen or $C_{1-4}$alkyl (e.g., methyl). Formula (I-A) represents compounds wherein L is —$C(R^{2c})$, alternatively written as

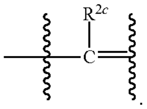.

Formula (I-A) also represents compounds wherein L is an unsaturated $C_1$hydrocarbylene substituted with $R^{2c}$. Formula (I-A) may have formula (II-A)

(II-A)

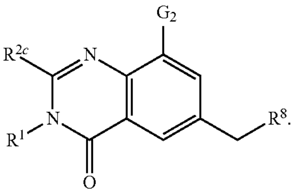

In the compounds described herein, formula (I) may have formula (I-B)

(I-B)

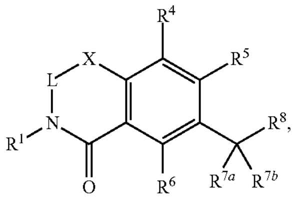

wherein L is $-(CR^{2a}R^{2b})_n-$ and $R^1$, $R^{2a}$, $R^{2b}$, $R^4$, $R^5$, $R^6$, $R^{7a}$, $R^{7b}$, $R^8$, X, and n are as defined herein. In the compounds described herein L may be $-CH_2-$ and X is NH. Formula (I-B) also includes compounds wherein L is a saturated $C_1$hydrocarbylene, i.e., $-CH_2-$.

In the compounds described herein, formula (I) may have formula (I-B1)

(I-B1)

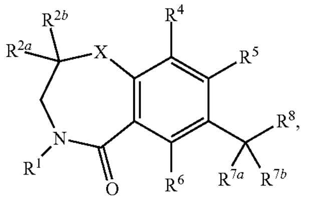

wherein $R^1$, $R^{2a}$, $R^{2b}$, $R^4$, $R^5$, $R^6$, $R^{7a}$, $R^{7b}$, $R^8$, and X are as defined herein. In the compounds described herein, $R^{2a}$ and $R^{2b}$ may be independently hydrogen or $C_{1-4}$alkyl; or $R^{2a}$ and $R^{2b}$ together may form an oxo group. In the compounds described herein, X may be O. In the compounds described herein, X may be NH. Formula (I-B1) represents compounds wherein L is a $C_2$hydrocarbylene optionally substituted with 1-2 $C_{1-4}$ alkyl or oxo. Formula (I-B1) may have formula (II-B1), (II-B2), (II-B3), (II-B4), or (II-B5):

(II-B1)

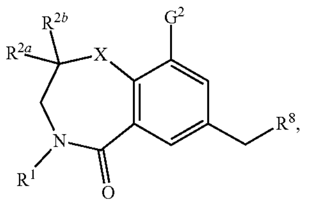

(II-B2)

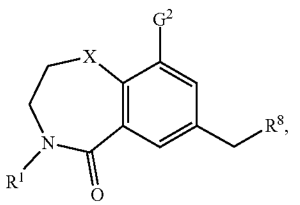

-continued (II-B3)

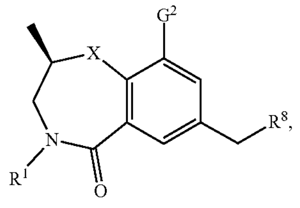

(II-B4)

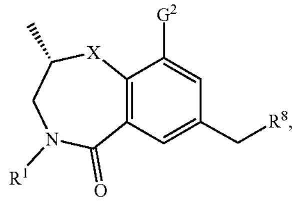

(II-B5)

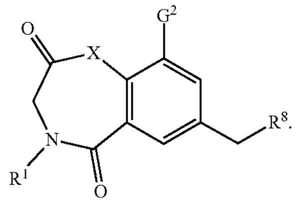

In the compounds described herein, $R^5$ may be hydrogen or halogen. In the compounds described herein, $R^5$ may be hydrogen.

In the compounds described herein, $R^6$ may be hydrogen.

In the compounds describe herein, $R^{7a}$ and $R^{7b}$ may each be hydrogen.

In the compounds of formula (I) are compounds of formula (II), (II)

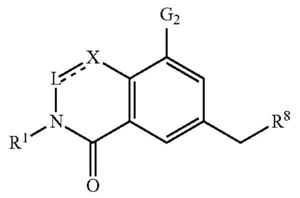

wherein X is an oxygen, nitrogen, or sulfur atom, the nitrogen atom being unsaturated or saturated and substituted with hydrogen; L is a $C_{2-1}$hydrocarbylene optionally substituted with 1-2 $C_{1-4}$alkyl or with oxo; $R^1$ is

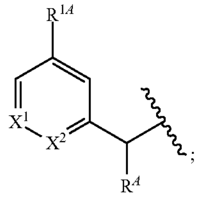

$X^1$ is $CR^{1B}$ or N; $X^2$ is $CR^{1C}$ or N; $R^{1A}$ is $OC_{1-4}$alkyl or $C_{1-4}$alkyl; $R^{1B}$ is hydrogen, $OC_{1-4}$alkyl, $C_{1-4}$alkyl, $-C(O)OR^{1a}$, or $-C(O)N(R^{1a})_2$; $R^{1C}$ is hydrogen and $R^A$ is hydrogen, $C_{1-4}$alkyl, or $C_{3-6}$cycloalkyl; or $R^{1C}$ and $R^A$ join to form a 6-membered ring optionally containing two additional double bonds and a nitrogen or oxygen heteroatom, the 6-membered ring being optionally substituted with $C_{1-4}$alkyl; $R^{1a}$, at each occurrence, is independently hydrogen, $C_{1-4}$alkyl, $C_{1-4}$fluoroalkyl, or —$C_{2-4}$alkylene-Y; Y, at each occurrence, is independently —OH, —O$C_{1-4}$alkyl, —$NH_2$, —NH$C_{1-4}$alkyl, or —N($C_{1-4}$alkyl)$_2$, $G^2$ is a 5- to 6-membered monocyclic aromatic ring, optionally containing 1-3 heteroatoms independently selected from N and S, and optionally substituted with 1-3 substituents independently selected from the group consisting of halogen, $C_{1-4}$alkyl, and $C_{1-4}$fluoroalkyl; and $R^8$ is a 5-membered heterocyclic ring containing 2-3 heteroatoms and 2 or 1 double bonds, wherein one of the 2-3 heteroatoms is a nitrogen and the remaining heteroatoms are independently selected from nitrogen and oxygen, wherein $R^8$ is optionally substituted with 1-3 substituents independently selected from the group consisting of $C_{1-4}$alkyl, imino, $C_{1-4}$ fluoroalkyl, $C_{3-4}$cycloalkyl, and —$C_{1-3}$alkylene-$C_{3-4}$cycloalkyl.

Included in formula (II) are compounds wherein $R^8$ is imidazolyl optionally substituted with 1-3 substituents independently selected from the group consisting of $C_{1-4}$alkyl, $C_{3-4}$cycloalkyl, and —$C_{1-3}$alkylene-$C_{3-4}$cycloalkyl. Further included are compounds wherein $R^8$ is

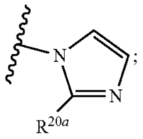

and $R^{20a}$ is hydrogen, $C_{1-4}$alkyl, or $C_{3-4}$cycloalkyl. Still further included are compounds wherein $R^8$ is

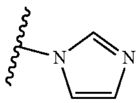

or

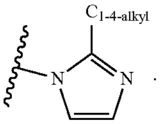

Also included in formula (II) are compounds wherein $R^8$ is

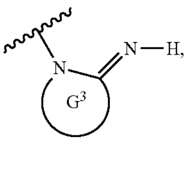

wherein $G^3$ is a 5-membered heterocyclic ring containing a first nitrogen at the point of attachment and optionally 1-2 additional heteroatoms selected from the group consisting of nitrogen and oxygen, $G^3$ having the imine substituent =NH adjacent to the first nitrogen and being optionally substituted with 1-3 substituents independently selected from the group consisting of $C_{1-4}$alkyl, $C_{1-4}$fluoroalkyl, $C_{3-4}$cycloalkyl, and —$C_{1-3}$alkylene-$C_{3-4}$cycloalkyl. Further included are compounds wherein $R^8$ is

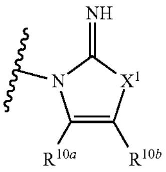

or

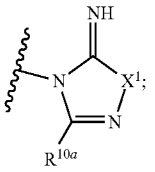

$X^1$ is $NR^{13}$ or O; $R^{10a}$ and $R^{10b}$ are independently hydrogen, $C_{1-4}$alkyl, or $C_{1-4}$fluoroalkyl; and $R^{13}$ is hydrogen, $C_{1-4}$alkyl, $C_{1-4}$ fluoroalkyl, $C_{3-4}$cycloalkyl, or —$C_{1-3}$alkylene-$C_{3-4}$ cycloalkyl. Still further included are compounds wherein $R^8$ is

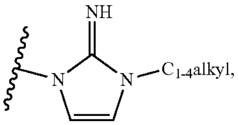

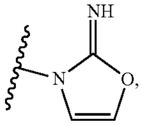

or

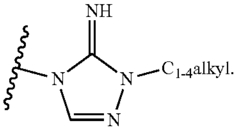

Also included in any of these groups or subgroups of compounds of formula (II) are compounds wherein $X^1$ is $CR^{1B}$; $X^2$ is $CR^{1C}$; $R^{1C}$ is hydrogen; and $R^A$ is hydrogen, $C_{1-4}$alkyl, or $C_{3-6}$cycloalkyl. Further included are compounds wherein $R^{1A}$ is O$C_{1-4}$alkyl; and $R^{1B}$ is O$C_{1-4}$alkyl. Still further included are compounds wherein $R^1$ is

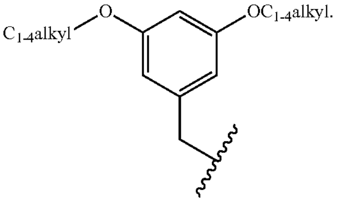

Still further included are compounds wherein $R^1$ is

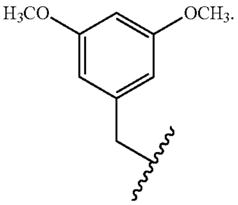 [SMILES: *Cc1cc(OC)cc(OC)c1]

Alternatively, included in any of these groups or subgroups of compounds of formula (II) are compounds wherein $X^2$ is $CR^{1C}$; and $R^{1C}$ and $R^A$ join to form a 6-membered ring optionally containing two additional double bonds and a nitrogen or oxygen heteroatom, the 6-membered ring being optionally substituted with $C_{1-4}$alkyl. Further included are compounds wherein $R^1$ is

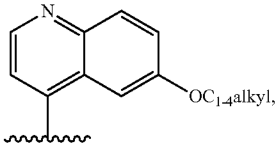
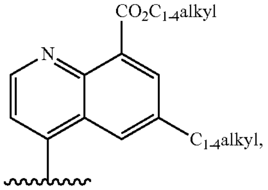
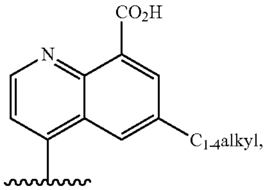
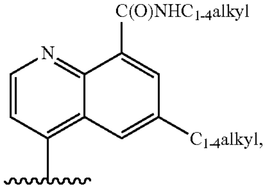
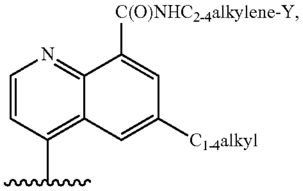
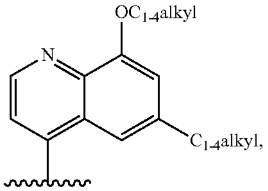
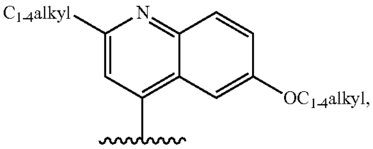
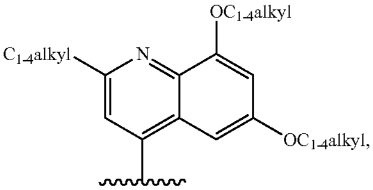
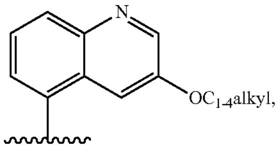
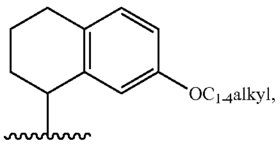 or
-continued
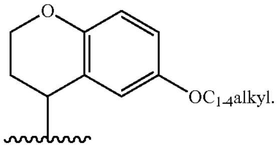
Still further included are compounds wherein
$R^1$ is
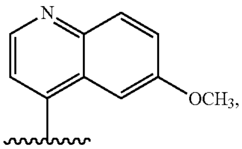
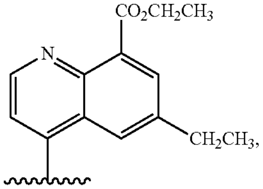
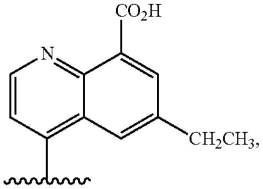
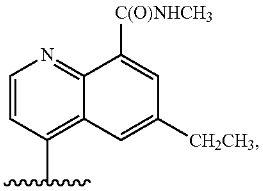
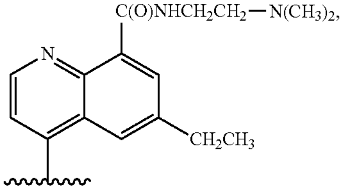
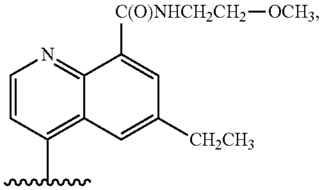
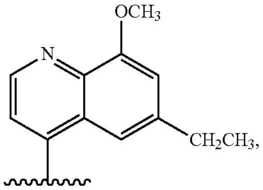
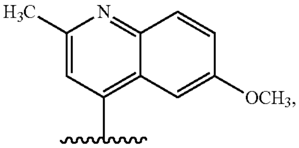
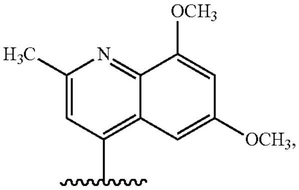

-continued

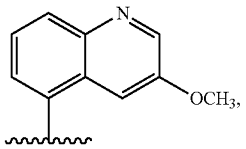 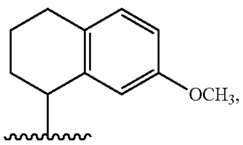 or

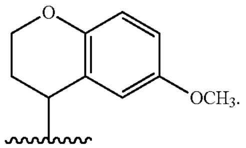

Alternatively, included in any of these groups or subgroups of compounds of formula (II) are compounds wherein $X^1$ is $CR^{1B}$; and $X^2$ is N. Further included are compounds wherein $R^{1A}$ is $C_{1-4}$alkyl or $OC_{1-4}$alkyl; and $R^{1B}$ is hydrogen or $C_{1-4}$alkyl. Still further included are compounds wherein $R^1$ is

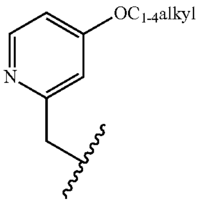 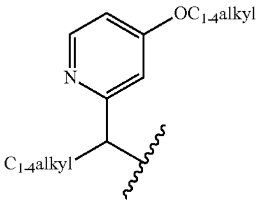, (e.g., 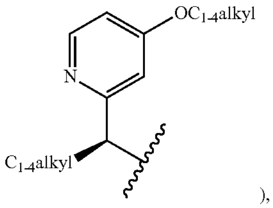),

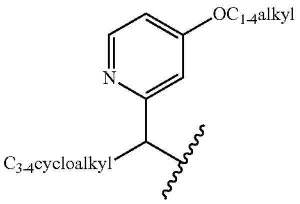

(e.g., 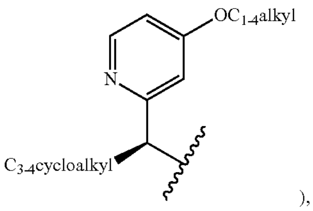),

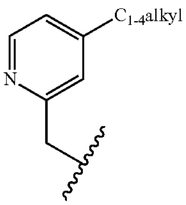), or

-continued

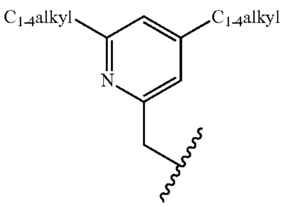.

Still further included are compounds wherein $R^1$ is

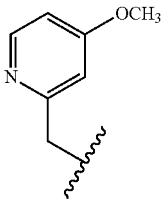, 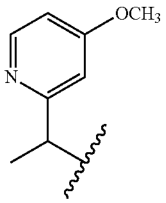

(e.g., 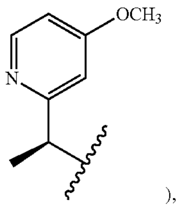), 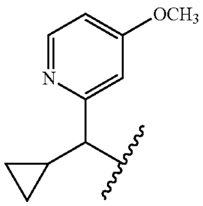

(e.g., 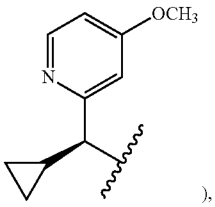), 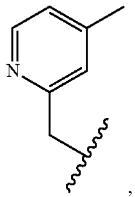, or

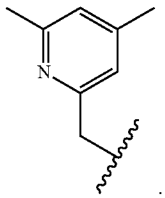.

Also included in any of these groups or subgroups of compounds, or combinations halo thereof, are further compounds wherein $G^2$ is

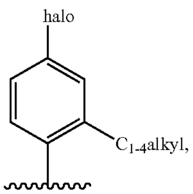 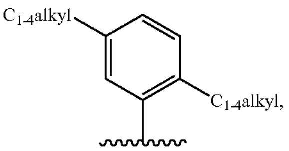

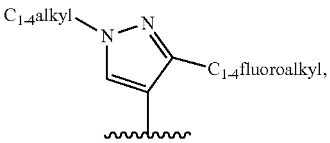

-continued

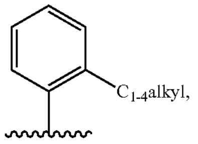
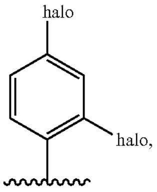
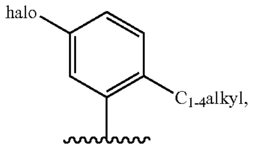
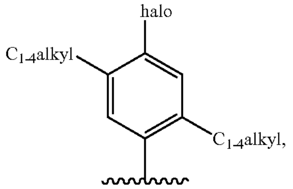
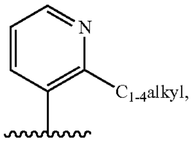
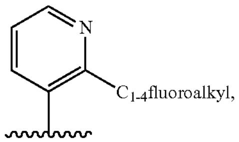
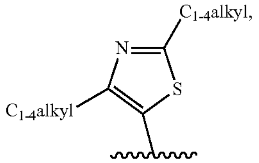
or
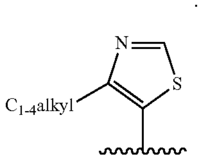

Further included are compounds wherein $G^2$ is

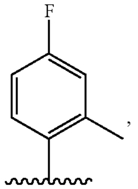
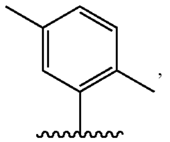
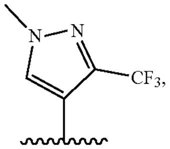
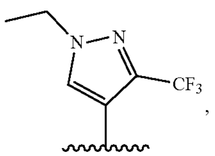
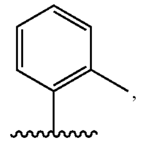
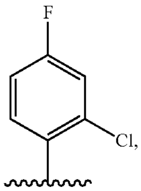
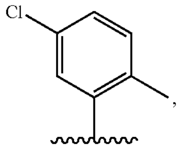
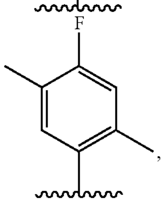
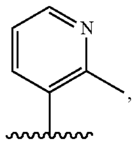
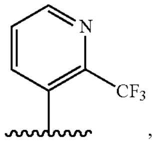
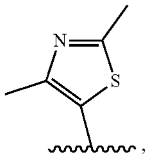
or
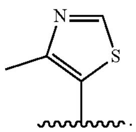

Included in any of these groups or subgroups of compounds of formula (II) are compounds of formula (II-A)

(II-A)

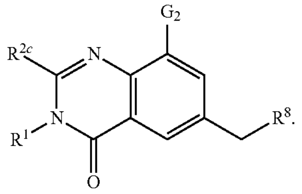

Included in any of these groups or subgroups of compounds of formula (II) are compounds of formula (II-B1)

(II-B1)

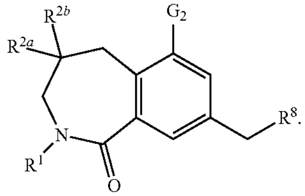

In compounds of formula (II-B1), $R^{2a}$ and $R^{2b}$ may be independently hydrogen or $C_{1-4}$ alkyl, as in formulas (II-B2), (II-B3), and (II-B4).

In compounds of formula (II-B1), $R^{2a}$ and $R^{2b}$ may form an oxo, as in formula (II-B5).

In certain embodiments, the compound of formula (I) is selected from the group consisting of the compounds in Table 1, or a pharmaceutically acceptable salt thereof.

TABLE 1

| Exemplary compounds. | |
|---|---|
| 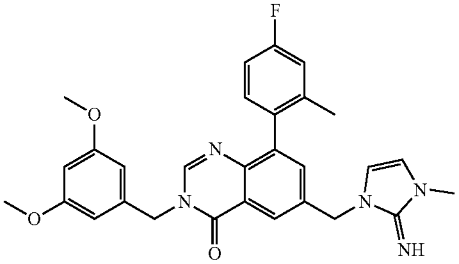 | I-1 |
| 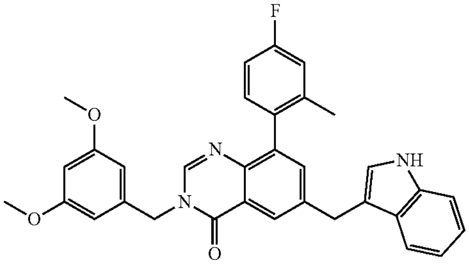 [SMILES: COc1cc(Cn2cnc3c(-c4ccc(F)cc4C)cc(Cc4c[nH]c5ccccc45)cc3c2=O)cc(OC)c1] | I-2 |

TABLE 1-continued
| Exemplary compounds. |
| --- |
| 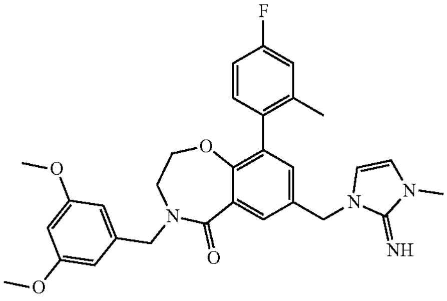 I-3 |
| 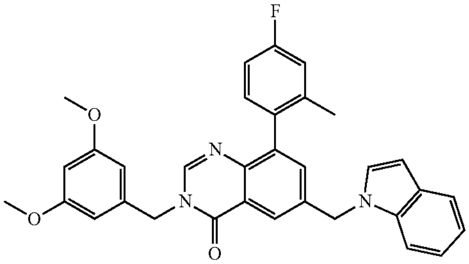 [SMILES: COc1cc(Cn2cnc3c(-c4ccc(F)cc4C)cc(Cn4ccc5ccccc54)cc3c2=O)cc(OC)c1] I-4 |
| 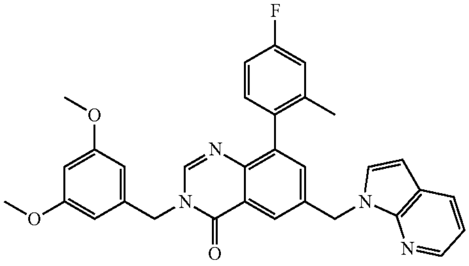 [SMILES: COc1cc(Cn2cnc3c(-c4ccc(F)cc4C)cc(Cn4ccc5cccnc54)cc3c2=O)cc(OC)c1] I-5 |
| 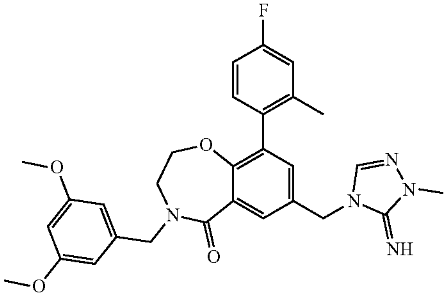 I-6 |
| 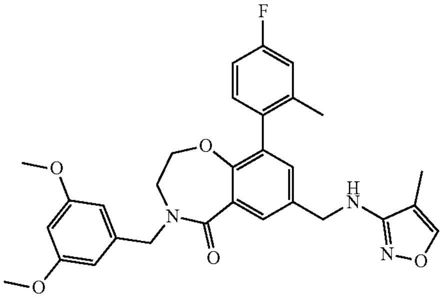 [SMILES: COc1cc(CN2CCOc3c(cc(CNc4nocc4C)cc3-c3ccc(F)cc3C)C2=O)cc(OC)c1] I-7 |
TABLE 1-continued
| Exemplary compounds. |
| --- |
| 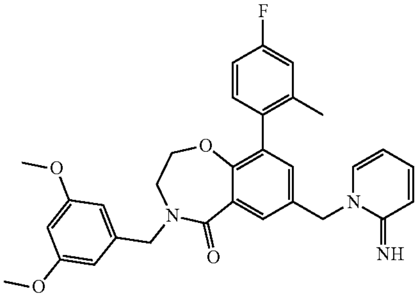 [SMILES: COc1cc(CN2CCOc3c(cc(Cn4ccccc4=N)cc3-c3ccc(F)cc3C)C2=O)cc(OC)c1] I-8 |
| 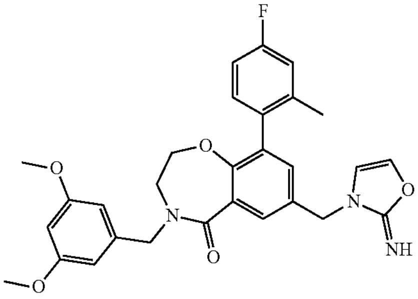 [SMILES: COc1cc(CN2CCOc3c(cc(Cn4ccoc4=N)cc3-c3ccc(F)cc3C)C2=O)cc(OC)c1] I-9 |
| 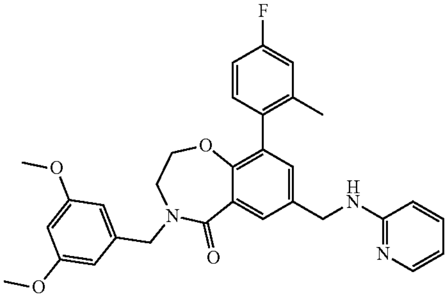 [SMILES: COc1cc(CN2CCOc3c(cc(CNc4ccccn4)cc3-c3ccc(F)cc3C)C2=O)cc(OC)c1] I-10 |
| 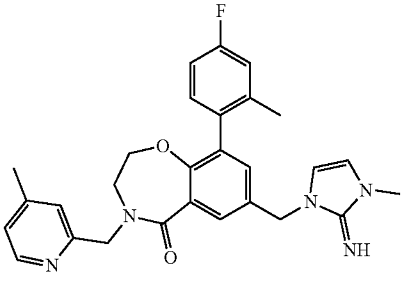 [SMILES: Cc1ccnc(CN2CCOc3c(cc(Cn4ccn(C)c4=N)cc3-c3ccc(F)cc3C)C2=O)c1] I-11 |
| 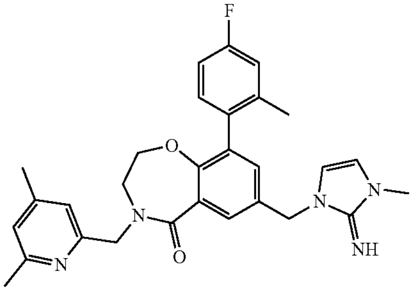 I-12 |

TABLE 1-continued
| Exemplary compounds. |
|---|
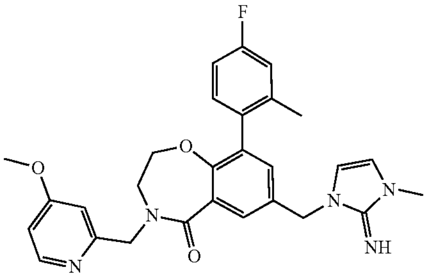
I-13
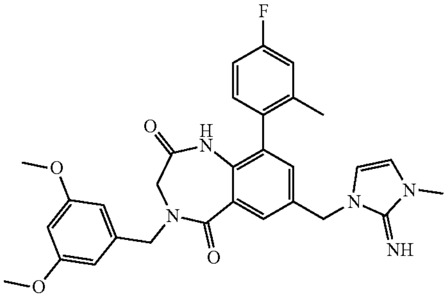
I-14
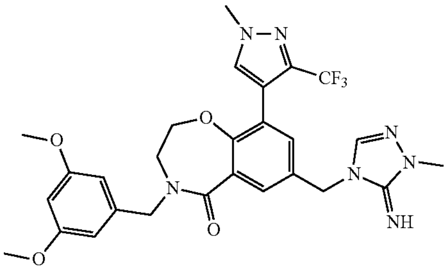
I-15
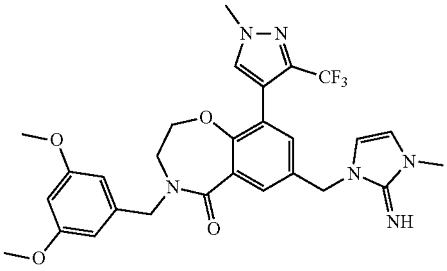
I-16
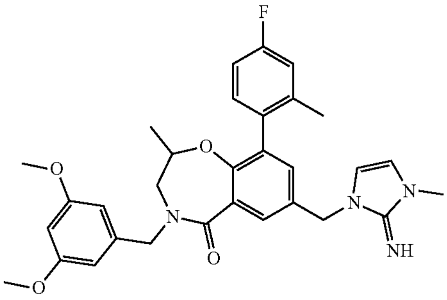
I-17
TABLE 1-continued
| Exemplary compounds. |
|---|
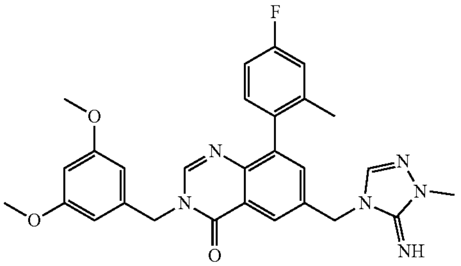
I-18
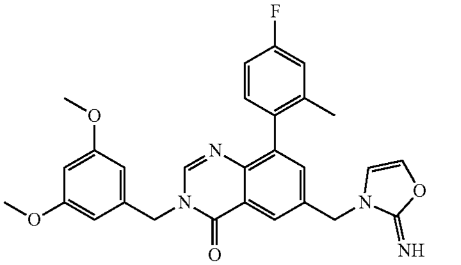 [SMILES: COc1cc(Cn2cnc3c(-c4ccc(F)cc4C)cc(Cn4ccoc4=N)cc3c2=O)cc(OC)c1]
I-19
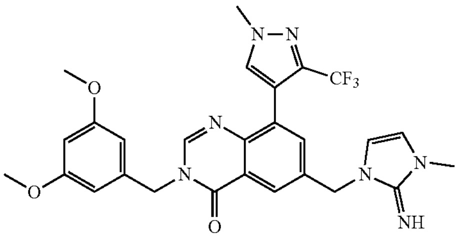
I-20
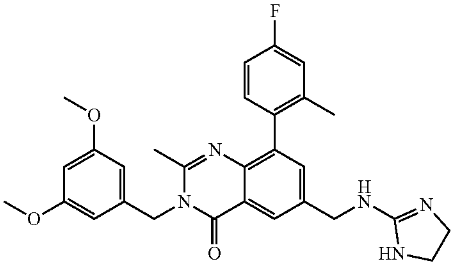 [SMILES: COc1cc(Cn2c(C)nc3c(-c4ccc(F)cc4C)cc(CNC4=NCCN4)cc3c2=O)cc(OC)c1]
I-21
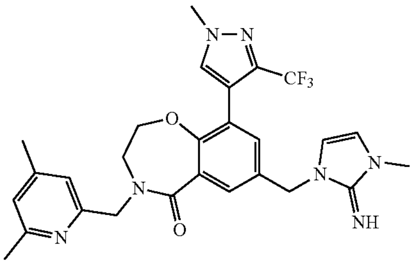
I-22
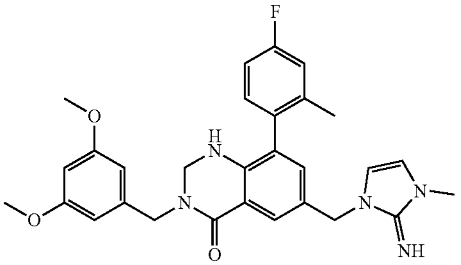
I-23

TABLE 1-continued
| Exemplary compounds. |
| --- |
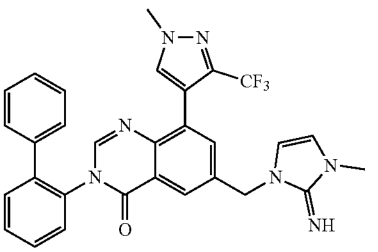 [SMILES: Cn1cc(-c2cc(Cn3ccn(C)c3=N)cc3c(=O)n(-c4ccccc4-c4ccccc4)cnc23)c(C(F)(F)F)n1]
I-24
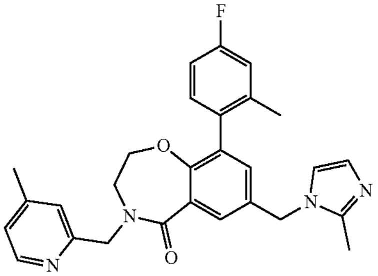 [SMILES: Cc1ccnc(CN2CCOc3c(cc(Cn4ccnc4C)cc3-c3ccc(F)cc3C)C2=O)c1]
I-25
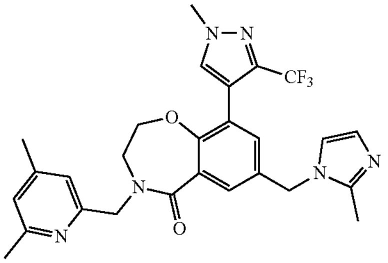 [SMILES: Cc1cc(C)nc(CN2CCOc3c(cc(Cn4ccnc4C)cc3-c3cn(C)nc3C(F)(F)F)C2=O)c1]
I-26
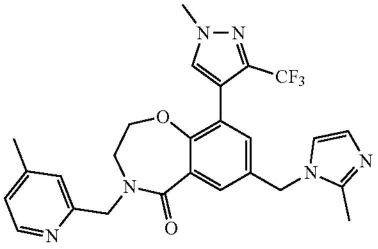 [SMILES: Cc1ccnc(CN2CCOc3c(cc(Cn4ccnc4C)cc3-c3cn(C)nc3C(F)(F)F)C2=O)c1]
I-27
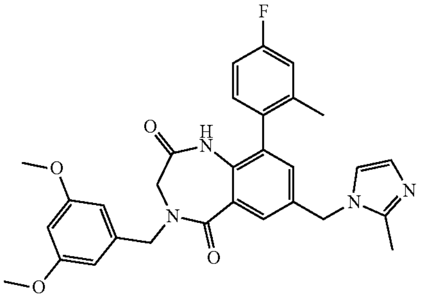 [SMILES: COc1cc(CN2CC(=O)Nc3c(cc(Cn4ccnc4C)cc3-c3ccc(F)cc3C)C2=O)cc(OC)c1]
I-28
TABLE 1-continued
| Exemplary compounds. |
| --- |
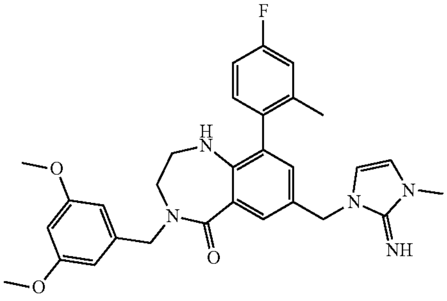
I-29
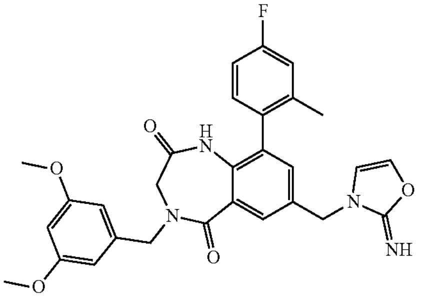 [SMILES: COc1cc(CN2CC(=O)Nc3c(cc(Cn4ccoc4=N)cc3-c3ccc(F)cc3C)C2=O)cc(OC)c1]
I-30
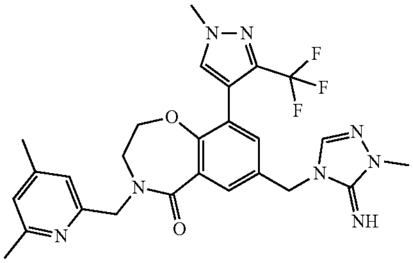
I-31
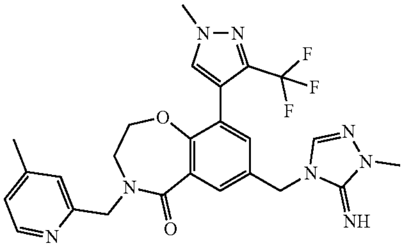 [SMILES: Cc1ccnc(CN2CCOc3c(cc(Cn4cnn(C)c4=N)cc3-c3cn(C)nc3C(F)(F)F)C2=O)c1]
I-32
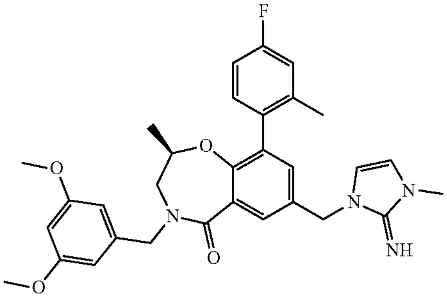
I-33

TABLE 1-continued
Exemplary compounds.
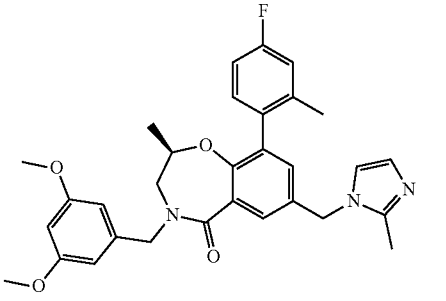 [SMILES: COc1cc(CN2C[C@@H](C)Oc3c(cc(Cn4ccnc4C)cc3-c3ccc(F)cc3C)C2=O)cc(OC)c1]
I-34
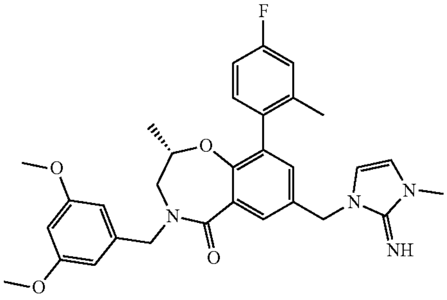
I-35
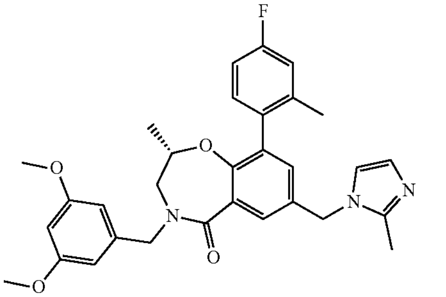 [SMILES: COc1cc(CN2C[C@H](C)Oc3c(cc(Cn4ccnc4C)cc3-c3ccc(F)cc3C)C2=O)cc(OC)c1]
I-36
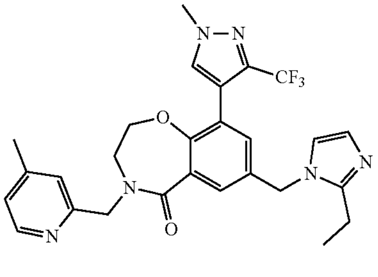 [SMILES: CCc1nccn1Cc1cc2c(c(-c3cn(C)nc3C(F)(F)F)c1)OCCN(Cc1cc(C)ccn1)C2=O]
I-37
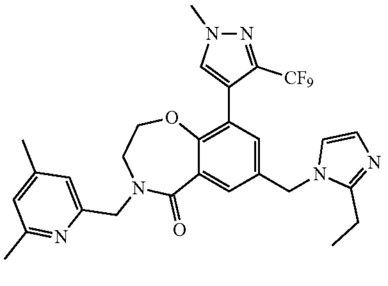
I-38
TABLE 1-continued
Exemplary compounds.
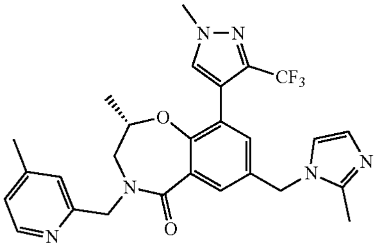 [SMILES: Cc1ccnc(CN2C[C@H](C)Oc3c(cc(Cn4ccnc4C)cc3-c3cn(C)nc3C(F)(F)F)C2=O)c1]
I-39
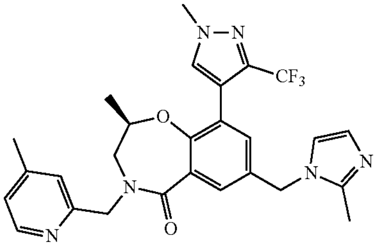 [SMILES: Cc1ccnc(CN2C[C@@H](C)Oc3c(cc(Cn4ccnc4C)cc3-c3cn(C)nc3C(F)(F)F)C2=O)c1]
I-40
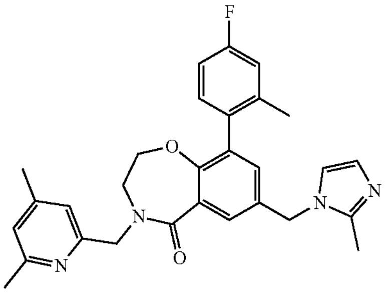 [SMILES: Cc1cc(C)nc(CN2CCOc3c(cc(Cn4ccnc4C)cc3-c3ccc(F)cc3C)C2=O)c1]
I-41
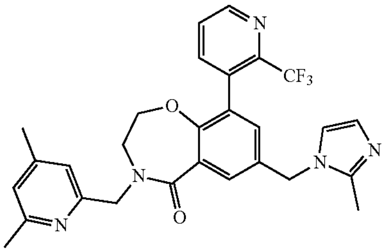
I-42
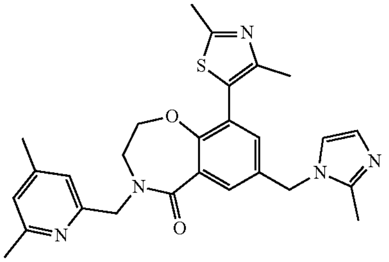 [SMILES: Cc1cc(C)nc(CN2CCOc3c(cc(Cn4ccnc4C)cc3-c3sc(C)nc3C)C2=O)c1]
I-43
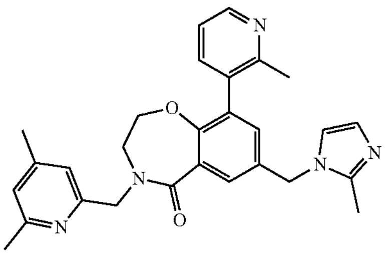 [SMILES: Cc1cc(C)nc(CN2CCOc3c(cc(Cn4ccnc4C)cc3-c3cccnc3C)C2=O)c1]
I-44

TABLE 1-continued
Exemplary compounds.
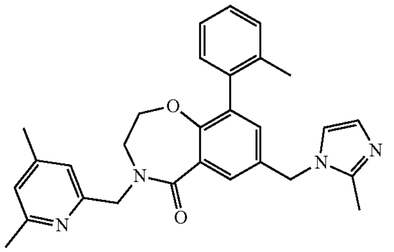
I-45
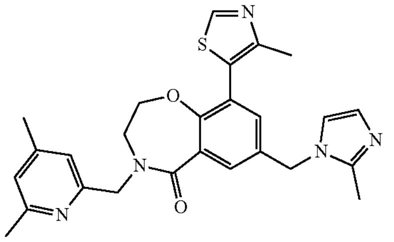 [SMILES: Cc1cc(C)nc(CN2CCOc3c(cc(Cn4ccnc4C)cc3-c3scnc3C)C2=O)c1]
I-46
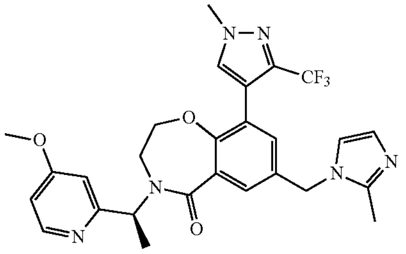 [SMILES: COc1ccnc([C@H](C)N2CCOc3c(cc(Cn4ccnc4C)cc3-c3cn(C)nc3C(F)(F)F)C2=O)c1]
I-47
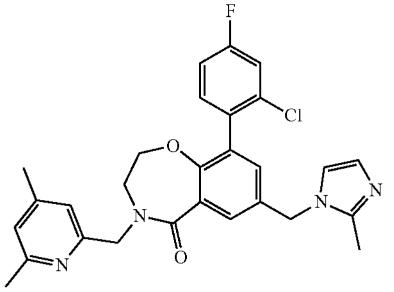
I-48
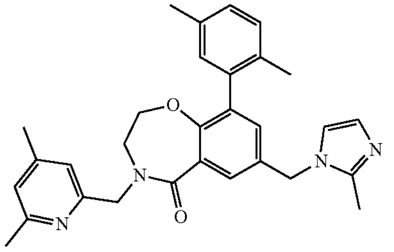 [SMILES: Cc1cc(C)nc(CN2CCOc3c(cc(Cn4ccnc4C)cc3-c3cc(C)ccc3C)C2=O)c1]
I-49
TABLE 1-continued
Exemplary compounds.
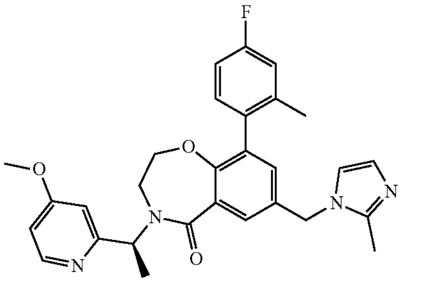 [SMILES: COc1ccnc([C@H](C)N2CCOc3c(cc(Cn4ccnc4C)cc3-c3ccc(F)cc3C)C2=O)c1]
I-50
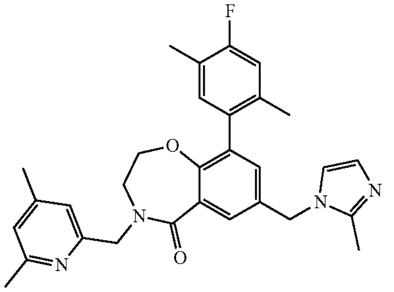 [SMILES: Cc1cc(C)nc(CN2CCOc3c(cc(Cn4ccnc4C)cc3-c3cc(C)c(F)cc3C)C2=O)c1]
I-51
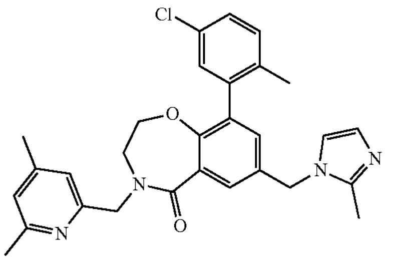 [SMILES: Cc1cc(C)nc(CN2CCOc3c(cc(Cn4ccnc4C)cc3-c3cc(Cl)ccc3C)C2=O)c1]
I-52
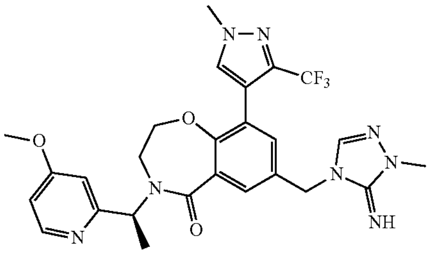
I-53
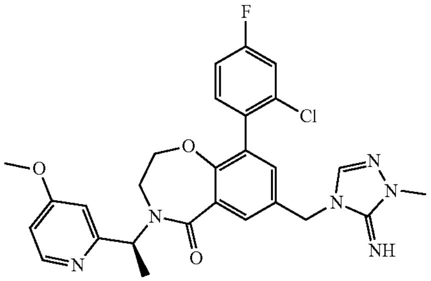
I-54

TABLE 1-continued
| Exemplary compounds. |
| --- |
I-55
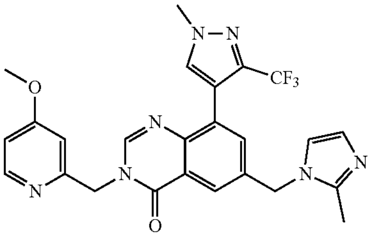 [SMILES: COc1ccnc(Cn2cnc3c(-c4cn(C)nc4C(F)(F)F)cc(Cn4ccnc4C)cc3c2=O)c1]
I-56
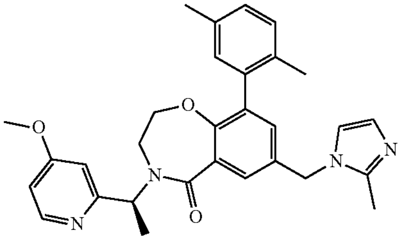 [SMILES: COc1ccnc([C@H](C)N2CCOc3c(cc(Cn4ccnc4C)cc3-c3cc(C)ccc3C)C2=O)c1]
I-57
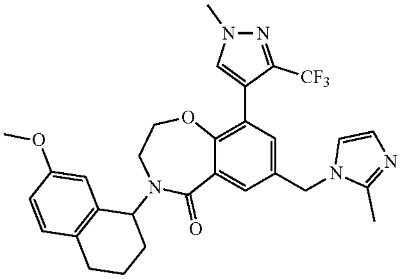 [SMILES: COc1ccc2c(c1)C(N1CCOc3c(cc(Cn4ccnc4C)cc3-c3cn(C)nc3C(F)(F)F)C1=O)CCC2]
I-58
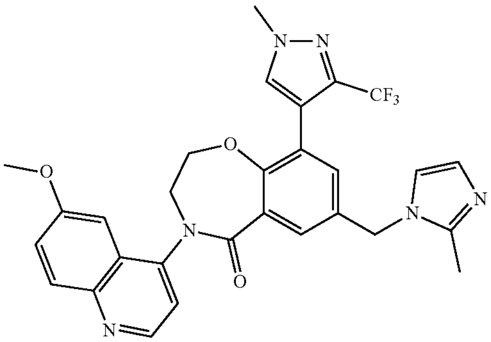 [SMILES: COc1ccc2nccc(N3CCOc4c(cc(Cn5ccnc5C)cc4-c4cn(C)nc4C(F)(F)F)C3=O)c2c1]
I-59
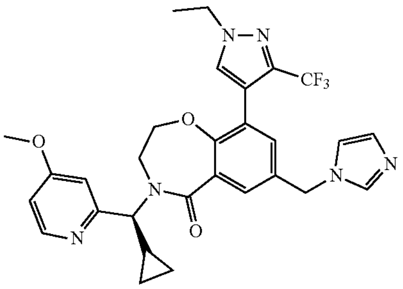 [SMILES: CCn1cc(-c2cc(Cn3ccnc3)cc3c2OCCN([C@H](c2cc(OC)ccn2)C2CC2)C3=O)c(C(F)(F)F)n1]
TABLE 1-continued
| Exemplary compounds. |
| --- |
I-60
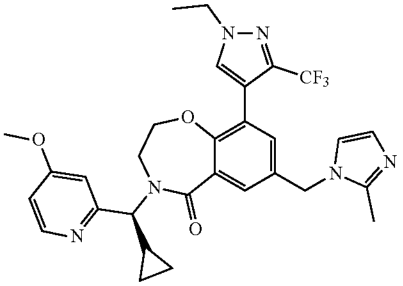 [SMILES: CCn1cc(-c2cc(Cn3ccnc3C)cc3c2OCCN([C@H](c2cc(OC)ccn2)C2CC2)C3=O)c(C(F)(F)F)n1]
I-61
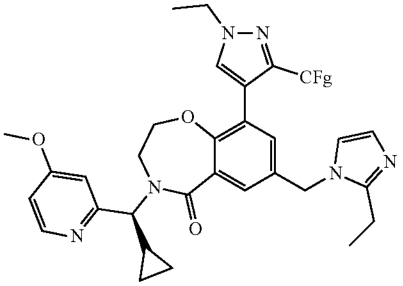
I-62
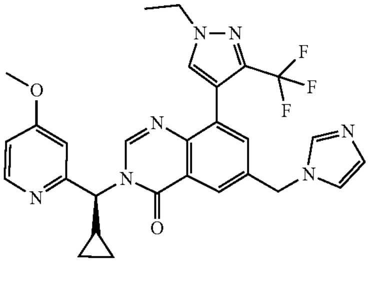 [SMILES: CCn1cc(-c2cc(Cn3ccnc3)cc3c(=O)n([C@H](c4cc(OC)ccn4)C4CC4)cnc23)c(C(F)(F)F)n1]
I-63
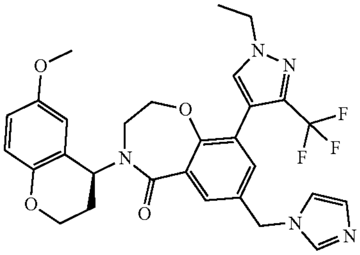 [SMILES: CCn1cc(-c2cc(Cn3ccnc3)cc3c2OCCN([C@H]2CCOc4ccc(OC)cc42)C3=O)c(C(F)(F)F)n1]
I-64
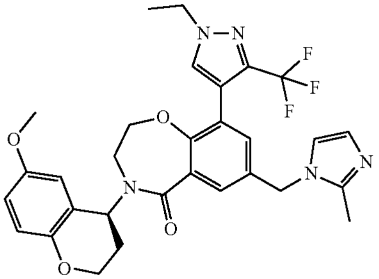 [SMILES: CCn1cc(-c2cc(Cn3ccnc3C)cc3c2OCCN([C@H]2CCOc4ccc(OC)cc42)C3=O)c(C(F)(F)F)n1]

TABLE 1-continued
| Exemplary compounds. |
| --- |
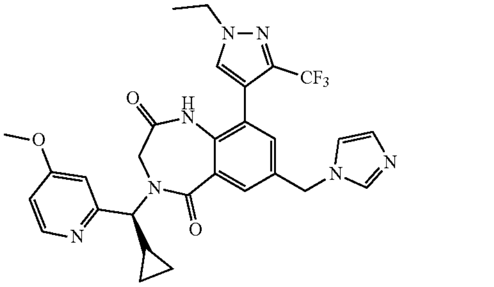 [SMILES: CCn1cc(-c2cc(Cn3ccnc3)cc3c2NC(=O)CN([C@H](c2cc(OC)ccn2)C2CC2)C3=O)c(C(F)(F)F)n1]
I-65
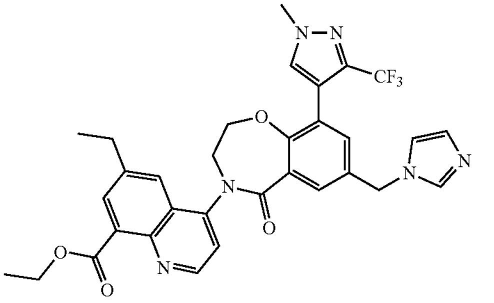 [SMILES: CCOC(=O)c1cc(CC)cc2c(N3CCOc4c(cc(Cn5ccnc5)cc4-c4cn(C)nc4C(F)(F)F)C3=O)ccnc12]
I-66
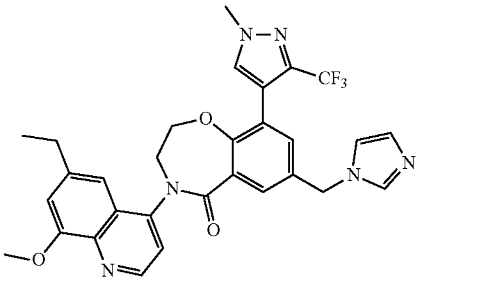 [SMILES: CCc1cc(OC)c2nccc(N3CCOc4c(cc(Cn5ccnc5)cc4-c4cn(C)nc4C(F)(F)F)C3=O)c2c1]
I-67
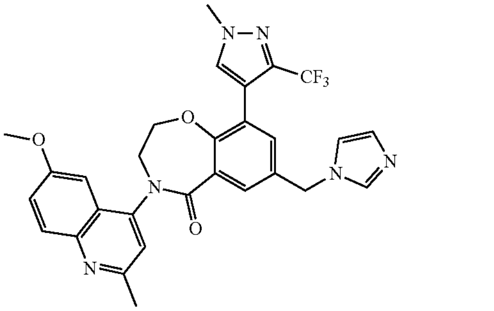 [SMILES: COc1ccc2nc(C)cc(N3CCOc4c(cc(Cn5ccnc5)cc4-c4cn(C)nc4C(F)(F)F)C3=O)c2c1]
I-68
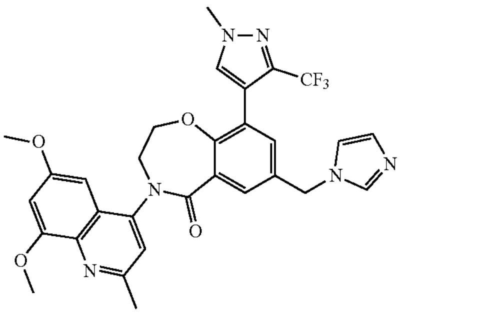 [SMILES: COc1cc(OC)c2nc(C)cc(N3CCOc4c(cc(Cn5ccnc5)cc4-c4cn(C)nc4C(F)(F)F)C3=O)c2c1]
I-69
TABLE 1-continued
| Exemplary compounds. |
| --- |
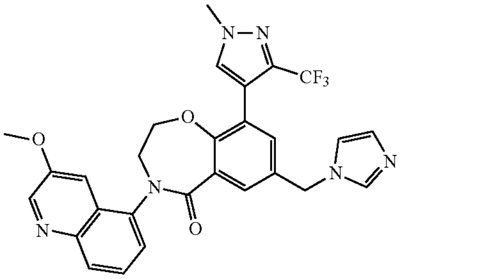 [SMILES: COc1cnc2cccc(N3CCOc4c(cc(Cn5ccnc5)cc4-c4cn(C)nc4C(F)(F)F)C3=O)c2c1]
I-70
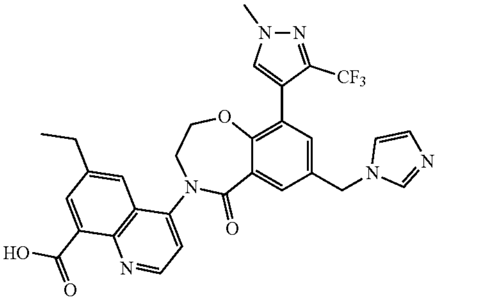 [SMILES: CCc1cc(C(=O)O)c2nccc(N3CCOc4c(cc(Cn5ccnc5)cc4-c4cn(C)nc4C(F)(F)F)C3=O)c2c1]
I-71
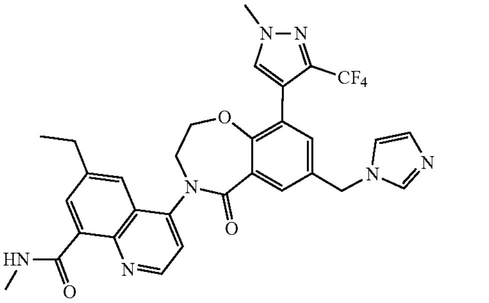
I-72
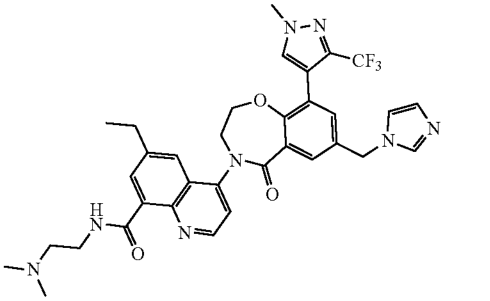 [SMILES: CCc1cc(C(=O)NCCN(C)C)c2nccc(N3CCOc4c(cc(Cn5ccnc5)cc4-c4cn(C)nc4C(F)(F)F)C3=O)c2c1]
I-73
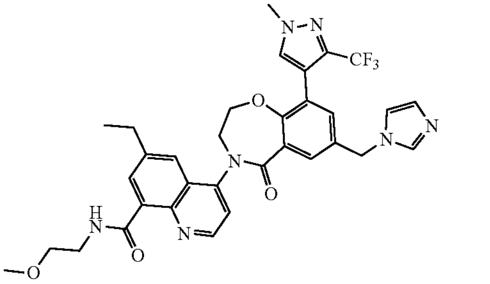 [SMILES: CCc1cc(C(=O)NCCOC)c2nccc(N3CCOc4c(cc(Cn5ccnc5)cc4-c4cn(C)nc4C(F)(F)F)C3=O)c2c1]
I-74
Compound names can be assigned by using Struct=Name naming algorithm as part of CHEMDRAW® ULTRA.
The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. BINDING TO WDR5

The disclosed compounds may bind to WDR5 and prevent the association of MLL1 or other transcription factors and proteins dependent on WDR5. The compounds may bind to WDR5 and prevent oncogenic processes associated with MLL1, c-MYC, or other oncogenic proteins dependent on WDR5.

Compounds of formula (I) can bind to WDR5 resulting in a $K_i$ ranging from about 0.01 nM to about 250 μM. The compounds may have a $K_i$ of about 250 μM, about 200 μM, about 150 μM, about 100 μM, about 90 μM, about 80 μM, about 70 μM, about 60 μM, about 50 μM, about 40 μM, about 30 μM, about 20 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) can bind to WDR5 resulting in a $K_i$ of less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

B. GENERAL SYNTHESIS

Compounds of formula (I) may be prepared by synthetic processes or by metabolic processes. Preparation of the compounds by metabolic processes includes those occurring in the human or animal body (in vivo) or processes occurring in vitro.

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein. Compounds of formula (I) may be also prepared by metabolic processes. Preparation of the compounds by metabolic processes includes those occurring in the human or animal body (in vivo) or processes occurring in vitro.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, which are compatible with the reaction conditions, will be readily apparent to one skilled in the art and alternate methods can be used.

Scheme 1

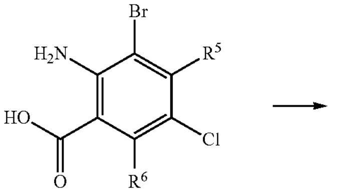

1

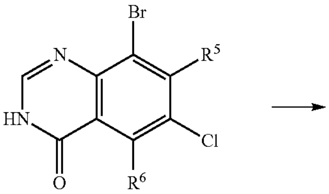

2

-continued

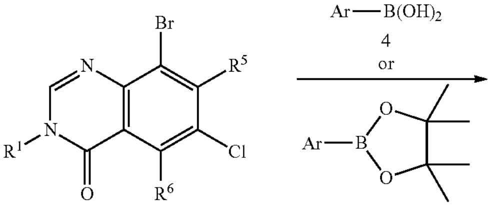

3

5

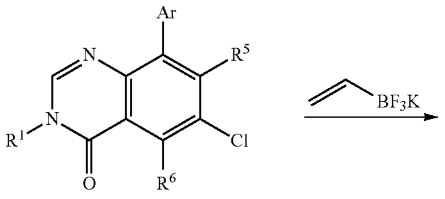

6

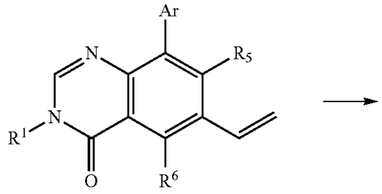

7

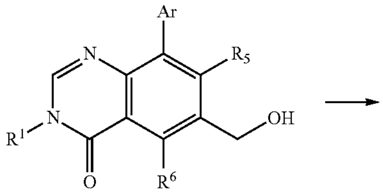

8

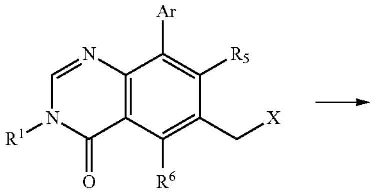

9

X = Br, Cl, OMs, OTs

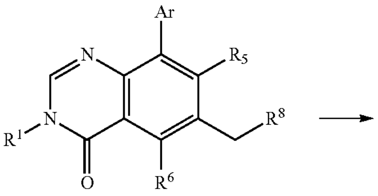

10a-k

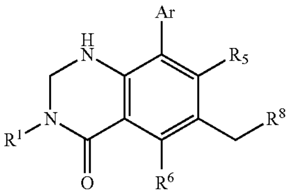

11a-k

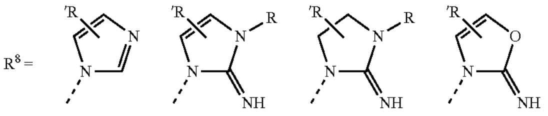

a b c d

-continued

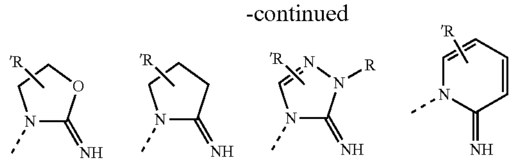

e f g h

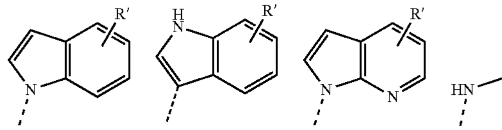

i j k l

In some embodiments, provided compounds of this invention may be prepared as shown in Scheme 1. Optionally substituted 2-amino-3-bromo-5-chlorobenzoic acid 1 is cyclized to 8-bromo-6-chloroquinazolin-4(3H)-one 2 in formamide under the thermal condition. The corresponding quinazolinone NH of 2 can be alkylated by appropriate $R^1$ group under a number of conditions that are routine for those skilled in the art to give intermediate 3. A variety of boronic acids 4 or borates 5, which are commercially available or can be prepared, can be selectively coupled with intermediates 3 by reacting with the bromo via e.g., Suzuki-Miyaura coupling protocol to afford biaryl adducts 6 (Miyaura, N., Suzuki, A., *Chem. Rev.* (1995), 2457) in the presence of a catalytic Pd species, such as $Pd(PPh_3)_4$, $PdCl_2(dppf)$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. The commercially available vinyl boronic acid or potassium trifluoro(vinyl)borate can be coupled with intermediates 6 to provide vinyl adduct 7 via e.g., Suzuki coupling protocol for arylchloride developed by Fu (Littke, A. F., Fu, G. C. *Angew. Chem. Int. Ed.* (1998), 37, 3387-3388) using a catalytic Pd species including, but not limited to, $Pd(t\text{-}Bu_3P)_2$ and with appropriate bases such as $Na_2CO_3$, $Cs_2CO_3$, $K_2CO_3$, $Ba(OH)_2$ or $Et_3N$. Oxidation of the vinyl group of 7 can be achieved by $OsO_4/NaIO_4$ or ozonolysis followed by hydride reduction using, but not limited to, $NaBH_4$ or $NaCNBH_3$ to prepare alcohol 8. Hydroxy group of Formula 8 may be activated by converting to bromide, chloride, mesylate or tosylate group under a number of conditions that are routine for those skilled in the art of organic synthesis. Intermediate 9 can be reacted with variety of nucleophiles such as optionally substituted imidazole (a), 1,3-dihydro-2H-imidazol-2-imine (b), imidazolidin-2-imine (c), oxazol-2-imine (d), oxazolidine-2-imine (e), pyrrolidin-2-imine (f), 2,4-dihydro-1,2,4-triazol-3-imine (g), pyridin-2(1H)-imine (h), indol-1-yl (i), indol-3-yl (j), 1H-pyrrolo[2,3-b]pyridine-1-yl (k), or isoxazol-3-amino (l) in the presence of appropriate bases, such as DIEA, TEA, $Cs_2CO_3$, $K_2CO_3$, LiOH or NaOH, to yield corresponding products of Formula 10a-k, respectively. The quinazolin-4(3H)-one core of 10a-k, can be reduced to give the corresponding 2,3-dihydroquinazolin-4(1H)-one 11a-k using, but not limited to, $NaBH_4$ and TFA in an appropriate organic solvent, such as THE and DME under the reflux condition.

Scheme 2

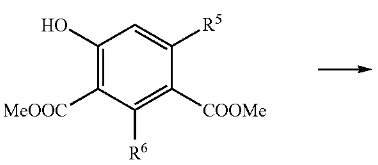

12

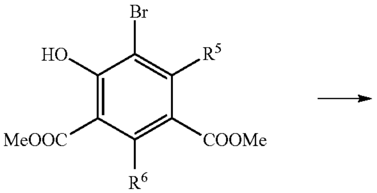

13

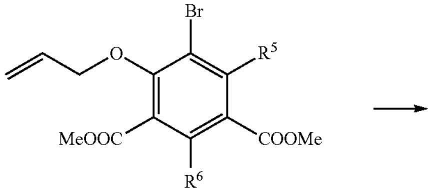

14

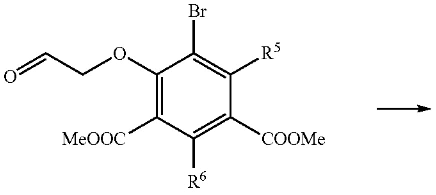

15

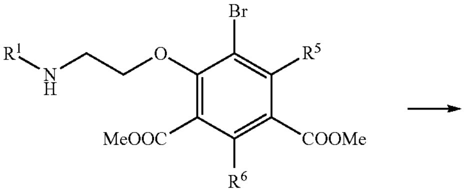

16

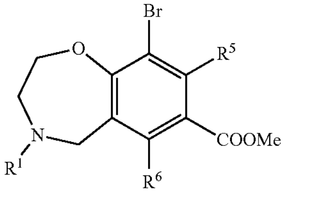

17

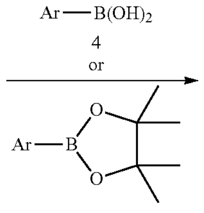

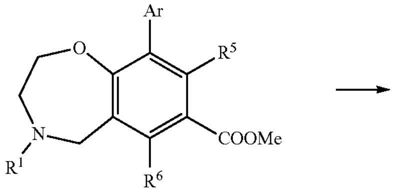

18

-continued

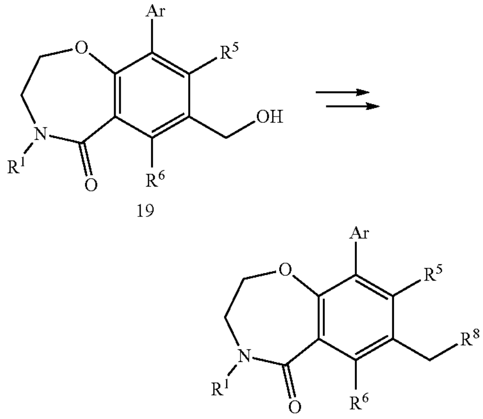

19

20a-k

In some embodiments, 3,4-dihydrobenzo[f][1,4]oxazepin-5(2H)-one containing compounds of this invention may be prepared as shown in Scheme 2. Optionally substituted dimethyl 4-hydroxyisophthalate 12 can be regioselectively brominated at the 5-position using, but not limited to, NBS to yield intermediate 13. The hydroxyl group of intermediate 13 is then allylated by reacting with 3-bromoprop-1-ene in the presence of appropriate bases, such as DIEA, TEA, $Cs_2CO_3$, or $K_2CO_3$ to yield corresponding adduct 14. The aldehyde 15 can be produced by oxidation of the vinyl group of 14 using, but not limited to, $OsO_4/NaIO_4$ or ozonolysis. Primary amines with appropriate $R^1$ groups can react with the aldehyde group in 15 to give corresponding secondary amine 16 via reductive amination protocol using, but not limited to, $NaBH(OAc)_3$ or $NaCNBH_3$. Dihydrobenzo-oxazepinone 17 can be constructed by intramolecular cyclization of 16 in the presence of bases, such as DIEA, TEA, $Cs_2CO_3$, or $K_2CO_3$. The intermediate 17 coupled with a variety of boronic acids 4 or borates 5 under the Suzuki-Miyaura coupling protocol outlined in Scheme 1 to afford biaryl intermediate 18. The methyl ester functional group of 18 can be converted to alcohol under various reduction conditions that are routine for those skilled in the art of organic synthesis. Finally, alcohol 19 can be further elaborated to produce compounds of formula 20a-k using the reaction sequence illustrated in Scheme 1.

Scheme 3

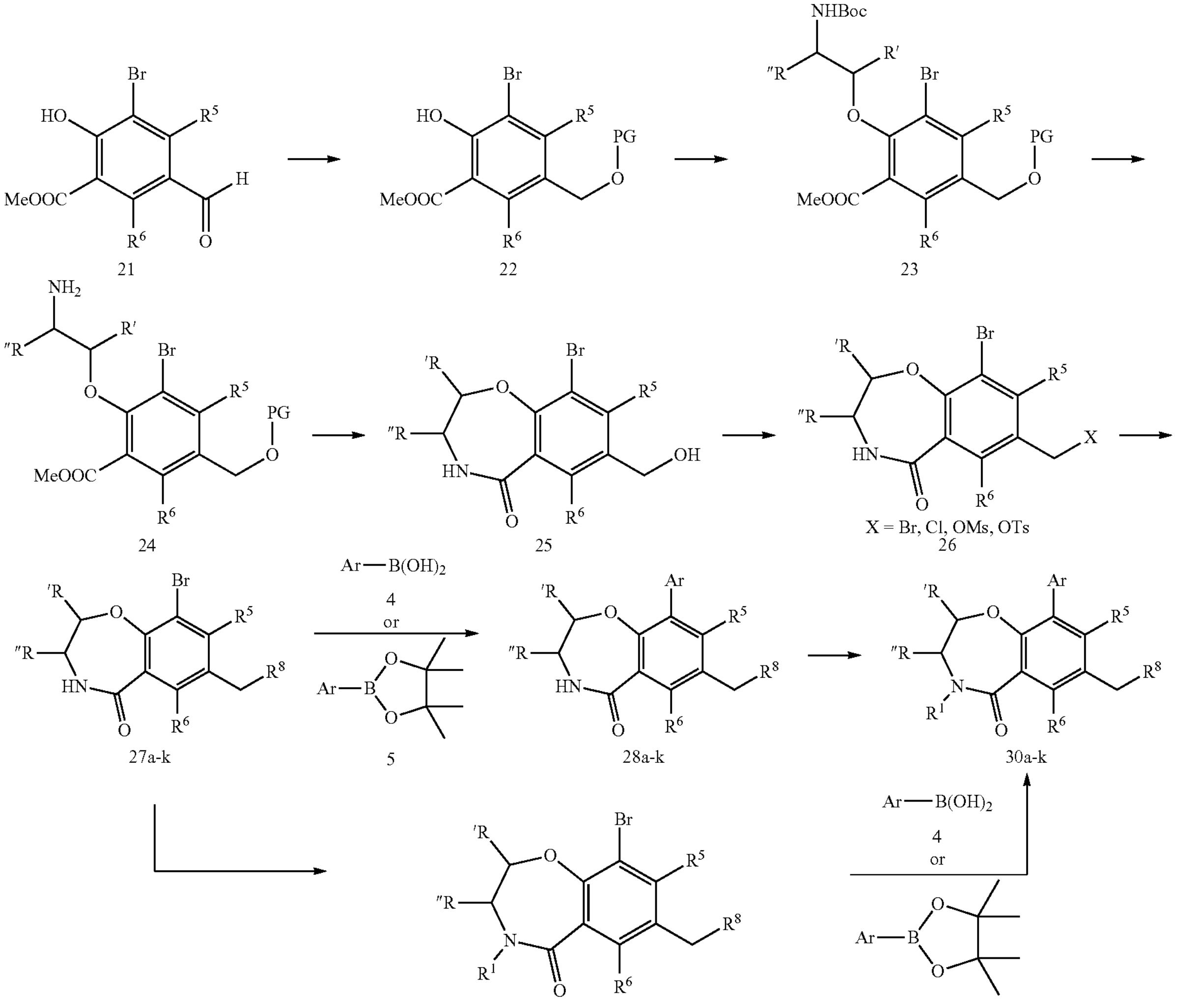

21 22 23 24 25 26 27a-k 28a-k 30a-k 29a-k

Scheme 3 depicts a route to produce compounds of formula 30a-k containing an optionally substituted 3,4-dihydrobenzo[f][1,4]oxazepin-5(2H)-one core unit. Optionally substituted methyl 3-bromo-5-formyl-2-hydroxybenzoate 21 can be reduced using, but not limited to, $NaBH_4$, $NaBH(OAc)_3$ or $NaCNBH_3$, and the resulting alcohol can be selectively protected with tert-butyl-diphenylsilyl group using tert-butyl(chloro)diphenylsilane and base such as $Et_3N$ or $(i\text{-}Pr)_2EtN$ or other proper protecting groups under appropriate conditions that are routine for those skilled in the art to yield intermediate 22. The phenol group 22 can be substituted using optionally substituted tert-butyl (2-bromoethyl)carbamate in the presence of appropriate bases, such as DIEA, TEA, $Cs_2CO_3$, or $K_2CO_3$ to yield corresponding adduct 23. The Boc group is removed under acidic conditions and the resulting free amine 24 can undergo intramolecular cyclization in the presence of bases, such as DIEA, TEA, $Cs_2CO_3$, or $K_2CO_3$, followed by deprotection of the alcohol to give dihydrobenzo-oxazepinone 25. The hydroxy group of 25 can be further elaborated to produce compounds of formula 27a-k using the reaction sequence illustrated in Scheme 1 (intermediate 8 to 10a-k). The intermediate 27a-k can be subjected in Suzuki-Miyaura coupling protocol, depicted in Scheme 1, using boronic acids 4 or borates 5 to afford biaryl adducts 28a-k. Finally, the NH— of 28a-k core unit can be substituted by appropriate $R^1$ groups using a number of conditions that are routine for those skilled in the art to give compounds of formula 30a-k. Alternatively, the reaction sequence can be switched by alkylation the NH of 27a-k prior to Suzuki-Miyaura coupling reaction.

-continued

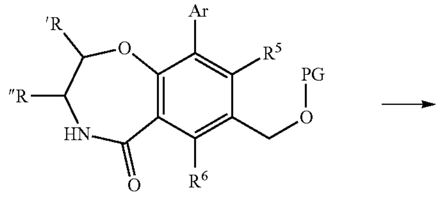

32

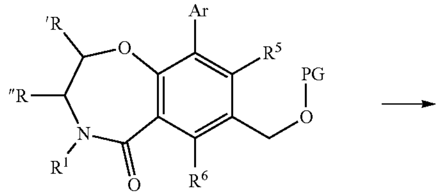

33

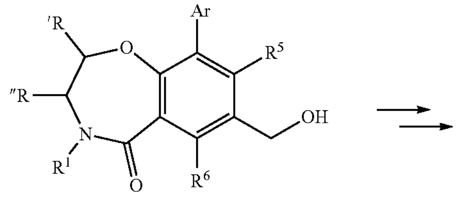

34

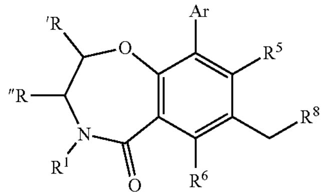

30a-k

Scheme 4

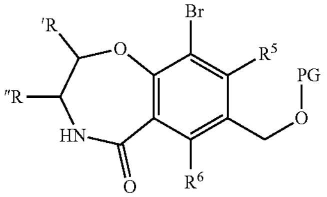

31

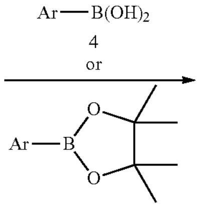

5

Alternatively, the intermediate 31 with a protected hydroxyl group can be subjected in Suzuki-Miyaura coupling protocol followed by substitution of NH of 32 as illustrated in Scheme 3 to give the intermediate 33. Then, the protecting group of 33 can be removed under various conditions that are routine for those skilled in the art of organic synthesis. The resulting hydroxyl group of 33 can be further elaborated to produce compounds of formula 30a-k using the reaction sequence shown in Scheme 1.

Scheme 5

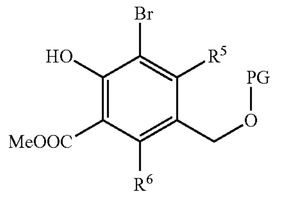

22

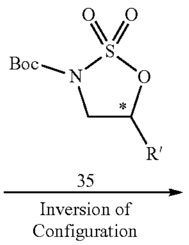

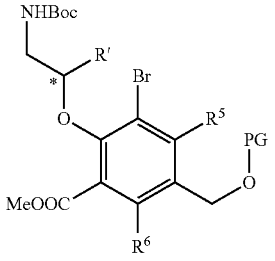

36

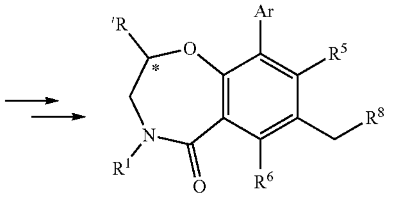

37a-k

-continued

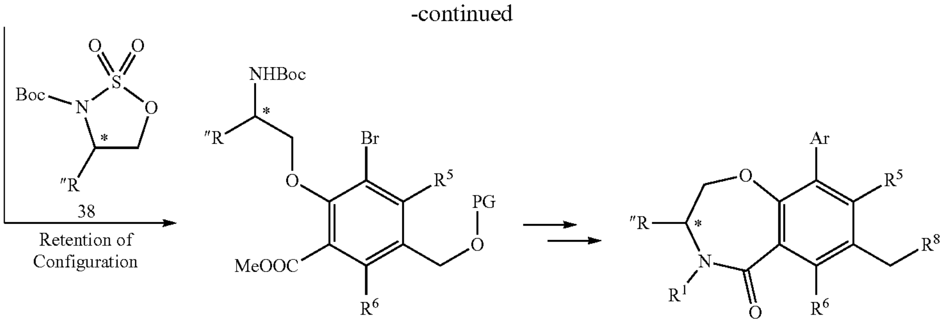

38

39

40a-k

In some embodiments, compounds of Formula 37a-k and 40a-k encompassing R' or R" groups with defined stereo-configurations may be synthesized by procedures illustrated in Scheme 5. The optically pure Boc protected 5-R'-1,2,3-oxathiazolidine-2,2-dioxide reagent 35 can react with the phenol 22 (PG=protecting group) with inversion of configuration to give the adduct 36 in the presence of appropriate bases such as $Cs_2CO_3$, $K_2CO_3$, $Et_3N$ or $(i\text{-}Pr)_2EtN$. Similarly, the same reaction protocol can be applied using 4-R"-1,2,3-oxathiazolidine-2,2-dioxide reagent 38 to generate the intermediate 39 with retention of configuration. Then, resulting intermediates 36 and 39 can be subjected to reaction sequences illustrated in Schemes 3 and 4 to produce final compounds 37a-k and 40a-k.

Scheme 6.

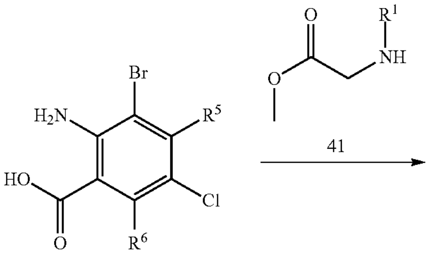

1

41

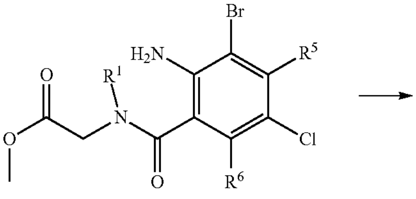

42

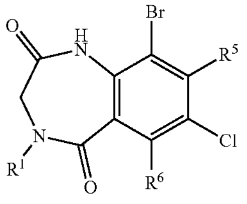

43

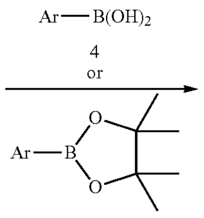

5

-continued

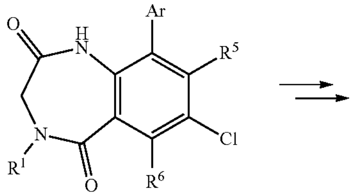

44

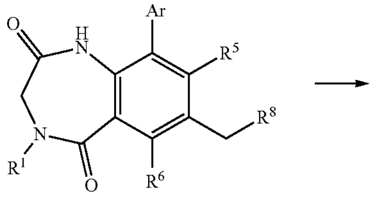

45a-k

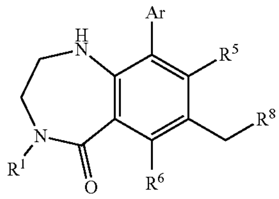

46a-k

Exemplary methods for preparing compounds of Formula 45a-k and 46a-k, containing dihydro-benzodiazepine-dione and tetrahydro-benzodiazepin-one core unit respectively, are shown in Scheme 6 and proceed from optionally substituted 2-amino-3-bromo-5-chlorobenzoic acid 1. Amide coupling reaction with $R^1$-substituted aminoacetate 41 using coupling reagents including, but not limited to, HATU, EDC, PyBOP, DCC, HBTU, or TBTU under a number of conditions that are routine for those skilled in the art of organic synthesis gives amide 42. Subsequent intramolecular cyclization of 42 in the presence of base, such as KOtBu, can produce dihydro-benzodiazepine-dione 43. The reaction sequence demonstrated in Scheme 1 can be applied to prepare dione 45a-k, which can be converted to compounds of Formula 46a-k by hydride reduction reaction using, but not limited to, $NaBH_4$, $NaBH(OAc)_3$ or $NaCNBH_3$.

Scheme 7.

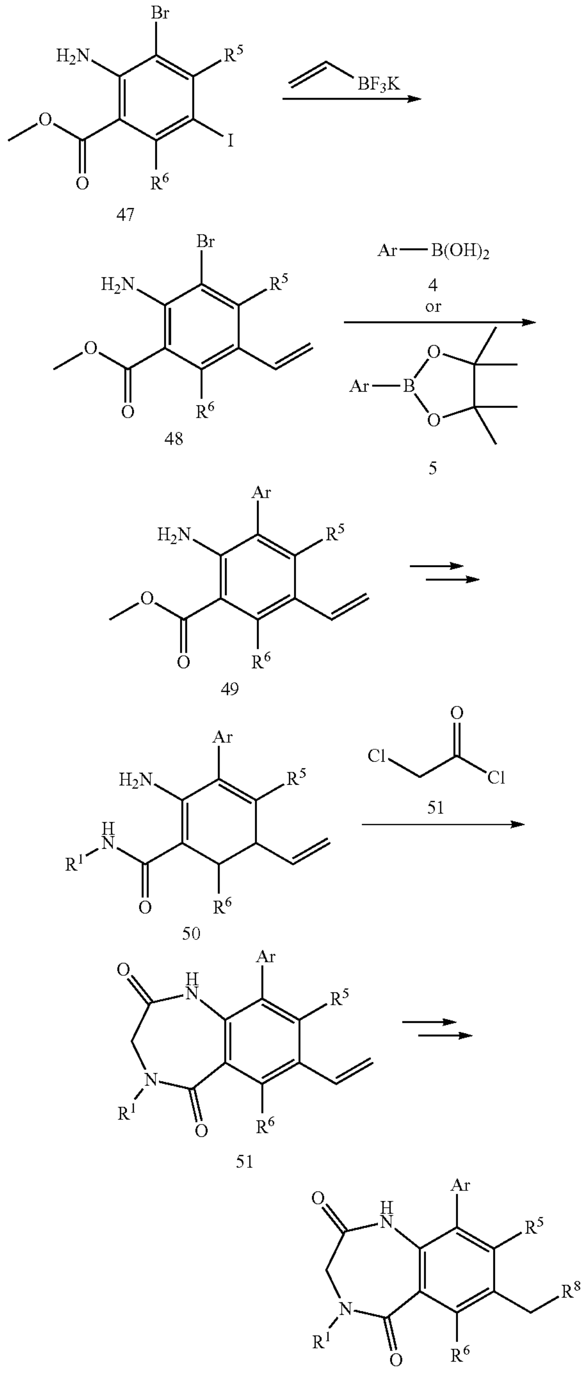

47

48

49

50

51

45a-k

Alternatively, compounds of Formula 45a-k may be prepared by procedures illustrated in Scheme 7. The synthesis is started from optionally substituted 2-amino-3-bromo-5-iodobenzoic acid 47, which can undergo 2 subsequent Suzuki-Miyaura coupling protocols outlined in Scheme 1 in region-selective manner to provide Intermediates 48 and 49. Saponification followed by amide coupling reaction described previously gives amide 50. Subsequent intramolecular cyclization using, but not limited to, chloroacetyl chloride through amide formation of the aniline moiety followed by alkylation of the benzamide group in the presence of base, such as NaH, can produce dihydrobenzodiazepine-dione 51. Dione 45a-k may be produced following the reaction sequence demonstrated in Scheme 1

Scheme 8.

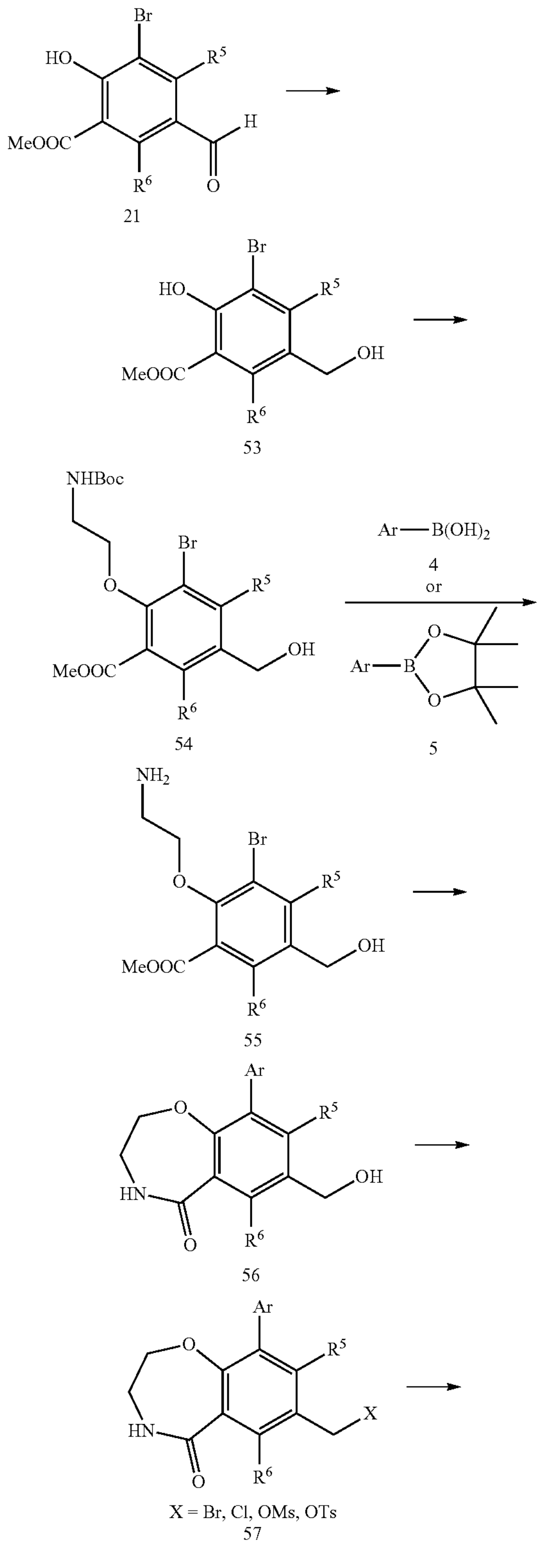

21

53

54

55

56

X = Br, Cl, OMs, OTs
57

-continued

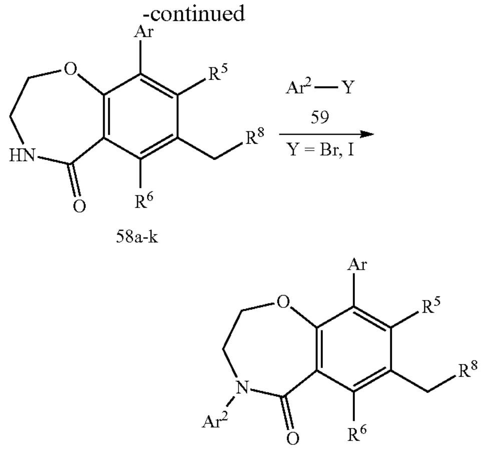

58a-k 60a-k

In some embodiments, compounds of Formula 60a-k containing aromatic $R^1$ group ($Ar^2$) may be synthesized by procedures illustrated in Scheme 8. Reduction of optionally substituted methyl 3-bromo-5-formyl-2-hydroxybenzoate 21 as shown in Scheme 3 can produce alcohol 53, where the phenol group can be selectively alkylated using tert-butyl (2-bromoethyl)carbamate in the presence of appropriate bases such as $K_2CO_3$ to yield corresponding adduct 54. Boronic acids 4 or borates 5 may be coupled under the Suzuki-Miyaura coupling protocol outlined in Scheme 1 followed by removal of Boc protecting group to afford biaryl intermediate 18. Subsequent intramolecular cyclization in the presence of base such as $(i\text{-Pr})_2EtN$ under thermolysis condition may yield oxazepinone intermediate 56. Intermediate 58a-k may be produced using the reaction sequence illustrated in Scheme 1 to install desired $R^8$ group from alcohol 56. The lactam NH of 58a-k may undergo cross-coupling reactions with a variety of aryl or heteroaryl halides of formula 59, wherein Y is Br or I, in the presence of a catalytic Pd species, such as $Pd(OAc)_2$ or $Pd_2(dba)_3$ and a suitable ligand such as Xantphos or BrettPhos and a base such as $Na_2CO_3$, $Cs_2CO_3$, or $K_2CO_3$ to generate compounds of formula 60a-k. Alternatively, compounds of formula 60a-k can be also produced using the Ullman coupling conditions in the presence of CuI and a suitable ligand such as (trans)-1,2-N,N'-dimethylaminocyclohexane or L-Proline and a base such as $Cs_2CO_3$, $K_2CO_3$ or $K_2PO_4$ in a suitable solvent such as toluene or DMF.

Precursor reagents and intermediates for core aryl or phenyl structure were either commercially available or prepared using known methods in the literature. Procedures towards key intermediates are detailed within specified examples or below.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

C. EXAMPLES

Abbreviations

The following abbreviations are employed in the Examples and elsewhere herein:

AcCl=acetyl chloride
AcOK=potassium acetate
AIBN=Azobisisobutyronitrile
$AsPh_3$=triphenylarsine
DCC=N,N'-dicyclohexylcarbodiimide
DCM=dichloromethane
DIPEA/DIEA=N,N-diisopropylethylamine
DMA=dimethylacetamide
DMAP=dimethylaminopyridine
DME=dimethoxyethane
DMF=dimethylformamide
DMSO=dimethylsulfoxide
EDC=1-Ethyl-3-(3-dimethylaminopropyl)carbodiimide
ether=diethyl ether
$Et_3N$=triethylamine
EtOAc=ethyl acetate
EtOH=ethanol
HATU=1-[Bis(dimethylamino)methylene]-1H-1,2,3-triazolo[4,5-b]pyridinium 3-oxid hexafluorophosphate
HBTU=N,N,N',N'-Tetramethyl-O-(1H-benzotriazol-1-yl) uronium hexafluorophosphate
Hex=hexanes
$(i-Pr)_2EtN$=diisopropylethylamine
KOtBu=potassium tert-butoxide
MeCN=acetonitrile
MeOH=methanol
$NaBH(OAc)_3$=sodium triacetoxyborohydride
NBS=N-bromosuccinimide
$Pd(t-Bu_3P)_2$=Bis(tri-tert-butylphosphine)palladium(O)
$PdCl_2(dppf)/Pd(dppf)Cl_2$=[1,1'-Bis(diphenylphosphino) ferrocene]dichloropalladium(II)
$Pd_2(dba)_3$=Tris(dibenzylideneacetone)dipalladium(O)
$Pd(OAc)_2$=palladium(II) acetate
$Pd(PPh_3)_4$=Tetrakis(triphenylphosphine)palladium(O)
$Pd(PPh_3)_2Cl_2$=Bis(triphenylphosphine)palladium(II) dichloride
$PPh_3$=triphenylphosphine
PyBOP=(Benzotriazol-1-yloxy)tripyrrolidinophosphonium hexafluorophosphate
TBAF=tetrabutylammonium fluoride
TBS=tert-butyldimethylsilyl
TBTU=2-(1H-Benzotriazole-1-yl)-1,1,3,3-tetramethylaminium tetrafluoroborate
TEA=triethylamine
THF=tetrahydrofuran
XantPhos=4,5-Bis(diphenylphosphino)-9,9-dimethylxanthene
aq.=aqueous
equiv. or eq.=equivalent(s)
min=minute(s)
h or hr=hour(s)
quant.=quantitative
r.t.=room temperature
LRMS=low resolution mass spectrometry
$R_T$=retention time (in minutes)
sat.=saturated Microwave assisted reactions are performed in a single-mode reactor: Emrys™ Optimizer microwave reactor (Personal Chemistry A.B., currently Biotage).

Hydrogenation reactions are performed using an atmospheric balloon or using a Parr hydrogenation shaker apparatus.

Normal phase flash silica gel-based column chromatography is performed using ready-to-connect cartridges from ISCO, on irregular silica gel, particle size 15-40 μm on a Combi-flash Companion chromatography system from ISCO.

Low resolution mass spectra are obtained on an Agilent 1200 series 6130 mass spectrometer. Analytical HPLC is performed on an HP1100 with UV detection at 214 and 254 nm along with ELSD detection, LC/MS (J-Sphere80-C18, 3.0×50 mm, 4.1 min gradient, 5%[0.05% $TFA/CH_3CN$]: 95%[0.05% $TFA/H_2O$] to 100%[0.05% $TFA/CH_3CN$]. Preparative RP-HPLC purification is performed on a custom HP1100 automated purification system with collection triggered by mass detection or using a Gilson Inc. preparative UV-based system using a Phenomenex Luna C18 column (50×30 mm I.D., 5 μm) with an acetonitrile (unmodified)-water (0.1% TFA) custom gradient.

For LC-MS-characterization of the compounds of the present invention, the following methods are used.

Method 1: The HPLC measurement is performed using an Agilent 1200 system comprising a binary pump with degasser, an autosampler, a column oven, a diode-array detector (DAD) and a column as specified in the respective methods below. Flow from the column is split to a SQ mass spectrometer and Polymer Labs ELSD. The MS detector is configured with an ES ionization source. Nitrogen is used as the nebulizer gas. The source temperature is maintained at 350° C. Data acquisition is performed with Agilent Chemstation software. Reversed phase HPLC is carried out on a Kinetex C18 column (2.6 μm, 2.1×30 μm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 μL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 2: Using method 1 instrument and column conditions. The gradient conditions used are: 95% A (water+0.1% TFA), 5% B (acetonitrile), to 95% B in 2.0 minutes, returning to initial conditions at 2.11 minutes. Injection volume 1 μL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 3: Using method 1 instrument and column conditions. The gradient conditions used are: 50% A (water+0.1% TFA), 50% B (acetonitrile), to 95% B in 2.0 minutes, returning to initial conditions at 2.11 minutes. Injection volume 1 μL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

$^1H$ NMR spectra are recorded either on a Bruker DPX-400 or on a Bruker AV-500 spectrometer with standard pulse sequences, operating at 400 MHz and 500 MHz respectively. Chemical shifts (δ) are reported in parts per million (ppm)

downfield from tetramethylsilane (TMS), which is used as internal standard. Coupling constants (J-values) are reported in Hz.

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

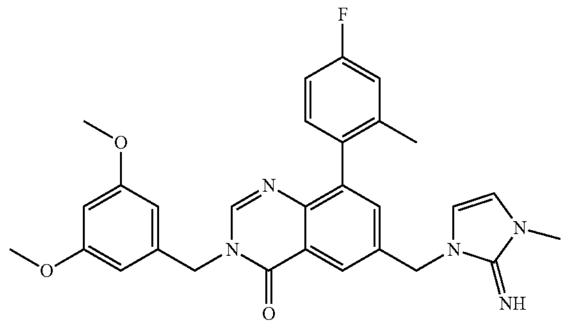

Example 1

3-(3,5-Dimethoxybenzyl)-8-(4-fluoro-2-methylphenyl)-6-((2-imino-3-methyl-2,3-dihydro-1H-imidazol-1-yl)methyl)quinazolin-4(3H)-one Step A. Preparation of 8-bromo-6-chloroquinazolin-4(3H)-one 2-Amino-3-bromo-5-chlorobenzoic acid (1000 mg, 4.02 mmol, 1.0 equiv.) and formamide (3.20 mL, 80.3 mmol, 20 equiv.) were heated to 150° C. overnight and then cooled to room temperature and diluted with $H_2O$ (5 mL). The resulting solid was collected by vacuum filtration and washed with $H_2O$ and then further dried in a vacuum oven overnight to yield the title compound (652 mg, 63% yield). LCMS: $R_T$=1.196 min, MS (ES) 258.9 $[M+H]^+$; $^1H$ NMR (400 MHz, DMSO-d) δ 8.28 (d, J=2.4 Hz, 1H), 8.25 (s, 1H), 8.08 (d, J=2.4 Hz, 1H).

Step B. Preparation of 8-bromo-6-chloro-3-(3,5-dimethoxybenzyl)quinazolin-4(3H)-one 8-Bromo-6-chloroquinazolin-4(3H)-one (651 mg, 2.52 mmol, 1.0 equiv.) was dissolved in DMF (10 mL) and then $K_2CO_3$ (1040 mg, 7.56 mmol, 3.0 equiv.) was added followed by 3,5-dimethoxybenzyl bromide (695 mg, 3.02 mmol, 1.2 equiv.). The reaction was stirred at room temperature for 1 h and then $H_2O$ (20 mL) was added and the solid was collected by vacuum filtration and washed with water. The solid was further dried in a vacuum oven overnight to yield the title compound (852 mg, 83% yield). LCMS: $R_T$=1.814 min, MS (ES) 408.9 $[M+H]^+$; $^1H$ NMR (400 MHz, DMSO-d) δ 8.69 (s, 1H), 8.30 (d, J=2.0 Hz, 1H), 8.12 (d, J=2.4 Hz, 1H), 6.54 (d, J=2.4 Hz, 2H), 6.44 (t, J=2.0 Hz, 1H), 5.11 (s, 2H), 3.71 (s, 6H).

Step C. Preparation of 6-chloro-3-(3,5-dimethoxybenzyl)-8-(4-fluoro-2-methylphenyl)quinazolin-4(3H)-one Pd(dppf)$Cl_2$ (76.2 mg, 0.104 mmol, 0.05 equiv.) was added to a mixture of 8-bromo-6-chloro-3-(3,5-dimethoxybenzyl)quinazolin-4(3H)-one (851 mg, 2.08 mmol, 1.0 equiv.), 4-fluoro-2-methylphenyl-boronic acid (417 mg, 2.71 mmol, 1.3 equiv.), and $K_2CO_3$ (864 mg, 6.25 mmol, 3.0 equiv.) in 1,4-dioxane:$H_2O$ (3:1, 10 mL). The resulting mixture was degassed and back filled with argon gas, and heated at 95° C. overnight. The reaction was cooled to room temperature and filtered through a pad of celite and washed with EtOAc (20 mL). $H_2O$ (20 mL) was added and the layers were separated. The aqueous layer was extracted with EtOAc (3×10 mL) and the combined organic layers were washed with brine (10 mL), dried ($MgSO_4$), filtered and concentrated. The residue was purified by flash chromatography (Combi-flash Rf, Hex/EtOAc=0-75% gradient) to afford the title compound (513 mg, 56% yield). LCMS: $R_T$=2.010 min, MS (ES) 438.9 $[M+H]^+$; $^1H$ NMR (400 MHz, chloroform-d) δ 8.34 (d, J=2.4 Hz, 1H), 8.04 (s, 1H), 7.58 (d, J=2.4 Hz, 1H), 7.16-7.12 (m, 1H), 7.02-6.94 (m, 2H), 6.46 (d, J=2.0 Hz, 2H), 6.40 (t, J=1.6 Hz, 1H), 5.16 (s, 1H), 5.03 (s, 1H), 3.76 (s, 6H), 2.08 (s, 3H).

Step D. Preparation of 3-(3,5-dimethoxybenzyl)-8-(4-fluoro-2-methylphenyl)-6-vinylquinazolin-4(3H)-one Pd(t-$Bu_3P)_2$ (59.5 mg, 0.116 mmol, 0.1 equiv.) was added to a mixture of 6-chloro-3-(3,5-dimethoxybenzyl)-8-(4-fluoro-2-methylphenyl)quinazolin-4(3H)-one (513 mg, 1.16 mmol, 1.0 equiv.), potassium vinyltrifluoroborate (468 mg, 3.49 mmol, 3.0 equiv.), $Cs_2CO_3$ (1140 mg, 3.49 mmol, 3.0 equiv.) and 1,4-dioxane (12 mL) under an argon atmosphere. The resulting mixture was heated at 90° C. for 4 h, then partitioned between EtOAc (10 mL) and $H_2O$ (10 mL). The aqueous layer was extracted with EtOAc (3×10 mL) and the combined organic layers were washed with brine (10 mL), dried ($MgSO_4$), filtered and concentrated. The residue was purified by flash chromatography (Combi-flash Rf, Hex/EtOAc=0-75% gradient) to afford the title compound (154 mg, 30% yield). LCMS: $R_T$=1.981 min, MS (ES) 430.9 $[M+H]^+$.

Step E. Preparation of 3-(3,5-dimethoxybenzyl)-8-(4-fluoro-2-methylphenyl)-6-(hydroxymethyl)quinazolin-4(3H)-one Solid supported $OsO_4$ (118 mg, 0.465 mmol, 0.5 equiv.) was added to a mixture of 3-(3,5-dimethoxybenzyl)-8-(4-fluoro-2-methylphenyl)-6-vinylquinazolin-4(3H)-one (400 mg, 0.930 mmol, 1.0 equiv.) and pyridine (149 μL, 1.86 mmol, 2.0 equiv.) in 1,4-dioxane:$H_2O$ (3:1, 9.4 mL). at room temperature followed by the addition of $NaIO_4$ (796 mg, 3.72 mmol, 4.0 equiv.). After stirring overnight, the reaction mixture was cooled to 0° C. and MeOH (3 mL) was added followed by $NaBH_4$ (387 mg, 10.2 mmol, 11 equiv.). The ice bath was removed and the reaction was stirred at room temperature for 1 hour and then filtered and concentrated. The residue was taken up in EtOAc (10 mL) and washed with $H_2O$ (10 mL). The organic layer was dried ($MgSO_4$), filtered and concentrated. The residue was purified by flash chromatography (Combi-flash Rf, Hex/EtOAc=25-100% gradient) to afford the title compound (92 mg, 22% yield). LCMS: $R_T$=1.622 min, MS (ES) 435.0 $[M+H]^+$.

Step F. Preparation of 6-(bromomethyl)-3-(3,5-dimethoxybenzyl)-8-(4-fluoro-2-methylphenyl)quinazolin-4(3H)-one $PBr_3$ (39 μL, 0.415 mmol, 2.0 equiv.) was added to a solution of 3-(3,5-dimethoxybenzyl)-8-(4-fluoro-2-methylphenyl)-6-(hydroxymethyl)quinazolin-4(3H)-one (90 mg, 0.207 mmol, 1.0 equiv.) in DCM (2.0 mL) at 0° C. The reaction was allowed to warm to room temperature over 3 hours and then quenched with sat. $NaHCO_3$ (5 mL). The mixture was extracted with EtOAc (3×5 mL) and the combined organic layers were washed with brine, dried ($MgSO_4$), filtered and concentrated to yield the title compound (65 mg, 63% yield). LCMS $R_T$=1.984 min, MS (ES) 496.9 $[M+H]^+$.

Step G. Preparation of 3-(3,5-dimethoxybenzyl)-8-(4-fluoro-2-methylphenyl)-6-((2-imino-3-methyl-2,3-dihydro-1H-imidazol-1-yl)methyl)quinazolin-4(3H)-one 1-Methyl-1H-imidazol-2-amine (32.7 mg, 0.121 mmol, 3.0 equiv.) was added to a solution of 6-(bromomethyl)-3-(3,5-dimethoxybenzyl)-8-(4-fluoro-2-methylphenyl)quinazolin-4(3H)-one (20 mg, 0.0403 mmol, 1.0 equiv.), NaI (0.0006 mg, 0.00403 mmol, 0.1 equiv.) and diisopropylethylamine (14 μL, 0.0806 mmol, 2.0 equiv.) in acetonitrile (0.2 mL). The reaction mixture was heated at 80° C. for 30 min then concentrated under reduced pressure. The residue was purified by reverse phase HPLC (Phenomenex Gemini C18, $H_2O/CH_3CN$ gradient from 15-95% $CH_3CN$, 0.1% TFA) to yield the title compound (11 mg, 53% yield). *To remove TFA, the organic layer was washed with $K_2CO_3$ (sat.). LCMS: $R_T$=1.364 min, MS (ES) 514.0 $[M+H]^+$; $^1H$ NMR (400 MHz, Chloroform-d) δ 8.20 (s, 1H), 8.15 (s, 1H), 8.06 (d, J=7.6 Hz, 1H), 7.61 (d, J=11.2 Hz, 1H), 7.45 (t, J=8.0 Hz, 1H), 7.09 (t, J=8.0 Hz, 1H), 6.99-6.91 (m, 2H), 6.57 (d, J=4.4 Hz, 1H), 6.43 (d, J=1.6 Hz, 2H), 6.38 (s, 1H), 5.31 (s, 2H), 5.17 (d, J=13.6 Hz, 1H), 5.03 (d, J=13.6 Hz, 1H), 3.74 (s, 6H), 3.59 (s, 3H), 2.02 (s, 3H).

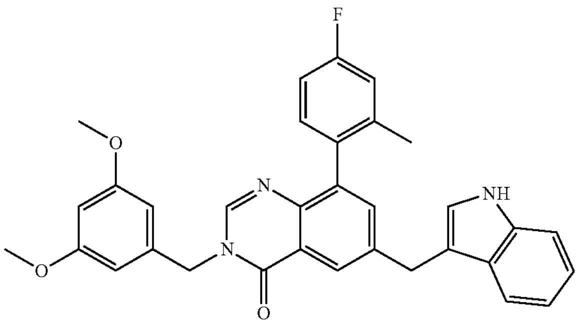 [SMILES: COc1cc(Cn2cnc3c(-c4ccc(F)cc4C)cc(Cc4c[nH]c5ccccc45)cc3c2=O)cc(OC)c1]

Example 2

6-((1H-Indol-3-yl)methyl)-3-(3,5-dimethoxybenzyl)-8-(4-fluoro-2-methylphenyl)quinazolin-4(3H)-one The title compound (5.0 mg, 23% yield) was prepared from the procedure described in Example 1, Step G using indole (14.2 mg, 0.121 mmol, 3 equiv.). The reaction mixture was stirred at 80° C. for 30 min. LCMS: $R_T$=2.039 min, MS (ES) 534.0 $[M+H]^+$; $^1H$ NMR (400 MHz, Chloroform-d) δ 8.31 (d, J=1.6 Hz, 1H), 8.18 (s, 1H), 8.13-8.06 (m, 1H), 7.55 (d, J=2.0 Hz, 1H), 7.48 (d, J=8.0 Hz, 1H), 7.37 (d, J=8.0 Hz, 1H), 7.20 (t, J=7.6 Hz, 1H), 7.12-7.06 (m, 2H), 7.04 (d, J=8.4 Hz, 1H), 6.98-6.90 (m, 2H), 6.47 (d, J=2.0 Hz, 2H), 6.38 (t, J=2.4 Hz, 1H), 5.19 (d, J=13.6 Hz, 1H), 5.04 (d, J=13.2 Hz, 1H), 4.27 (s, 2H), 3.75 (s, 6H), 2.01 (s, 3H).

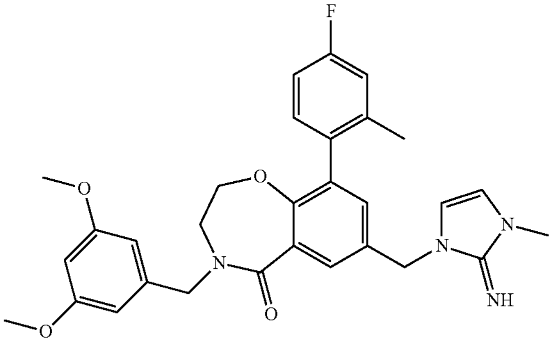

Example 3

4-(3,5-Dimethoxybenzyl)-9-(4-fluoro-2-methylphenyl)-7-((2-imino-3-methyl-2,3-dihydro-1H-imidazol-1-yl)methyl)-3,4-dihydrobenzo[f][1,4]oxazepin-5(2H)-one Step A. Preparation of dimethyl 5-bromo-4-hydroxyisophthalate N-bromosuccinimide (931.4 mg, 5.23 mmol, 1.1 equiv.) was added to a solution of dimethyl 4-hydroxyisophthalate (1000.0 mg, 4.76 mmol, 1.0 equiv.) in THE (30.0 mL) at 0° C. After stirring for 5 min at 0° C., the reaction mixture was warmed to room temperature and stirred for 2.5 h. The reaction mixture was concentrated under the reduced pressure. The residue was purified by flash chromatography (Combi-flash Rf, Hex/EtOAc=0-100% gradient) to afford the title compound (1250 mg, 90% yield). LCMS: $R_T$=1.646 min, MS (ES) 290.1 $[M+H]^+$.

Step B. Preparation of dimethyl 4-(allyloxy)-5-bromoisophthalate

3-Bromoprop-1-ene (340.0 μL, 3.91 mmol, 1.5 equiv.) and $Cs_2CO_3$ (2544.8 mg, 7.81 mmol, 3.0 equiv.) were added to a solution of dimethyl 5-bromo-4-hydroxyisophthalate (752.6 mg, 2.60 mmol, 1.0 equiv.) in DMF (20.0 mL). The reaction mixture was stirred at 50° C. for 2 h. The reaction mixture was filtered through Celite and concentrated under the reduced pressure. The crude reaction mixture was partitioned between $CH_2Cl_2$ (20.0 mL) and $H_2O$ (4.0 mL). The organic layer was extracted with $CH_2Cl_2$ (3×20.0 mL) and dried over $Na_2SO_4$ and concentrated under the reduced pressure. The residue was purified by flash chromatography (Combi-flash Rf, Hex/EtOAc=0-100% gradient) to afford the title compound (576 mg, 67% yield). LCMS: $R_T$=1.745 min, MS (ES) 330.2 $[M+H]^+$; $^1H$ NMR (400 MHz, Chloroform-d) δ 8.41 (d, J=2.2 Hz, 1H), 8.39 (d, J=2.2 Hz, 1H), 6.20-6.09 (m, 1H), 5.44 (dq, J=17.2, 1.5 Hz, 1H), 5.33-5.28 (m, 1H), 4.62 (dt, J=5.9, 1.2 Hz, 2H), 3.93 (s, 3H), 3.93 (s, 3H).

Step C. Preparation of dimethyl 5-bromo-4-(2-oxoethoxy)isophthalate $OsO_4$ (38.6 mg, 0.15 mmol, 0.25 equiv.) was added to a mixture of dimethyl 4-(allyloxy)-5-bromoisophthalate (200.0 mg, 0.61 mmol, 1.0 equiv.), pyridine (100.0 μL, 1.22 mmol, 2.0 equiv.), water (2.0 mL), and 1,4-dioxane (6.0 mL) at room temperature followed by $NaIO_4$ (519.9 mg, 2.43 mmol, 4.0 equiv.). After stirring 12 h, the reaction mixture was partitioned between $CH_2Cl_2$ (20.0 mL) and $H_2O$ (5.0 mL). The reaction mixture was extracted with $CH_2Cl_2$ (3×20.0 mL), dried over $Na_2SO_4$ and concentrated under reduced pressure to yield the crude title compound, which was used for the next step without further purification. LCMS: $R_T$=1.343 min, MS (ES) 332.1 $[M+H]^+$.

Step D. Preparation of dimethyl 5-bromo-4-(2-((3,5-dimethoxybenzyl)amino)ethoxy) isophthalate To a solution of dimethyl 5-bromo-4-(2-oxoethoxy)isophthalate (201.2 mg, 0.61 mmol, 1.0 equiv.) in $CH_2Cl_2$ (10.0 mL) was added (3,5-dimethoxyphenyl)methanamine (152.3 mg, 0.91 mmol, 1.5 equiv.) followed by sodium triacetoxyborohydride (257.6 mg, 1.22 mmol, 2.0 equiv.), and acetic acid (70.0 μL, 1.22 mmol, 2.0 equiv.). The reaction mixture was stirred at room temperature for 12 h then quenched with acetone (0.5 mL) and concentrated under the reduced pressure. The residue was purified by flash chromatography (Combi-flash Rf, Hex/EtOAc=0-100% gradient) to afford the title compound (238 mg, 81% yield over 2 steps). LCMS: $R_T$=1.297 min, MS (ES) 483.3 $[M+H]^+$; $^1$H NMR (400 MHz, Chloroform-d) δ 8.43 (d, J=2.1 Hz, 1H), 8.38 (d, J=2.1 Hz, 1H), 6.58 (d, J=2.2 Hz, 2H), 6.38 (t, J=2.1 Hz, 1H), 4.66 (br s, 1H), 4.34-4.24 (m, 2H), 3.93 (s, 3H), 3.91 (s, 3H), 3.79 (m, 8H), 3.14 (t, J=4.8 Hz, 2H).

Step E. Preparation of 9-bromo-4-(3,5-dimethoxybenzyl)-5-oxo-2,3,4,5-tetrahydrobenzo[f][1,4]oxazepine-7-carboxylic acid $K_2CO_3$ (340.6 mg, 2.46 mmol, 5.0 equiv.) was added to a solution of dimethyl 5-bromo-4-(2-((3,5-dimethoxybenzyl)amino)ethoxy)isophthalate (237.7 mg, 0.49 mmol, 1.0 equiv.) in MeOH (20.0 mL). The reaction mixture was stirred at 64° C. for 12 h then concentrated under reduced pressure. The residue was partitioned between $CH_2Cl_2$ (20.0 mL) and $H_2O$ (3.0 mL). The organic layer was extracted with $CH_2Cl_2$ (3×20.0 mL) and dried over $Na_2SO_4$. The combined organics were concentrated under the reduced pressure to afford the crude title compound, which was used for the next step without further purification. LCMS: $R_T$=1.496 min, MS (ES) 437.3 $[M+H]^+$.

Step F. Preparation of methyl 9-bromo-4-(3,5-dimethoxybenzyl)-5-oxo-2,3,4,5-tetrahydrobenzo[f][1,4]oxazepine-7-carboxylate $SOCl_2$ (0.11 mL, 1.53 mmol, 3.0 equiv.) was added to a solution of 9-bromo-4-(3,5-dimethoxybenzyl)-5-oxo-2,3,4,5-tetrahydrobenzo[f][1,4]oxazepine-7-carboxylic acid (221.9 mg, 0.51 mmol, 1.0 equiv.) in MeOH (10.0 mL). The reaction mixture was stirred at 65° C. for 12 h at which point it was complete by LCMS analysis. The reaction mixture was concentrated under the reduced pressure. The crude residue was purified by silica gel chromatography with a Teledyne ISCO Combi-Flash eluting with 0 to 20% MeOH in $CH_2Cl_2$ to yield the title compound (168.2 mg, 73% yield over 2 steps). LCMS: $R_T$=1.722 min, MS (ES) 451.3 $[M+H]^+$; $^1$H NMR (400 MHz, Chloroform-d) δ 8.46 (d, J=2.1 Hz, 1H), 8.33 (d, J=2.1 Hz, 1H), 6.47 (d, J=2.1 Hz, 2H), 6.38 (t, J=2.1 Hz, 1H), 4.74 (s, 2H), 4.30 (t, J=5.1 Hz, 2H), 3.90 (s, 3H), 3.76 (s, 6H), 3.47 (d, J=5.2 Hz, 2H).

Step G. Preparation of methyl 4-(3,5-dimethoxybenzyl)-9-(4-fluoro-2-methylphenyl)-5-oxo-2,3,4,5-tetrahydrobenzo[f][1,4]oxazepine-7-carboxylate (4-Fluoro-2-methylphenyl)boronic acid (115.0 mg, 0.75 mmol, 2.0 equiv.), $K_2CO_3$ (206.5 mg, 1.49 mmol, 4.0 equiv.), $Pd(PPh_3)_4$ (21.6 mg, 0.02 mmol, 0.05 equiv.) were added to a solution of methyl 9-bromo-4-(3,5-dimethoxybenzyl)-5-oxo-2,3,4,5-tetrahydrobenzo[f][1,4]oxazepine-7-carboxylate (168.2 mg, 0.37 mmol, 1.0 equiv.) in 1,4-dioxane (4.0 mL) and $H_2O$ (1.0 mL). The reaction mixture was degassed using Ar gas then stirred at 80° C. for 4.5 h. The reaction was quenched with sat. aq. $NH_4Cl$ (1.0 mL) and extracted with $CH_2Cl_2$ (3×10.0 mL). The combined organics were dried over $Na_2SO_4$ and concentrated under the reduced pressure. The residue was purified by flash chromatography (Combi-flash Rf, Hex/EtOAc=0-100% gradient) to afford the title compound (153 mg, 85% yield). LCMS: $R_T$=1.887 min; MS (ES) 480.5 $[M+H]^+$ $^1$H NMR (400 MHz, Chloroform-d) δ 8.59 (d, J=2.3 Hz, 1H), 7.96 (d, J=2.3 Hz, 1H), 7.06 (dd, J=8.3, 5.9 Hz, 1H), 6.96 (dd, J=9.7, 2.4 Hz, 1H), 6.91 (td, J=8.4, 2.6 Hz, 1H), 6.49 (d, J=2.2 Hz, 2H), 6.38 (t, J=2.2 Hz, 1H), 4.77 (br s, 2H), 4.05 (br s, 2H), 3.92 (s, 3H), 3.77 (s, 6H), 3.48 (br s, 2H), 2.08 (s, 3H).

Step H. Preparation of 4-(3,5-dimethoxybenzyl)-9-(4-fluoro-2-methylphenyl)-7-(hydroxymethyl)-3,4-dihydrobenzo[f][1,4]oxazepin-5(2H)-one $NaBH_4$ (907 mg, 24.0 mmol, 75 equiv.) was added portionwise to a solution of methyl 4-(3,5-dimethoxybenzyl)-9-(4-fluoro-2-methylphenyl)-5-oxo-2,3,4,5-tetrahydrobenzo[f][1,4] oxazepine-7-carboxylate (153 mg, 0.32 mmol, 1.0 equiv.) in EtOH (20.0 mL). The reaction mixture was stirred at 65° C. for 12 h then diluted with acetone (5.0 mL) and concentrated under the reduced pressure. The residue was partitioned between $CH_2Cl_2$ (20.0 mL) and $H_2O$ (3.0 mL). The organic layer was extracted with $CH_2Cl_2$ (3×20.0 mL), dried over $Na_2SO_4$ and concentrated under the reduced pressure. The residue was purified by flash chromatography (Combi-flash Rf, Hex/EtOAc=0-100% gradient) to afford the title compound (144 mg, quantitative). LCMS: $R_T$=1.590 min, MS (ES) 452.5 $[M+H]^+$.

Step I Preparation of 7-(bromomethyl)-4-(3,5-dimethoxybenzyl)-9-(4-fluoro-2-methylphenyl)-3,4-dihydrobenzo[f][1,4]oxazepin-5(2H)-one $PBr_3$ (60 μL, 0.64 mmol, 2.0 equiv.) was added to a solution of 4-(3,5-dimethoxybenzyl)-9-(4-fluoro-2-methylphenyl)-7-(hydroxymethyl)-3,4-dihydrobenzo[f][1,4] oxazepin-5(2H)-one (145 mg, 0.32 mmol, 1.0 equiv.) in THE (3.0 mL). The reaction mixture was stirred at room temperature for 0.5 h then quenched with $H_2O$ (1.0 mL) and extracted with $CH_2Cl_2$ (3×10.0 mL). The organics were passed through a phase separator and the combined organics were concentrated under reduced pressure. The residue was purified by flash chromatography (Combi-flash Rf, Hex/EtOAc=0-100% gradient) to afford the title compound (145 mg, 87% yield). LCMS: $R_T$=1.953 min, MS (ES) 515.4 $[M+H]^+$.

Step J. Preparation of 4-(3,5-dimethoxybenzyl)-9-(4-fluoro-2-methylphenyl)-7-((2-imino-3-methyl-2,3-dihydro-1H-imidazol-1-yl)methyl)-3,4-dihydrobenzo[f][1,4]oxazepin-5(2H)-one 1-Methyl-1H-imidazol-2-amine hydrochloride (11.3 mg, 0.08 mmol, 2.0 equiv.), KI (2.1 mg, 0.01 mmol, 0.3 equiv.), and N,N-diisopropylethylamine (40.0 μL, 0.21 mmol, 5.0 equiv.) were added to a solution of 7-(bromomethyl)-4-(3,5-dimethoxybenzyl)-9-(4-fluoro-2-methylphenyl)-3,4-dihydrobenzo[f][1,4]oxazepin-5(2H)-one (21.8 mg, 0.04 mmol, 1.0 equiv.) in $CH_3CN$ (1.0 mL). The reaction mixture was stirred at 90° C. for 12 h then quenched with MeOH (0.5 mL) and concentrated under reduced pressure. The residue was purified by reverse phase HPLC (Phenomenex Gemini C18, $H_2O/CH_3CN$ gradient from 5-95% $CH_3CN$, 0.1% TFA) to yield the title compound (14.2 mg, 63% yield). To remove TFA, the organic layer was washed with $K_2CO_3$ (sat.). LCMS: $R_T$=0.869 min, MS (ES) 531.6 $[M+H]^+$; $^1H$ NMR (400 MHz, Chloroform-d) δ 7.69 (d, J=2.2 Hz, 1H), 7.21 (d, J=2.2 Hz, 1H), 7.04 (dd, J=8.3, 6.0 Hz, 1H), 6.92 (dd, J=9.8, 2.3 Hz, 1H), 6.86 (td, J=8.4, 2.5 Hz, 1H), 6.48 (d, J=2.1 Hz, 2H), 6.36 (t, J=2.1 Hz, 1H), 6.19 (q, J=2.6 Hz, 2H), 4.94 (s, 2H), 4.75 (br s, 2H), 3.88 (br s, 2H), 3.76 (s, 6H), 3.33 (s, 3H), 3.12 (br s, 2H), 2.05 (s, 3H).

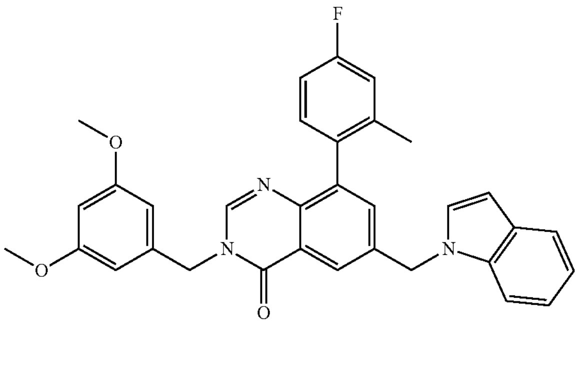 [SMILES: COc1cc(Cn2cnc3c(-c4ccc(F)cc4C)cc(Cn4ccc5ccccc54)cc3c2=O)cc(OC)c1]

Example 4

6-((1H-Indol-1-yl)methyl)-3-(3,5-dimethoxybenzyl)-8-(4-fluoro-2-methylphenyl)quinazolin-4(3H)-one The title compound (5.0 mg, 23% yield) was prepared from the procedure described in Example 1, Step G using indole (14.2 mg, 0.121 mmol, 3 equiv.). The reaction mixture was stirred at 80° C. for 30 min. LCMS: $R_T$=2.117 min, MS (ES) 534.0 $[M+H]^+$; $^1H$ NMR (400 MHz, Chloroform-d) δ 8.25 (d, J=1.6 Hz, 1H), 8.04 (s, 1H), 7.65 (d, J=7.6 Hz, 1H), 7.36-7.28 (m, 2H), 7.22-7.16 (m, 2H), 7.14-7.03 (m, 2H), 7.00-6.87 (m, 2H), 6.56 (d, J=2.8 Hz, 1H), 6.45 (d, J=2.0 Hz, 2H), 6.38 (t, J=2.0 Hz, 1H), 5.52-5.46 (m, 2H), 5.41 (d, J=10.8 Hz, 1H), 5.13 (d, J=10.8 Hz, 1H), 3.75 (s, 6H), 1.95 (s, 3H).

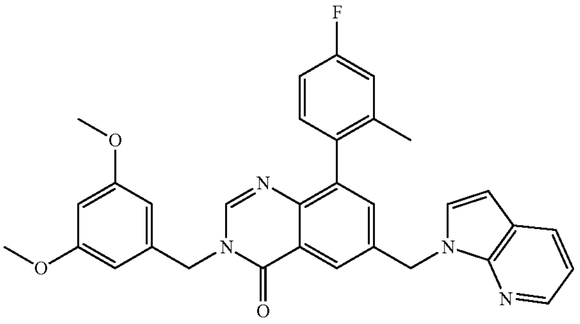 [SMILES: COc1cc(Cn2cnc3c(-c4ccc(F)cc4C)cc(Cn4ccc5cccnc54)cc3c2=O)cc(OC)c1]

Example 5

6-((1H-Pyrrolo[2,3-b]pyridin-1-yl)methyl)-3-(3,5-dimethoxybenzyl)-8-(4-fluoro-2-methylphenyl)quinazolin-4(3H)-one The title compound (8.1 mg, 37% yield) was prepared from the procedure described in Example 1, Step G using 7-azaindole (14.2 mg, 0.121 mmol, 3 equiv.). The reaction mixture was stirred at 80° C. for 30 min. LCMS: $R_T$=1.411 min, MS (ES) 535.0 $[M+H]^+$. $^1H$ NMR (400 MHz, Chloroform-d) δ 8.49 (d, J=7.6 Hz, 1H), 8.12-8.08 (m, 3H), 7.81 (d, J=3.6 Hz, 2H), 7.47-7.42 (m, 1H), 7.13-7.09 (m, 1H), 6.99-6.91 (m, 2H), 6.85 (d, J=3.2 Hz, 1H), 6.42 (d, J=2.0 Hz, 2H), 6.38 (t, J=2.0 Hz, 1H), 5.15 (d, J=14.0 Hz, 1H), 5.0 (d, J=13.6 Hz, 1H), 4.18-4.06 (m, 2H), 3.74 (s, 6H), 2.04 (s, 3H).

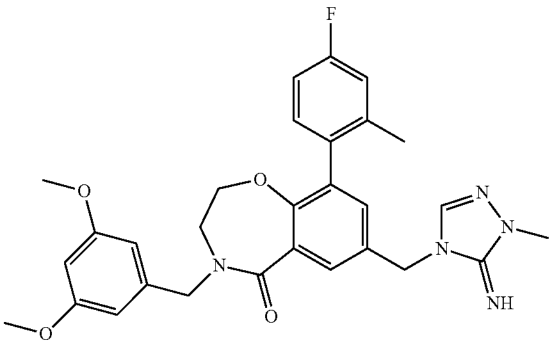

Example 6

4-(3,5-Dimethoxybenzyl)-9-(4-fluoro-2-methylphenyl)-7-((5-imino-1-methyl-1,5-dihydro-4H-1,2,4-triazol-4-yl)methyl)-3,4-dihydrobenzo[f][1,4]oxazepin-5(2H)-one 1-Methyl-1H-1,2,4-triazol-5-amine (17.2 mg, 0.17 mmol, 3.0 equiv.) was added to a solution of 7-(bromomethyl)-4-(3,5-dimethoxybenzyl)-9-(4-fluoro-2-methylphenyl)-3,4-dihydrobenzo[f][1,4]oxazepin-5(2H)-one (30.0 mg, 0.06 mmol, 1.0 equiv.) in $CH_3CN$ (1.0 mL). The reaction mixture was stirred at 60° C. for 12 h then quenched with MeOH (0.5 mL) and concentrated under the reduced pressure. The residue was purified by reverse phase HPLC (Phenomenex Gemini C18, $H_2O/CH_3CN$ gradient from 5-95% $CH_3CN$, 0.1% TFA) to yield the title compound (11.3 mg, 36% yield).

To remove TFA, the organic layer was washed with $K_2CO_3$ (sat.). LCMS: $R_T$=1.381 min, MS (ES) 532.6 $[M+H]^+$; $^1H$ NMR (400 MHz, Chloroform-d) δ 7.78 (d, J=2.4 Hz, 1H), 7.25 (s, 1H), 7.23 (d, J=2.4 Hz, 1H), 7.04 (dd, J=8.4, 5.9 Hz, 1H), 6.94 (dd, J=9.8, 2.5 Hz, 1H), 6.88 (td, J=8.3, 2.5 Hz, 1H), 6.48 (d, J=2.2 Hz, 2H), 6.37 (t, J=2.2 Hz, 1H), 4.89 (s, 2H), 4.74 (br s, 2H), 3.94 (br s, 2H), 3.76 (s, 6H), 3.47 (s, 3H), 3.42 (br s, 2H), 2.06 (s, 3H).

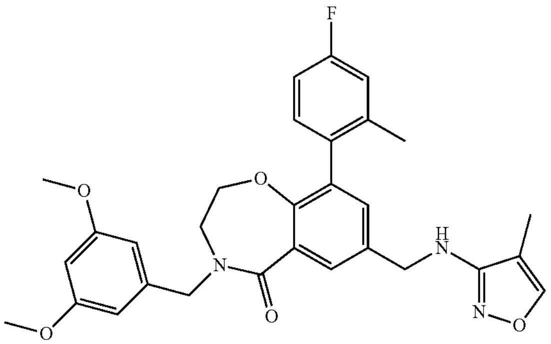 [SMILES: COc1cc(CN2CCOc3c(cc(CNc4nocc4C)cc3-c3ccc(F)cc3C)C2=O)cc(OC)c1]

Example 7

4-(3,5-Dimethoxybenzyl)-9-(4-fluoro-2-methylphenyl)-7-(((4-methylisoxazol-3-yl)amino)methyl)-3,4-dihydrobenzo[f][1,4]oxazepin-5(2H)-one The title compound (4.3 mg, 13% yield) was prepared from the procedure described in Example 6 using 7-(bromomethyl)-4-(3,5-dimethoxybenzyl)-9-(4-fluoro-2-methylphenyl)-3,4-dihydrobenzo[f][1,4]oxazepin-5(2H)-one (30.0 mg, 0.06 mmol, 1.0 equiv.) and 4-methylisoxazol-3-amine (28.6 mg, 0.29 mmol, 5.0 equiv.). LCMS: $R_T$=1.766 min, MS (ES) 532.6 $[M+H]^+$; $^1H$ NMR (400 MHz, Chloroform-d) δ 7.84 (d, J=1.1 Hz, 1H), 7.83 (d, J=2.4 Hz, 1H), 7.32 (d, J=2.4 Hz, 1H), 7.07 (dd, J=8.3, 6.0 Hz, 1H), 6.95 (dd, J=9.8, 2.5 Hz, 1H), 6.89 (td, J=8.4, 2.6 Hz, 1H), 6.49 (d, J=2.2 Hz, 2H), 6.37 (t, J=2.2 Hz, 1H), 4.77 (s, 2H), 4.51 (s, 2H), 3.92 (s, 2H), 3.77 (s, 6H), 3.43 (s, 2H), 2.08 (s, 3H), 1.90 (d, J=1.0 Hz, 3H).

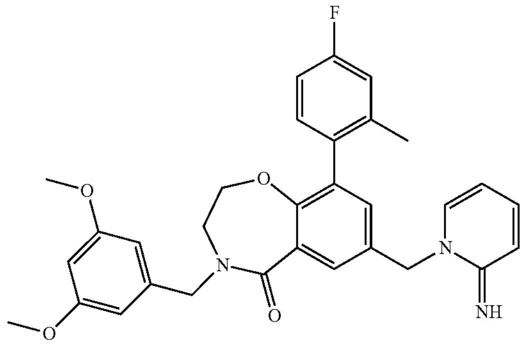 [SMILES: COc1cc(CN2CCOc3c(cc(Cn4ccccc4=N)cc3-c3ccc(F)cc3C)C2=O)cc(OC)c1]

Example 8

4-(3,5-Dimethoxybenzyl)-9-(4-fluoro-2-methylphenyl)-7-((2-iminopyridin-1(2H)-yl)methyl)-3,4-dihydrobenzo[f][1,4]oxazepin-5(2H)-one The title compound (11.2 mg, 36% yield) was prepared from the procedure described in Example 6 as a major product using 7-(bromomethyl)-4-(3,5-dimethoxybenzyl)-9-(4-fluoro-2-methylphenyl)-3,4-dihydrobenzo[f][1,4]oxazepin-5(2H)-one (30.0 mg, 0.06 mmol, 1.0 equiv.) and pyridin-2-amine (27.5 mg, 0.29 mmol, 5.0 equiv.). LCMS: $R_T$=1.396 min, MS (ES) 528.6 $[M+H]^+$.

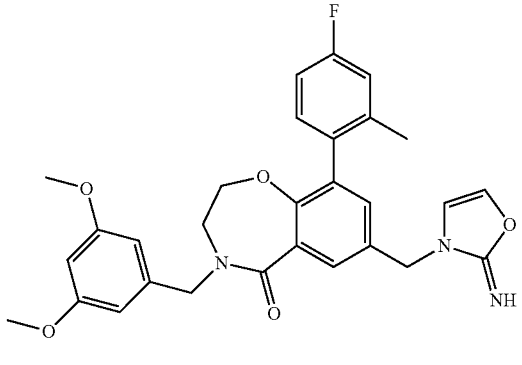 [SMILES: COc1cc(CN2CCOc3c(cc(Cn4ccoc4=N)cc3-c3ccc(F)cc3C)C2=O)cc(OC)c1]

Example 9

4-(3,5-Dimethoxybenzyl)-9-(4-fluoro-2-methylphenyl)-7-((2-iminooxazol-3(2H)-yl)methyl)-3,4-dihydrobenzo[f][1,4]oxazepin-5(2H)-one The title compound (13.1 mg, 43% yield) was prepared from the procedure described in Example 6 using 7-(bromomethyl)-4-(3,5-dimethoxybenzyl)-9-(4-fluoro-2-methylphenyl)-3,4-dihydrobenzo[f][1,4]oxazepin-5(2H)-one (30.0 mg, 0.06 mmol, 1.0 equiv.) and oxazol-2-amine (24.5 mg, 0.29 mmol, 5.0 equiv.). LCMS: $R_T$=1.372 min, MS (ES) 518.6 $[M+H]^+$; $^1H$ NMR (400 MHz, Chloroform-d) δ 7.75 (d, J=2.3 Hz, 1H), 7.24 (d, J=2.3 Hz, 1H), 7.05 (dd, J=8.3, 5.9 Hz, 1H), 6.94 (dd, J=9.7, 2.4 Hz, 1H), 6.88 (td, J=8.4, 2.5 Hz, 1H), 6.68 (d, J=1.8 Hz, 1H), 6.49 (d, J=2.1 Hz, 2H), 6.41 (d, J=1.8 Hz, 1H), 6.37 (t, J=2.1 Hz, 1H), 4.81 (s, 2H), 4.75 (br s, 2H), 3.92 (br s, 2H), 3.77 (s, 6H), 3.41 (br s, 2H), 2.06 (s, 3H).

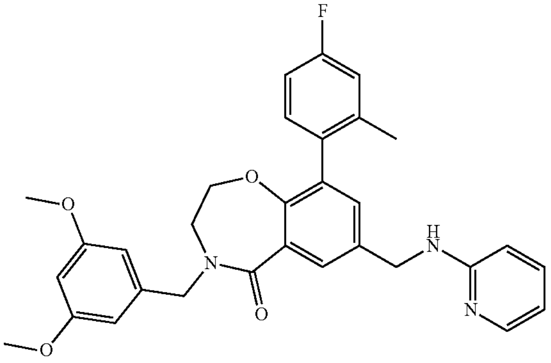 [SMILES: COc1cc(CN2CCOc3c(cc(CNc4ccccn4)cc3-c3ccc(F)cc3C)C2=O)cc(OC)c1]

Example 10

4-(3,5-Dimethoxybenzyl)-9-(4-fluoro-2-methylphenyl)-7-((pyridin-2-ylamino)methyl)-3,4-dihydrobenzo[f][1,4]oxazepin-5(2H)-one The title compound (3.8 mg, 12% yield) was prepared from the procedure described in Example 6 as a minor product using 7-(bromomethyl)-4-(3,5-dimethoxybenzyl)-9-(4-fluoro-2-methylphenyl)-3,4-dihydrobenzo[f][1,4]oxazepin-5(2H)-one (30.0 mg, 0.06 mmol, 1.0 equiv.) and pyridin-2-amine (27.5 mg, 0.29 mmol, 5.0 equiv.). LCMS: $R_T$=1.460 min, MS (ES) 528.6 $[M+H]^+$.

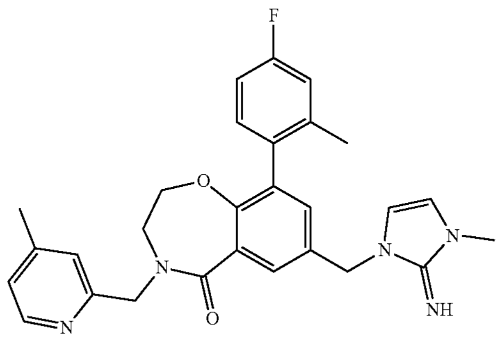 [SMILES: Cc1ccnc(CN2CCOc3c(cc(Cn4ccn(C)c4=N)cc3-c3ccc(F)cc3C)C2=O)c1]

Example 11

9-(4-Fluoro-2-methylphenyl)-7-((2-imino-3-methyl-2,3-dihydro-1H-imidazol-1-yl)methyl)-4-((4-methylpyridin-2-yl)methyl)-3,4-dihydrobenzo[f][1,4]oxazepin-5(2H)-one Step A. Preparation of 9-bromo-7-((2-imino-3-methyl-2,3-dihydro-1H-imidazol-1-yl)methyl)-3,4-dihydrobenzo[f][1,4]oxazepin-5(2H)-one The crude title compound was prepared from the procedure described in Example 3, Step J using 9-bromo-7-(bromomethyl)-3,4-dihydrobenzo[f][1,4]oxazepin-5(2H)-one (436.0 mg, 1.30 mmol, 1.0 equiv.) (Example 25, Step B), 1-methyl-1H-imidazol-2-amine hydrochloride (189.6 mg, 1.95 mmol, 1.5 equiv.), KI (64.8 mg, 0.39 mmol, 0.3 equiv.) and N,N-diisopropylethylamine (1.13 mL, 6.51 mmol, 5.0 equiv.). The reaction mixture was stirred at 90° C. for 1 h. LCMS: $R_T$=0.825 min, MS (ES) 352.2 $[M+H]^+$.

Step B. Preparation of tert-butyl (1-((9-bromo-5-oxo-2,3,4,5-tetrahydrobenzo[f][1,4] oxazepin-7-yl)methyl)-3-methyl-1,3-dihydro-2H-imidazol-2-ylidene)carbamate Di-tert-butyl dicarbonate (1.49 mL, 6.51 mmol, 5.0 equiv.) and DMAP (79.5 mg, 0.65 mmol, 0.5 equiv.) were added to a solution of 9-bromo-7-((2-imino-3-methyl-2,3-dihydro-1H-imidazol-1-yl)methyl)-3,4-dihydrobenzo[f][1,4]oxazepin-5(2H)-one (457.1 mg, 1.30 mmol, 1.0 equiv.) in CH2Cl2 (10.0 mL). The reaction mixture was stirred for 3.5 h at room temperature then quenched with H2O (2.0 mL) and extracted with CH2Cl2 (3×20.0 mL). The combined organics were concentrated under reduced pressure. The residue was purified by flash chromatography (Combi-flash Rf, DCM/MeOH=0-20% gradient) to afford the title compound (187 mg, 31% yield over 2 steps). LCMS: RT=1.005 min, MS (ES) 452.3 [M+H]+; 1H NMR (400 MHz, Chloroform-d) δ 7.84 (d, J=1.9 Hz, 1H), 7.74 (d, J=1.9 Hz, 1H), 7.10 (s, 1H), 7.07 (s, 1H), 5.27 (s, 2H), 4.54-4.49 (m, 2H), 3.77 (s, 3H), 3.55-3.50 (m, 2H), 2.00 (s, 9H).

Step C. Preparation of tert-butyl (1-((9-(4-fluoro-2-methylphenyl)-5-oxo-2,3,4,5-tetrahydrobenzo[f][1,4]oxazepin-7-yl)methyl)-3-methyl-1,3-dihydro-2H-imidazol-2-ylidene)carbamate The title compound (127 mg, 63% yield) was prepared from the procedure described in Example 3, Step F using tert-butyl (1-((9-bromo-5-oxo-2,3,4,5-tetrahydrobenzo[f][1,4]oxazepin-7-yl)methyl)-3-methyl-1,3-dihydro-2H-imidazol-2-ylidene)carbamate (187 mg, 0.41 mmol, 1.0 equiv.) and (4-fluoro-2-methylphenyl)boronic acid (127.4 mg, 0.83 mmol, 2.0 equiv.). LCMS: RT=1.249 min, MS (ES) 481.5 [M+H]+.

Step D. Preparation of tert-butyl (1-((9-(4-fluoro-2-methylphenyl)-4-((4-methylpyridin-2-yl)methyl)-5-oxo-2,3,4,5-tetrahydrobenzo[f][1,4]oxazepin-7-yl)methyl)-3-methyl-1,3-dihydro-2H-imidazol-2-ylidene)carbamate 2-(Chloromethyl)-4-methylpyridine hydrochloride (14 mg, 0.08 mmol, 1.5 equiv.) was added to a solution of tert-butyl (1-((9-(4-fluoro-2-methylphenyl)-5-oxo-2,3,4,5-tetrahydrobenzo[f][1,4]oxazepin-7-yl)methyl)-3-methyl-1,3-dihydro-2H-imidazol-2-ylidene)carbamate (25 mg, 0.05 mmol, 1.0 equiv.) in DMF (1.0 mL). The reaction mixture was cooled to 0° C., and NaH (2.5 mg, 0.10 mmol, 2.0 equiv.) was added and stirred for 2 h at 0° C. The reaction mixture was quenched with MeOH (0.5 mL) and concentrated under the reduced pressure. The residue was purified by reverse phase HPLC (Phenomenex Gemini C18, H2O/CH3CN gradient from 5-95% CH3CN, 0.1% TFA) to yield the TFA salt of title compound, which was directly used for the next step. LCMS: RT=1.357 min, MS (ES) 586.7 [M+H]+.

Step E. Preparation of 9-(4-fluoro-2-methylphenyl)-7-((2-imino-3-methyl-2,3-dihydro-1H-imidazol-1-yl)methyl)-4-((4-methylpyridin-2-yl)methyl)-3,4-dihydrobenzo[f][1,4]oxazepin-5(2H)-one To a solution of tert-butyl (1-((9-(4-fluoro-2-methylphenyl)-4-((4-methylpyridin-2-yl)methyl)-5-oxo-2,3,4,5-tetrahydrobenzo[f][1,4]oxazepin-7-yl)methyl)-3-methyl-1,3-dihydro-2H-imidazol-2-ylidene)carbamate (30.5 mg, 0.05 mmol, 1.0 equiv.) in CH3CN (1.0 mL), 2 drops of concentrated HCl were added and stirred at room temperature for 12 h. The reaction mixture was concentrated under the reduced pressure, and the residue was purified by reverse phase HPLC (Phenomenex Gemini C18, H2O/CH3CN gradient from 5-95% CH3CN, 0.1% TFA) to yield the title compound (22.7 mg, 89% yield over 2 steps). To remove TFA, the organic layer has to be washed with K2CO3 (sat.). LCMS: RT=1.082 min, MS (ES) 486.6 [M+H]+; 1H NMR (400 MHz, Chloroform-d) δ 8.35 (d, J=5.1 Hz, 1H), 7.69 (d, J=2.4 Hz, 1H), 7.27 (s, 1H), 7.21 (d, J=2.4 Hz, 1H), 7.06-7.00 (m, 2H), 6.92 (dd, J=9.8, 2.6 Hz, 1H), 6.86 (td, J=8.4, 2.6 Hz, 1H), 6.24-6.20 (m, 2H), 4.97 (s, 2H), 4.86 (s, 2H), 4.01 (m, 2H), 3.60 (br s, 2H), 3.35 (s, 3H), 2.33 (s, 3H), 2.05 (s, 3H).

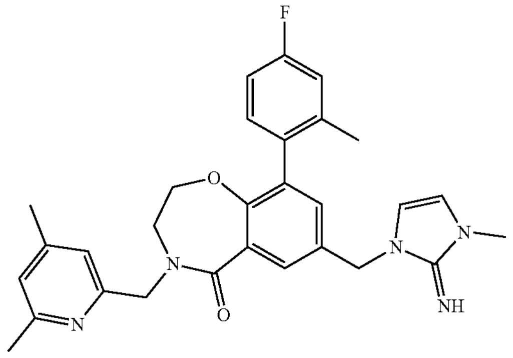

Example 12

4-((4,6-Dimethylpyridin-2-yl)methyl)-9-(4-fluoro-2-methylphenyl)-7-((2-imino-3-methyl-2,3-dihydro-1H-imidazol-1-yl)methyl)-3,4-dihydrobenzo[f][1,4]oxazepin-5(2H)-one

Step A. Preparation of tert-butyl (1-((4-((4,6-dimethylpyridin-2-yl)methyl)-9-(4-fluoro-2-methylphenyl)-5-oxo-2,3,4,5-tetrahydrobenzo[f][1,4]oxazepin-7-yl)methyl)-3-methyl-1,3-dihydro-2H-imidazol-2-ylidene)carbamate The TFA salt of the title compound was prepared from the procedure described in Example 11, Step D using tert-butyl (1-((9-(4-fluoro-2-methylphenyl)-5-oxo-2,3,4,5-tetrahydrobenzo[f][1,4]oxazepin-7-yl)methyl)-3-methyl-1,3-dihydro-2H-imidazol-2-ylidene)carbamate (30.0 mg, 0.06 mmol, 1.0 equiv.) and 2-(chloromethyl)-4,6-dimethylpyridine (10.0 μL, 0.09 mmol, 1.5 equiv.). LCMS: $R_T$=1.376 min, MS (ES) 600.7 $[M+H]^+$.

Step B. Preparation of 4-((4,6-dimethylpyridin-2-yl)methyl)-9-(4-fluoro-2-methylphenyl)-7-((2-imino-3-methyl-2,3-dihydro-1H-imidazol-1-yl)methyl)-3,4-dihydrobenzo[f][1,4]oxazepin-5(2H)-one The title compound (25.6 mg, 78% yield over 2 steps) was prepared from the procedure described in Example 11, Step E using tert-butyl (1-((4-((4,6-dimethylpyridin-2-yl)methyl)-9-(4-fluoro-2-methylphenyl)-5-oxo-2,3,4,5-tetrahydrobenzo[f][1,4]oxazepin-7-yl)methyl)-3-methyl-1,3-dihydro-2H-imidazol-2-ylidene)carbamate (39.4 mg, 0.07 mmol, 1.0 equiv.). LCMS: $R_T$=1.128 min, MS (ES) 500.6 $[M+H]^+$; $^1$H NMR (400 MHz, Chloroform-d) δ 7.69 (d, J=2.4 Hz, 1H), 7.22 (d, J=2.4 Hz, 1H), 7.06-7.01 (m, 2H), 6.91 (dd, J=9.8, 2.5 Hz, 1H), 6.89-6.82 (m, 2H), 6.31 (q, J=2.6 Hz, 2H), 5.08 (s, 2H), 4.82 (s, 2H), 4.04 (m, 2H), 3.60 (br s, 2H), 3.44 (s, 3H), 2.46 (s, 3H), 2.27 (s, 3H), 2.04 (s, 3H).

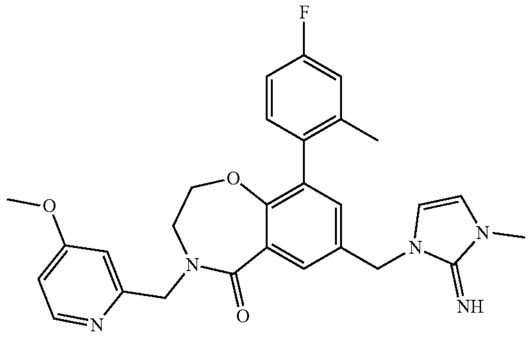

Example 13

9-(4-Fluoro-2-methylphenyl)-7-((2-imino-3-methyl-2,3-dihydro-1H-imidazol-1-yl)methyl)-4-((4-methoxypyridin-2-yl)methyl)-3,4-dihydrobenzo[f][1,4]oxazepin-5(2H)-one

Step A. Preparation of tert-butyl (1-((9-(4-fluoro-2-methylphenyl)-4-((4-methoxypyridin-2-yl)methyl)-5-oxo-2,3,4,5-tetrahydrobenzo[f][1,4]oxazepin-7-yl)methyl)-3-methyl-1,3-dihydro-2H-imidazol-2-ylidene)carbamate The TFA salt of the title compound was prepared from the procedure described in Example 11, Step D using tert-butyl (1-((9-(4-fluoro-2-methylphenyl)-5-oxo-2,3,4,5-tetrahydrobenzo[f][1,4]oxazepin-7-yl)methyl)-3-methyl-1,3-dihydro-2H-imidazol-2-ylidene)carbamate (25.0 mg, 0.05 mmol, 1.0 equiv.) and 2-(chloromethyl)-4-methoxypyridine (10.0 μL, 0.08 mmol, 1.5 equiv.). LCMS: $R_T$=1.321 min, MS (ES) 602.7 $[M+H]^+$.

Step B. Preparation of 9-(4-fluoro-2-methylphenyl)-7-((2-imino-3-methyl-2,3-dihydro-1H-imidazol-1-yl)methyl)-4-((4-methoxypyridin-2-yl)methyl)-3,4-dihydrobenzo[f][1,4]oxazepin-5(2H)-one The title compound (18 mg, 67% yield over 2 steps) was prepared from the procedure described in Example 11, Step E using tert-butyl (1-((9-(4-fluoro-2-methylphenyl)-4-((4-methoxypyridin-2-yl)methyl)-5-oxo-2,3,4,5-tetrahydrobenzo[f][1,4]oxazepin-7-yl)methyl)-3-methyl-1,3-dihydro-2H-imidazol-2-ylidene)carbamate (31.3 mg, 0.05 mmol, 1.0 equiv.). LCMS: $R_T$=1.054 min, MS (ES) 502.6 $[M+H]^+$.

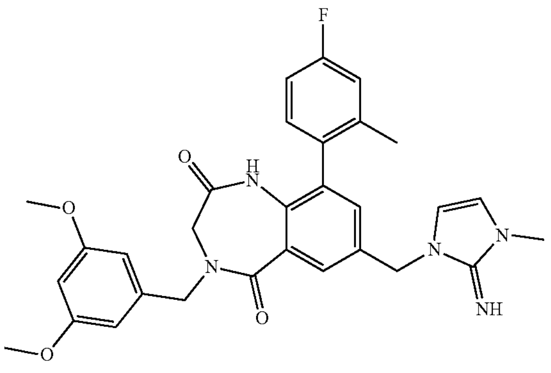

Example 14

4-(3,5-Dimethoxybenzyl)-9-(4-fluoro-2-methylphenyl)-7-((2-imino-3-methyl-2,3-dihydro-1H-imidazol-1-yl)methyl)-3,4-dihydro-1H-benzo[e][1,4]diazepine-2,5-dione Step A. Preparation of methyl (3,5-dimethoxybenzyl)glycinate Methyl glycine (1070 mg, 12.0 mmol, 2 equiv.) and 3,5-dimethoxybenzaldehyde (1000 mg, 6.02 mmol, 1.0 equiv.) were suspended in DCM (24 mL) and $Et_3N$ (2.52 mL, 18.1 mmol, 3.0 equiv.) was added. The reaction was stirred at room temperature overnight and then MeOH (12 mL) was added followed by $NaBH_4$ (228 mg, 6.02 mmol, 1.0 equiv.). The reaction was stirred for additional 30 min at room temperature, quenched with $H_2O$ (20 mL) and extracted with DCM (3×15 mL). The combined organic layers were washed with brine (10 mL), dried ($MgSO_4$), filtered and concentrated. The residue was purified by flash chromatography (Combi-flash Rf, DCM/MeOH=0-5% gradient) to afford the title compound (1102 mg, 82% yield) as a clear oil. LCMS: $R_T$=0.751 min, MS (ES) 240.1 $[M+H]^+$.

Step B. Preparation of 9-bromo-7-chloro-4-(3,5-dimethoxybenzyl)-3,4-dihydro-1H-benzo[e][1,4]diazepine-2,5-dione 2-Amino-3-bromo-5-chlorobenzoic acid (1000 mg, 4.02 mmol, 1.0 equiv.) was suspended in DCM (8 mL), and HATU (1528 mg, 4.02 mmol, 1.0 equiv.) and diisopropylethylamine (1038 mg, 8.04 mmol, 2.0 equiv.) were added followed by a solution of methyl (3,5-dimethoxybenzyl) glycinate (960 mg, 4.02 mmol, 1.0 equiv.) in DCM (4 mL). The reaction was stirred at 35° C. for 2 h and then cooled to room temperature. KOtBu (902 mg, 8.04 mmol, 2.0 equiv.) was added, and the reaction was stirred for 6 h at room temperature. The reaction was diluted with water (12 mL) and extracted with EtOAc (3×15 mL). The combined organic layer was washed with brine, dried ($MgSO_4$), filtered and concentrated. The residue was purified by flash chromatography (Combi-flash Rf, Hex/EtOAc=0-75% gradient) to afford the title compound (942 mg, 53% yield). LCMS: $R_T$=1.555 min, MS (ES) 438.9 $[M+H]^+$.

Step C. Preparation of 7-chloro-4-(3,5-dimethoxybenzyl)-9-(4-fluoro-2-methylphenyl)-3,4-dihydro-1H-benzo[e][1,4]diazepine-2,5-dione 9-Bromo-7-chloro-4-(3,5-dimethoxybenzyl)-3,4-dihydro-1H-benzo[e][1,4]diazepine-2,5-dione (940 mg, 2.15 mmol, 1.0 equiv.), 2-methyl-4-fluorophenylboronic acid (496 mg, 3.22 mmol, 1.5 equiv.), $K_2CO_3$ (890 mg, 6.44 mmol, 3.0 equiv.) and $Pd(dppf)Cl_2$ (78.5 mg, 0.107 mmol, 0.05 equiv.) were suspended in 1,4-dioxane:$H_2O$ (3:1, 8.5 mL). The mixture was degassed for 10 minutes with Ar then heated to 95° C. for 2 h under Ar. The reaction was then cooled to room temperature, diluted with water (10 mL) and extracted with EtOAc (3×10 mL). The combined organic layer was washed with brine, dried ($MgSO_4$), filtered and concentrated. The residue was purified by flash chromatography (Combi-flash Rf, Hex/EtOAc=0-75% gradient) to afford the title compound (586 mg, 58% yield). LCMS: $R_T$=1.807 min, MS (ES) 468.9 $[M+H]^+$.

Step D. Preparation of 4-(3,5-dimethoxybenzyl)-9-(4-fluoro-2-methylphenyl)-7-vinyl-3,4-dihydro-1H-benzo[e][1,4]diazepine-2,5-dione $Pd(t-Bu_3P)_2$ (17.5 mg, 0.0342 mmol, 0.20 equiv.) was added to a mixture of 7-chloro-4-(3,5-dimethoxybenzyl)-9-(4-fluoro-2-methylphenyl)-3,4-dihydro-1H-benzo[e][1,4]diazepine-2,5-dione (80.0 mg, 0.171 mmol, 1.0 equiv.), potassium vinyltrifluoroborate (68.7 mg, 0.513 mmol, 3.0 equiv.) and $Cs_2CO_3$ (167 mg, 0.513 mmol, 3.0 equiv.), in 1,4-dioxane:$H_2O$ (3:1, 1.7 mL) under Ar. The resulting mixture was heated at 90° C. for 2 h, quenched with $H_2O$ (5 mL) and extracted with EtOAc (3×5 mL). The combined organic layer was washed with brine, dried ($MgSO_4$), filtered and concentrated. The residue was purified by flash chromatography (Combi-flash Rf, Hex/EtOAc=0-75% gradient) to afford the title compound (51.5 mg, 64% yield). LCMS: $R_T$=1.785 min, MS (ES) 461.0 $[M+H]^+$.

Step E. Preparation of 4-(3,5-dimethoxybenzyl)-9-(4-fluoro-2-methylphenyl)-7-(hydroxymethyl)-3,4-dihydro-1H-benzo[e][1,4]diazepine-2,5-dione $OsO_4$ (5% polymer bound, 6.9 mg, 0.0272 mmol, 0.25 equiv.) was added to a solution of 4-(3,5-dimethoxybenzyl)-9-(4-fluoro-2-methylphenyl)-7-vinyl-3,4-dihydro-1H-benzo[e][1,4] diazepine-2,5-dione (50.0 mg, 0.109 mmol, 1.0 equiv.) and pyridine (17.5 μL, 0.217 mmol, 2.0 equiv.) in 1,4-dioxane:$H_2O$ (3:1, 2 mL) at room temperature followed by $NaIO_4$ (93.0 mg, 0.435 mmol, 4.0 equiv.). After stirring overnight, the reaction mixture was cooled to 0° C., then MeOH (1 mL) was added followed by $NaBH_4$ (41.1 mg, 1.09 mmol, 10.0 equiv.). The ice bath was removed and the reaction was stirred at room temperature for additional 45 min then filtered. The filtrate was concentrated under reduced pressure, and the residue was dissolved in EtOAc (5 mL). The organic layer was washed with $H_2O$ (2×5 mL), dried ($MgSO_4$) and concentrated. The residue was purified by flash chromatography (Combi-flash Rf, Hex/EtOAc=0-100% gradient) to afford the title compound (35.0 mg, 69% yield). LCMS: $R_T$=1.432 min, MS (ES) 465.0 $[M+H]^+$; $^1H$ NMR (400 MHz, Chloroform-d) δ 8.02 (d, J=1.6 Hz, 1H), 7.36 (d, J=2.0 Hz, 1H), 7.08-6.95 (m, 4H), 6.48 (d, J=2.4 Hz, 2H), 6.39 (t, J=2.4 Hz, 1H), 4.94 (d, J=13.6 Hz, 1H), 4.75 (s, 2H), 4.67 (d, J=14.8 Hz, 1H), 3.83 (d, J=6.4 Hz, 2H), 3.77 (s, 6H), 2.00 (s, 3H).

Step F. Preparation of 7-(bromomethyl)-4-(3,5-dimethoxybenzyl)-9-(4-fluoro-2-methylphenyl)-3,4-dihydro-1H-benzo[e][1,4]diazepine-2,5-dione 4-(3,5-Dimethoxybenzyl)-9-(4-fluoro-2-methylphenyl)-7-(hydroxymethyl)-3,4-dihydro-1H-benzo[e][1,4]diazepine-2,5-dione (35.0 mg, 0.0754 mmol, 1.0 equiv.) was dissolved in DCM (0.8 mL) and $PBr_3$ (21.5 μL, 0.226 mmol, 3.0 equiv.) was added. After stirring at room temperature for 30 min, the reaction was quenched with saturated $NaHCO_3$ (5 mL) and extracted with EtOAc (3×5 mL). The combined organic layer was washed with brine, dried ($MgSO_4$), filtered and concentrated to yield the title compound (25.1 mg, 63% yield). LCMS: $R_T$=1.775 min, MS (ES) 526.9 $[M+H]^+$.

Step G. Preparation of 4-(3,5-dimethoxybenzyl)-9-(4-fluoro-2-methylphenyl)-7-((2-imino-3-methyl-2,3-dihydro-1H-imidazol-1-yl)methyl)-3,4-dihydro-1H-benzo[e][1,4]diazepine-2,5-dione 7-(Bromomethyl)-4-(3,5-dimethoxybenzyl)-9-(4-fluoro-2-methylphenyl)-3,4-dihydro-1H-benzo[e][1,4]diazepine-2, 5-dione (25.0 mg, 0.0475 mmol, 1.0 equiv.) was dissolved in MeCN (0.5 mL) and then 1-methyl-1H-imidazole-2-amine (13.8 mg, 0.143 mmol, 3.0 equiv.), KI (0.80 mg, 0.00475 mmol, 0.1 equiv.) and diisopropylethylamine (24.8 µL, 0.143 mmol, 3.0 equiv.) were added. The reaction was heated to 80° C. overnight, cooled to room temperature and concentrated under reduced pressure. The residue was purified by reverse phase HPLC (Phenomenex Gemini C18, $H_2O/CH_3CN$ gradient from 20-95% $CH_3CN$, 0.1% TFA) to yield the title compound (4.5 mg, 17% yield). To remove TFA, the organic layer was washed with $K_2CO_3$ (sat.). LCMS: $R_T$=1.300 min, MS (ES) 544.0 $[M+H]^+$; $^1H$ NMR (400 MHz, Chloroform-d) δ 7.90 (d, J=2.0 Hz, 1H), 7.11-6.94 (m, 5H), 6.54-6.46 (m, 3H), 6.39 (d, J=2.0 Hz, 1H), 4.90-4.84 (m, 1H), 4.71-4.65 (m, 1H), 3.86 (t, J=4.8 Hz, 2H), 3.77 (s, 6H), 3.74 (s, 3H), 3.59-3.45 (m, 2H), 1.99 (s, 3H). $^{19}F$ NMR (376 MHz, Chloroform-d) δ−112.33.

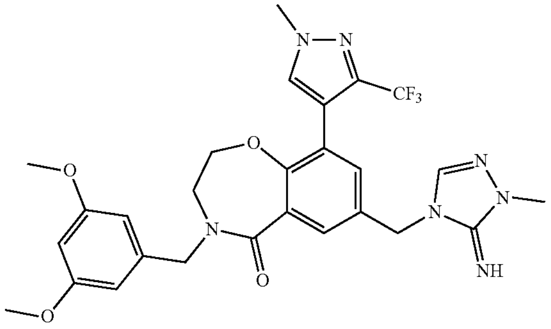

Example 15

4-(3,5-Dimethoxybenzyl)-7-((5-imino-1-methyl-1,5-dihydro-4H-1,2,4-triazol-4-yl)methyl)-9-(1-methyl-3-(trifluoromethyl)-1H-pyrazol-4-yl)-3,4-dihydrobenzo[f][1,4]oxazepin-5(2H)-one

Step A. Preparation of methyl 3-bromo-5-formyl-2-hydroxybenzoate

N-bromosuccinimide (10867 mg, 61.1 mmol) was added to a solution of methyl 5-formyl-2-hydroxybenzoate (1000 mg, 55.5 mmol) in THE (300.0 mL) at 0° C. then stirred for 5 min. The reaction mixture was warmed to room temperature and stirred for additional 2.5 h and concentrated under reduced pressure. The residue was purified by flash chromatography (Combi-flash Rf, Hex/EtOAc=0-100% gradient) to afford the title compound (14360 mg, quantitative). LCMS: $R_T$=1.499 min, MS (ES) 260.1 $[M+H]^+$; $^1H$ NMR (400 MHz, Chloroform-d) δ 9.85 (s, 1H), 8.36 (d, J=2.0 Hz, 1H), 8.27 (d, J=1.9 Hz, 1H), 4.04 (s, 3H).

Step B. Preparation of methyl 2-(allyloxy)-3-bromo-5-formylbenzoate

The crude title compound was prepared from the procedure described in Example 3, Step B using methyl 3-bromo-5-formyl-2-hydroxybenzoate (500.0 mg, 1.93 mmol, 1.0 equiv.), 3-bromoprop-1-ene (0.25 mL, 2.90 mmol, 1.5 equiv.), and $Cs_2CO_3$ (1886.6 mg, 5.79 mmol, 3 equiv.). The reaction mixture was stirred at 80° C. for 1 h. LCMS: $R_T$=1.602 min, MS (ES) 300.1 $[M+H]^+$.

Step C. Preparation of methyl 2-(allyloxy)-3-bromo-5-(hydroxymethyl)benzoate $NaBH_4$ (73 mg, 1.93 mmol, 1.0 equiv.) was added to a solution of methyl 2-(allyloxy)-3-bromo-5-formylbenzoate (577 mg, 1.93 mmol, 1.0 equiv.) in MeOH (20 mL). The reaction mixture was stirred at room temperature for 1 h, quenched with acetone (1.0 mL) and concentrated under reduced pressure. The crude reaction mixture was used for the next step without further purification.

Step D. Preparation of methyl 2-(allyloxy)-3-bromo-5-(((tert-butyldimethylsilyl)oxy)methyl)benzoate tert-Butyldimethylsilyl chloride (349 mg, 2.32 mmol, 1.2 equiv.), $Et_3N$ (0.4 mL, 2.90 mmol, 1.5 equiv.), and DMAP (47 mg, 0.39 mmol, 0.2 equiv.) were added to a solution of methyl 2-(allyloxy)-3-bromo-5-(hydroxymethyl)benzoate (581.2 mg, 1.93 mmol, 1.0 equiv.) in $CH_2Cl_2$ (20.0 mL) at 0° C. The reaction mixture was stirred for 12 h while warmed to room temperature during this time period. The reaction mixture was quenched with MeOH (2.0 mL) and concentrated under reduced pressure. The crude residue was partitioned between $CH_2Cl_2$ (20 mL) and $H_2O$ (5.0 mL). The organic layer was extracted with $CH_2Cl_2$ (3×20.0 mL) and dried over $Na_2SO_4$ and concentrated under reduced pressure. The residue was purified by flash chromatography (Combi-flash Rf, Hex/EtOAc=0-100% gradient) to afford the title compound (791 mg, 98% yield over 3 steps). LCMS: $R_T$=2.460 min, MS (ES) 416.4 $[M+H]^+$; $^1H$ NMR (400 MHz, Chloroform-d) δ 7.72-7.69 (m, 1H), 7.67 (m, 1H), 6.15 (ddt, J=17.1, 10.4, 5.8 Hz, 1H), 5.43 (dq, J=17.2, 1.5 Hz, 1H), 5.30-5.26 (m, 1H), 4.68 (s, 2H), 4.55 (dt, J=5.8, 1.3 Hz, 2H), 3.90 (s, 3H), 0.94 (s, 9H), 0.11 (s, 6H).

Step E. Preparation of methyl 3-bromo-5-(((tert-butyldimethylsilyl)oxy)methyl)-2-(2-oxoethoxy)benzoate $OsO_4$ (96.4 mg, 0.38 mmol, 0.75 equiv.) was added to a mixture of methyl 2-(allyloxy)-3-bromo-5-(((tert-butyldimethylsilyl)oxy)methyl)benzoate (210.0 mg, 0.51 mmol, 1.0 equiv.), pyridine (80.0 µL, 1.01 mmol, 2.0 equiv.), $H_2O$ (1.0 mL), and 1,4-dioxane (3.0 mL) at room temperature followed by $NaIO_4$ (432.5 mg, 2.02 mmol, 4.0 equiv.). After stirring 12 h at room temperature, the reaction mixture was partitioned between $CH_2Cl_2$ (10 mL) and $H_2O$ (2.0 mL) and extracted with $CH_2Cl_2$ (3×20 mL). The combined organics were dried over $Na_2SO_4$ and concentrated under reduced pressure to give the crude title compound, which was used for the next step without further purification. LCMS: $R_T$=1.869 min, MS (ES) 418.4 $[M+H]^+$.

Step F. Preparation of methyl 3-bromo-5-(((tert-butyldimethylsilyl)oxy)methyl)-2-(2-((3,5-dimethoxybenzyl)amino)ethoxy)benzoate The crude title compound was prepared from the procedure described in Example 3, Step D using methyl 3-bromo-5-(((tert-butyldimethylsilyl)oxy)methyl)-2-(2-oxoethoxy)benzoate (211.0 mg, 0.51 mmol, 1.0 equiv.) and (3,5- dimethoxyphenyl)methanamine (126.7 mg, 0.76 mmol, 1.5 equiv.). LCMS: $R_T$=2.176 min, MS (ES) 569.6 $[M+H]^+$.

Step G. Preparation of 9-bromo-4-(3,5-dimethoxybenzyl)-7-(hydroxymethyl)-3,4-dihydrobenzo[f][1,4]oxazepin-5(2H)-one The title compound (102 mg, 37% yield over 3 steps) was prepared from the procedure described in Example 3, Step E using methyl 3-bromo-5-(((tert-butyldimethylsilyl)oxy)methyl)-2-(2-((3,5-dimethoxybenzyl)amino)ethoxy)benzoate (287 mg, 0.51 mmol, 1.0 equiv.) and $K_2CO_3$ (349 mg, 2.53 mmol, 5.0 equiv.). The reaction mixture was stirred at 64° C. for 12 h. The TBS group was removed under the reaction conditions. LCMS: $R_T$=1.417 min, MS (ES) 423.3 $[M+H]^+$. $^1$H NMR (400 MHz, Chloroform-d) δ 7.68 (s, 1H), 7.66 (s, 1H), 6.48 (d, J=2.1 Hz, 2H), 6.38 (t, J=2.1 Hz, 1H), 4.73 (s, 2H), 4.63 (s, 2H), 4.19 (t, J=5.4 Hz, 2H), 3.77 (s, 6H), 3.40 (t, J=5.4 Hz, 2H), 3.11 (br s, 1H).

Step H. Preparation of 4-(3,5-dimethoxybenzyl)-7-(hydroxymethyl)-9-(1-methyl-3-(trifluoromethyl)-1H-pyrazol-4-yl)-3,4-dihydrobenzo[f][1,4]oxazepin-5(2H)-one The title compound (48 mg, 40% yield) was prepared from the procedure described in Example 3, Step F using 9-bromo-4-(3,5-dimethoxybenzyl)-7-(hydroxymethyl)-3,4-dihydrobenzo[f][1,4]oxazepin-5(2H)-one (102 mg, 0.24 mmol, 1.0 equiv.) and (1-methyl-3-(trifluoromethyl)-1H-pyrazol-4-yl)boronic acid (56 mg, 0.29 mmol, 1.2 equiv.). The reaction mixture was stirred at 80° C. for 3 h. LCMS: $R_T$=1.420 min, MS (ES) 492.5 $[M+H]^+$.

Step I. Preparation of 7-(bromomethyl)-4-(3,5-dimethoxybenzyl)-9-(1-methyl-3-(trifluoromethyl)-1H-pyrazol-4-yl)-3,4-dihydrobenzo[f][1,4]oxazepin-5(2H)-one The crude title compound was prepared from the procedure described in Example 3, Step H using 4-(3,5-dimethoxybenzyl)-7-(hydroxymethyl)-9-(1-methyl-3-(trifluoromethyl)-1H-pyrazol-4-yl)-3,4-dihydrobenzo[f][1,4]oxazepin-5(2H)-one (48 mg, 0.10 mmol, 1.0 equiv.) and $PBr_3$ (20 μL, 0.20 mmol, 2.0 equiv.). The reaction mixture was stirred at room temperature for 1 h. LCMS: $R_T$=1.743 min, MS (ES) 555.4 $[M+H]^+$.

Step J. Preparation of 4-(3,5-dimethoxybenzyl)-7-((5-imino-1-methyl-1,5-dihydro-4H-1,2,4-triazol-4-yl)methyl)-9-(1-methyl-3-(trifluoromethyl)-1H-pyrazol-4-yl)-3,4-dihydrobenzo[f][1,4]oxazepin-5(2H)-one The title compound (10 mg, 32% yield over 2 steps) was prepared from the procedure described in Example 6, Step A using 7-(bromomethyl)-4-(3,5-dimethoxybenzyl)-9-(1-methyl-3-(trifluoromethyl)-1H-pyrazol-4-yl)-3,4-dihydrobenzo[f][1,4]oxazepin-5(2H)-one (25 mg, 0.06 mmol, 1.0 equiv.) and 1-methyl-1H-1,2,4-triazol-5-amine (13 mg, 0.12 mmol, 3.0 equiv.). The reaction mixture was stirred at 60° C. for 12 h. LCMS: $R_T$=1.279 min, MS (ES) 572.6 $[M+H]^+$; $^1$H NMR (400 MHz, Chloroform-d) δ 7.80 (d, J=2.4 Hz, 1H), 7.46 (s, 1H), 7.35 (d, J=2.2 Hz, 1H), 7.23 (s, 1H), 6.48 (d, J=2.2 Hz, 2H), 6.38 (t, J=2.2 Hz, 1H), 4.89 (s, 2H), 4.74 (s, 2H), 4.04 (t, J=5.1 Hz, 2H), 3.97 (s, 3H), 3.77 (s, 6H), 3.48 (s, 3H), 3.45 (t, J=5.1 Hz, 2H).

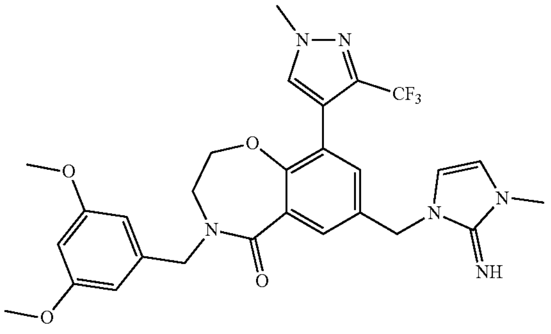

Example 16

4-(3,5-Dimethoxybenzyl)-7-((2-imino-3-methyl-2,3-dihydro-1H-imidazol-1-yl)methyl)-9-(1-methyl-3-(trifluoromethyl)-1H-pyrazol-4-yl)-3,4-dihydrobenzo[f][1,4]oxazepin-5(2H)-one The title compound (15 mg, 56% yield over 2 steps) was prepared from the procedure described in Example 3, Step J using 7-(bromomethyl)-4-(3,5-dimethoxybenzyl)-9-(1-methyl-3-(trifluoromethyl)-1H-pyrazol-4-yl)-3,4-dihydrobenzo[f][1,4]oxazepin-5(2H)-one (25 mg, 0.05 mmol, 1.0 equiv.) and 1-methyl-1H-imidazol-2-amine hydrochloride (8.8 mg 0.09 mmol, 2.0 equiv.). LCMS: $R_T$=1.308 min, MS (ES) 571.6 $[M+H]^+$; $^1$H NMR (400 MHz, Chloroform-d) δ 7.73 (d, J=2.3 Hz, 1H), 7.48 (s, 1H), 7.31 (d, J=2.2 Hz, 1H), 6.48 (d, J=2.2 Hz, 2H), 6.37 (t, J=2.2 Hz, 1H), 6.23 (s, 2H), 4.95 (s, 2H), 4.73 (s, 2H), 4.02 (t, J=5.1 Hz, 2H), 3.95 (s, 3H), 3.76 (s, 6H), 3.43 (t, J=5.1 Hz, 2H), 3.36 (s, 3H).

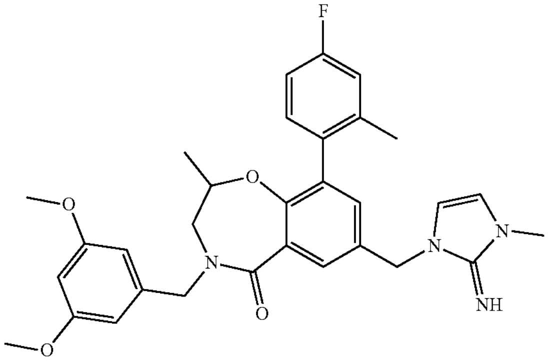

Example 17

4-(3,5-Dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one Step A. Preparation of methyl 3-bromo-2-hydroxy-5-(hydroxymethyl)benzoate Sodium borohydride (2097 mg, 55.4 mmol) was slowly added to a solution of methyl 3-bromo-5-formyl-2-hydroxybenzoate (14360 mg, 55.4 mmol) in MeOH (500 mL). The reaction mixture was stirred at room temperature for 1 h. The reaction mixture was concentrated under the reduced pressure. The residue was redissolved in $CH_2Cl_2$/MeOH and filtered through Celite and the filtrate was concentrated under the reduced pressure. The crude title compound was used for the next step without further purification. LCMS: $R_T$=1.246 min, MS (ES) 244.0 $[M+H-H_2O]^+$; $^1$H NMR (400 MHz, Chloroform-d) δ 11.40 (s, 1H), 7.82 (s, 1H), 7.76 (d, J=1.6 Hz, 1H), 4.62 (s, 2H), 3.98 (s, 3H).

Step B. Preparation of methyl 3-bromo-5-(((tert-butyldiphenylsilyl)oxy)methyl)-2-hydroxybenzoate tert-Butyl(chloro)diphenylsilane (40 μL, 0.14 mmol), $Et_3N$ (20 μL, 0.17 mmol), and DMAP (2.8 mg, 0.02 mmol) were added to a solution of methyl 3-bromo-2-hydroxy-5-(hydroxymethyl)benzoate (30 mg, 0.11 mmol) in 1,4-dioxane (1.0 mL). The reaction mixture was stirred at room temperature for 12 h, quenched with MeOH (1.0 mL) and concentrated under reduced pressure. The residue was purified by flash chromatography (Combi-flash Rf, Hex/EtOAc=0-5% gradient) to afford the title compound (53 mg, 92%). LCMS: $R_T$=1.944 min, MS (ES) 499.5 $[M+H]^+$; $^1$H NMR (400 MHz, Chloroform-d) δ 11.36 (s, 1H), 7.74 (d, J=2.1 Hz, 1H), 7.68 (dd, J=7.9, 1.4 Hz, 5H), 7.48-7.35 (m, 7H), 4.66 (s, 2H), 3.96 (s, 3H), 1.11 (s, 9H).

Step C. Preparation of methyl 3-bromo-2-((1-((tert-butoxycarbonyl)amino)propan-2-yl)oxy)-5-(((tert-butyldiphenylsilyl)oxy)methyl)benzoate The title compound (48 mg, 68% yield) was prepared from the procedure described in Example 3, Step B using methyl 3-bromo-5-(((tert-butyldiphenylsilyl)oxy)methyl)-2-hydroxybenzoate (53 mg, 0.11 mmol, 1.0 equiv.) and tert-butyl (2-bromopropyl)carbamate (51 mg, 0.21 mmol, 2.0 equiv.). $K_2CO_3$ (44 mg, 0.32 mmol, 3.0 equiv.) was used as a base. The reaction mixture was stirred at 80° C. for 6.5 h. LCMS: $R_T$=1.860 min, MS (ES) 601.6 $[M+H\text{-}tBu]^+$.

Step D. Preparation of methyl 2-((1-aminopropan-2-yl)oxy)-3-bromo-5-(((tert-butyldiphenylsilyl)oxy)methyl)benzoate TFA (0.1 mL) was added to a solution of methyl 3-bromo-2-((1-((tert-butoxycarbonyl)amino)propan-2-yl)oxy)-5-(((tert-butyldiphenylsilyl)oxy)methyl)benzoate (48 mg, 0.07 mmol, 1.0 equiv.) in $CH_2Cl_2$ (1.0 mL). The reaction mixture was stirred at room temperature for 1.5 h then concentrated under reduced pressure. The residue was partitioned between $CH_2Cl_2$ (5.0 mL) and sat. aq. $NaHCO_3$ (1.0 mL). The organic layer was extracted with $CH_2Cl_2$ (3×10.0 mL), dried over $Na_2SO_4$ and concentrated under reduced pressure. The crude title compound was used for the next step without further purification. LCMS: $R_T$=2.014 min, MS (ES) 557.6 $[M+H]^+$.

Step E. Preparation of 9-bromo-7-(((tert-butyldiphenylsilyl)oxy)methyl)-2-methyl-3,4-dihydrobenzo[f][1,4]oxazepin-5(2H)-one The title compound (30 mg, 79% yield) was prepared from the procedure described in Example 3, Step E using methyl 2-((1-aminopropan-2-yl)oxy)-3-bromo-5-(((tert-butyldiphenylsilyl)oxy)methyl)benzoate (40 mg, 0.07 mmol, 1.0 equiv.) and $K_2CO_3$ (50 mg, 0.36 mmol, 5.0 equiv.). The reaction mixture was stirred at 78° C. for 12 h. LCMS: $R_T$=2.303 min, MS (ES) 525.5 $[M+H]^+$.

Step F. Preparation of 9-bromo-7-(((tert-butyldiphenylsilyl)oxy)methyl)-4-(3,5-dimethoxybenzyl)-2-methyl-3,4-dihydrobenzo[f][1,4]oxazepin-5(2H)-one The title compound (36 mg, 93% yield) was prepared from the procedure described in Example 11, Step D using 9-Bromo-7-(((tert-butyldiphenylsilyl)oxy)methyl)-2-methyl-3,4-dihydrobenzo[f][1,4]oxazepin-5(2H)-one (30 mg, 0.06 mmol, 1.0 equiv.) and 1-(bromomethyl)-3,5-dimethoxybenzene (20 mg, 0.09 mmol, 1.5 equiv.). The reaction mixture was stirred at 0° C. for 2 h. LCMS: $R_T$=1.346 min, MS (ES) 675.7 $[M+H]^+$.

Step G. Preparation of 7-(((tert-butyldiphenylsilyl)oxy)methyl)-4-(3,5-dimethoxybenzyl)-9-(4-fluoro-2-methylphenyl)-2-methyl-3,4-dihydrobenzo[f][1,4]oxazepin-5(2H)-one The title compound (36 mg, 95% yield) was prepared from the procedure described in Example 3, Step F using 9-bromo-7-(((tert-butyldiphenylsilyl)oxy)methyl)-4-(3,5-dimethoxybenzyl)-2-methyl-3,4-dihydrobenzo[f][1,4]oxazepin-5(2H)-one (36 mg, 0.05 mmol, 1.0 equiv.) and (4-fluoro-2-methylphenyl)boronic acid (17 mg, 0.11 mmol, 2.0 equiv.). The reaction mixture was stirred at 80° C. for 4.5 h. LCMS: $R_T$=1.338 min, MS (ES) 704.9 $[M+H]^+$.

Step H. Preparation of 4-(3,5-dimethoxybenzyl)-9-(4-fluoro-2-methylphenyl)-7-(hydroxymethyl)-2-methyl-3,4-dihydrobenzo[f][1,4]oxazepin-5(2H)-one 1M tetrabutyl ammonium fluoride solution (0.1 mL, 0.10 mmol, 2.0 equiv.) was added to a solution of 7-(((tert-butyldiphenylsilyl)oxy)methyl)-4-(3,5-dimethoxybenzyl)-9-(4-fluoro-2-methylphenyl)-2-methyl-3,4-dihydrobenzo[f][1,4]oxazepin-5(2H)-one (36 mg, 0.05 mmol, 1.0 equiv.) in THF (1.0 mL). The reaction mixture was stirred at room temperature for 12 h, quenched with $H_2O$ (0.5 mL) and extracted with $CH_2Cl_2$ (3×3.0 mL). The combined organics were dried over $Na_2SO_4$ and concentrated under reduced pressure. The residue was purified by flash chromatography (Combi-flash Rf, Hex/EtOAc=0-100% gradient) to afford the title compound (22.1 mg, 92% yield). LCMS: $R_T$=1.115 min, MS (ES) 466.5 $[M+H]^+$.

Step I. Preparation of 7-(bromomethyl)-4-(3,5-dimethoxybenzyl)-9-(4-fluoro-2-methylphenyl)-2-methyl-3,4-dihydrobenzo[f][1,4]oxazepin-5(2H)-one The crude title compound was prepared from the procedure described in Example 3, Step I using 4-(3,5-dimethoxybenzyl)-9-(4-fluoro-2-methylphenyl)-7-(hydroxymethyl)-2-methyl-3,4-dihydrobenzo[f][1,4]oxazepin-5(2H)-one (22.1 mg, 0.05 mmol, 1.0 equiv.) and $PBr_3$ (10.0 μL, 0.09 mmol, 2.0 equiv.). The reaction mixture was stirred at room temperature for 2 h.

Step J. Preparation of 4-(3,5-dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4] oxazepin-5(2H)-one The title compound (17 mg, 67% yield over 2 steps) was prepared from the procedure described in Example 3, Step J using 7-(bromomethyl)-4-(3,5-dimethoxybenzyl)-9-(4-fluoro-2-methylphenyl)-2-methyl-3,4-dihydrobenzo[f][1,4]oxazepin-5(2H)-one (25.1 mg, 0.05 mmol, 1.0 equiv.) and 1-methyl-1H-imidazol-2-amine hydrochloride (13 mg, 0.09 mmol, 2.0 equiv.). The reaction mixture was stirred at 90° C. for 12 h. LCMS: $R_T$=1.033 min, MS (ES) 545.6 $[M+H]^+$; $^1H$ NMR (400 MHz, Chloroform-d) δ 7.67-7.64 (m, 1H), 7.21 (d, J=2.2 Hz, 1H), 7.10-7.03 (m, 1H), 6.90 (d, J=9.6 Hz, 1H), 6.85 (td, J=8.4, 2.4 Hz, 1H), 6.48-6.45 (m, 2H), 6.37 (t, J=2.0 Hz, 1H), 6.19 (d, J=2.5 Hz, 1H), 6.17 (d, J=2.6 Hz, 1H), 4.91 (s, 2H), 4.54 (s, 1H), 4.29 (s, 1H), 3.77 (s, 6H), 3.51 (br s, 1H), 3.30 (s, 3H), 3.24 (br s, 1H), 3.09 (br s, 1H), 2.06 (br s, 3H), 0.70 (m, 3H).

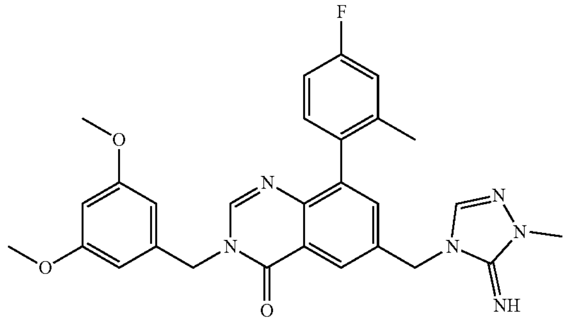

Example 18

3-(3,5-Dimethoxybenzyl)-8-(4-fluoro-2-methylphenyl)-6-((5-imino-1-methyl-1,5-dihydro-4H-1,2,4-triazol-4-yl)methyl)quinazolin-4(3H)-one The title compound (1.8 mg, 7% yield) was prepared from the procedure described in Example 1, Step G using 1-methyl-1H-1,2,4-triazol-5-amine (15 mg, 0.151 mmol, 3.0 equiv.). The reaction mixture was stirred at 80° C. for 16 hours. LCMS: $R_T$=0.917 min, MS (ES) 515.0 $[M+H]^+$; $^1H$ NMR (400 MHz, Chloroform-d) δ 8.35 (d, J=2.4 Hz, 1H), 8.07 (d, J=2.4 Hz, 1H), 7.76 (s, 1H), 7.52 (s, 1H), 7.17-7.11 (m, 1H), 7.01-6.91 (m, 2H), 6.48 (d, J=2.0 Hz, 2H), 6.43 (t, J=2.0 Hz, 1H), 5.31-5.01 (m, 2H), 3.87 (s, 2H), 3.75 (s, 6H), 2.07 (s, 3H), 2.05 (s, 3H). $^{19}F$ NMR (376 MHz, Chloroform-d) δ−114.60.

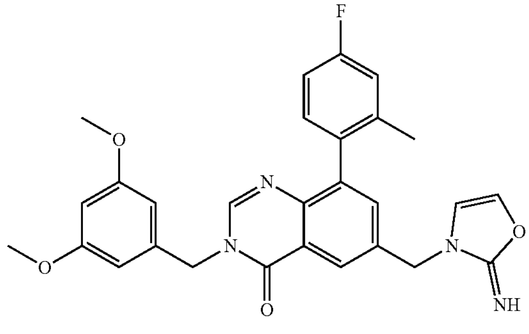 [SMILES: COc1cc(Cn2cnc3c(-c4ccc(F)cc4C)cc(Cn4ccoc4=N)cc3c2=O)cc(OC)c1]

Example 19

3-(3,5-Dimethoxybenzyl)-8-(4-fluoro-2-methylphenyl)-6-((2-iminooxazol-3(2H)-yl)methyl)quinazolin-4(3H)-one The title compound (1.5 mg, 6% yield) was prepared from the procedure described in Example 1, Step G using 2-aminoxazole (13 mg, 0.151 mmol, 3.0 equiv.). The reaction mixture was stirred at 80° C. for 16 hours. LCMS: $R_T$=0.924 min, MS (ES) 501.0 $[M+H]^+$; $^1H$ NMR (400 MHz, Chloroform-d) δ 8.36 (s, 1H), 8.16 (d, J=6.8 Hz, 1H), 7.65 (s, 1H), 7.17-7.14 (m, 2H), 7.02-6.94 (m, 3H), 6.48 (d, J=2.0 Hz, 2H), 6.39 (t, J=2.0 Hz, 1H), 5.25-5.00 (m, 2H), 3.87 (s, 2H), 3.75 (s, 6H), 2.07 (s, 3H). $^{19}F$ NMR (376 MHz, Chloroform-d) δ−115.15.

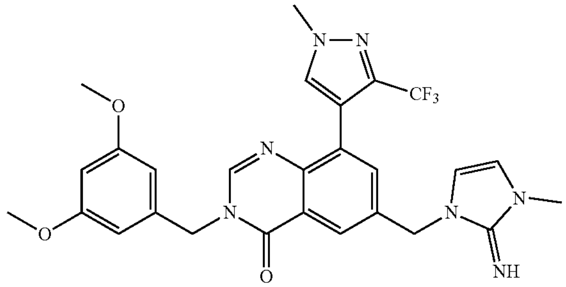

Example 20

3-(3,5-Dimethoxybenzyl)-6-((2-imino-3-methyl-2,3-dihydro-1H-imidazol-1-yl)methyl)-8-(1-methyl-3-(trifluoromethyl)-1H-pyrazol-4-yl)quinazolin-4(3H)-one Step A. Preparation of 6-chloro-3-(3,5-dimethoxybenzyl)-8-(1-methyl-3-(trifluoromethyl)-1H-pyrazol-4-yl)quinazolin-4(3H)-one The title compound (261 mg, 74% yield) was prepared from the procedure described in Example 1, Step C using 1-Methyl-3-trifluoromethyl-1H-pyrazole-4-boronic acid (214 mg, 1.10 mmol, 1.5 equiv.). The reaction mixture was stirred at 95° C. for 2 hours. $^1H$ NMR (400 MHz, Chloroform-d) δ 8.30 (d, J=2.4 Hz, 1H), 8.04 (s, 1H), 7.73 (d, J=2.4 Hz, 1H), 7.67 (s, 1H), 6.46 (d, J=2.4 Hz, 2H), 6.40 (t, J=2.0 Hz, 1H), 5.10 (s, 2H), 4.01 (s, 3H), 3.75 (s, 6H). $^{19}F$ NMR (376 MHz, chloroform-d) δ−59.43.

Step B. Preparation of 3-(3,5-dimethoxybenzyl)-8-(1-methyl-3-(trifluoromethyl)-1H-pyrazol-4-yl)-6-vinylquinazolin-4(3H)-one The title compound (212 mg, 84% yield) was prepared from the procedure described in Example 1, Step D. $^1H$ NMR (400 MHz, Chloroform-d) δ 8.33 (d, J=1.6 Hz, 1H), 8.04 (s, 1H), 7.87 (d, J=2.0 Hz, 1H), 7.70 (s, 1H), 6.86-6.79 (m, 1H), 6.48 (d, J=2.0 Hz, 2H), 6.40 (t, J=2.0 Hz, 1H), 5.92 (d, J=17.6 Hz, 1H), 5.42 (d, J=10.8 Hz, 1H), 5.12 (s, 2H), 4.02 (s, 3H), 3.76 (s, 6H).

Step C. Preparation of 3-(3,5-dimethoxybenzyl)-8-(1-methyl-3-(trifluoromethyl)-1H-pyrazol-4-yl)-6-(hydroxymethyl)quinazolin-4(3H)-one The title compound (134 mg, 61% yield) was prepared from the procedure described in Example 1, Step E. $^1H$ NMR (400 MHz, Chloroform-d) δ 8.30 (d, J=1.6 Hz, 1H), 8.02 (s, 1H), 7.77 (d, J=1.6 Hz, 1H), 7.63 (s, 1H), 6.44 (d, J=2.0 Hz, 2H), 6.37 (t, J=2.4 Hz, 1H), 5.08 (s, 2H), 4.80 (s, 2H), 3.98 (s, 3H), 3.72 (s, 6H).

Step D. Preparation of 6-(bromomethyl)-3-(3,5-dimethoxybenzyl)-8-(1-methyl-3-(trifluoromethyl)-1H-pyrazol-4-yl)quinazolin-4(3H)-one The title compound (77.0 mg, 52% yield) was prepared from the procedure described in Example 1, Step F. LCMS: $R_T$=1.758 min, MS (ES) 537.1 $[M+H]^+$.

Step E. Preparation of 3-(3,5-dimethoxybenzyl)-6-((2-imino-3-methyl-2,3-dihydro-1H-imidazol-1-yl)methyl)-8-(1-methyl-3-(trifluoromethyl)-1H-pyrazol-4-yl)quinazolin-4(3H)-one The title compound (27 mg, 34% yield) was prepared from the procedure described in Example 1, Step G. LCMS: $R_T$=1.254 min, MS (ES) 553.9 $[M+H]^+$; $^1H$ NMR (400 MHz, Chloroform-d) δ 8.21 (d, J=2.0 Hz, 1H), 8.07 (s, 1H), 7.73 (s, 1H), 7.69 (d, J=2.0 Hz, 1H), 6.48 (d, J=2.4 Hz, 1H), 6.46-6.40 (m, 4H), 5.39 (s, 2H), 5.10 (s, 2H), 4.00 (s, 3H), 3.77 (s, 6H), 3.62 (s, 3H).

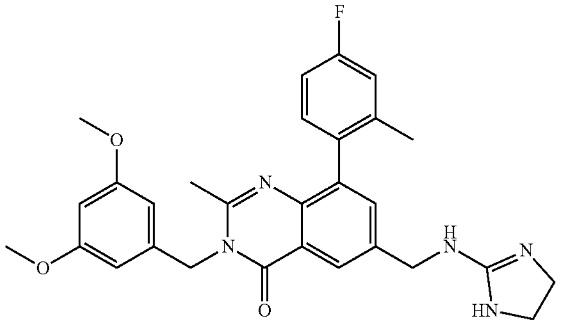 [SMILES: COc1cc(Cn2c(C)nc3c(-c4ccc(F)cc4C)cc(CNC4=NCCN4)cc3c2=O)cc(OC)c1]

Example 21

6-(((4,5-Dihydro-1H-imidazol-2-yl)amino)methyl)-3-(3,5-dimethoxybenzyl)-8-(4-fluoro-2-methylphenyl)-2-methylquinazolin-4(3H)-one Step A. Preparation of methyl 2-amino-3-bromo-5-iodobenzoate N-Bromosuccinimide (16.9 g, 94.8 mmol, 1.05 equiv.) was added in three portions over 1.5 h to a stirred solution of methyl 2-amino-5-iodobenzoate (25.0 g, 90.3 mmol, 1.0 equiv.) in $CHCl_3$ (360 mL) at room temperature. The reaction was stirred for 16 h and then concentrated. The residue was purified by flash chromatography (Combi-flash Rf, Hex/EtOAc=0-50% gradient) to afford the title compound (14.5 g, 45% yield). LCMS: $R_T$=1.994 min, MS (ES) 355.8 $[M+H]^+$; $^1H$ NMR (400 MHz, Chloroform-d) δ 8.13 (d, J=2.0 Hz, 1H), 7.82 (d, J=2.0 Hz, 1H), 6.38 (bs, 2H), 3.88 (s, 3H).

Step B. Preparation of methyl 2-amino-3-bromo-5-vinylbenzoate $Pd(dppf)Cl_2$ (206 mg, 0.282 mmol, 0.05 equiv.) was added to a mixture of methyl 2-amino-3-bromo-5-iodobenzoate (2000 mg, 5.64 mmol, 1.0 equiv.), potassium vinyltrifluoroborate (981 mg, 7.33 mmol, 1.3 equiv.), $K_2CO_3$ (2337 mg, 16.9 mmol, 3.0 equiv.) in 1,4-dioxane:$H_2O$ (3:1, 22 mL) under Ar. The resulting mixture was heated at 95° C. for 2 h, then diluted with $H_2O$ (20 mL) and extracted with EtOAc (3×15 mL). The combined organics were dried ($MgSO_4$), filtered and concentrated. The residue was purified by flash chromatography (Combi-flash Rf, Hex/EtOAc=0-50% gradient) to afford the title compound (910 mg, 63% yield). LCMS: $R_T$=1.752 min, MS (ES) 256.0 $[M+H]^+$; $^1H$ NMR (400 MHz, Chloroform-d) δ 7.87 (d, J=2.0 Hz, 1H), 7.71 (d, J=2.0 Hz, 1H), 6.57-6.50 (m, 1H), 6.37 (bs, 2H), 5.58 (d, J=17.6 Hz, 1H), 5.12 (d, J=11.2 Hz, 1H), 3.90 (s, 3H).

Step C. Preparation of methyl 2-amino-3-bromo-5-formylbenzoate $OsO_4$ (4% polymer bound, 90 mg, 0.353 mmol, 0.1 equiv.) was added to a mixture of methyl 2-amino-3-bromo-5-vinylbenzoate (900 mg, 3.53 mmol, 1.0 equiv.) and pyridine (570 μL, 7.1 mmol, 2.0 equiv.) in 1,4-dioxane:$H_2O$ (3:1, 35 mL) followed by the addition of $NaIO_4$ (3020 mg, 14.1 mmol, 4.0 equiv.). After stirring at room temperature overnight, the reaction was filtered and the solvent was removed under reduced pressure. The residue was purified by flash chromatography (Combi-flash Rf, Hex/EtOAc=0-50% gradient) to afford the title compound (410 mg, 45% yield). LCMS: $R_T$=1.371 min, MS (ES) 258.0 $[M+H]^+$; $^1H$ NMR (400 MHz, Chloroform-d) δ 9.72 (s, 1H), 8.37 (d, J=2.0 Hz, 1H), 8.13 (d, J=2.0 Hz, 1H), 3.93 (s, 3H).

Step D. Preparation of methyl 2-amino-5-(aminomethyl)-3-bromobenzoate

A solution of methyl 2-amino-3-bromo-5-formylbenzoate (400 mg, 1.56 mmol, 1.0 equiv.) and hydroxylammonium chloride (433 mg, 6.23 mmol, 4.0 equiv.) in methanol (15 mL) was stirred for 1 h at 50° C. The reaction was then cooled to room temperature and concentrated. Then AcOH:MeOH (1:1, 6 mL) was added followed by the addition of zinc dust (407 mg, 6.23 mmol, 4.0 equiv.). The reaction was sonicated for 1 h, filtered and concentrated to yield the title compound (372 mg, 92% yield). LCMS: $R_T$=0.685 min, MS (ES) 241.9 $[M-NH_2]$.

Step E. Preparation of methyl 2-amino-3-bromo-5-(((tert-butoxycarbonyl)amino)methyl)benzoate Methyl 2-amino-5-(aminomethyl)-3-bromobenzoate (370 mg, 1.43 mmol, 1.0 equiv.) was dissolved in DCM (6 mL) and $Boc_2O$ (344 mg, 1.58 mmol, 1.1 equiv.) and DMAP (17.5 mg, 0.143 mmol, 0.1 equiv.) were added. The reaction was stirred at room temperature for 16 h then concentrated. The residue was purified by flash chromatography (Combi-flash Rf, Hex/EtOAc=0-50% gradient) to afford the title compound (395 mg, 77% yield). LCMS: $R_T$=1.661 min, MS (ES) 358.9 $[M+H]^+$; $^1H$ NMR (400 MHz, Chloroform-d) δ 7.76 (d, J=2.0 Hz, 1H), 7.54 (d, J=1.6 Hz, 1H), 6.29 (bs, 2H), 4.17 (d, J=4.8 Hz, 2H), 3.87 (s, 3H). 1.46 (s, 9H).

Step F. Preparation of methyl 2-amino-5-(((tert-butoxycarbonyl)amino)methyl)-4'-fluoro-2'-methyl-[1,1'-biphenyl]-3-carboxylate To a suspension of methyl 2-amino-3-bromo-5-(((tert-butoxycarbonyl)amino)methyl)benzoate (395 mg, 1.11 mmol, 1.0 equiv.), 2-methyl-4-fluorophenylboronic acid (258 mg, 1.68 mmol, 1.5 equiv.) and $K_2CO_3$ (463 mg, 3.35 mmol, 3.0 equiv.) in 1,4-dioxane:$H_2O$ (3:1, 4.5 mL) was added Pd(dppf)$Cl_2$ (40.9 mg, 0.0559 mmol, 0.05 equiv.). The reaction mixture was degassed with Ar and heated to 95° C. for 1 h under Ar. The reaction was cooled to room temperature and filtered through a pad of celite. $H_2O$ (10 mL) was added to the filtrate and extracted with EtOAc (3×10 mL). The combined organic layer was washed with brine, dried ($MgSO_4$), filtered and concentrated. The residue was purified by flash chromatography (Combi-flash Rf, Hex/EtOAc=0-50% gradient) to afford the title compound (296 mg, 68% yield). LCMS: $R_T$=1.885 min, MS (ES) 389.1 $[M+H]^+$; $^1H$ NMR (400 MHz, Chloroform-d) δ 7.82 (d, J=2.0 Hz, 1H), 7.14-6.94 (m, 4H), 5.64 (bs, 2H), 4.21 (d, J=4.8 Hz, 2H), 3.88 (s, 3H), 2.12 (s, 3H), 1.45 (s, 9H).

Step G. Preparation of 2-amino-5-(((tert-butoxycarbonyl)amino)methyl)-4'-fluoro-2'-methyl-[1,1'-biphenyl]-3-carboxylic acid To a solution of methyl 2-amino-5-(((tert-butoxycarbonyl)amino)methyl)-4'-fluoro-2'-methyl-[1,1'-biphenyl]-3-carboxylate (100 mg, 0.258 mmol, 1.0 equiv.) in MeOH (0.5 mL) was added 2 M KOH (0.5 mL), and the reaction was heated at 50° C. for 2 h. The reaction was cooled to room temperature and diluted with $H_2O$ (5 mL). The resulting solution was washed with EtOAc (5 mL) then acidified to pH~2 with 1 M HCl and extracted with EtOAc (3×5 mL). The combined organic layer was washed with brine, dried ($MgSO_4$), filtered and concentrated to yield the title compound (91 mg, 94% yield). LCMS: $R_T$=1.672 min, MS (ES) 375.0 $[M+H]^+$.

Step H. Preparation of tert-butyl ((6-amino-5-((3,5-dimethoxybenzyl)carbamoyl)-4'-fluoro-2'-methyl-[1,1'-biphenyl]-3-yl)methyl)carbamate To a solution of 2-amino-5-(((tert-butoxycarbonyl)amino)methyl)-4'-fluoro-2'-methyl-[1,1'-biphenyl]-3-carboxylic acid (91.0 mg, 0.243 mmol, 1.0 equiv.) in DMF (1 mL) was added TBTU (78.1 mg, 0.243 mmol, 1.0 equiv.) and diisopropylethylamine (85 μL, 0.486 mmol, 2.0 equiv.). The reaction mixture was stirred at room temperature for 10 min then 3,5-dimethoxybenzylamine (40.6 mg, 0.243 mmol, 1.0 equiv.) was added. The reaction was stirred for an additional 1 h then diluted with $H_2O$ (5 mL) and extracted with EtOAc (3×5 mL). The combined organic layer was washed with brine, dried ($MgSO_4$), filtered and concentrated. The residue was purified by flash chromatography (Combi-flash Rf, Hex/EtOAc=0-75% gradient) to afford the title compound (111 mg, 87% yield). LCMS: $R_T$=1.905 min, MS (ES) 524.0 $[M+H]^+$; $^1H$ NMR (400 MHz, Chloroform-d) δ 7.30-7.28 (m, 2H), 7.15-7.12 (m, 1H), 7.05-6.96 (m, 3H), 6.54 (d, J=2.4 Hz, 2H), 6.43-641 (m, 2H), 5.45 (bs, 2H), 4.57 (d, J=5.6 Hz, 2H), 4.20 (d, J=5.2 Hz, 2H), 3.81 (s, 6H), 2.15 (s, 3H), 1.44 (s, 9H).

Step I. Preparation of tert-butyl ((6-acetamido-5-((3,5-dimethoxybenzyl)carbamoyl)-4'-fluoro-2'-methyl-[1,1'-biphenyl]-3-yl)methyl)carbamate To a solution of tert-butyl ((6-amino-5-((3,5-dimethoxybenzyl)carbamoyl)-4'-fluoro-2'-methyl-[1,1'-biphenyl]-3-yl)methyl)carbamate (42 mg, 0.0803 mmol, 1.0 equiv.) in THE (0.8 mL) was added NaH (2.8 mg, 0.120 mmol, 1.5 equiv.) and stirred at room temperature for 15 min. AcCl (17 μL, 0.241 mmol, 3.0 equiv) was added to the reaction and stirred for 30 min at room temperature. The reaction was quenched with sat. $NH_4Cl$ (5 mL) and extracted with EtOAc (3×5 mL). The combined organic layer was washed with brine, dried ($MgSO_4$), filtered and concentrated. The residue was purified by flash chromatography (Combi-flash Rf, Hex/EtOAc=0-75% gradient) to afford the title compound (32.2 mg, 71% yield). LCMS: $R_T$=1.659 min, MS (ES) 565.9 $[M+H]^+$.

Step J. Preparation of 2-acetamido-5-(aminomethyl)-N-(3,5-dimethoxybenzyl)-4'-fluoro-2'-methyl-[1,1'-biphenyl]-3-carboxamide TFA (0.25 mL) was added to a solution of tert-butyl ((6-acetamido-5-((3,5-dimethoxybenzyl)carbamoyl)-4'-fluoro-2'-methyl-[1,1'-biphenyl]-3-yl)methyl)carbamate (30.0 mg, 0.0531 mmol, 1.0 equiv.) in DCM (0.25 mL). The reaction mixture was stirred at room temperature for 1 h then concentrated to yield the crude title compound (23.4 mg, 93% yield). LCMS: $R_T$=1.134 min, MS (ES) 466.0 $[M+H]^+$.

Step K. Preparation of 6-(((4,5-dihydro-1H-imidazol-2-yl)amino)methyl)-3-(3,5-dimethoxybenzyl)-8-(4-fluoro-2-methylphenyl)-2-methylquinazolin-4(3H)-one To a solution of 2-acetamido-5-(aminomethyl)-N-(3,5-dimethoxybenzyl)-4'-fluoro-2'-methyl-[1,1'-biphenyl]-3-carboxamide (11.0 mg, 0.0236 mmol, 1.0 equiv.) in pyridine (0.25 mL) was added 2-(methylthio)-4,5-dihydro-1H-imidazole (13.7 mg, 0.118 mmol, 5.0 equiv.). The reaction was heated to 125° C. in the microwave for 1 h then concentrated. The residue was purified by reverse phase HPLC (Phenomenex Gemini C18, $H_2O/CH_3CN$ gradient from 15-95% $CH_3CN$, 0.1% TFA) to yield the title compound (3.8 mg, 31% yield). To remove TFA, the organic layer was washed with $K_2CO_3$ (sat.). LCMS: $R_T$=1.205 min, MS (ES) 534.0 $[M+H]^+$; $^1H$ NMR (400 MHz, MeOD) δ 8.24 (d, J=2.4 Hz, 1H), 7.60 (d, J=2.0 Hz, 1H), 7.22-7.17 (m, 1H), 7.06-6.96 (m, 2H), 6.42 (t, J=2.4 Hz, 1H), 6.31 (d, J=2.0 Hz, 2H), 5.39 (s, 2H), 4.60 (s, 2H), 3.75-3.73 (m, 4H), 3.72 (s, 6H), 2.44 (s, 3H), 2.08 (s, 3H); $^{19}F$ NMR (376 MHz, MeOD) δ−117.69.

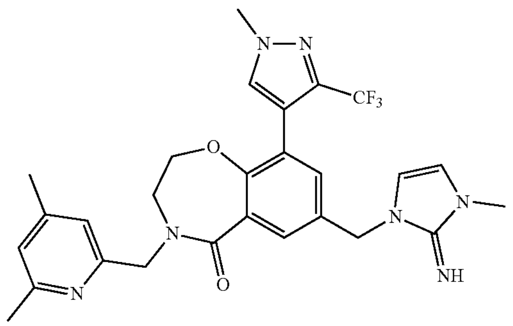

Example 22

4-((4,6-Dimethylpyridin-2-yl)methyl)-7-((2-imino-3-methyl-2,3-dihydro-1H-imidazol-1-yl)methyl)-9-(1-methyl-3-(trifluoromethyl)-1H-pyrazol-4-yl)-3,4-dihydrobenzo[f][1,4]oxazepin-5(2H)-one Step A. Preparation of methyl 3-bromo-2-(2-((tert-butoxycarbonyl)amino)ethoxy)-5-(((tert-butyldiphenylsilyl)oxy)methyl)benzoate The crude title compound was prepared from the procedure described in Example 17, Step C using 3-bromo-5-(((tert-butyldiphenylsilyl)oxy)methyl)-2-hydroxybenzoate (50.0 mg, 0.1 mmol, 1.0 equiv.) and tert-butyl 1,2,3-oxathiazolidine-3-carboxylate 2,2-dioxide (33.5 mg, 0.15 mmol, 1.5 equiv.). The reaction mixture was stirred at 80° C. for 12 h. LCMS: $R_T$=1.994 min, MS (ES) 542.5 $[M+H-Boc]^+$.

Step B. Preparation of methyl 2-(2-aminoethoxy)-3-bromo-5-(((tert-butyldiphenylsilyl)oxy)methyl)benzoate The crude title compound was prepared from the procedure described in Example 17, Step D using methyl 3-bromo-2-(2-((tert-butoxycarbonyl)amino)ethoxy)-5-(((tert-butyldiphenylsilyl)oxy)methyl)benzoate (64.3 mg, 0.1 mmol, 1.0 equiv.) and TFA (1.0 mL). The reaction mixture was stirred at room temperature for 1 h. LCMS: $R_T$=0.986 min, MS (ES) 543.6 $[M+H]^+$.

Step C. Preparation of 9-bromo-7-(((tert-butyldiphenylsilyl)oxy)methyl)-3,4-dihydrobenzo[f][1,4]oxazepin-5(2H)-one To a solution of methyl 2-(2-aminoethoxy)-3-bromo-5-(((tert-butyldiphenylsilyl)oxy)methyl)benzoate (55.7 mg, 0.10 mmol, 1.0 equiv.) in EtOH (2.0 mL) was added $K_2CO_3$ (71.0 mg, 0.51 mmol, 5.0 equiv.) and stirred at 78° C. for 12 h. The reaction mixture was filtered through the Celite and concentrated under reduced pressure. The residue was redissolved in $CH_2Cl_2$ (5.0 mL) and $H_2O$ (1.0 mL) and extracted with $CH_2Cl_2$ (3×5.0 mL). Combined organics were dried over $Na_2SO_4$ and concentrated under the reduced pressure to yield the crude title compound which was used for the next step without further purification. LCMS: $R_T$=2.264 min, MS (ES) 511.5 $[M+H]^+$; $^1H$ NMR (400 MHz, Chloroform-d) δ 7.73 (d, J=2.0 Hz, 1H), 7.69 (d, J=1.9 Hz, 1H), 7.67 (dd, J=7.9, 1.4 Hz, 4H), 7.45-7.36 (m, 6H), 6.67 (br s, 1H), 4.70 (s, 2H), 4.44 (t, J=5.2 Hz, 2H), 3.47 (q, J=5.4 Hz, 2H), 1.10 (s, 9H).

Step D. Preparation of 9-bromo-7-(((tert-butyldiphenylsilyl)oxy)methyl)-4-((4,6-dimethylpyridin-2-yl)methyl)-3,4-dihydrobenzo[f][1,4]oxazepin-5(2H)-one The title compound (36.8 mg, 56% yield over 4 steps) was prepared from the procedure described in Example 11, Step D using 9-bromo-7-(((tert-butyldiphenylsilyl)oxy)methyl)-3,4-dihydrobenzo[f][1,4]oxazepin-5(2H)-one (52.4 mg, 0.10 mmol, 1.0 equiv.) and 2-(chloromethyl)-4,6-dimethylpyridine (20.0 μL, 0.15 mmol, 1.5 equiv.). The reaction mixture was stirred at 0° C. for 3 h. LCMS: $R_T$=2.244 min, MS (ES) 630.7 $[M+H]^+$.

Step E. Preparation of 7-(((tert-butyldiphenylsilyl)oxy)methyl)-4-((4,6-dimethylpyridin-2-yl)methyl)-9-(1-methyl-3-(trifluoromethyl)-1H-pyrazol-4-yl)-3,4-dihydrobenzo[f][1,4] oxazepin-5(2H)-one The crude title compound was prepared from the procedure described in Example 3, Step F using 9-bromo-7-(((tert-butyldiphenylsilyl)oxy)methyl)-4-((4,6-dimethylpyridin-2-yl)methyl)-3,4-dihydrobenzo[f][1,4]oxazepin-5(2H)-one (44.5 mg, 0.07 mmol, 1.0 equiv.), (1-methyl-3-(trifluoromethyl)-1H-pyrazol-4-yl)boronic acid (16.5 mg, 0.08 mmol, 5.0 equiv.), $K_2CO_3$ (39.1 mg, 0.28 mmol, 4.0 equiv.), and $Pd(PPh_3)_4$ (4.1 mg, 0.01 mmol, 0.05 equiv.). The reaction mixture was stirred at 80° C. for 2 h. LCMS: $R_T$=2.159 min, MS (ES) 699.9 $[M+H]^+$.

Step F. Preparation of 4-((4,6-dimethylpyridin-2-yl)methyl)-7-(hydroxymethyl)-9-(1-methyl-3-(trifluoromethyl)-1H-pyrazol-4-yl)-3,4-dihydrobenzo[f][1,4]oxazepin-5(2H)-one The title compound (25.9 mg, 79% yield over 2 steps) was prepared from the procedure described in Example 17, Step H using 7-(((tert-butyldiphenylsilyl)oxy)methyl)-4-((4,6-dimethylpyridin-2-yl)methyl)-9-(1-methyl-3-(trifluoromethyl)-1H-pyrazol-4-yl)-3,4-dihydrobenzo[f][1,4]oxazepin-5(2H)-one (49.4 mg, 0.07 mmol, 1.0 equiv.) and 1.0 M tetrabutylammonium fluoride (140.0 μL, 0.14 mmol, 2.0 equiv.). LCMS: $R_T$=1.031 min, MS (ES) 461.5 $[M+H]^+$.

Step G. Preparation of 7-(bromomethyl)-4-((4,6-dimethylpyridin-2-yl)methyl)-9-(1-methyl-3-(trifluoromethyl)-1H-pyrazol-4-yl)-3,4-dihydrobenzo[f][1,4]oxazepin-5(2H)-one The crude title compound was prepared from the procedure described in Example 3, Step I using 4-((4,6-dimethylpyridin-2-yl)methyl)-7-(hydroxymethyl)-9-(1-methyl-3-(trifluoromethyl)-1H-pyrazol-4-yl)-3,4-dihydrobenzo[f][1,4]oxazepin-5(2H)-one (25.9 mg, 0.06 mmol, 1.0 equiv.) and $PBr_3$ (10.0 μL, 0.11 mmol, 2.0 equiv.). LCMS: $R_T$=0.953 min, MS (ES) 524.4 $[M+H]^+$.

Step H. Preparation of 4-((4,6-dimethylpyridin-2-yl)methyl)-7-((2-imino-3-methyl-2,3-dihydro-1H-imidazol-1-yl)methyl)-9-(1-methyl-3-(trifluoromethyl)-1H-pyrazol-4-yl)-3,4-dihydrobenzo[f][1,4]oxazepin-5(2H)-one The title compound (8.3 mg, 27% yield) was prepared from the procedure described in Example 3, Step J using 7-(bromomethyl)-4-((4,6-dimethylpyridin-2-yl)methyl)-9-(1-methyl-3-(trifluoromethyl)-1H-pyrazol-4-yl)-3,4-dihydrobenzo[f][1,4]oxazepin-5(2H)-one (29.7 mg, 0.06 mmol, 1.0 equiv.), 1-methyl-1H-imidazol-2-amine hydrochloride (15.2 mg, 0.11 mmol, 2.0 equiv.), KI (2.8 mg, 0.02 mmol, 0.3 equiv.), and N,N-diisopropylethylamine (50.0 μL, 0.28 mmol, 5.0 equiv.). The reaction mixture was stirred at 90° C. for 5.5 h. LCMS: $R_T$=0.885 min, MS (ES) 540.6 $[M+H]^+$.

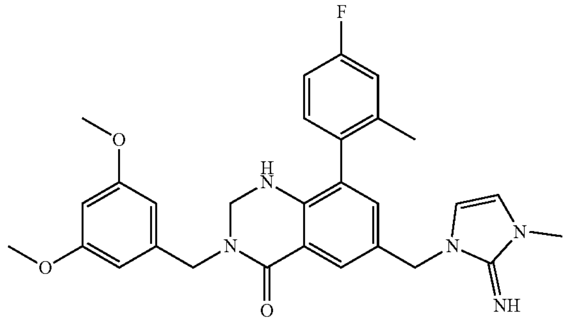

Example 23

3-(3,5-Dimethoxybenzyl)-8-(4-fluoro-2-methylphenyl)-6-((2-imino-3-methyl-2,3-dihydro-1H-imidazol-1-yl)methyl)-2,3-dihydroquinazolin-4(1H)-one $NaBH_4$ (7.4 mg, 0.195 mmol, 10 equiv.) was added to a solution of 3-(3,5-dimethoxybenzyl)-8-(4-fluoro-2-methylphenyl)-6-((2-imino-3-methyl-2,3-dihydro-1H-imidazol-1-yl)methyl)quinazolin-4(3H)-one (10 mg, 0.0195 mmol, 1.0 equiv.) in DME (0.2 mL) at room temperature followed by the dropwise addition of TFA (5 μL) in DME (0.5 mL). The mixture was refluxed for 30 min then cooled, carefully quenched with water then basified with sat. aq. $K_2CO_3$ (5 mL). The aqueous layer was extracted with EtOAc (3×5 mL). The combined organic layer was washed with brine, dried ($MgSO_4$), filtered and concentrated. The residue was purified by reverse phase HPLC (Phenomenex Gemini C18, $H_2O/CH_3CN$ gradient from 15-95% $CH_3CN$, 0.1% TFA) to yield the title compound (6.8 mg, 68% yield). To remove TFA, the organic layer was washed with $K_2CO_3$ (sat.). LCMS: $R_T$=1.394 min, MS (ES) 516.0 $[M+H]^+$; $^1H$ NMR (400 MHz, MeOD) δ 7.79 (d, J=2.0 Hz, 1H), 7.17-7.12 (m, 2H), 7.09-7.06 (m, 1H), 7.03-6.97 (m, 1H), 6.92 (t, J=2.8 Hz, 2H), 6.51 (d, J=2.4 Hz, 2H), 6.40 (t, J=2.0 Hz, 1H), 5.03 (s, 2H), 4.65 (s, 2H), 4.50 (s, 2H), 3.74 (s, 6H), 3.53 (s, 3H), 2.12 (s, 3H); $^{19}F$ NMR (376 MHz, MeOD) δ–119.54.

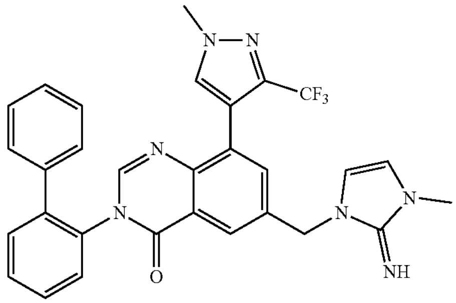 [SMILES: Cn1cc(-c2cc(Cn3ccn(C)c3=N)cc3c(=O)n(-c4ccccc4-c4ccccc4)cnc23)c(C(F)(F)F)n1]

Example 24

3-([1,1'-Biphenyl]-2-yl)-6-((2-imino-3-methyl-2,3-dihydro-1H-imidazol-1-yl)methyl)-8-(1-methyl-3-(trifluoromethyl)-1H-pyrazol-4-yl)quinazolin-4(3H)-one Step A. Preparation of N-([1,1'-biphenyl]-2-ylmethyl)-2-amino-3-bromo-5-chlorobenzamide The title compound (411 mg, 51% yield) was prepared from the procedure described in Example 21, Step H using 2-aminobiphenyl (340 mg, 2.01 mmol, 1.0 equiv.) The reaction mixture was stirred at room temperature for 16 h. LCMS: $R_T$=2.027 min, MS (ES) 400.8 $[M+H]^+$.

Step B. Preparation of 3-([1,1'-biphenyl]-2-ylmethyl)-8-bromo-6-chloroquinazolin-4(3H)-one N-([1,1'-biphenyl]-2-ylmethyl)-2-amino-3-bromo-5-chlorobenzamide (400 mg, 1.0 mmol, 1.0 equiv.) was dissolved in toluene (4 mL) and triethyl orthoformate (170 μL, 1.0 mmol, 1.0 equiv.) was added followed by p-toluenesulfonic acid (17.2 mg, 0.10 mmol, 0.1 equiv.). The reaction was heated at 100° C. for 16 h. The reaction was then cooled to room temperature and diluted with $H_2O$ (10 mL) and extracted with EtOAc (3×10 mL). The combined organics were washed with brine, dried ($MgSO_4$), filtered and concentrated. The residue was purified by flash chromatography (Combi-flash Rf, Hex/EtOAc=0-75% gradient) to afford the title compound (261 mg, 64% yield). LCMS: $R_T$=1.931 min, MS (ES) 410.8 $[M+H]^+$.

Step C. Preparation of 3-([1,1'-biphenyl]-2-ylmethyl)-6-chloro-8-(1-methyl-3-(trifluoromethyl)-1H-pyrazol-4-yl)quinazolin-4(3H)-one The title compound (212 mg, 78% yield) was prepared from the procedure described in Example 1, Step C using (1-methyl-3-(trifluoromethyl)-1H-pyrazol-4-yl)boronic acid (148 mg, 0.761 mmol, 1.2 equiv.). The reaction mixture was stirred at 95° C. for 2 h. LCMS: $R_T$=1.915 min, MS (ES) 480.9 $[M+H]^+$.

Step D. Preparation of 3-([1,1'-biphenyl]-2-ylmethyl)-8-(1-methyl-3-(trifluoromethyl)-1H-pyrazol-4-yl)-6-vinylquinazolin-4(3H)-one The title compound (83.0 mg, 42% yield) was prepared from the procedure described in Example 1, Step D. The reaction mixture was stirred at 90° C. overnight. LCMS: $R_T$=1.863 min, MS (ES) 472.9 $[M+H]^+$.

Step E. Preparation of 3-([1,1'-biphenyl]-2-ylmethyl)-6-(hydroxymethyl)-8-(1-methyl-3-(trifluoromethyl)-1H-pyrazol-4-yl)quinazolin-4(3H)-one The title compound (112 mg, 55% yield) was prepared from the procedure described in Example 1, Step E. The reaction mixture was stirred at room temperature overnight. LCMS: $R_T$=1.541 min, MS (ES) 477.0 $[M+H]^+$.

Step F. Preparation of 3-([1,1'-biphenyl]-2-ylmethyl)-6-(bromomethyl)-8-(1-methyl-3-(trifluoromethyl)-1H-pyrazol-4-yl)quinazolin-4(3H)-one The title compound (106 mg, 85% yield) was prepared from the procedure described in Example 1, Step F. The reaction mixture was stirred at room temperature for 30 min. LCMS: $R_T$=1.856 min, MS (ES) 538.8 $[M+H]^+$.

Step G. Preparation of 3-([1,1'-biphenyl]-2-yl)-6-((2-imino-3-methyl-2,3-dihydro-1H-imidazol-1-yl)methyl)-8-(1-methyl-3-(trifluoromethyl)-1H-pyrazol-4-yl)quinazolin-4(3H)-one The title compound (17.3 mg, 33% yield) was prepared from the procedure described in Example 1, Step G. The reaction mixture was stirred at 80° C. for 4 h. LCMS: $R_T$=1.383 min, MS (ES) 555.9 $[M+H]^+$; $^1$H NMR (400 MHz, DMSO-d) δ 8.11 (d, J=2.0 Hz, 1H), 8.04 (s, 1H), 7.89 (s, 1H), 7.68-7.55 (m, 4H), 7.53 (d, J=1.6 Hz, 1H), 7.25 (s, 5H), 7.00 (s, 2H), 5.29 (s, 2H), 4.00 (s, 3H), 3.58 (s, 3H); $^{19}$F NMR (376 MHz, DMSO-d) δ−60.65.

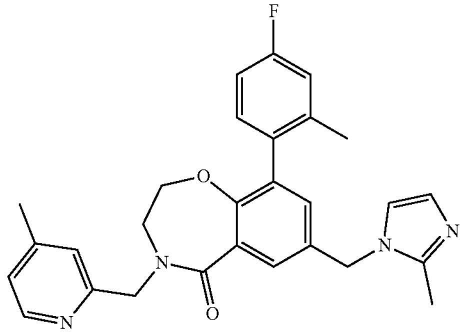 [SMILES: Cc1ccnc(CN2CCOc3c(cc(Cn4ccnc4C)cc3-c3ccc(F)cc3C)C2=O)c1]

Example 25

9-(4-Fluoro-2-methylphenyl)-7-((2-methyl-1H-imidazol-1-yl)methyl)-4-((4-methylpyridin-2-yl)methyl)-3,4-dihydrobenzo[f][1,4]oxazepin-5(2H)-one Step A. Preparation of 9-bromo-7-(hydroxymethyl)-3,4-dihydrobenzo[f][1,4]oxazepin-5(2H)-one The title compound (128.4 mg, 47% yield) was prepared from the procedure described in Example 3, Step E using methyl 2-(2-aminoethoxy)-3-bromo-5-(((tert-butyldiphenylsilyl)oxy)methyl)benzoate (543.1 mg, 1.0 mmol, 1.0 equiv.) and $K_2CO_3$ (2767.1 mg, 20.0 mmol, 20.0 equiv.). The reaction mixture was stirred at 78° C. for 12 h. LCMS: $R_T$=0.863 min, MS (ES) 273.1 $[M+H]^+$; $^1$H NMR (400 MHz, Methanol-$d_4$) δ 7.76 (d, J=2.1 Hz, 1H), 7.62 (d, J=2.1 Hz, 1H), 4.57 (s, 2H), 4.38 (t, J=5.3 Hz, 2H), 3.36 (t, J=5.3 Hz, 3H).

Step B. Preparation of 9-bromo-7-(bromomethyl)-3,4-dihydrobenzo[f][1,4]oxazepin-5(2H)-one The crude title compound was prepared from the procedure described in Example 3, Step I using 9-bromo-7-(hydroxymethyl)-3,4-dihydrobenzo[f][1,4]oxazepin-5(2H)-one (128.4 mg, 0.47 mmol, 1.0 equiv.) and $PBr_3$ (90.0 μL, 0.94 mmol, 2.0 equiv.). The reaction mixture was stirred at room temperature for 1 h. LCMS: $R_T$=1.315 min, MS (ES) 336.0 $[M+H]^+$.

Step C. Preparation of 9-bromo-7-((2-methyl-1H-imidazol-1-yl)methyl)-3,4-dihydrobenzo[f][1,4]oxazepin-5(2H)-one The crude title compound was prepared from the procedure described in Example 11, Step E using 9-bromo-7-(bromomethyl)-3,4-dihydrobenzo[f][1,4]oxazepin-5(2H)-one (158.1 mg, 0.47 mmol, 1.0 equiv.), 2-methyl-1H-imidazole (116.2 mg, 1.42 mmol, 3.0 equiv.), and N,N-diisopropylethylamine (0.41 mL, 2.36 mmol, 5.0 equiv.). The reaction mixture was stirred at 90° C. for 1 h. LCMS: $R_T$=0.765 min, MS (ES) 337.2 $[M+H]^+$.

Step D. Preparation of 9-(4-fluoro-2-methylphenyl)-7-((2-methyl-1H-imidazol-1-yl)methyl)-3,4-dihydrobenzo[f][1,4]oxazepin-5(2H)-one The title compound (21.4 mg, 12% yield over 2 steps) was prepared from the procedure described in Example 3, Step F using 9-bromo-7-((2-methyl-1H-imidazol-1-yl)methyl)-3,4-dihydrobenzo[f][1,4]oxazepin-5(2H)-one (158.6 mg, 0.47 mmol, 1.0 equiv.), (4-fluoro-2-methylphenyl)boronic acid (145.3 mg, 0.94 mmol, 2.0 equiv.), $K_2CO_3$ (260.9 mg, 1.89 mmol, 4.0 equiv.), and $Pd(PPh_3)_4$ (27.3 mg, 0.02 mmol, 0.05 equiv.). LCMS: $R_T$=1.073 min, MS (ES) 366.4 $[M+H]^+$; $^1$H NMR (400 MHz, Methanol-$d_4$) δ 7.67 (d, J=2.1 Hz, 1H), 7.45 (s, 1H), 7.34 (s, 1H), 7.30 (d, J=2.1 Hz, 1H), 7.12 (dd, J=8.3, 6.0 Hz, 1H), 7.00 (dd, J=9.9, 2.3 Hz, 1H), 6.94 (td, J=8.5, 2.5 Hz, 1H), 5.37 (s, 2H), 4.14 (m, 2H), 3.39 (t, J=4.8 Hz, 2H), 2.60 (s, 3H), 2.07 (s, 3H).

Step E. Preparation of 9-(4-fluoro-2-methylphenyl)-7-((2-methyl-1H-imidazol-1-yl)methyl)-4-((4-methylpyridin-2-yl)methyl)-3,4-dihydrobenzo[f][1,4]oxazepin-5(2H)-one The title compound (13.0 mg, 47% yield) was prepared from the procedure described in Example 11, Step D using 9-(4-fluoro-2-methylphenyl)-7-((2-methyl-1H-imidazol-1-yl)methyl)-3,4-dihydrobenzo[f][1,4]oxazepin-5(2H)-one (21.4 mg, 0.06 mmol, 1.0 equiv.), 2-(chloromethyl)-4-methylpyridine hydrochloride (15.7 mg, 0.09 mmol, 1.5 equiv.), and NaH (2.8 mg, 0.12 mmol, 2.0 equiv.). The reaction mixture was stirred at 0° C. for 1 h. LCMS: $R_T$=1.092 min, MS (ES) 471.6 $[M+H]^+$; $^1$H NMR (400 MHz, Chloroform-d) δ 8.36 (d, J=5.1 Hz, 1H), 7.70 (d, J=2.4 Hz, 1H), 7.28 (s, 1H), 7.05-6.96 (m, 3H), 6.93 (m, 2H), 6.88 (m, 2H), 5.06 (s, 2H), 4.86 (s, 2H), 4.03 (br s, 2H), 3.64 (br s, 2H), 2.43 (s, 3H), 2.34 (s, 3H), 2.02 (s, 3H).

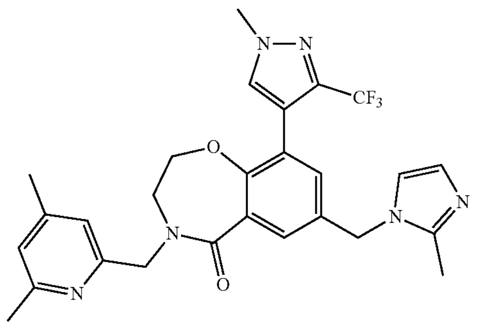 [SMILES: Cc1cc(C)nc(CN2CCOc3c(cc(Cn4ccnc4C)cc3-c3cn(C)nc3C(F)(F)F)C2=O)c1]

Example 26

4-((4,6-Dimethylpyridin-2-yl)methyl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one Step A. Preparation of 7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one The title compound (44.2 mg, 51% yield) was prepared from the procedure described in Example 26, Step A using 9-bromo-7-((2-methyl-1H-imidazol-1-yl)methyl)-3,4-dihydrobenzo[f][1,4]oxazepin-5(2H)-one (70.6 mg, 0.21 mmol, 1.0 equiv.), (1-methyl-3-(trifluoromethyl)-1H-pyrazol-4-yl) boronic acid (61.1 mg, 0.32 mmol, 1.5 equiv.), $K_2CO_3$ (116.1 mg, 0.84 mmol, 4.0 equiv.), and $PdCl_2$(dppf) (7.7 mg, 0.01 mmol, 0.05 equiv.). The reaction mixture was stirred at 80° C. for 5 h. LCMS: $R_T$=0.806 min, MS (ES) 406.4 $[M+H]^+$.

Step B. Preparation of 4-((4,6-dimethylpyridin-2-yl) methyl)-7-((2-methyl-1H-imidazol-1-yl)methyl)-9-(1-methyl-3-(trifluoromethyl)-1H-pyrazol-4-yl)-3,4-dihydrobenzo[f][1,4] oxazepin-5(2H)-one The title compound (16.8 mg, 59% yield) was prepared from the procedure described in Example 11, Step D using 7-((2-methyl-1H-imidazol-1-yl)methyl)-9-(1-methyl-3-(trifluoromethyl)-1H-pyrazol-4-yl)-3,4-dihydrobenzo[f][1,4] oxazepin-5(2H)-one (22.0 mg, 0.05 mmol, 1.0 equiv.), 2-(chloromethyl)-4,6-dimethylpyridine (10.0 μL, 0.08 mmol, 1.5 equiv.), and NaH (2.6 mg, 0.11 mmol, 2.0 equiv.). LCMS: $R_T$=0.928 min, MS (ES) 525.6 $[M+H]^+$; $^1$H NMR (400 MHz, Chloroform-d) δ 7.69 (d, J=2.2 Hz, 1H), 7.42 (s, 1H), 7.05 (s, 1H), 7.03 (d, J=2.1 Hz, 1H), 6.96-6.93 (m, 1H), 6.89 (s, 1H), 6.88-6.85 (m, 1H), 5.03 (s, 2H), 4.83 (s, 2H), 4.15 (t, J=5.0 Hz, 2H), 3.96 (s, 3H), 3.62 (t, J=5.0 Hz, 2H), 2.46 (s, 3H), 2.37 (s, 6H), 2.28 (s, 3H).

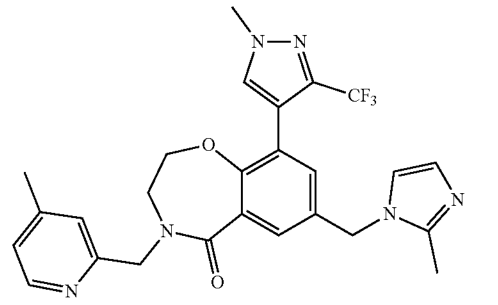 [SMILES: Cc1ccnc(CN2CCOc3c(cc(Cn4ccnc4C)cc3-c3cn(C)nc3C(F)(F)F)C2=O)c1]

Example 27

7-((2-Methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The title compound (15.4 mg, 55% yield) was prepared from the procedure described in Example 11, Step D using 7-((2-methyl-1H-imidazol-1-yl)methyl)-9-(1-methyl-3-(trifluoromethyl)-1H-pyrazol-4-yl)-3,4-dihydrobenzo[f][1,4] oxazepin-5(2H)-one (22.0 mg, 0.05 mmol, 1.0 equiv.) and 2-(chloromethyl)-4-methylpyridine hydrochloride (14.5 mg, 0.08 mmol, 1.5 equiv.). LCMS: $R_T$=0.911 min, MS (ES) 511.5 $[M+H]^+$; $^1$H NMR (400 MHz, Chloroform-d) δ 8.36 (d, J=5.1 Hz, 1H), 7.69 (d, J=2.3 Hz, 1H), 7.42 (s, 1H), 7.26 (s, 1H), 7.03 (d, J=2.6 Hz, 2H), 6.95 (d, J=1.2 Hz, 1H), 6.87 (d, J=1.2 Hz, 1H), 5.03 (s, 2H), 4.86 (s, 2H), 4.13 (t, J=5.1 Hz, 2H), 3.96 (s, 3H), 3.63 (t, J=5.1 Hz, 2H), 2.38 (s, 3H), 2.34 (s, 6H).

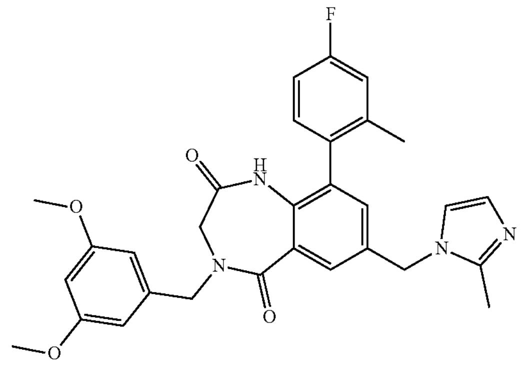 [SMILES: COc1cc(CN2CC(=O)Nc3c(cc(Cn4ccnc4C)cc3-c3ccc(F)cc3C)C2=O)cc(OC)c1]

Example 28

4-(3,5-Dimethoxybenzyl)-9-(4-fluoro-2-methylphenyl)-7-((2-methyl-1H-imidazol-1-yl)methyl)-3,4-dihydro-1H-benzo[e][1,4]diazepine-2,5-dione The title compound (8.1 mg, 40% yield) was prepared from the procedure described in Example 14, Step G using 2-methylimidazole (9.4 mg, 0.114 mmol, 3.0 equiv.). LCMS: $R_T$=1.180 min, MS (ES) 529.0 $[M+H]^+$; $^1$H NMR (400 MHz, Chloroform-d) δ 7.90 (d, J=2.0 Hz, 1H), 7.03-6.87 (m, 6H), 6.48 (d, J=2.4 Hz, 2H), 6.40 (t, J=2.4 Hz, 1H), 5.11 (s, 2H), 4.91 (d, J=15.2 Hz, 1H), 4.70 (d, J=14.8 Hz, 1H), 3.85 (d, J=2.4 Hz, 2H), 3.78 (s, 6H), 2.37 (s, 3H), 1.96 (s, 3H).

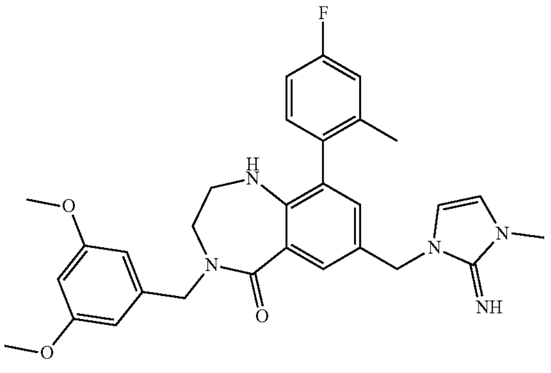

Example 29

4-(3,5-Dimethoxybenzyl)-9-(4-fluoro-2-methylphenyl)-7-((2-imino-3-methyl-2,3-dihydro-1H-imidazol-1-yl)methyl)-1,2,3,4-tetrahydro-5H-benzo[e][1,4]diazepin-5-one $NaBH_4$ (1.1 mg, 0.0276 mmol, 1.5 equiv.) was added to a solution of 4-(3,5-dimethoxybenzyl)-9-(4-fluoro-2-methylphenyl)-7-((2-imino-3-methyl-2,3-dihydro-1H-imidazol-1-yl)methyl)-3,4-dihydro-1H-benzo[e][1,4]diazepine-2,5-dione (10.0 mg, 0.0184 mmol, 1.0 equiv.) in DME (0.2 mL) at room temperature followed by a dropwise addition of TFA (4 μL) in DME (0.5 mL). The mixture was refluxed for 30 min, cooled, quenched with $H_2O$ (2 mL) and basified with sat. aq. $K_2CO_3$ (2 mL). The aqueous layer was extracted with EtOAc (3×5 mL) and the combined organic layer was washed with brine, dried ($MgSO_4$), filtered and concentrated. The residue was purified by reverse phase HPLC (Phenomenex Gemini C18, $H_2O/CH_3CN$ gradient from 15-95% $CH_3CN$, 0.1% TFA) to yield the title compound (3.9 mg, 40% yield). *To remove TFA, the organic layer was washed with $K_2CO_3$ (sat.). LCMS: $R_T$=1.358 min, MS (ES) 530.0 $[M+H]^+$; $^1H$ NMR (400 MHz, chloroform-d) δ 7.80 (d, J=2.4 Hz, 1H), 7.09-6.86 (m, 5H), 6.50 (d, J=2.0 Hz, 2H), 6.37 (t, J=2.0 Hz, 1H), 6.25 (d, J=2.4 Hz, 1H), 4.74 (s, 2H), 3.80 (s, 2H), 3.77 (s, 6H), 3.51-3.47 (m, 2H), 3.38-3.30 (m, 2H), 3.24 (s, 3H), 2.04 (s, 3H); $^{19}F$ NMR (376 MHz, chloroform-d) δ−114.05.

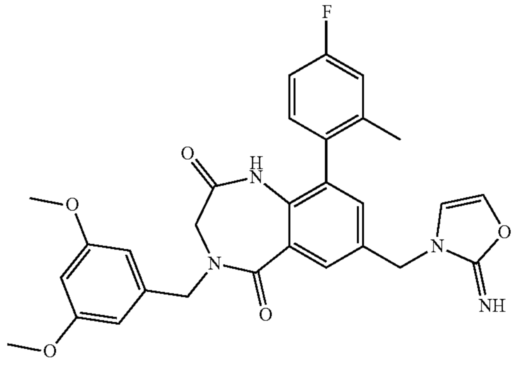 [SMILES: COc1cc(CN2CC(=O)Nc3c(cc(Cn4ccoc4=N)cc3-c3ccc(F)cc3C)C2=O)cc(OC)c1]

Example 30

4-(3,5-Dimethoxybenzyl)-9-(4-fluoro-2-methylphenyl)-7-((2-iminooxazol-3(2H)-yl)methyl)-3,4-dihydro-1H-benzo[e][1,4]diazepine-2,5-dione The title compound (8.7 mg, 43% yield) was prepared from the procedure described in Example 14, Step G using 2-aminooxazole (9.6 mg, 0.114 mmol, 3.0 equiv.). The reaction mixture was stirred at 80° C. for 4 h. LCMS: $R_T$=1.174 min, MS (ES) 531.0 $[M+H]^+$; $^1H$ NMR (400 MHz, Chloroform-d) δ 7.95 (d, J=2.0 Hz, 1H), 7.29 (d, J=2.0 Hz, 1H), 7.07-6.97 (m, 4H), 6.66 (d, J=2.0 Hz, 1H), 6.49 (d, J=2.4 Hz, 2H), 6.41 (t, J=2.0 Hz, 1H), 4.92 (d, J=15.2 Hz, 1H), 4.79 (s, 2H), 4.70 (d, J=14.8 Hz, 1H), 3.85 (d, J=3.2 Hz, 2H), 3.78 (s, 6H), 1.99 (s, 3H).

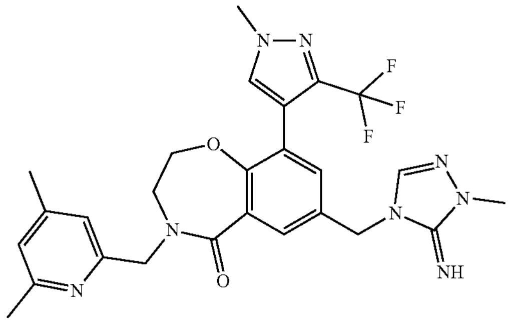

Example 31

4-((4,6-dimethylpyridin-2-yl)methyl)-7-((5-imino-1-methyl-1,5-dihydro-4H-1,2,4-triazol-4-yl)methyl)-9-(1-methyl-3-(trifluoromethyl)-1H-pyrazol-4-yl)-3,4-dihydrobenzo[f][1,4]oxazepin-5(2H)-one The title compound (16.8 mg, 52% yield) was prepared from the procedure described in Example 6, Step A using 7-(bromomethyl)-4-((4,6-dimethylpyridin-2-yl)methyl)-9-(1-methyl-3-(trifluoromethyl)-1H-pyrazol-4-yl)-3,4-dihydrobenzo[f][1,4]oxazepin-5(2H)-one (34.1 mg, 0.06 mmol, 1.0 equiv.) and 1-methyl-1H-1,2,4-triazol-5-amine (12.9 mg, 0.12 mmol, 3.0 equiv.). The reaction mixture was stirred at 60° C. for 12 h. LCMS: $R_T$=0.866 min, MS (ES) 541.6 $[M+H]^+$; $^1H$ NMR (400 MHz, Chloroform-d) δ 7.79 (d, J=2.4 Hz, 1H), 7.45 (s, 1H), 7.31 (d, J=2.3 Hz, 1H), 7.17 (s, 1H), 7.05 (s, 1H), 6.89 (s, 1H), 4.83 (s, 2H), 4.78 (s, 2H), 4.17 (t, J=5.0 Hz, 2H), 3.97 (s, 3H), 3.66-3.60 (m, 2H), 3.41 (s, 3H), 2.47 (s, 3H), 2.29 (s, 3H).

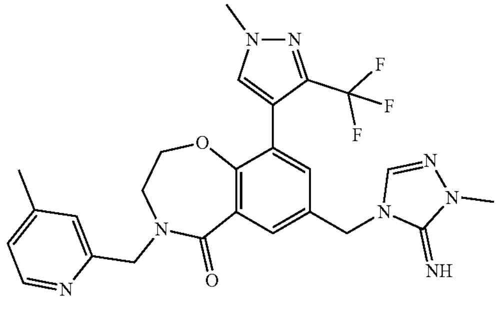 [SMILES: Cc1ccnc(CN2CCOc3c(cc(Cn4cnn(C)c4=N)cc3-c3cn(C)nc3C(F)(F)F)C2=O)c1]

Example 32

7-((5-imino-1-methyl-1,5-dihydro-4H-1,2,4-triazol-4-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one Step A. Preparation of 7-(((tert-butyldiphenylsilyl)oxy)methyl)-9-(1-methyl-3-(trifluoromethyl)-1H-pyrazol-4-yl)-3,4-dihydrobenzo[f][1,4]oxazepin-5(2H)-one The title compound (291.5 mg, 93% yield) was prepared from the procedure described in Example 3, Step F using 9-bromo-7-(((tert-butyldiphenylsilyl)oxy)methyl)-3,4-dihydrobenzo[f][1,4]oxazepin-5(2H)-one (391.4 mg, 0.77 mmol, 1.0 equiv.), (1-methyl-3-(trifluoromethyl)-1H-pyrazol-4-yl) boronic acid (223.0 mg, 1.15 mmol, 1.5 equiv.), $K_2CO_3$ (423.9 mg, 3.07 mmol, 4.0 equiv.), and $PdCl_2$(dppf) (28.1 mg, 0.04 mmol, 0.05 equiv.). The reaction mixture was stirred at 80° C. for 5 h. LCMS: $R_T$=2.179 min, MS (ES) 580.7 $[M+H]^+$.

Step B. Preparation of 7-(((tert-butyldiphenylsilyl) oxy)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The crude title compound was prepared from the procedure described in Example 11, Step D using 7-(((tert-butyldiphenylsilyl)oxy)methyl)-9-(1-methyl-3-(trifluoromethyl)-1H-pyrazol-4-yl)-3,4-dihydrobenzo[f][1,4]oxazepin-5(2H)-one (155.4 mg, 0.27 mmol, 1.0 equiv.), 2-(chloromethyl)-4-methylpyridine hydrochloride (71.6 mg, 0.40 mmol, 1.5 equiv.), and NaH (19.3 mg, 0.80 mmol, 3.0 equiv.). The reaction mixture was stirred at 0° C. for 2 h. LCMS: $R_T$=1.286 min, MS (ES) 685.8 $[M+H]^+$.

Step C. Preparation of 7-(hydroxymethyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The title compound (100.9 mg, 84% yield over 2 steps) was prepared from the procedure described in Example 17, Step H using 7-(((tert-butyldiphenylsilyl)oxy)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one (183.6 mg, 0.27 mmol, 1.0 equiv.) and 1.0 M solution of tetrabutylammonium fluoride (0.54 mL, 0.54 mmol, 2.0 equiv.). The reaction mixture was stirred at room temperature for 12 h. LCMS: $R_T$=1.047 min, MS (ES) 447.4 $[M+H]^+$.

Step D. Preparation of 7-(bromomethyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The crude title compound was prepared from the procedure described in Example 3, Step I using 7-(hydroxymethyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one (30.0 mg, 0.07 mmol, 1.0 equiv.) and $PBr_3$ (10.0 µL, 0.13 mmol, 2.0 equiv.). The reaction mixture was stirred at room temperature for 1.5 h. LCMS: $R_T$=1.325 min, MS (ES) 510.3 $[M+H]^+$.

Step E. Preparation of 7-((5-imino-1-methyl-1,5-dihydro-4H-1,2,4-triazol-4-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The title compound (19.0 mg, 59% yield) was prepared from the procedure described in Example 6, Step A using 7-(bromomethyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one (34.2 mg, 0.06 mmol, 1.0 equiv.) and 1-methyl-1H-1,2,4-triazol-5-amine (12.9 mg, 0.12 mmol, 3.0 equiv.). The reaction mixture was stirred at 60° C. for 12 h. LCMS: $R_T$=0.903 min, MS (ES) 527.5 $[M+H]^+$; $^1H$ NMR (400 MHz, Chloroform-d) δ 8.36 (d, J=5.1 Hz, 1H), 7.79 (d, J=2.4 Hz, 1H), 7.45 (s, 1H), 7.31 (d, J=2.3 Hz, 1H), 7.26 (s, 1H), 7.17 (s, 1H), 7.03 (d, J=5.0 Hz, 1H), 4.86 (s, 2H), 4.78 (s, 2H), 4.15 (t, J=5.0 Hz, 2H), 3.97 (s, 3H), 3.64 (t, J=5.1 Hz, 2H), 3.40 (s, 3H), 2.34 (s, 3H).

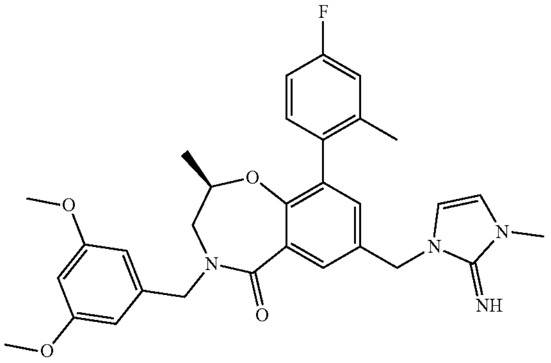

Example 33

(R)-4-(3,5-Dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one Step A. Preparation of methyl (R)-3-bromo-2-((1-((tert-butoxycarbonyl)amino)propan-2-yl)oxy)-5-(((tert-butyldiphenylsilyl)oxy)methyl)benzoate The crude title compound was prepared from the procedure described in Example 3, Step B using methyl 3-bromo-5-(((tert-butyldiphenylsilyl)oxy)methyl)-2-hydroxybenzoate (150.0 mg, 0.30 mmol, 1.0 equiv.), tert-butyl (S)-5-methyl-1,2,3-oxathiazolidine-3-carboxylate 2,2-dioxide (213.8 mg, 0.90 mmol, 3.0 equiv.), and $K_2CO_3$ (124.5 mg, 0.90 mmol, 3.0 equiv.). The reaction mixture was stirred at 90° C. for 1.5 h. LCMS: $R_T$=2.003 min, MS (ES) 679.7 [M+Na].

Step B. Preparation of methyl (R)-2-((1-aminopropan-2-yl)oxy)-3-bromo-5-(((tert-butyldiphenylsilyl)oxy)methyl)benzoate The crude title compound was prepared from the procedure described in Example 17, Step D using methyl (R)-3-bromo-2-((1-((tert-butoxycarbonyl)amino)propan-2-yl)oxy)-5-(((tert-butyldiphenylsilyl)oxy)methyl)benzoate (197.2 mg, 0.30 mmol, 1.0 equiv.) and TFA (0.86 mL, 6.01 mmol, 20.0 equiv.). The reaction mixture was stirred at room temperature for 1 h. LCMS: $R_T$=0.837 min, MS (ES) 557.6 $[M+H]^+$.

Step C. Preparation of (R)-9-bromo-7-(((tert-butyldiphenylsilyl)oxy)methyl)-2-methyl-3,4-dihydrobenzo[f][1,4]oxazepin-5(2H)-one The title compound (138.6 mg, 87% yield over 3 steps) was prepared from the procedure described in Example 22, Step C using methyl (R)-2-((1-aminopropan-2-yl)oxy)-3-bromo-5-(((tert-butyldiphenylsilyl)oxy)methyl) benzoate (167.1 mg, 0.30 mmol, 1.0 equiv.) and N,N-diisopropylethylamine (0.78 mL, 4.50 mmol, 15.0 equiv.). The reaction mixture was stirred at 110° C. for 12 h. LCMS: $R_T$=2.328 min, MS (ES) 525.5 [M+H]$^+$; $^1$H NMR (400 MHz, Chloroform-d) δ 7.81 (t, J=5.2 Hz, 1H), 7.74 (d, J=1.9 Hz, 1H), 7.68 (d, J=6.8 Hz, 4H), 7.60 (d, J=1.9 Hz, 1H), 7.47-7.36 (m, 6H), 4.72 (m, 3H), 3.36 (m, 1H), 3.14 (m, 1H), 1.43 (d, J=6.3 Hz, 3H), 1.11 (s, 9H).

Step D. Preparation of (R)-7-(((tert-butyldiphenylsilyl)oxy)methyl)-9-(4-fluoro-2-methylphenyl)-2-methyl-3,4-dihydrobenzo[f][1,4]oxazepin-5(2H)-one The title compound (72.5 mg, 51% yield) was prepared from the procedure described in Example 3, Step F using (R)-9-bromo-7-(((tert-butyldiphenylsilyl)oxy)methyl)-2-methyl-3,4-dihydrobenzo[f][1,4]oxazepin-5(2H)-one (132.2 mg, 0.25 mmol, 1.0 equiv.), (4-fluoro-2-methylphenyl)boronic acid (77.6 mg, 0.50 mmol, 2.0 equiv.), $K_2CO_3$ (139.3 mg, 1.01 mmol, 4.0 equiv.), and $PdCl_2$(dppf) (9.2 mg, 0.01 mmol, 0.05 equiv.). The reaction mixture was stirred at 100° C. for 7.5 h. LCMS: $R_T$=2.502 min, MS (ES) 554.8 [M+H]$^+$.

Step E. Preparation of (R)-7-(((tert-butyldiphenylsilyl)oxy)methyl)-4-(3,5-dimethoxybenzyl)-9-(4-fluoro-2-methylphenyl)-2-methyl-3,4-dihydrobenzo[f][1,4]oxazepin-5(2H)-one The crude title compound was prepared from the procedure described in Example 11, Step D using (R)-7-(((tert-butyldiphenylsilyl)oxy)methyl)-9-(4-fluoro-2-methylphenyl)-2-methyl-3,4-dihydrobenzo[f][1,4]oxazepin-5(2H)-one (72.5 mg, 0.13 mmol, 1.0 equiv.), 1-(bromomethyl)-3,5-dimethoxybenzene (45.4 mg, 0.20 mmol, 1.5 equiv.), and NaH (6.3 mg, 0.26 mmol, 2.0 equiv.). The reaction mixture was stirred at 0° C. for 1.5 h. LCMS: $R_T$=2.465 min, MS (ES) 704.9 M+H]$^+$.

Step F. Preparation of (R)-4-(3,5-dimethoxybenzyl)-9-(4-fluoro-2-methylphenyl)-7-(hydroxymethyl)-2-methyl-3,4-dihydrobenzo[f][1,4]oxazepin-5(2H)-one The title compound (53.9 mg, 88% yield over 2 steps) was prepared from the procedure described in Example 17, Step H using (R)-7-(((tert-butyldiphenylsilyl)oxy)methyl)-4-(3,5-dimethoxybenzyl)-9-(4-fluoro-2-methylphenyl)-2-methyl-3,4-dihydrobenzo[f][1,4]oxazepin-5(2H)-one (92.2 mg, 0.13 mmol, 1.0 equiv.) and 1.0 M tetrabutylammonium fluoride (0.52 mL, 0.52 mmol, 4.0 equiv.). The reaction mixture was stirred at room temperature for 2.5 h. LCMS: $R_T$=1.742 min, MS (ES) 466.5 [M+H]$^+$.

Step G. Preparation of (R)-7-(bromomethyl)-4-(3,5-dimethoxybenzyl)-9-(4-fluoro-2-methylphenyl)-2-methyl-3,4-dihydrobenzo[f][1,4]oxazepin-5(2H)-one The crude title compound was prepared from the procedure described in Example 3, Step I using (R)-4-(3,5-dimethoxybenzyl)-9-(4-fluoro-2-methylphenyl)-7-(hydroxymethyl)-2-methyl-3,4-dihydrobenzo[f][1,4]oxazepin-5(2H)-one (53.9 mg, 0.12 mmol, 1.0 equiv.) and $PBr_3$ (20.0 μL, 0.23 mmol, 2.0 equiv.). The reaction mixture was stirred at room temperature for 1.5 h. LCMS: $R_T$=2.011 min, MS (ES) 529.4 [M+H]$^+$.

Step H. Preparation of (R)-4-(3,5-dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one The title compound (25.3 mg, 80% yield over 2 steps) was prepared from the procedure described in Example 11, Step D using (R)-7-(bromomethyl)-4-(3,5-dimethoxybenzyl)-9-(4-fluoro-2-methylphenyl)-2-methyl-3,4-dihydrobenzo[f][1,4]oxazepin-5(2H)-one (30.6 mg, 0.06 mmol, 1.0 equiv.), 1-methyl-1H-imidazol-2-amine hydrochloride (15.5 mg, 0.12 mmol, 2.0 equiv.), KI (2.9 mg, 0.02 mmol, 0.3 equiv.), and N,N-diisopropylethylamine (50.0 μL, 0.29 mmol, 5.0 equiv.). The reaction mixture was stirred at 90° C. for 12 h. LCMS: $R_T$=1.381 min, MS (ES) 545.6 [M+H]$^+$; $^1$H NMR (400 MHz, Chloroform-d) δ 7.65 (d, J=1.9 Hz, 1H), 7.18 (d, J=2.2 Hz, 1H), 7.10-7.02 (m, 1H), 6.93-6.81 (m, 2H), 6.46 (d, J=1.9 Hz, 2H), 6.36 (t, J=2.2 Hz, 1H), 6.14 (d, J=2.6 Hz, 1H), 6.13 (d, J=2.6 Hz, 1H), 4.92 (m, 1H), 4.83 (s, 2H), 4.54 (m, 1H), 4.29 (m, 1H), 3.76 (s, 6H), 3.52 (m, 2H), 3.24 (s, 3H), 2.06 (s, 3H), 0.71 (m, 3H).

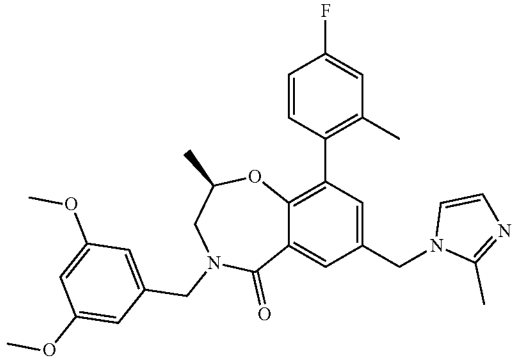 [SMILES: COc1cc(CN2C[C@@H](C)Oc3c(cc(Cn4ccnc4C)cc3-c3ccc(F)cc3C)C2=O)cc(OC)c1]

Example 34

(R)-4-(3,5-Dimethoxybenzyl)-9-(4-fluoro-2-methylphenyl)-2-methyl-7-((2-methyl-1H-imidazol-1-yl)methyl)-3,4-dihydrobenzo[f][1,4]oxazepin-5(2H)-one The title compound (20.6 mg, 67% yield over 2 steps) was prepared from the procedure described in Example 11, Step D using (R)-7-(bromomethyl)-4-(3,5-dimethoxybenzyl)-9-(4-fluoro-2-methylphenyl)-2-methyl-3,4-dihydrobenzo[f][1,4]oxazepin-5(2H)-one in Example 33, Step G (30.6 mg, 0.06 mmol, 1.0 equiv.), 2-methyl-1H-imidazole (14.3 mg, 0.17 mmol, 3.0 equiv.), and N,N-diisopropylethylamine (50.0 μL, 0.29 mmol, 5.0 equiv.). The reaction mixture was stirred at 90° C. for 12 h. LCMS: $R_T$=1.387 min, MS (ES) 530.6 [M+H]$^+$; $^1$H NMR (400 MHz, Chloroform-d) δ 7.64 (d, J=1.9 Hz, 1H), 7.06-6.81 (m, 6H), 6.46 (d, J=2.0 Hz, 2H), 6.37 (t, J=2.2 Hz, 1H), 5.06 (s, 2H), 4.92 (s, 1H), 4.56 (s, 1H), 4.30 (s, 1H), 3.77 (s, 6H), 3.20 (s, 2H), 2.38 (s, 3H), 2.03 (s, 3H), 0.72 (m, 3H).

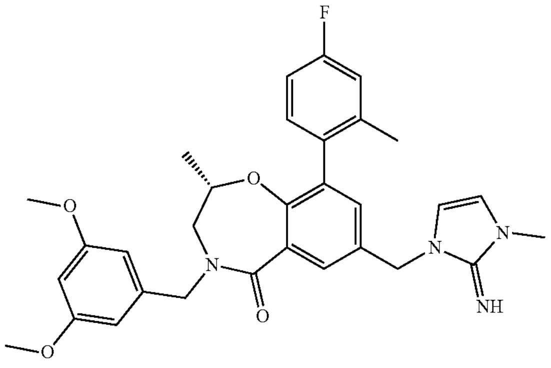

Example 35

(S)-4-(3,5-Dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one The title compound was prepared from the procedure described in Example 33, Step A-H by substituting tert-butyl (S)-5-methyl-1,2,3-oxathiazolidine-3-carboxylate 2,2-dioxide with tert-butyl (R)-5-methyl-1,2,3-oxathiazolidine-3-carboxylate 2,2-dioxide in Step A. LCMS: $R_T$=1.381 min, MS (ES) 545.6 $[M+H]^+$; $^1H$ NMR (400 MHz, Chloroform-d) δ 7.65 (d, J=1.9 Hz, 1H), 7.18 (d, J=2.2 Hz, 1H), 7.10-7.02 (m, 1H), 6.93-6.81 (m, 2H), 6.46 (d, J=1.9 Hz, 2H), 6.36 (t, J=2.2 Hz, 1H), 6.14 (d, J=2.6 Hz, 1H), 6.13 (d, J=2.6 Hz, 1H), 4.92 (m, 1H), 4.83 (s, 2H), 4.54 (m, 1H), 4.29 (m, 1H), 3.76 (s, 6H), 3.52 (m, 2H), 3.24 (s, 3H), 2.06 (s, 3H), 0.71 (m, 3H).

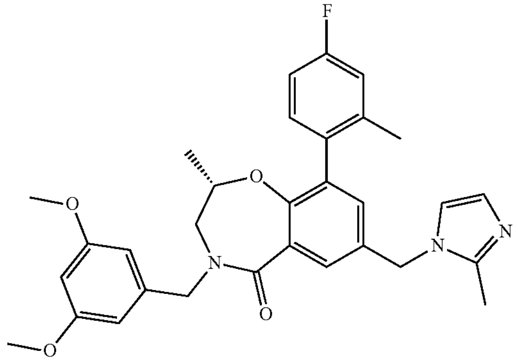 [SMILES: COc1cc(CN2C[C@H](C)Oc3c(cc(Cn4ccnc4C)cc3-c3ccc(F)cc3C)C2=O)cc(OC)c1]

Example 36

(S)-4-(3,5-Dimethoxybenzyl)-9-(4-fluoro-2-methylphenyl)-2-methyl-7-((2-methyl-1H-imidazol-1-yl)methyl)-3,4-dihydrobenzo[f][1,4]oxazepin-5(2H)-one The title compound (26.0 mg, 65% yield over 2 steps) was prepared from the procedure described in Example 11, Step D using (S)-7-(bromomethyl)-4-(3,5-dimethoxybenzyl)-9-(4-fluoro-2-methylphenyl)-2-methyl-3,4-dihydrobenzo[f][1,4]oxazepin-5(2H)-one (39.6 mg, 0.07 mmol, 1.0 equiv.), 2-methyl-1H-imidazole (18.5 mg, 0.22 mmol, 3.0 equiv.), and N,N-diisopropylethylamine (70.0 µL, 0.37 mmol, 5.0 equiv.). The reaction mixture was stirred at 90° C. for 12 h. LCMS: $R_T$=1.380 min, MS (ES) 530.6 $[M+H]^+$; $^1H$ NMR (400 MHz, Chloroform-d) δ 7.67-7.61 (m, 1H), 7.05-6.81 (m, 6H), 6.46 (d, J=2.0 Hz, 2H), 6.37 (t, J=2.2 Hz, 1H), 5.05 (s, 2H), 4.93 (m, 1H), 4.56 (m, 1H), 4.31 (m, 1H), 3.76 (s, 6H), 3.22 (m, 2H), 2.37 (s, 3H), 2.03 (s, 3H), 0.74 (m, 3H).

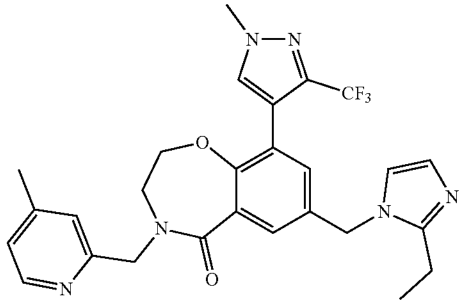 [SMILES: CCc1nccn1Cc1cc2c(c(-c3cn(C)nc3C(F)(F)F)c1)OCCN(Cc1cc(C)ccn1)C2=O]

Example 37

7-((2-Ethyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The title compound (24.1 mg, 59% yield over 2 steps) was prepared from the procedure described in Example 11, Step D using 7-(bromomethyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one (39.6 mg, 0.08 mmol, 1.0 equiv.), 2-ethyl-1H-imidazole (22.4 mg, 0.23 mmol, 3.0 equiv.), and N,N-diisopropylethylamine (70.0 µL, 0.39 mmol, 5.0 equiv.). The reaction mixture was stirred at 90° C. for 1 h. LCMS: $R_T$=0.149 min, MS (ES) 525.6 $[M+H]^+$; $^1H$ NMR (400 MHz, Chloroform-d) δ 8.36 (d, J=5.1 Hz, 1H), 7.69 (d, J=2.4 Hz, 1H), 7.40 (s, 1H), 7.26 (s, 1H), 7.05-6.99 (m, 2H), 6.96 (d, J=1.2 Hz, 1H), 6.84 (d, J=1.3 Hz, 1H), 5.04 (s, 2H), 4.86 (s, 2H), 4.12 (t, J=5.1 Hz, 2H), 3.95 (s, 3H), 3.63 (t, J=5.1 Hz, 2H), 2.64 (q, J=7.5 Hz, 2H), 2.34 (s, 3H), 1.28 (t, J=7.5 Hz, 3H).

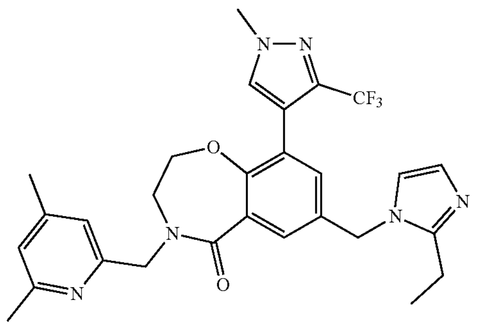 [SMILES: CCc1nccn1Cc1cc2c(c(-c3cn(C)nc3C(F)(F)F)c1)OCCN(Cc1cc(C)cc(C)n1)C2=O]

Example 38

4-((4,6-Dimethylpyridin-2-yl)methyl)-7-((2-ethyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one The title compound (15.6 mg, 41% yield over 2 steps) was prepared from the procedure described in Example 11, Step D using 7-(bromomethyl)-4-((4,6-dimethylpyridin-2-yl)methyl)-9-(1-methyl-3-(trifluoromethyl)-1H-pyrazol-4-yl)-3,4-dihydrobenzo[f][1,4]oxazepin-5(2H)-one (36.8 mg, 0.07 mmol, 1.0 equiv.), 2-ethyl-1H-imidazole (20.3 mg, 0.21 mmol, 3.0 equiv.), and N,N-diisopropylethylamine (60.0 μL, 0.35 mmol, 5.0 equiv.). The reaction mixture was stirred at 90° C. for 1 h. LCMS: $R_T$=0.152 min, MS (ES) 538.6 $[M+H]^+$; $^1$H NMR (400 MHz, Chloroform-d) δ 7.70 (d, J=2.4 Hz, 1H), 7.40 (s, 1H), 7.06 (s, 1H), 7.02 (d, J=2.3 Hz, 1H), 6.97 (d, J=1.3 Hz, 1H), 6.89 (s, 1H), 6.85 (d, J=1.3 Hz, 1H), 5.04 (s, 2H), 4.83 (s, 2H), 4.15 (t, J=5.1 Hz, 2H), 3.96 (s, 3H), 3.62 (t, J=5.1 Hz, 2H), 2.65 (q, J=7.5 Hz, 2H), 2.47 (s, 3H), 2.29 (s, 3H), 1.29 (t, J=7.5 Hz, 3H).

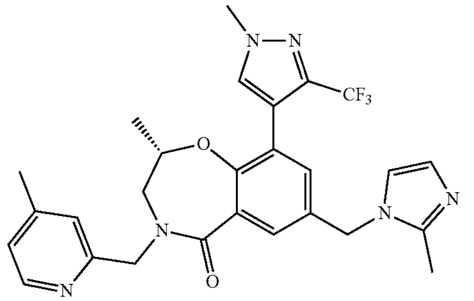 [SMILES: Cc1ccnc(CN2C[C@H](C)Oc3c(cc(Cn4ccnc4C)cc3-c3cn(C)nc3C(F)(F)F)C2=O)c1]

Example 39

(S)-2-Methyl-7-((2-methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one Step A. Preparation of (S)-9-bromo-7-(((tert-butyldiphenylsilyl)oxy)methyl)-2-methyl-4-((4-methylpyridin-2-yl)methyl)-3,4-dihydrobenzo[f][1,4]oxazepin-5(2H)-one The crude title compound was prepared from the procedure described in Example 11, Step D using (S)-9-bromo-7-(((tert-butyldiphenylsilyl)oxy)methyl)-2-methyl-3,4-dihydrobenzo[ ][1,4]oxazepin-5(2H)-one (30.6 mg, 0.06 mmol, 1.0 equiv.), 2-(chloromethyl)-4-methylpyridine hydrochloride (15.6 mg, 0.09 mmol, 1.5 equiv.), and NaH (4.2 mg, 0.18 mmol, 3.0 equiv.). The reaction mixture was stirred at 0° C. for 1 h. LCMS: $R_T$=1.476 min, MS (ES) 630.7 $[M+H]^+$.

Step B. Preparation of (S)-9-bromo-7-(hydroxymethyl)-2-methyl-4-((4-methylpyridin-2-yl)methyl)-3,4-dihydrobenzo[f][1,4]oxazepin-5(2H)-one The crude title compound was prepared from the procedure described in Example 17, Step H using (S)-9-bromo-7-(((tert-butyldiphenylsilyl)oxy)methyl)-2-methyl-4-((4-methylpyridin-2-yl)methyl)-3,4-dihydrobenzo[f][1,4]oxazepin-5(2H)-one (36.7 mg, 0.06 mmol, 1.0 equiv.) and 1.0 M tetrabutylammonium fluoride (0.23 mL, 0.23 mmol, 4.0 equiv.). The reaction mixture was stirred at room temperature for 12 h. LCMS: $R_T$=1.080 min, MS (ES) 392.3 $[M+H]^+$.

Step C. Preparation of (S)-9-bromo-7-(bromomethyl)-2-methyl-4-((4-methylpyridin-2-yl)methyl)-3,4-dihydrobenzo[f][1,4]oxazepin-5(2H)-one The crude title compound was prepared from the procedure described in Example 3, Step I using (S)-9-bromo-7-(hydroxymethyl)-2-methyl-4-((4-methylpyridin-2-yl)methyl)-3,4-dihydrobenzo[f][1,4]oxazepin-5(2H)-one (22.8 mg, 0.06 mmol, 1.0 equiv.) and $PBr_3$ (10.0 μL, 0.12 mmol, 2.0 equiv.). The reaction mixture was stirred at room temperature for 0.5 h. LCMS: $R_T$=1.408 min, MS (ES) 455.2 $[M+H]^+$.

Step D. Preparation of (S)-9-bromo-2-methyl-7-((2-methyl-1H-imidazol-1-yl)methyl)-4-((4-methylpyridin-2-yl)methyl)-3,4-dihydrobenzo[f][1,4]oxazepin-5(2H)-one The title compound (24.1 mg, 90% yield over 4 steps) was prepared from the procedure described in Example 11, Step D using (S)-9-bromo-7-(bromomethyl)-2-methyl-4-((4-methylpyridin-2-yl)methyl)-3,4-dihydrobenzo[f][1,4]oxazepin-5(2H)-one (26.5 mg, 0.06 mmol, 1.0 equiv.), 2-methyl-1H-imidazole (14.4 mg, 0.17 mmol, 3.0 equiv.), and N,N-diisopropylethylamine (50.0 μL, 0.29 mmol, 5.0 equiv.). The reaction mixture was stirred at 90° C. for 4 h. LCMS: $R_T$=0.946 min, MS (ES) 456.4 $[M+H]^+$.

Step E. Preparation of (S)-2-methyl-7-((2-methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The title compound (11.1 mg, 39% yield) was prepared from the procedure described in Example 3, Step F using (S)-9-bromo-2-methyl-7-((2-methyl-1H-imidazol-1-yl)methyl)-4-((4-methylpyridin-2-yl)methyl)-3,4-dihydrobenzo[f][1,4]oxazepin-5(2H)-one (24.1 mg, 0.05 mmol, 1.0 equiv.), (1-methyl-3-(trifluoromethyl)-1H-pyrazol-4-yl)boronic acid (20.5 mg, 0.11 mmol, 2.0 equiv.), $K_2CO_3$ (29.3 mg, 0.21 mmol, 4.0 equiv.), and $PdCl_2$(dppf) (2.0 mg, 0.01 mmol, 0.05 equiv.). The reaction mixture was stirred at 100° C. for 4 h. LCMS: $R_T$=0.955 min, MS (ES) 525.6 $[M+H]^+$; $^1$H NMR (400 MHz, Chloroform-d) δ 8.37 (d, J=5.1 Hz, 1H), 7.63 (d, J=2.4 Hz, 1H), 7.48 (s, 1H), 7.26 (s, 1H), 7.11 (d, J=2.0 Hz, 1H), 7.04 (d, J=4.4 Hz, 1H), 6.99 (s, 1H), 6.90 (s, 1H), 5.11-5.00 (m, 2H), 5.00-4.93 (m, 1H), 4.77 (d, J=14.6 Hz, 1H), 4.46 (dtt, J=12.7, 6.3, 3.1 Hz, 1H), 3.98 (s, 3H), 3.48 (dd, J=15.7, 3.7 Hz, 1H), 3.35 (dd, J=15.7, 8.4 Hz, 1H), 2.41 (s, 3H), 2.35 (s, 3H), 0.90 (d, J=6.4 Hz, 3H).

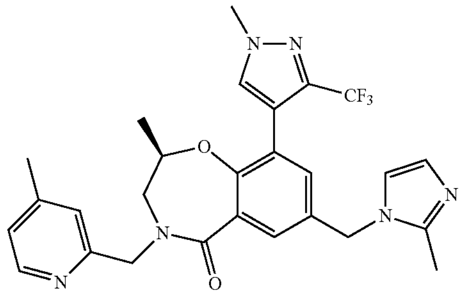 [SMILES: Cc1ccnc(CN2C[C@@H](C)Oc3c(cc(Cn4ccnc4C)cc3-c3cn(C)nc3C(F)(F)F)C2=O)c1]

Example 40

(R)-2-Methyl-7-((2-methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one The title compound was prepared from the procedure described in Example 39, Step A-E by substituting (S)-9-bromo-7-(((tert-butyldiphenylsilyl)oxy)methyl)-2-methyl-3,4-dihydrobenzo[f][1,4]oxazepin-5(2H)-one with (R)-9-bromo-7-(((tert-butyldiphenylsilyl)oxy)methyl)-2-methyl-3,4-dihydrobenzo[f][1,4]oxazepin-5(2H)-one in Step A. LCMS: $R_T$=1.011 min, MS (ES) 525.6 $[M+H]^+$; $^1H$ NMR (400 MHz, Chloroform-d) δ 8.37 (d, J=5.0 Hz, 1H), 7.62 (d, J=2.4 Hz, 1H), 7.47 (s, 1H), 7.26 (s, 1H), 7.10 (d, J=2.0 Hz, 1H), 7.04 (d, J=5.0 Hz, 1H), 6.95 (d, J=1.1 Hz, 1H), 6.87 (d, J=1.2 Hz, 1H), 5.09-4.99 (m, 2H), 4.97 (d, J=14.6 Hz, 1H), 4.77 (d, J=14.6 Hz, 1H), 4.45 (dtt, J=12.7, 6.4, 3.2 Hz, 1H), 3.97 (s, 3H), 3.47 (dd, J=15.6, 3.8 Hz, 1H), 3.34 (dd, J=15.7, 8.4 Hz, 1H), 2.37 (s, 3H), 2.35 (s, 3H), 0.89 (d, J=6.4 Hz, 3H).

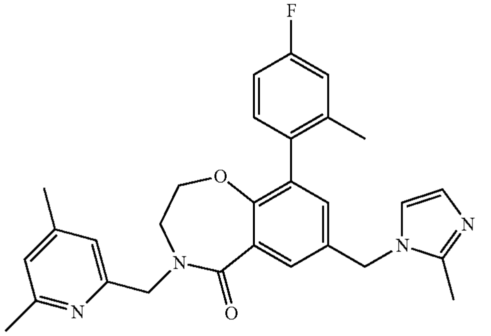 [SMILES: Cc1cc(C)nc(CN2CCOc3c(cc(Cn4ccnc4C)cc3-c3ccc(F)cc3C)C2=O)c1]

Example 41

4-((4,6-Dimethylpyridin-2-yl)methyl)-9-(4-fluoro-2-methylphenyl)-7-((2-methyl-1H-imidazol-1-yl)methyl)-3,4-dihydrobenzo[f][1,4]oxazepin-5(2H)-one Step A. Preparation of 9-bromo-4-((4,6-dimethylpyridin-2-yl)methyl)-7-(hydroxymethyl)-3,4-dihydrobenzo[f][1,4]oxazepin-5(2H)-one The title compound (286.4 mg, 74% yield) was prepared from the procedure described in Example 11, Step D using 9-bromo-7-(((tert-butyldiphenylsilyl)oxy)methyl)-3,4-dihydrobenzo[f][1,4]oxazepin-5(2H)-one (500.0 mg, 0.98 mmol, 1.0 equiv.), 2-(chloromethyl)-4,6-dimethylpyridine (228.6 mg, 1.47 mmol, 1.5 equiv.), and NaH (70.5 mg, 2.94 mmol, 3.0 equiv.). The reaction mixture was stirred at 0° C. for 1 h. LCMS: $R_T$=1.112 min, MS (ES) 630.7 $[M+H]^+$.

Step B. Preparation of 9-bromo-7-(bromomethyl)-4-((4,6-dimethylpyridin-2-yl)methyl)-3,4-dihydrobenzo[f][1,4]oxazepin-5(2H)-one The crude title compound was prepared from the procedure described in Example 3, Step I using 9-bromo-4-((4,6-dimethylpyridin-2-yl)methyl)-7-(hydroxymethyl)-3,4-dihydrobenzo[f][1,4]oxazepin-5(2H)-one (286.4 mg, 0.73 mmol, 1.0 equiv.) and $PBr_3$ (0.14 mL, 1.46 mmol, 2.0 equiv.). The reaction mixture was stirred at room temperature for 1.5 h. LCMS: $R_T$=1.263 min, MS (ES) 455.2 $[M+H]^+$.

Step C. Preparation of 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one The title compound (317.2 mg, 95% yield over 2 steps) was prepared from the procedure described in Example 11, Step D using 9-bromo-7-(bromomethyl)-4-((4,6-dimethylpyridin-2-yl)methyl)-3,4-dihydrobenzo[f][1,4]oxazepin-5(2H)-one (332.4 mg, 0.73 mmol, 1.0 equiv.) and 2-methyl-1H-imidazole (180.3 mg, 2.20 mmol, 3.0 equiv.) and N,N-diisopropylethylamine (0.64 mL, 3.66 mmol, 5.0 equiv.). The reaction mixture was stirred at 90° C. for 12 h. LCMS: $R_T$=0.152 min, MS (ES) 456.4 $[M+H]^+$.

Step D. Preparation of 4-((4,6-dimethylpyridin-2-yl)methyl)-9-(4-fluoro-2-methylphenyl)-7-((2-methyl-1H-imidazol-1-yl)methyl)-3,4-dihydrobenzo[f][1,4]oxazepin-5(2H)-one The title compound (12.9 mg, 40% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), (4-fluoro-2-methylphenyl)boronic acid (25.4 mg, 0.16 mmol, 2.5 equiv.), $K_2CO_3$ (36.4 mg, 0.26 mmol, 4.0 equiv.), and $PdCl_2(dppf)$ (2.4 mg, 0.01 mmol, 0.05 equiv.). The reaction mixture was stirred at 100° C. for 6 h. LCMS: $R_T$=0.982 min, MS (ES) 485.6 $[M+H]^+$.

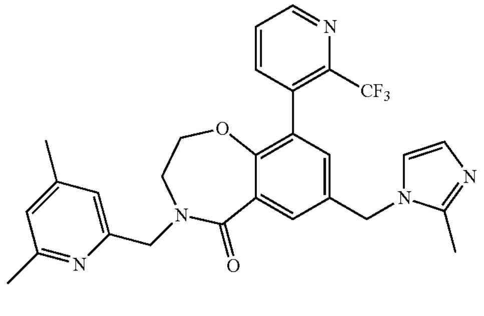 [SMILES: Cc1cc(C)nc(CN2CCOc3c(cc(Cn4ccnc4C)cc3-c3cccnc3C(F)(F)F)C2=O)c1]

Example 42

4-((4,6-Dimethylpyridin-2-yl)methyl)-7-((2-methyl-1H-imidazol-1-yl)methyl)-9-(2-(trifluoromethyl)pyridin-3-yl)-3,4-dihydrobenzo[f][1,4]oxazepin-5(2H)-one The title compound (2.5 mg, 7% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), (2-(trifluoromethyl)pyridin-3-yl)boronic acid (31.5 mg, 0.16 mmol, 2.5 equiv.), $K_2CO_3$ (36.4 mg, 0.26 mmol, 4.0 equiv.), and $PdCl_2$(dppf) (2.4 mg, 0.01 mmol, 0.05 equiv.). The reaction mixture was stirred at 100° C. for 6 h. LCMS: $R_T$=0.191 min, MS (ES) 522.5 [M+H]$^+$.

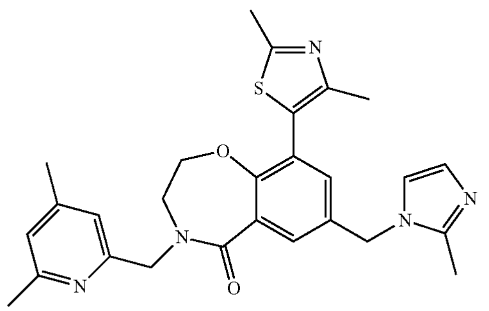 [SMILES: Cc1cc(C)nc(CN2CCOc3c(cc(Cn4ccnc4C)cc3-c3sc(C)nc3C)C2=O)c1]

Example 43

4-((4,6-Dimethylpyridin-2-yl)methyl)-9-(2,4-dimethylthiazol-5-yl)-7-((2-methyl-1H-imidazol-1-yl)methyl)-3,4-dihydrobenzo[f][1,4]oxazepin-5(2H)-one 2,4-Dimethylthiazole (20.0 μL, 0.20 mmol, 3.0 equiv.), $Pd(OAc)_2$ (1.5 mg, 0.01 mmol, 0.1 equiv.), and AcOK (19.4 mg, 0.20 mmol, 3.0 equiv.) were added to a solution of 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.) in DMA (1.0 mL). The reaction mixture was stirred at 150° C. for 12 h, cooled to room temperature, quenched with sat. aq. $NH_4Cl$ (0.5 mL) and extracted with $CH_2Cl_2$ (3×3.0 mL). The combined organics were dried over $Na_2SO_4$ and concentrated under reduced pressure. The residue was purified by reverse phase HPLC (Phenomenex Gemini C18, $H_2O$/$CH_3CN$ gradient from 5-95% $CH_3CN$, 0.1% TFA) to yield the title compound (14.7 mg, 45% yield). LCMS: $R_T$=0.884 min, MS (ES) 488.6 [M+H]$^+$; $^1$H NMR (400 MHz, Chloroform-d) δ 7.67 (d, J=2.4 Hz, 1H), 7.07 (s, 1H), 7.03 (d, J=2.4 Hz, 1H), 6.95 (d, J=1.2 Hz, 1H), 6.90 (s, 1H), 6.86 (d, J=1.3 Hz, 1H), 5.05 (s, 2H), 4.84 (s, 2H), 4.21 (t, J=5.2 Hz, 2H), 3.66 (t, J=5.2 Hz, 2H), 2.66 (s, 3H), 2.47 (s, 3H), 2.37 (s, 3H), 2.28 (s, 3H), 2.22 (s, 3H).

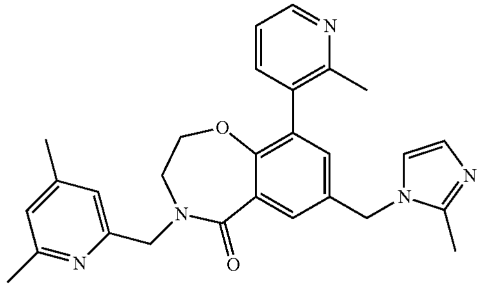 [SMILES: Cc1cc(C)nc(CN2CCOc3c(cc(Cn4ccnc4C)cc3-c3cccnc3C)C2=O)c1]

Example 44

4-((4,6-Dimethylpyridin-2-yl)methyl)-7-((2-methyl-1H-imidazol-1-yl)methyl)-9-(2-methylpyridin-3-yl)-3,4-dihydrobenzo[f][1,4]oxazepin-5(2H)-one The title compound (3.0 mg, 9% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), (2-methylpyridin-3-yl)boronic acid (22.6 mg, 0.16 mmol, 2.5 equiv.), $K_2CO_3$ (36.4 mg, 0.26 mmol, 4.0 equiv.), and $PdCl_2$(dppf) (2.4 mg, 0.01 mmol, 0.05 equiv.). The reaction mixture was stirred at 100° C. for 7.5 h. LCMS: $R_T$=0.150 min, MS (ES) 468.6 [M+H]$^+$.

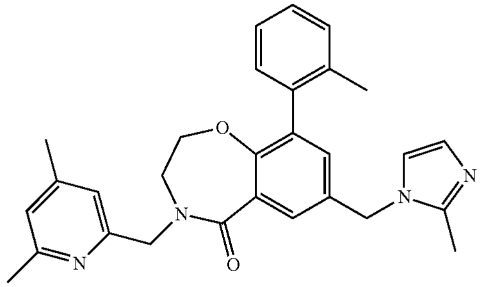 [SMILES: Cc1cc(C)nc(CN2CCOc3c(cc(Cn4ccnc4C)cc3-c3ccccc3C)C2=O)c1]

Example 45

4-((4,6-Dimethylpyridin-2-yl)methyl)-7-((2-methyl-1H-imidazol-1-yl)methyl)-9-(o-tolyl)-3,4-dihydrobenzo[f][1,4]oxazepin-5(2H)-one The title compound (11.9 mg, 38% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), o-tolylboronic acid (22.4 mg, 0.16 mmol, 2.5 equiv.), $K_2CO_3$ (36.4 mg, 0.26 mmol, 4.0 equiv.), and $PdCl_2$(dppf) (2.4 mg, 0.01 mmol, 0.05 equiv.). The reaction mixture was stirred at 100° C. for 7.5 h. LCMS: $R_T$=0.989 min, MS (ES) 467.6 [M+H]$^+$; $^1$H NMR (400 MHz, Chloroform-d) δ 7.69 (d, J=2.4 Hz, 1H), 7.29-7.22 (m, 2H), 7.18 (m, 1H), 7.07 (s, 1H), 7.04 (d, J=7.3 Hz, 1H), 6.97 (d, J=1.7 Hz, 2H), 6.91-6.86 (m, 2H), 5.06 (s, 2H), 4.84 (s, 2H), 4.05 (m, 2H), 3.64 (br s, 2H), 2.46 (s, 3H), 2.42 (s, 3H), 2.28 (s, 3H), 2.04 (s, 3H).

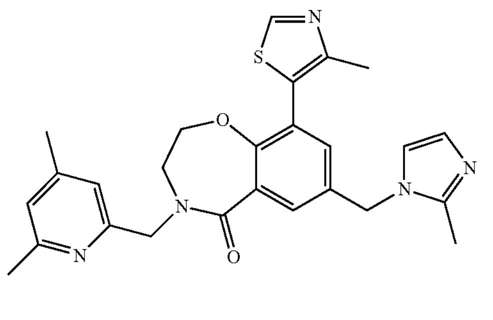 [SMILES: Cc1cc(C)nc(CN2CCOc3c(cc(Cn4ccnc4C)cc3-c3scnc3C)C2=O)c1]

Example 46

4-((4,6-Dimethylpyridin-2-yl)methyl)-7-((2-methyl-1H-imidazol-1-yl)methyl)-9-(4-methylthiazol-5-yl)-3,4-dihydrobenzo[f][1,4]oxazepin-5(2H)-one The title compound (9.7 mg, 31% yield) was prepared from the procedure described in Example 43 using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), 4-methylthiazole (20.0 μL, 0.20 mmol, 3.0 equiv.), $Pd(OAc)_2$ (1.5 mg, 0.01 mmol, 0.1 equiv.), and AcOK (19.4 mg, 0.20 mmol, 3.0 equiv.). The reaction mixture was stirred at 150° C. for 12 h. LCMS: $R_T$=0.141 min, MS (ES) 474.6 $[M+H]^+$; $^1$H NMR (400 MHz, Chloroform-d) δ 8.73 (s, 1H), 7.71 (d, J=2.4 Hz, 1H), 7.10-7.04 (m, 2H), 6.96 (d, J=1.4 Hz, 1H), 6.90 (s, 1H), 6.88 (d, J=1.4 Hz, 1H), 5.07 (s, 2H), 4.84 (s, 2H), 4.24-4.18 (m, 2H), 3.68 (t, J=5.2 Hz, 2H), 2.47 (s, 3H), 2.38 (s, 3H), 2.31 (s, 3H), 2.29 (s, 3H).

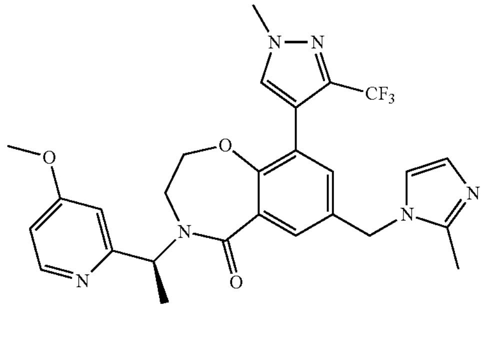 [SMILES: COc1ccnc([C@H](C)N2CCOc3c(cc(Cn4ccnc4C)cc3-c3cn(C)nc3C(F)(F)F)C2=O)c1]

Example 47

(S)-4-(1-(4-Methoxypyridin-2-yl)ethyl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one Step A. Preparation of methyl 2-(allyloxy)-3-bromo-5-(((tert-butyldiphenylsilyl)oxy)methyl)benzoate The title compound (499 mg, 92% yield) was prepared from the procedure described in Example 3, Step B using methyl 3-bromo-5-(((tert-butyldiphenylsilyl)oxy)methyl)-2-hydroxybenzoate (500 mg, 1.0 mmol, 1.0 equiv.), 3-bromoprop-1-ene (0.26 mL, 3.0 mmol, 3.0 equiv.), and $K_2CO_3$ (692 mg, 5.01 mmol, 5.0 equiv. The reaction mixture was stirred at 80° C. for 1.5 h. LCMS: $R_T$=1.989 min, *Product is not ionizable.

Step B. Preparation of methyl 3-bromo-5-(((tert-butyldiphenylsilyl)oxy)methyl)-2-(2-oxoethoxy)benzoate The crude mixture of title compound was prepared from the procedure described in Example 3, Step C using methyl 2-(allyloxy)-3-bromo-5-(((tert-butyldiphenylsilyl)oxy)methyl)benzoate (200 mg, 0.37 mmol, 1.0 equiv.), 4 wt. % $OsO_4$ in $H_2O$ (1.75 mL, 0.28 mmol, 0.75 equiv.), pyridine (60 μL, 0.74 mmol, 2.0 equiv.), $NaIO_4$ (317 mg, 1.48 mmol, 4.0 equiv.), $H_2O$ (1.0 mL), and 1,4-dioxane (3.0 mL). The reaction mixture was stirred at room temperature for 2.5 h. LCMS: $R_T$=1.589 min, MS (ES) 542.5 $[M+H]^+$.

Step C. Preparation of methyl (S)-3-bromo-5-(((tert-butyldiphenylsilyl)oxy) methyl)-2-(2-((1-(4-methoxypyridin-2-yl)ethyl)amino)ethoxy)benzoate The crude title compound was prepared from the procedure described in Example 3, Step D using methyl 3-bromo-5-(((tert-butyldiphenylsilyl)oxy)methyl)-2-(2-oxoethoxy)benzoate (201 mg, 0.37 mmol, 1.0 equiv.), (S)-1-(4-methoxypyridin-2-yl)ethan-1-amine dihydrochloride (170 mg, 0.74 mmol, 2.0 equiv.), $NaBH(OAc)_3$ (157 mg, 0.74 mmol, 2.0 equiv.), and acetic acid (40 μL, 0.74 mmol, 2.0 equiv.). The reaction mixture was stirred at room temperature for 0.5 h. LCMS: $R_T$=0.107 min, MS (ES) 678.7 $[M+H]^+$.

Step D. Preparation of (S)-9-bromo-7-(((tert-butyldiphenylsilyl)oxy)methyl)-4-(1-(4-methoxypyridin-2-yl)ethyl)-3,4-dihydrobenzo[f][1,4]oxazepin-5(2H)-one The title compound (198 mg, 50% yield over 3 steps) was prepared from the procedure described in Example 22, Step C using methyl (S)-3-bromo-5-(((tert-butyldiphenylsilyl)oxy)methyl)-2-(2-((1-(4-methoxypyridin-2-yl)ethyl)amino)ethoxy)benzoate (411 mg, 0.61 mmol, 1.0 equiv.) and N,N-diisopropylethylamine (1.1 mL, 6.1 mmol, 10.0 equiv.) in DMF. The reaction mixture was stirred at 110° C. for 24 h. LCMS: $R_T$=2.157 min, MS (ES) 646.7 $[M+H]^+$; $^1$H NMR (400 MHz, Chloroform-d) δ 8.35 (d, J=5.8 Hz, 1H), 7.71-7.61 (m, 5H), 7.57 (d, J=1.9 Hz, 1H), 7.42-7.31 (m, 6H), 6.97 (d, J=2.4 Hz, 1H), 6.74 (dd, J=5.8, 2.5 Hz, 1H), 6.07 (q, J=7.0 Hz, 1H), 4.69 (s, 2H), 4.27-4.18 (m, 1H), 3.94-3.87 (m, 1H), 3.80 (s, 3H), 3.51 (m, 2H), 1.64 (d, J=7.1 Hz, 3H), 1.08 (s, 9H).

Step E. Preparation of (S)-7-(((tert-butyldiphenylsilyl)oxy)methyl)-4-(1-(4-methoxypyridin-2-yl)ethyl)-9-(1-methyl-3-(trifluoromethyl)-1H-pyrazol-4-yl)-3,4-dihydrobenzo[f][1,4] oxazepin-5(2H)-one The crude title compound was prepared from the procedure described in Example 3, Step F using (S)-9-bromo-7-(((tert-butyldiphenylsilyl)oxy)methyl)-4-(1-(4-methoxypyridin-2-yl)ethyl)-3,4-dihydrobenzo[f][1,4]oxazepin-5(2H)-one (100 mg, 0.15 mmol, 1.0 equiv.), (1-methyl-3-(trifluoromethyl)-1H-pyrazol-4-yl)boronic acid (60 mg, 0.31 mmol, 2.0 equiv.), $K_2CO_3$ (86 mg, 0.62 mmol, 4.0 equiv.), and $PdCl_2(dppf)$ (5.7 mg, 0.01 mmol, 0.05 equiv.).

The reaction mixture was stirred at 100° C. for 4.5 h. LCMS: $R_T$=2.006 min, MS (ES) 715.9 $[M+H]^+$.

Step F. Preparation of (S)-7-(hydroxymethyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one The title compound (56 mg, 75% yield over 2 steps) was prepared from the procedure described in Example 11, Step D using (S)-7-(((tert-butyldiphenylsilyl)oxy)methyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one (110.7 mg, 0.15 mmol, 1.0 equiv.), and 1.0 M tetrabutylammonium fluoride (0.62 mL, 0.62 mmol, 4.0 equiv.). The reaction mixture was stirred at room temperature for 12 h. LCMS: $R_T$=1.089 min, MS (ES) 477.5 $[M+H]^+$.

Step G. Preparation of (S)-7-(bromomethyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one The crude title compound was prepared from the procedure described in Example 3, Step I using (S)-7-(hydroxymethyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one (27.8 mg, 0.06 mmol, 1.0 equiv.) and $PBr_3$ (10.0 μL, 0.12 mmol, 2.0 equiv.). The reaction mixture was stirred at room temperature for 0.5 h. LCMS: $R_T$=1.351 min, MS (ES) 540.4 $[M+H]^+$.

Step H. Preparation of (S)-4-(1-(4-methoxypyridin-2-yl)ethyl)-7-((2-methyl-1H-imidazol-1-yl)methyl)-9-(1-methyl-3-(trifluoromethyl)-1H-pyrazol-4-yl)-3,4-dihydrobenzo[f][1,4] oxazepin-5(2H)-one The title compound (19.2 mg, 60% yield over 2 steps) was prepared from the procedure described in Example 11, Step D using (S)-7-(bromomethyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one (31.5 mg, 0.06 mmol, 1.0 equiv.), 2-methyl-1H-imidazole (14.4 mg, 0.18 mmol, 3.0 equiv.), and N,N-diisopropylethylamine (50.0 μL, 0.29 mmol, 5.0 equiv.). The reaction mixture was stirred at 90° C. for 12 h. LCMS: $R_T$=0.980 min, MS (ES) 541.6 $[M+H]^+$; $^1H$ NMR (400 MHz, Chloroform-d) δ 8.35 (d, J=5.7 Hz, 1H), 7.65 (s, 1H), 7.41 (s, 1H), 7.03 (s, 1H), 6.96 (s, 1H), 6.95-6.90 (m, 1H), 6.87 (s, 1H), 6.76-6.70 (m, 1H), 6.07 (q, J=7.0 Hz, 1H), 5.03 (s, 2H), 4.07 (m, 1H), 3.95 (s, 3H), 3.83 (s, 3H), 3.78 (m, 1H), 3.56 (m, 2H), 2.38 (s, 3H), 1.62 (d, J=7.0 Hz, 3H).

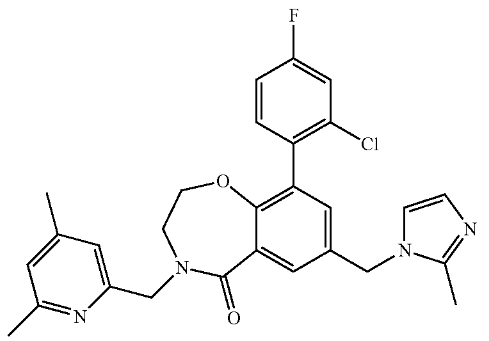 [SMILES: Cc1cc(C)nc(CN2CCOc3c(cc(Cn4ccnc4C)cc3-c3ccc(F)cc3Cl)C2=O)c1]

Example 48

9-(2-Chloro-4-fluorophenyl)-4-((4,6-dimethylpyridin-2-yl)methyl)-7-((2-methyl-1H-imidazol-1-yl)methyl)-3,4-dihydrobenzo[f][1,4]oxazepin-5(2H)-one The title compound (15.1 mg, 45% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), (2-chloro-4-fluorophenyl)boronic acid (25.7 mg, 0.16 mmol, 2.5 equiv.), $K_2CO_3$ (36.4 mg, 0.26 mmol, 4.0 equiv.), and $PdCl_2$(dppf) (2.4 mg, 0.01 mmol, 0.05 equiv.). The reaction mixture was stirred at 110° C. for 5 h. LCMS: $R_T$=1.803 min, MS (ES) 506.0 $[M+H]^+$; $^1H$ NMR (400 MHz, Chloroform-d) δ 7.75 (d, J=2.4 Hz, 1H), 7.18 (dd, J=8.5, 2.5 Hz, 1H), 7.13 (dd, J=8.5, 6.0 Hz, 1H), 7.06 (s, 1H), 7.00 (td, J=8.3, 2.6 Hz, 1H), 6.96 (d, J=1.3 Hz, 1H), 6.94 (d, J=2.4 Hz, 1H), 6.88 (d, J=1.3 Hz, 2H), 5.06 (s, 2H), 4.83 (s, 2H), 4.19 (br s, 2H), 3.68 (br s, 2H), 2.46 (s, 3H), 2.39 (s, 3H), 2.28 (s, 3H).

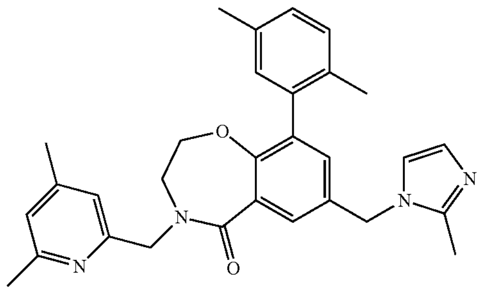 [SMILES: Cc1cc(C)nc(CN2CCOc3c(cc(Cn4ccnc4C)cc3-c3cc(C)ccc3C)C2=O)c1]

Example 49

9-(2,5-Dimethylphenyl)-4-((4,6-dimethylpyridin-2-yl)methyl)-7-((2-methyl-1H-imidazol-1-yl)methyl)-3,4-dihydrobenzo[f][1,4]oxazepin-5(2H)-one The title compound (17.4 mg, 54% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30.0 mg, 0.07 mmol, 1.0 equiv.), (2,5-dimethylphenyl)boronic acid (24.7 mg, 0.16 mmol, 2.5 equiv.), $K_2CO_3$ (36.4 mg, 0.26 mmol, 4.0 equiv.), and $PdCl_2$(dppf) (2.4 mg, 0.01 mmol, 0.05 equiv.). The reaction mixture was stirred at 100° C. for 5 h. LCMS: $R_T$=1.099 min, MS (ES) 481.6 $[M+H]^+$; $^1H$ NMR (400 MHz, Chloroform-d) δ 7.70 (d, J=2.4 Hz, 1H), 7.13-7.05 (m, 3H), 7.04-7.01 (m, 1H), 6.99 (d, J=2.4 Hz, 1H), 6.92 (d, J=1.2 Hz, 1H), 6.89 (s, 1H), 6.85 (s, 1H), 5.07 (s, 2H), 4.84 (s, 2H), 4.08 (m, 2H), 3.65 (s, 2H), 2.48 (s, 3H), 2.46 (s, 3H), 2.31 (s, 3H), 2.28 (s, 3H), 1.99 (s, 3H).

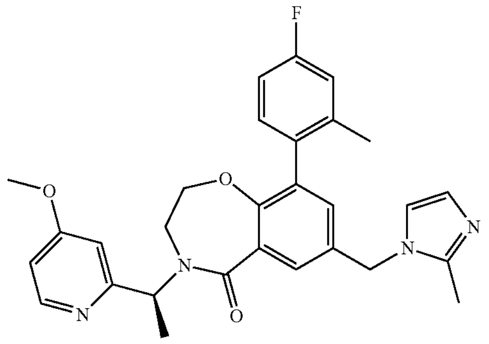 [SMILES: COc1ccnc([C@H](C)N2CCOc3c(cc(Cn4ccnc4C)cc3-c3ccc(F)cc3C)C2=O)c1]

Example 50

(S)-9-(4-Fluoro-2-methylphenyl)-4-(1-(4-methoxy-pyridin-2-yl)ethyl)-7-((2-methyl-1H-imidazol-1-yl)methyl)-3,4-dihydrobenzo[f][1,4]oxazepin-5(2H)-one Step A. Preparation of (S)-7-(((tert-butyldiphenylsilyl)oxy)methyl)-9-(4-fluoro-2-methylphenyl)-4-(1-(4-methoxypyridin-2-yl)ethyl)-3,4-dihydrobenzo[f][1,4]oxazepin-5(2H)-one The title compound (80 mg, 76% yield) was prepared from the procedure described in Example 3, Step F using (S)-9-bromo-7-(((tert-butyldiphenylsilyl)oxy)methyl)-4-(1-(4-methoxypyridin-2-yl)ethyl)-3,4-dihydrobenzo[f][1,4]oxazepin-5(2H)-one (100.0 mg, 0.15 mmol, 1.0 equiv.), (4-fluoro-2-methylphenyl)boronic acid (48 mg, 0.31 mmol, 2.0 equiv.), $K_2CO_3$ (86 mg, 0.62 mmol, 4.0 equiv.), and $PdCl_2$(dppf) (5.7 mg, 0.01 mmol, 0.05 equiv.). The reaction mixture was stirred at 100° C. for 4.0 h. LCMS: $R_T$=2.258 min, MS (ES) 675.9 $[M+H]^+$; $^1$H NMR (400 MHz, Chloroform-d) δ 8.18 (d, J=5.7 Hz, 1H), 7.57-7.47 (m, 5H), 7.28-7.15 (m, 6H), 7.09 (d, J=2.2 Hz, 1H), 6.91-6.66 (m, 4H), 6.57 (dd, J=5.7, 2.5 Hz, 1H), 5.96 (q, J=7.0 Hz, 1H), 4.60 (s, 2H), 3.91 (m, 1H), 3.66 (s, 3H), 3.38 (m, 3H), 1.91 (s, 3H), 1.48 (d, J=7.0 Hz, 3H), 0.92 (s, 9H).

Step B. Preparation of (S)-9-(4-fluoro-2-methylphenyl)-7-(hydroxymethyl)-4-(1-(4-methoxypyridin-2-yl)ethyl)-3,4-dihydrobenzo[f][1,4]oxazepin-5(2H)-one The title compound (49 mg, 95% yield) was prepared from the procedure described in Example 11, Step D using (S)-7-(((tert-butyldiphenylsilyl)oxy)methyl)-9-(4-fluoro-2-methylphenyl)-4-(1-(4-methoxypyridin-2-yl)ethyl)-3,4-dihydrobenzo[f][1,4]oxazepin-5(2H)-one (80 mg, 0.12 mmol, 1.0 equiv.) and 1.0 M tetrabutylammonium fluoride (0.47 mL, 0.47 mmol, 4.0 equiv.). The reaction mixture was stirred at room temperature for 12 h. LCMS: $R_T$=1.234 min, MS (ES) 437.5 $[M+H]^+$; $^1$H NMR (400 MHz, Chloroform-d) δ 8.33 (d, J=5.7 Hz, 1H), 7.78 (d, J=1.8 Hz, 1H), 7.28 (s, 1H), 7.04 (dd, J=8.2, 6.1 Hz, 1H), 6.98 (s, 1H), 6.96-6.90 (m, 1H), 6.87 (td, J=8.4, 2.4 Hz, 1H), 6.73 (dd, J=5.7, 2.3 Hz, 1H), 6.09 (q, J=7.0 Hz, 1H), 4.69 (s, 2H), 4.05 (m, 1H), 3.84 (s, 3H), 3.60 (m, 3H), 2.24 (br s, 1H), 2.06 (s, 3H), 1.63 (d, J=6.9 Hz, 3H).

Step C. Preparation of (S)-7-(bromomethyl)-9-(4-fluoro-2-methylphenyl)-4-(1-(4-methoxypyridin-2-yl)ethyl)-3,4-dihydrobenzo[f][1,4]oxazepin-5(2H)-one The crude title compound was prepared from the procedure described in Example 3, Step I using (S)-9-(4-fluoro-2-methylphenyl)-7-(hydroxymethyl)-4-(1-(4-methoxypyridin-2-yl)ethyl)-3,4-dihydrobenzo[f][1,4]oxazepin-5(2H)-one (25 mg, 0.06 mmol, 1.0 equiv.) and $PBr_3$ (10 μL, 0.11 mmol, 2.0 equiv.). The reaction mixture was stirred at room temperature for 0.5 h. LCMS: $R_T$=1.518 min, MS (ES) 500.4 $[M+H]^+$.

Step D. Preparation of (S)-9-(4-fluoro-2-methylphenyl)-4-(1-(4-methoxypyridin-2-yl)ethyl)-7-((2-methyl-1H-imidazol-1-yl)methyl)-3,4-dihydrobenzo[f][11,4]oxazepin-5(2H)-one The title compound (25 mg, 88% yield over 2 steps) was prepared from the procedure described in Example 11, Step D using (S)-7-(bromomethyl)-9-(4-fluoro-2-methylphenyl)-4-(1-(4-methoxypyridin-2-yl)ethyl)-3,4-dihydrobenzo[f][1,4]oxazepin-5(2H)-one (28 mg, 0.06 mmol, 1.0 equiv.), 2-methyl-1H-imidazole (14 mg, 0.17 mmol, 3.0 equiv.), and N,N-diisopropylethylamine (50 μL, 0.28 mmol, 5.0 equiv.). The reaction mixture was stirred at 90° C. for 12 h. LCMS: $R_T$=1.091 min, MS (ES) 501.6 $[M+H]^+$; $^1$H NMR (400 MHz, Chloroform-d) δ 8.33 (d, J=5.7 Hz, 1H), 7.65 (d, J=2.3 Hz, 1H), 7.02-6.79 (m, 7H), 6.72 (dd, J=5.7, 2.5 Hz, 1H), 6.07 (q, J=7.0 Hz, 1H), 5.04 (s, 2H), 4.05 (m, 1H), 3.82 (s, 3H), 3.61 (m, 3H), 2.38 (s, 3H), 2.00 (s, 3H), 1.62 (d, J=7.0 Hz, 3H).

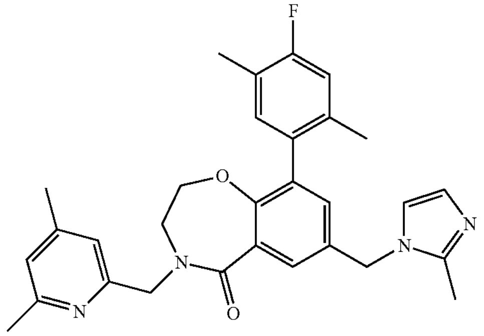 [SMILES: Cc1cc(C)nc(CN2CCOc3c(cc(Cn4ccnc4C)cc3-c3cc(C)c(F)cc3C)C2=O)c1]

Example 51

4-((4,6-Dimethylpyridin-2-yl)methyl)-9-(4-fluoro-2,5-dimethylphenyl)-7-((2-methyl-1H-imidazol-1-yl)methyl)-3,4-dihydrobenzo[f][1,4]oxazepin-5(2H)-one The title compound (16 mg, 48% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one in Example 43, Step C (30 mg, 0.07 mmol, 1.0 equiv.), (4-fluoro-2,5-dimethylphenyl)boronic acid (28 mg, 0.16 mmol, 2.5 equiv.), $K_2CO_3$ (36 mg, 0.26 mmol, 4.0 equiv.), and $PdCl_2$(dppf) (2.4 mg, 0.01 mmol, 0.05 equiv.). The reaction mixture was stirred at 100° C. for 5 h. LCMS: $R_T$=1.128 min, MS (ES) 499.6 $[M+H]^+$; $^1$H NMR (400 MHz, Chloroform-d) δ 7.68 (d, J=2.4 Hz, 1H), 7.07 (s, 1H), 6.95 (d, J=1.3 Hz, 1H), 6.92 (d, J=2.4 Hz, 1H), 6.90-6.82 (m, 4H), 5.04 (s, 2H), 4.83 (s, 2H), 4.06 (m, 2H), 3.63 (m, 2H), 2.46 (s, 3H), 2.39 (s, 3H), 2.28 (s, 3H), 2.22 (s, 3H), 1.98 (s, 3H).

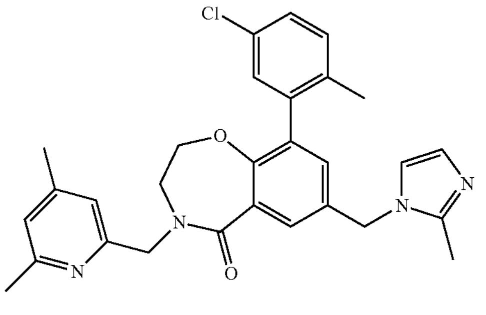 [SMILES: Cc1cc(C)nc(CN2CCOc3c(cc(Cn4ccnc4C)cc3-c3cc(Cl)ccc3C)C2=O)c1]

Example 52

9-(5-Chloro-2-methylphenyl)-4-((4,6-dimethylpyridin-2-yl)methyl)-7-((2-methyl-1H-imidazol-1-yl)methyl)-3,4-dihydrobenzo[f][1,4]oxazepin-5(2H)-one The title compound (16 mg, 48% yield) was prepared from the procedure described in Example 3, Step F using 9-bromo-4-((4,6-dimethylpyridin-2-yl)methyl)-7-((2-methyl-1H-imidazol-1-yl)methyl)-3,4-dihydrobenzo[f][1,4]oxazepin-5(2H)-one (30 mg, 0.07 mmol, 1.0 equiv.), (5-chloro-2-methylphenyl)boronic acid (28 mg, 0.16 mmol, 2.5 equiv.), $K_2CO_3$ (36 mg, 0.26 mmol, 4.0 equiv.), and $PdCl_2$(dppf) (2.4 mg, 0.01 mmol, 0.05 equiv.). The reaction mixture was stirred at 100° C. for 5 h. LCMS: $R_T$=1.128 min, MS (ES) 502.0 $[M+H]^+$; $^1$H NMR (400 MHz, Chloroform-d) δ 7.71 (d, J=2.4 Hz, 1H), 7.22 (dd, J=8.2, 2.2 Hz, 1H), 7.14 (d, J=8.2 Hz, 1H), 7.07 (s, 1H), 7.04 (d, J=2.2 Hz, 1H), 6.97-6.94 (m, 1H), 6.92 (d, J=2.4 Hz, 1H), 6.90-6.86 (m, 2H), 5.05 (s, 2H), 4.83 (s, 2H), 4.07 (br s, 2H), 3.64 (br s, 2H), 2.46 (s, 3H), 2.39 (s, 3H), 2.29 (s, 3H), 1.99 (s, 3H).

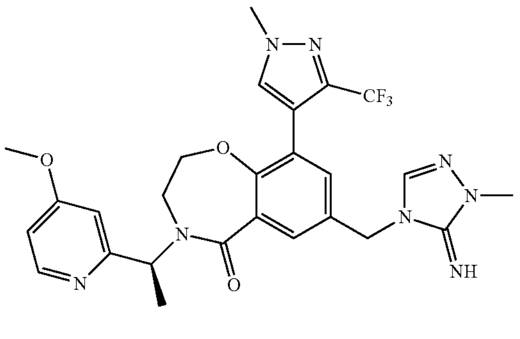

Example 53

(S)-7-((5-Imino-1-methyl-1,5-dihydro-4H-1,2,4-triazol-4-yl)methyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one The title compound (16 mg, 48% yield) was prepared from the procedure described in Example 6, Step A using (S)-7-(bromomethyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one (32 mg, 0.06 mmol, 1.0 equiv.) and 1-methyl-1H-1,2,4-triazol-5-amine (13 mg, 0.12 mmol, 3.0 equiv.). The reaction mixture was stirred at 60° C. for 12 h. LCMS: $R_T$=0.988 min, MS (ES) 556.55 $[M+H]^+$; $^1$H NMR (400 MHz, Chloroform-d) δ 8.34 (d, J=5.7 Hz, 1H), 7.75 (d, J=2.4 Hz, 1H), 7.44 (s, 1H), 7.30 (d, J=2.3 Hz, 1H), 7.18 (s, 1H), 6.94 (d, J=2.5 Hz, 1H), 6.73 (dd, J=5.7, 2.5 Hz, 1H), 6.07 (q, J=7.0 Hz, 1H), 4.79 (s, 2H), 4.08 (m, 1H), 3.96 (s, 3H), 3.83 (s, 3H), 3.79 (m, 1H), 3.61-3.51 (m, 2H), 3.42 (s, 3H), 1.62 (d, J=7.1 Hz, 3H).

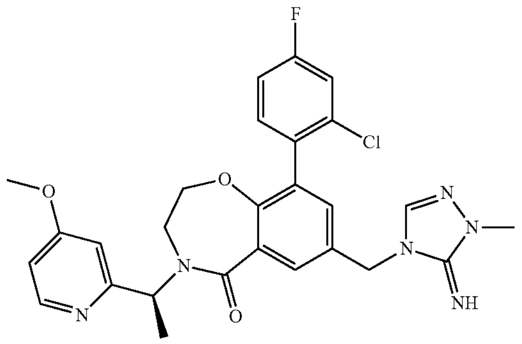

Example 54

(S)-9-(2-Chloro-4-fluorophenyl)-7-((5-imino-1-methyl-1,5-dihydro-4H-1,2,4-triazol-4-yl)methyl)-4-(1-(4-methoxypyridin-2-yl)ethyl)-3,4-dihydrobenzo[f][1,4]oxazepin-5(2H)-one The title compound (17 mg, 54% yield) was prepared from the procedure described in Example 6, Step A using (S)-7-(bromomethyl)-9-(2-chloro-4-fluorophenyl)-4-(1-(4-methoxypyridin-2-yl)ethyl)-3,4-dihydrobenzo[f][1,4]oxazepin-5(2H)-one (28 mg, 0.06 mmol, 1.0 equiv.) and 1-methyl-1H-1,2,4-triazol-5-amine (13 mg, 0.12 mmol, 3.0 equiv.). The reaction mixture was stirred at 60° C. for 12 h. LCMS: $R_T$=1.117 min, MS (ES) 517.6 $[M+H]^+$; $^1$H NMR (400 MHz, Chloroform-d) δ 8.33 (d, J=5.7 Hz, 1H), 7.73 (d, J=2.4 Hz, 1H), 7.19 (s, 1H), 7.17 (d, J=2.4 Hz, 1H), 7.01 (dd, J=8.3, 5.9 Hz, 1H), 6.96-6.89 (m, 2H), 6.86 (td, J=8.4, 2.6 Hz, 1H), 6.72 (dd, J=5.7, 2.5 Hz, 1H), 6.07 (q, J=7.0 Hz, 1H), 4.79 (s, 2H), 4.06 (m, 1H), 3.83 (s, 3H), 3.61 (m, 3H), 3.40 (s, 3H), 2.03 (s, 3H), 1.62 (d, J=7.0 Hz, 3H).

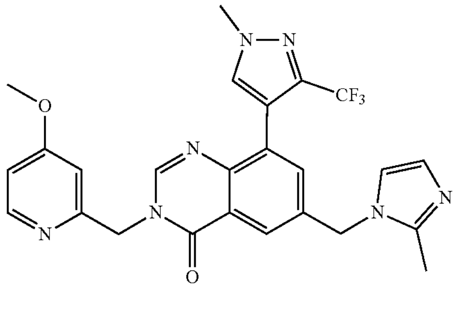 [SMILES: COc1ccnc(Cn2cnc3c(-c4cn(C)nc4C(F)(F)F)cc(Cn4ccnc4C)cc3c2=O)c1]

Example 55

3-((4-Methoxypyridin-2-yl)methyl)-6-((2-methyl-1H-imidazol-1-yl)methyl)-8-(1-methyl-3-(trifluoromethyl)-1H-pyrazol-4-yl)quinazolin-4(3H)-one Step A. Preparation of 2-amino-3-bromo-5-chloro-N-((4-methoxypyridin-2-yl)methyl)benzamide The title compound (760 mg, 98% yield) was prepared from the procedure described in Example 21, Step H using (4-methoxypyridin-2-yl)methanamine (305 mg, 2.01 mmol, 1.0 equiv.) The reaction mixture was stirred at room temperature for 16 h. LCMS: $R_T$=1.197 min, MS (ES) 383.8 $[M+H]^+$.

Step B. Preparation of 8-bromo-6-chloro-3-((4-methoxypyridin-2-yl)methyl)quinazolin-4(3H)-one The title compound (586 mg, 75% yield) was prepared from the procedure described in Example 24, Step B. The reaction mixture was stirred at 100° C. for 16 h. LCMS: RT=1.460 min, MS (ES) 393.9 [M+H]+.

Step C. Preparation of 6-chloro-3-((4-methoxypyridin-2-yl)methyl)-8-(1-methyl-3-(trifluoromethyl)-1H-pyrazol-4-yl)quinazolin-4(3H)-one The title compound (436 mg, 64% yield) was prepared from the procedure described in Example 24, Step C. The reaction mixture was stirred at 95° C. for 2 h. LCMS: RT=1.552 min, MS (ES) 463.9 [M+H]+.

Step D. Preparation of 3-((4-methoxypyridin-2-yl)methyl)-8-(1-methyl-3-(trifluoromethyl)-1H-pyrazol-4-yl)-6-vinylquinazolin-4(3H)-one The title compound (126 mg, 30% yield) was prepared from the procedure described in Example 24, Step D. The reaction mixture was stirred at 90° C. overnight. LCMS: RT=1.474 min, MS (ES) 456.0 [M+H]+.

Step E. Preparation of 6-(hydroxymethyl)-3-((4-methoxypyridin-2-yl)methyl)-8-(1-methyl-3-(trifluoromethyl)-1H-pyrazol-4-yl)quinazolin-4(3H)-one The title compound (71 mg, 59% yield) was prepared from the procedure described in Example 24, Step E. The reaction mixture was stirred at room temperature overnight. LCMS: RT=1.131 min, MS (ES) 460.0 [M+H]+.

Step F. Preparation of 6-(bromomethyl)-3-((4-methoxypyridin-2-yl)methyl)-8-(1-methyl-3-(trifluoromethyl)-1H-pyrazol-4-yl)quinazolin-4(3H)-one The title compound (32 mg, 40% yield) was prepared from the procedure described in Example 24, Step F. The reaction mixture was stirred at room temperature for 30 min. LCMS: RT=1.500 min, MS (ES) 521.8 [M+H]+.

Step G. Preparation of 3-((4-methoxypyridin-2-yl)methyl)-6-((2-methyl-1H-imidazol-1-yl)methyl)-8-(1-methyl-3-(trifluoromethyl)-1H-pyrazol-4-yl)quinazolin-4(3H)-one The title compound (17.2 mg, 55% yield) was prepared from the procedure described in Example 24, Step G using 2-methylimidazole (14.6 mg, 0.178 mmol, 3.0 equiv.). The reaction mixture was stirred at 50° C. for 4 h. LCMS: RT=1.026 min, MS (ES) 523.9 [M+H]+; 1H NMR (400 MHz, chloroform-d) δ 8.47 (s, 1H), 8.38 (d, J=5.6 Hz, 1H), 8.11 (d, J=2.4 Hz, 1H), 7.72 (s, 1H), 7.45 (d, J=1.6 Hz, 1H), 6.99-6.87 (m, 2H), 6.74-6.72 (m, 1H), 6.27-6.22 (m, 1H), 5.16 (s, 2H), 4.00 (s, 3H), 3.83 (s, 3H), 2.35 (s, 3H), 1.86 (d, J=7.2 Hz, 3H), 1.25 (s, 1H); 19F NMR (376 MHz, chloroform-d) δ−59.13.

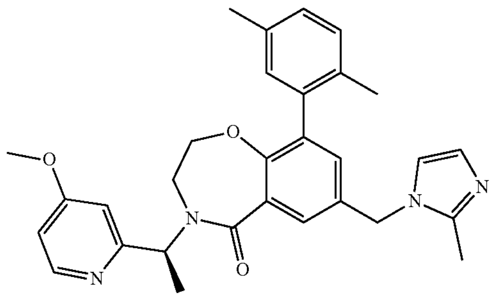 [SMILES: COc1ccnc([C@H](C)N2CCOc3c(cc(Cn4ccnc4C)cc3-c3cc(C)ccc3C)C2=O)c1]

Example 56

(S)-9-(2,5-Dimethylphenyl)-4-(1-(4-methoxypyridin-2-yl)ethyl)-7-((2-methyl-1H-imidazol-1-yl)methyl)-3,4-dihydrobenzo[f][1,4]oxazepin-5(2H)-one Step A. Preparation of (S)-9-bromo-7-(bromomethyl)-4-(1-(4-methoxypyridin-2-yl)ethyl)-3,4-dihydrobenzo[f][1,4]oxazepin-5(2H)-one The crude title compound was prepared from the procedure described in Example 3, Step I using (S)-9-bromo-7-(hydroxymethyl)-4-(1-(4-methoxypyridin-2-yl)ethyl)-3,4-dihydrobenzo[f][1,4]oxazepin-5(2H)-one (14.8 mg, 0.04 mmol, 1.0 equiv.) and PBr3 (10.0 µL, 0.07 mmol, 2.0 equiv.). LCMS: RT=1.318 min, MS (ES) 471.2 [M+H].

Step B. Preparation of (S)-9-bromo-4-(1-(4-methoxypyridin-2-yl)ethyl)-7-((2-methyl-1H-imidazol-1-yl)methyl)-3,4-dihydrobenzo[f][1,4]oxazepin-5(2H)-one The crude title compound was prepared from the procedure described in Example 11, Step D using (S)-9-bromo-7-(bromomethyl)-4-(1-(4-methoxypyridin-2-yl)ethyl)-3,4-dihydrobenzo[f][1,4]oxazepin-5(2H)-one (17.1 mg, 0.04 mmol, 1.0 equiv.), 2-methyl-1H-imidazole (9.0 mg, 0.11 mmol, 3.0 equiv.), and N,N-diisopropylethylamine (30.0 µL, 0.18 mmol, 5.0 equiv.). The reaction mixture was stirred at 90° C. for 12 h. LCMS: RT=0.914 min, MS (ES) 472.4 $[M+H]^+$.

Step C. Preparation of (S)-9-(2,5-dimethylphenyl)-4-(1-(4-methoxypyridin-2-yl)ethyl)-7-((2-methyl-1H-imidazol-1-yl)methyl)-3,4-dihydrobenzo[f][1,4]oxazepin-5(2H)-one The title compound (8.9 mg, 49% yield over 2 steps) was prepared from the procedure described in Example 3, Step F using (S)-9-bromo-4-(1-(4-methoxypyridin-2-yl)ethyl)-7-((2-methyl-1H-imidazol-1-yl)methyl)-3,4-dihydrobenzo[f][1,4]oxazepin-5(2H)-one (17.1 mg, 0.04 mmol, 1.0 equiv.), (2,5-dimethylphenyl)boronic acid (13.6 mg, 0.09 mmol, 2.5 equiv.), $K_2CO_3$ (20.1 mg, 0.15 mmol, 4.0 equiv.), and PdCl2(dppf) (1.4 mg, 0.01 mmol, 0.05 equiv.). The reaction mixture was stirred at 100° C. for 6 h. LCMS: RT=1.155 min, MS (ES) 497.6 $[M+H]^+$; 1H NMR (400 MHz, Chloroform-d) δ 8.33 (d, J=5.7 Hz, 1H), 7.64 (d, J=2.4 Hz, 1H), 7.10 (d, J=7.8 Hz, 1H), 7.08-7.02 (m, 1H), 6.98-6.89 (m, 3H), 6.88-6.79 (m, 2H), 6.72 (dd, J=5.7, 2.5 Hz, 1H), 6.08 (q, J=7.0 Hz, 1H), 5.03 (s, 2H), 4.05 (m, 1H), 3.83 (s, 3H), 3.58 (m, 3H), 2.36 (s, 3H), 2.30 (s, 3H), 1.97 (s, 3H), 1.63 (d, J=7.1 Hz, 3H).

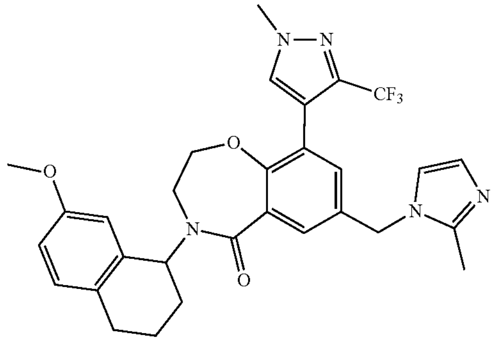 [SMILES: COc1ccc2c(c1)C(N1CCOc3c(cc(Cn4ccnc4C)cc3-c3cn(C)nc3C(F)(F)F)C1=O)CCC2]

Example 57

4-(7-Methoxy-1,2,3,4-tetrahydronaphthalen-1-yl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one 7-((2-Methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one (30 mg, 0.0740 mmol, 1.0 equiv.) was dissolved in DMF (0.75 mL) and then NaH (3.6 mg, 0.148 mmol, 2.0 equiv.) was added. The reaction was stirred at room temperature for 15 min, and 1-bromo-7-methoxy-1,2,3,4-tetrahydronaphthalene (35.5 mg, 0.148 mmol, 2.0 equiv.) was added. The reaction was stirred for 15 min then quenched with sat. aq. $NH_4Cl$ (5 mL). The resulting mixture was extracted with EtOAc (3x5 mL), and the combined organic layer was washed with brine, dried ($MgSO_4$), filtered and concentrated. The residue was purified by reverse phase HPLC (Phenomenex Gemini C18, $H_2O/CH_3CN$ gradient from 15-95% $CH_3CN$, 0.1% TFA) to yield the title compound (19.2 mg, 45% yield). To remove TFA, the organic layer was washed with $K_2CO_3$ (sat.). LCMS: $R_T$=1.565 min, MS (ES) 565.9 $[M+H]^+$; $^1H$ NMR (400 MHz, MeOD) δ 7.82 (s, 1H), 7.63 (d, J=2.0 Hz, 1H), 7.23 (d, J=2.0 Hz, 1H), 7.12 (d, J=1.6 Hz, 1H), 7.08 (d, J=8.4 Hz, 1H), 6.90 (d, J=1.2 Hz, 1H), 6.80-6.77 (m, 1H), 6.71 (d, J=2.8 Hz, 1H), 5.99-5.5.95 (m, 1H), 5.27 (s, 2H), 4.12-4.01 (m, 2H), 3.99 (s, 3H), 3.77 (s, 3H), 2.86-2.72 (m, 2H), 2.36 (s, 3H), 2.20-2.15 (m, 1H), 2.09-2.04 (m, 1H), 1.94-1.80 (m, 2H), 1.31-1.26 (m, 2H).

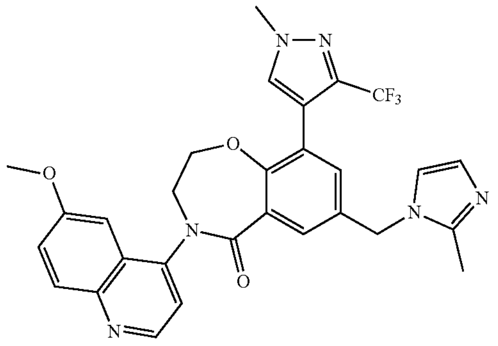 [SMILES: COc1ccc2nccc(N3CCOc4c(cc(Cn5ccnc5C)cc4-c4cn(C)nc4C(F)(F)F)C3=O)c2c1]

Example 58

4-(6-Methoxyquinolin-4-yl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one 7-((2-Methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one (10 mg, 0.0247 mmol, 1.0 equiv.) was dissolved in 1,4-dioxane (0.25 mL) then 4-bromo-6-methoxyquinoline (11.7 mg, 0.0494 mmol, 2.0 equiv.), $Cs_2CO_3$ (16.1 mg, 0.0494 mmol, 2.0 equiv.), $Pd_2(dba)_3$ (2.3 mg, 0.00247 mmol, 0.1 equiv.) and XantPhos (2.9 mg, 0.0494 mmol, 0.2 equiv.) were added. The reaction was degassed by bubbling argon through the mixture for 10 min then heated to 110° C. for 4 h. The reaction was cooled to room temperature and $H_2O$ (5 mL) was added. The aqueous layer was extracted with EtOAc (3x5 mL), and combined organic layer was washed with brine, dried ($MgSO_4$), filtered and concentrated. The residue was purified by reverse phase HPLC (Phenomenex Gemini C18, $H_2O/CH_3CN$ gradient from 15-95% $CH_3CN$, 0.1% TFA) to yield the title compound (1.9 mg, 14% yield). To remove TFA, the organic layer was washed with $K_2CO_3$ (sat.). LCMS: $R_T$=1.268 min, MS (ES) 562.9 $[M+H]^+$; $^1H$ NMR (400 MHz, MeOD) δ 8.83 (d, J=4.8 Hz, 1H), 8.06 (d, J=9.2 Hz, 1H), 7.91 (s, 1H), 7.63 (d, J=2.4 Hz, 1H), 7.57 (d, J=4.8 Hz, 1H), 7.52-7.49 (m, 1H), 7.35 (d, J=2.4 Hz, 1H), 7.14 (s, 1H), 6.90 (s, 1H), 5.29 (s, 2H), 4.48-4.40 (m, 1H), 4.29-4.24 (m, 1H), 4.17-4.07 (m, 1H), 4.05-3.99 (m, 4H), 3.90 (s, 3H), 2.37 (s, 3H).

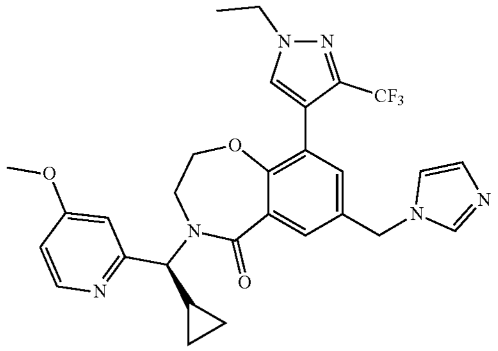 [SMILES: CCn1cc(-c2cc(Cn3ccnc3)cc3c2OCCN([C@H](c2cc(OC)ccn2)C2CC2)C3=O)c(C(F)(F)F)n1]

Example 59

(S)-7-((1H-Imidazol-1-yl)methyl)-4-(cyclopropyl(4-methoxypyridin-2-yl)methyl)-9-(1-ethyl-3-(trifluoromethyl)-1H-pyrazol-4-yl)-3,4-dihydrobenzo[f][1,4]oxazepin-5(2H)-one Step A. Preparation of methyl (S)-9-bromo-4-(cyclopropyl(4-methoxypyridin-2-yl)methyl)-5-oxo-2,3,4,5-tetrahydrobenzo[f][1,4]oxazepine-7-carboxylate DCM (8 mL) was added to dimethyl 5-bromo-4-(2-oxoethoxy)isophthalate (620 mg, 1.88 mmol, 1.0 equiv.), (S)-cyclopropyl(4-methoxypyridin-2-yl)methanamine (402 mg, 2.25 mmol, 1.2 equiv.) and diisopropyl ethyl amine (0.65 mL, 3.76 mmol, 2.0 equiv.). The reaction was stirred at room temperature overnight then $NaBH_4$ (35.5 mg, 0.939 mmol, 0.5 equiv.) was added. The reaction was stirred for 4 h at room temperature and concentrated. The residue was taken up in EtOAc (10 mL) and washed with water (10 mL), and the organic layer was dried ($MgSO_4$), filtered and concentrated. To the residue was added 1,5,7-Triazabicyclo[4.4.0]dec-5-ene (50 mg, 0.359 mmol) and the mixture was heated neat at 110° C. for 1 hour. The reaction was cooled to room temperature then $H_2O$ (5 mL) and EtOAc (5 mL) were added. The layers were separated and the aqueous layer was extracted with EtOAc (3×5 mL). The combined organic layer was washed with brine, dried ($MgSO_4$), filtered and concentrated. The residue was purified by flash chromatography (Combi-flash Rf, Hex/EtOAc=0-75% gradient) to afford the title compound (91 mg, 11% yield). LCMS: $R_T$=1.404 min, MS (ES) 460.9 $[M+H]^+$.

Step B. Preparation of methyl (S)-4-(cyclopropyl(4-methoxypyridin-2-yl)methyl)-9-(1-ethyl-3-(trifluoromethyl)-1H-pyrazol-4-yl)-5-oxo-2,3,4,5-tetrahydrobenzo[f][1,4]oxazepine-7-carboxylate The title compound (61 mg, 61% yield) was prepared from the procedure described in Example 3, Step G using 1-ethyl-3-(trifluoromethyl)pyrazole-4-boronic acid (57.7 mg, 0.277 mmol, 1.5 equiv.). The reaction mixture was stirred at 95° C. for 1 h. L CMS: $R_T$=1.553 min, MS (ES) 544.9 $[M+H]^+$.

Step C. Preparation of (S)-4-(cyclopropyl(4-methoxypyridin-2-yl)methyl)-9-(1-ethyl-3-(trifluoromethyl)-1H-pyrazol-4-yl)-7-(hydroxymethyl)-3,4-dihydrobenzo[f][1,4]oxazepin-5(2H)-one The title compound (46 mg, 79% yield) was prepared from the procedure described in Example 3, Step H. The reaction mixture was stirred at 75° C. for 5 hour. LCMS: RT=1.329 min, MS (ES) 517.0 [M+H]+.

Step D. Preparation of (S)-7-(bromomethyl)-4-(cyclopropyl(4-methoxypyridin-2-yl)methyl)-9-(1-ethyl-3-(trifluoromethyl)-1H-pyrazol-4-yl)-3,4-dihydrobenzo[f][1,4]oxazepin-5(2H)-one The title compound (46 mg, 89% yield) was prepared from the procedure described in Example 3, Step I. The reaction mixture was stirred at room temperature for 2 h. LCMS: RT=1.644 min, MS (ES) 578.8 [M+H]+.

Step E. Preparation of (S)-7-((1H-imidazol-1-yl)methyl)-4-(cyclopropyl(4-methoxypyridin-2-yl)methyl)-9-(1-ethyl-3-(trifluoromethyl)-1H-pyrazol-4-yl)-3,4-dihydrobenzo[f][1,4] oxazepin-5(2H)-one The title compound (4.4 mg, 30% yield) was prepared from the procedure described in Example 3, Step J using imidazole (5.3 mg, 0.0778 mmol, 3.0 equiv.). The reaction mixture was stirred at 50° C. for 1 hours. LCMS: RT=1.256 min, MS (ES) 567.0 [M+H]+; 1H NMR (400 MHz, chloroform-d) δ 8.37 (d, J=5.6 Hz, 1H), 7.70 (d, J=2.4 Hz, 1H), 7.55 (s, 1H), 7.46 (s, 1H), 7.16 (d, J=2.4 Hz, 1H), 7.08 (s, 1H), 6.95 (d, J=2.4 Hz, 1H), 6.92 (s, 1H), 6.75 (dd, J=5.6, 2.4 Hz, 1H), 5.09 (s, 2H), 5.02 (d, J=10.0 Hz, 1H), 4.37-4.31 (m, 1H), 4.26 (q, J=7.2 Hz, 2H), 4.03-3.98 (m, 1H), 3.92-3.87 (m, 1H), 3.85 (s, 3H), 3.74-3.67 (m, 1H), 1.73-1.65 (m, 1H), 1.56 (t, J=7.2 Hz, 3H), 0.78-0.73 (m, 1H), 0.68-0.59 (m, 2H), 0.58-0.55 (m, 1H).

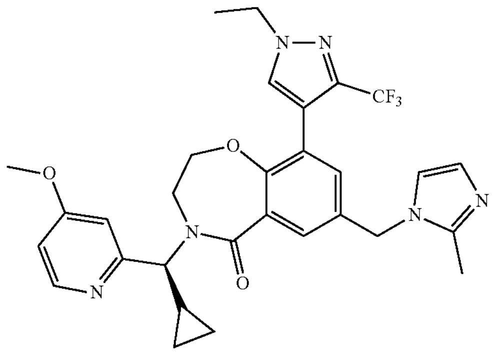 [SMILES: CCn1cc(-c2cc(Cn3ccnc3C)cc3c2OCCN([C@H](c2cc(OC)ccn2)C2CC2)C3=O)c(C(F)(F)F)n1]

Example 60

(S)-4-(Cyclopropyl(4-methoxypyridin-2-yl)methyl)-9-(1-ethyl-3-(trifluoromethyl)-1H-pyrazol-4-yl)-7-((2-methyl-1H-imidazol-1-yl)methyl)-3,4-dihydrobenzo[f][1,4]oxazepin-5(2H)-one The title compound (3.8 mg, 25% yield) was prepared from the procedure described in Example 59, Step E using 2-methylimidazole (6.4 mg, 0.0778 mmol, 3.0 equiv.). The reaction mixture was stirred at 50° C. for 1 h. LCMS: $R_T$=1.277 min, MS (ES) 580.9 $[M+H]^+$; $^1H$ NMR (400 MHz, chloroform-d) δ 8.38 (d, J=6.0 Hz, 1H), 7.64 (d, J=2.4 Hz, 1H), 7.46 (s, 1H), 7.03 (d, J=2.0 Hz, 1H), 6.95 (t, J=2.0 Hz, 2H), 6.86 (d, J=1.2 Hz, 1H), 6.75 (dd, J=5.6, 2.4 Hz, 1H), 5.02 (s, 2H), 4.35-4.30 (m, 1H), 4.26 (q, J=7.2 Hz, 2H), 4.03-3.99 (m, 1H), 3.95-3.89 (m, 2H), 3.87 (s, 3H), 3.76-3.69 (m, 1H), 2.36 (s, 3H), 1.73-1.65 (m, 1H), 1.56 (t, J=7.6 Hz, 3H), 0.80-0.75 (m, 1H), 0.72-0.59 (m, 2H), 0.57-0.52 (m, 1H).

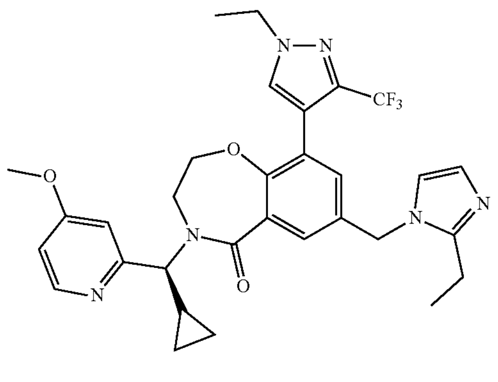 [SMILES: CCc1nccn1Cc1cc2c(c(-c3cn(CC)nc3C(F)(F)F)c1)OCCN([C@H](c1cc(OC)ccn1)C1CC1)C2=O]

Example 61

(S)-4-(Cyclopropyl(4-methoxypyridin-2-yl)methyl)-7-((2-ethyl-1H-imidazol-1-yl)methyl)-9-(1-ethyl-3-(trifluoromethyl)-1H-pyrazol-4-yl)-3,4-dihydrobenzo[f][1,4]oxazepin-5(2H)-one The title compound (3.3 mg, 21% yield) was prepared from the procedure described in Example 59, Step E using 2-ethylimidazole (7.5 mg, 0.0778 mmol, 3.0 equiv.). The reaction mixture was stirred at 50° C. for 1 h. LCMS: $R_T$=1.273 min, MS (ES) 595.0 $[M+H]^+$; $^1H$ NMR (400 MHz, chloroform-d) δ 8.37 (d, J=5.6 Hz, 1H), 7.64 (d, J=2.4 Hz, 1H), 7.45 (s, 1H), 7.02 (d, J=2.0 Hz, 1H), 6.98 (d, J=1.2 Hz, 1H), 6.95 (d, J=2.4 Hz, 1H), 6.85 (d, J=1.2 Hz, 1H), 6.77 (dd, J=5.6, 2.4 Hz, 1H), 5.05 (s, 2H), 4.35-4.30 (m, 1H), 4.25 (q, J=7.6 Hz, 2H), 4.00-3.96 (m, 1H), 3.92-3.86 (m, 1H), 3.85 (s, 3H), 3.73-3.66 (m, 1H), 2.68 (q, J=7.4 Hz, 2H), 1.91-1.83 (m, 1H), 1.74-1.62 (m, 1H), 1.56 (t, J=7.4 Hz, 3H), 1.34 (t, J=7.4 Hz, 3H), 0.79-0.73 (m, 1H), 0.72-0.57 (m, 2H), 0.54-0.48 (m, 1H).

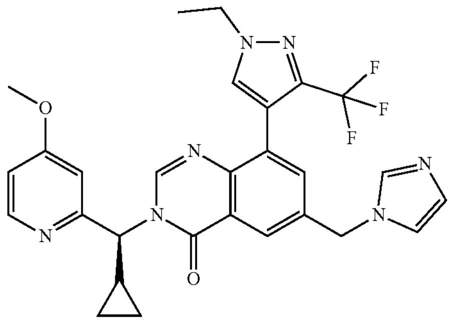 [SMILES: CCn1cc(-c2cc(Cn3ccnc3)cc3c(=O)n([C@H](c4cc(OC)ccn4)C4CC4)cnc23)c(C(F)(F)F)n1]

Example 62

(S)-6-((1H-imidazol-1-yl)methyl)-3-(cyclopropyl(4-methoxypyridin-2-yl)methyl)-8-(1-ethyl-3-(trifluoromethyl)-1H-pyrazol-4-yl)quinazolin-4(3H)-one Step A. Preparation of (S)-2-amino-3-bromo-5-chloro-N-(cyclopropyl(4-methoxypyridin-2-yl)methyl)benzamide The title compound (900 mg, 92% yield) was prepared from the procedure described in Example 21, Step H using (S)-cyclopropyl(4-methoxypyridin-2-yl)methanamine (513 mg, 2.87 mmol, 1.2 equiv.) The reaction mixture was stirred at room temperature for 16 h. LCMS: RT=1.420 min, 411.9 min, MS (ES) 411.9 [M+H]+; 1H NMR (400 MHz, chloroform-d) δ 8.49 (d, J=6.9 Hz, 1H), 8.04 (s, 1H), 7.62 (d, J=2.3 Hz, 1H), 7.56 (d, J=5.7 Hz, 1H), 7.50 (d, J=2.2 Hz, 1H), 7.33 (d, J=2.6 Hz, 1H), 7.26 (s, 2H), 4.28-4.24 (m, 1H), 4.14 (s, 1H), 1.64-1.52 (m, 1H), 0.92-0.77 (m, 2H), 0.64-0.50 (m, 2H).

Step B. Preparation of (S)-8-bromo-6-chloro-3-(cyclopropyl(4-methoxypyridin-2-yl)methyl)quinazolin-4(3H)-one The title compound (537 mg, 58% yield) was prepared from the procedure described in Example 24, Step B. The reaction was heated at 100° C. for 16 h. LCMS: RT=1.640 min, MS (ES) 419.8 [M+H]+; 1H NMR (400 MHz, chloroform-d) δ 8.88 (s, 1H), 8.36 (d, J=5.8 Hz, 1H), 8.20 (d, J=2.3 Hz, 1H), 7.98 (d, J=2.4 Hz, 1H), 6.97 (d, J=2.4 Hz, 1H), 6.73 (dd, J=5.8, 2.7 Hz, 1H), 4.30-4.22 (m, 1H), 3.85 (s, 3H), 1.84-1.75 (m, 1H), 0.90-0.83 (m, 1H), 0.76-0.63 (m, 2H), 0.50-0.44 (m, 1H).

Step C. Preparation of (S)-6-chloro-3-(cyclopropyl(4-methoxypyridin-2-yl)methyl)-8-(1-ethyl-3-(trifluoromethyl)-1H-pyrazol-4-yl)quinazolin-4(3H)-one The title compound (394 mg, 80% yield) was prepared from the procedure described in Example 1, Step C using (1-ethyl-3-(trifluoromethyl)-1H-pyrazol-4-yl)boronic acid (305 mg, 1.47 mmol, 1.5 equiv.) The reaction mixture was stirred at 80° C. for 12 h. LCMS: RT=1.807 min, MS (ES) 503.9 [M+H]+; 1H NMR (400 MHz, chloroform-d) δ 8.72 (s, 1H), 8.36 (d, J=5.7 Hz, 1H), 8.23 (d, J=2.5 Hz, 1H), 7.82 (s, 1H), 7.74 (d, J=2.4 Hz, 1H), 6.98 (d, J=2.4 Hz, 1H), 6.73 (dd, J=5.7, 2.7 Hz, 1H), 5.20 (d, J=10.1 Hz, 1H), 4.30 (q, J=7.3 Hz, 2H), 3.86 (s, 3H), 1.85-1.75 (m, 1H), 1.59 (t, J=7.3 Hz, 3H), 0.90-0.81 (m, 1H), 0.76-0.61 (m, 2H), 0.52-0.46 (m, 1H).

Step D. Preparation of (S)-3-(cyclopropyl(4-methoxypyridin-2-yl)methyl)-8-(1-ethyl-3-(trifluoromethyl)-1H-pyrazol-4-yl)-6-vinylquinazolin-4(3H)-one The title compound (170 mg, 44% yield) was prepared from the procedure described in Example 1, Step D. The reaction mixture was stirred at 100° C. overnight. LCMS: RT=1.604 min, MS (ES) 496.0 [M+H]+; 1H NMR (400 MHz, chloroform-d) δ 8.69 (s, 1H), 8.35 (d, J=5.6 Hz, 1H), 8.23 (d, J=1.6 Hz, 1H), 7.87 (s, 1H), 7.83 (s, 1H), 6.98 (s, 1H), 6.77 (d, J=17.6 Hz, 1H), 6.61 (dd, J=6.0, 2.0 Hz, 1H), 5.75 (d, J=17.2 Hz, 1H), 4.75 (d, J=12.0 Hz, 1H), 4.62 (d, J=10.4 Hz, 1H), 4.30 (d, J=7.2 Hz, 2H), 3.86 (s, 3H), 1.86-1.76 (m, 1H), 1.59 (d, J=7.2 Hz, 3H), 0.89-0.81 (m, 1H), 0.76-0.62 (m, 2H), 0.52-0.46 (m, 1H).

Step E. Preparation of (S)-3-(cyclopropyl(4-methoxypyridin-2-yl)methyl)-8-(1-ethyl-3-(trifluoromethyl)-1H-pyrazol-4-yl)-6-(hydroxymethyl)quinazolin-4(3H)-one Ozone was bubbled through a solution of dimethyl (S)-3-(cyclopropyl(4-methoxypyridin-2-yl)methyl)-8-(1-ethyl-3-(trifluoromethyl)-1H-pyrazol-4-yl)-6-vinylquinazolin-4(3H)-one (170 mg, 0.343 mmol, 1 equiv) in DCM (20 mL, 0.02 M) at −78° C. for 30 min. After the solution was purged with air, dimethyl sulfide (0.08 mL, 1.03 mmol, 3 equiv) was added. The reaction mixture was allowed to warm to 23° C. and stirred overnight. Crude (S)-3-(cyclopropyl(4-methoxypyridin-2-yl)methyl)-8-(1-ethyl-3-(trifluoromethyl)-1H-pyrazol-4-yl)-4-oxo-3,4-dihydroquinazoline-6-carbaldehyde was then concentrated and dissolved in DCM (2 mL). Sodium triacetoxyhydroborohydride (218 mg, 1.03 mmol, 3 equiv) was added, and the reaction mixture was stirred at 35° C. overnight. The reaction mixture was diluted with DCM and washed with sat. NaHCO3. The organic layer was dried over MgSO4, and concentrated. The residue was purified by flash chromatography (Combi-flash Rf, Hex/EtOAc=0-100% gradient) to afford the title compound (36 mg, 21% yield, over two steps). LCMS: RT=1.259 min, MS (ES) 499.9 [M+H]+; 1H NMR (400 MHz, chloroform-d) δ 8.69 (s, 1H), 8.33 (d, J=5.6 Hz, 1H), 8.22 (d, J=1.6 Hz, 1H), 7.77 (s, 2H), 6.98 (d, J=2.4 Hz, 1H), 6.69 (dd, J=5.6, 2.4 Hz, 1H), 5.27 (s, 1H), 5.20 (d, J=10.0 Hz, 1H), 4.77 (s, 2H), 4.26 (q, J=7.2 Hz, 2H), 3.82 (s, 3H), 1.83-1.73 (m, 1H), 1.56 (t, J=7.2 Hz, 3H), 0.86-0.78 (m, 1H), 0.72-0.56 (m, 2H), 0.50-0.43 (m, 1H).

Step F. Preparation of (S)-6-(bromomethyl)-3-(cyclopropyl(4-methoxypyridin-2-yl)methyl)-8-(1-ethyl-3-(trifluoromethyl)-1H-pyrazol-4-yl)quinazolin-4(3H)-one The title compound (35 mg, quant. yield) was prepared from the procedure described in Example 1, Step F. The reaction mixture was stirred at room temperature for 30 minutes. LCMS: RT=1.571 min, MS (ES) 561.9 [M+H]+.

Step G. Preparation of (S)-6-((1H-imidazol-1-yl)methyl)-3-(cyclopropyl(4-methoxypyridin-2-yl)methyl)-8-(1-ethyl-3-(trifluoromethyl)-1H-pyrazol-4-yl)quinazolin-4(3H)-one The title compound (14.3 mg, 36% yield) was prepared from the procedure described in Example 3, Step J using imidazole (14.7 mg, 0.216 mmol, 3.0 equiv.). The reaction mixture was stirred at 50° C. overnight. LCMS: RT=1.153 min, MS (ES) 550.0 [M+H]+; 1H NMR (400 MHz, chloroform-d) δ 8.74 (s, 1H), 8.35 (d, J=6.0 Hz, 1H), 8.05 (d, J=1.6 Hz, 1H), 7.73 (s, 1H), 7.48 (s, 2H), 7.01 (s, 1H), 6.90 (d, J=2.8 Hz, 1H), 6.83 (s, 1H), 6.63 (dd, J=5.6, 2.0 Hz, 1H), 5.13-5.09 (m, 3H), 4.19 (q, J=8.0 Hz, 2H), 3.76 (s, 3H), 1.76-1.66 (m, 1H), 1.49 (t, J=8.0 Hz, 3H), 0.80-0.73 (m, 1H), 0.67-0.53 (m, 2H), 0.43-0.36 (m, 1H); 19F NMR (376 MHz, chloroform-d) δ−58.98.

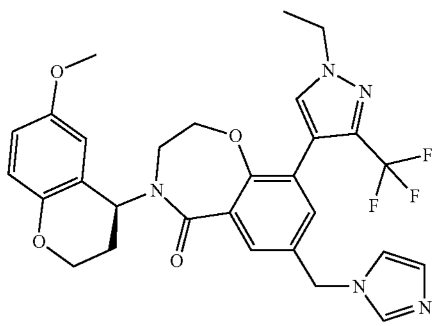 [SMILES: CCn1cc(-c2cc(Cn3ccnc3)cc3c2OCCN([C@H]2CCOc4ccc(OC)cc42)C3=O)c(C(F)(F)F)n1]

Example 63

(S)-7-((1H-imidazol-1-yl)methyl)-9-(1-ethyl-3-(trifluoromethyl)-1H-pyrazol-4-yl)-4-(6-methoxychroman-4-yl)-3,4-dihydrobenzo[f][1,4]oxazepin-5(2H)-one

Step A. Preparation of methyl (S)-9-bromo-4-(6-methoxychroman-4-yl)-5-oxo-2,3,4,5-tetrahydrobenzo[f][1,4]oxazepine-7-carboxylate The title compound (145 mg, 69% yield) was prepared from the procedure described in Example 59, Step A using (S)-6-methoxychroman-4-aminium chloride (107 mg, 0.498 mmol, 1.1 equiv.). The reaction mixture was stirred at 110° C. overnight. LCMS: RT=1.887 min, MS (ES) 461.8 [M+H]+; 1H NMR (400 MHz, chloroform-d) δ 8.53 (d, J=2.0 Hz, 1H), 8.40 (d, J=2.0 Hz, 1H), 6.85-6.69 (m, 3H), 6.19-6.15 (m, 1H), 4.41-4.30 (m, 4H), 4.25-4.15 (m, 2H), 3.96 (s, 3H), 3.76 (s, 3H), 3.38-3.28 (m, 2H), 2.35-2.27 (m, 1H), 2.20-2.09 (m, 1H).

Step B. Preparation of methyl (S)-9-(1-ethyl-3-(trifluoromethyl)-1H-pyrazol-4-yl)-4-(6-methoxychroman-4-yl)-5-oxo-2,3,4,5-tetrahydrobenzo[f][1,4]oxazepine-7-carboxylate The title compound (136 mg, 80% yield) was prepared from the procedure described in Example 3, Step G using 1-ethyl-3-(trifluoromethyl)pyrazole-4-boronic acid (77.7 mg, 0.374 mmol, 1.2 equiv.). The reaction mixture was stirred at 80° C. overnight. LCMS: RT=1.857 min, MS (ES) 546.0 [M+H]+; 1H NMR (400 MHz, chloroform-d) δ 8.64 (d, J=2.4 Hz, 1H), 8.09 (d, J=2.4 Hz, 1H), 7.48 (s, 1H), 6.81-6.74 (m, 2H), 6.64 (d, J=2.4 Hz, 1H), 6.17-6.13 (m, 1H), 4.30-4.07 (m, 6H), 3.91 (s, 3H), 3.70 (s, 3H), 3.37-3.24 (m, 2H), 2.29-2.20 (m, 1H), 2.12-2.03 (m, 1H), 1.54 (t, J=7.6 Hz, 3H).

Step C. Preparation of (S)-9-(1-ethyl-3-(trifluoromethyl)-1H-pyrazol-4-yl)-7-(hydroxymethyl)-4-(6-methoxychroman-4-yl)-3,4-dihydrobenzo[f][1,4]oxazepin-5(2H)-one Lithium triethylborohydride (1 M THF, 0.748 mmol, 3 equiv.) was added dropwise to a solution of methyl (S)-9-(1-ethyl-3-(trifluoromethyl)-1H-pyrazol-4-yl)-4-(6-methoxychroman-4-yl)-5-oxo-2,3,4,5-tetrahydrobenzo[f][1,4]oxazepine-7-carboxylate (136 mg, 0.249 mmol) in THE at 0° C. The reaction was stirred for 40 min, quenched with sat. $NaHCO_3$, and extracted with EtOAc. The combined organic layer was dried (MgSO4), concentrated to yield the crude title product, which was used without further purification (130 mg, quant. yield). LCMS: RT=1.628 min, MS (ES) 517.9 [M+H]+; 1H NMR (400 MHz, chloroform-d) δ 7.89-7.82 (m, 1H), 7.54-7.44 (m, 2H), 6.82-6.72 (m, 2H), 6.70-6.67 (m, 1H), 6.17 (dd, J=10.4, 5.5 Hz, 1H), 4.74 (d, J=5.8 Hz, 1H), 4.32-4.13 (m, 4H), 4.05-4.00 (m, 2H), 3.73 (s, 3H), 3.35-3.20 (m, 2H), 2.30-2.23 (m, 1H), 2.15-2.04 (m, 1H), 1.56 (t, J=7.4 Hz, 1H).

Step D. Preparation of (S)-7-(bromomethyl)-9-(1-ethyl-3-(trifluoromethyl)-1H-pyrazol-4-yl)-4-(6-methoxychroman-4-yl)-3,4-dihydrobenzo[f][1,4]oxazepin-5(2H)-one The title compound (119 mg, 82% yield) was prepared from the procedure described in Example 3, Step I. The reaction mixture was stirred at room temperature for 2 h. LCMS: RT=1.942 min, MS (ES) 579.9 [M+H]+; 1H NMR (400 MHz, chloroform-d) δ 7.91 (d, J=2.4 Hz, 1H), 7.52 (s, 1H), 7.48 (d, J=2.4 Hz, 1H), 6.80-6.73 (m, 2H), 6.68-6.60 (m, 1H), 6.15 (dd, J=10.4, 5.8 Hz, 1H), 4.52 (s, 2H), 4.31-4.00 (m, 6H), 3.72 (s, 3H), 3.34-3.09 (m, 2H), 2.29-2.23 (m, 1H), 2.17-2.05 (m, 1H), 1.56 (t, J=7.3 Hz, 3H).

Step E. Preparation of (S)-7-((1H-imidazol-1-yl)methyl)-9-(1-ethyl-3-(trifluoromethyl)-1H-pyrazol-4-yl)-4-(6-methoxychroman-4-yl)-3,4-dihydrobenzo[f][1,4]oxazepin-5(2H)-one The title compound (14.3 mg, 25% yield) was prepared from the procedure described in Example 3, Step J using imidazole (21 mg, 0.30 mmol, 3.0 equiv.). The reaction mixture was stirred at 50° C. overnight. LCMS: RT=1.441 min, MS (ES) 568.0 [M+H]+; 1H NMR (400 MHz, chloroform-d) δ 7.77 (d, J=2.2 Hz, 1H), 7.57 (s, 1H), 7.46 (s, 1H), 7.19 (d, J=2.0 Hz, 1H), 7.10 (s, 1H), 6.96 (m, 1H), 6.80-6.74 (m, 2H), 6.67 (d, J=2.5 Hz, 1H), 6.13 (dd, J=10.4, 5.4 Hz, 1H), 5.15 (s, 2H), 4.30-4.15 (m, 4H), 4.07-4.02 (m, 2H), 3.72 (s, 3H), 3.30-3.20 (m, 2H), 2.28-2.23 (m, 1H), 2.14-2.05 (m, 1H), 1.54 (t, J=7.3 Hz, 3H); 19F NMR (376 MHz, chloroform-d) δ-59.61.

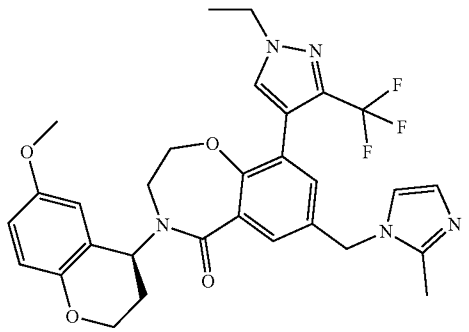 [SMILES: CCn1cc(-c2cc(Cn3ccnc3C)cc3c2OCCN([C@H]2CCOc4ccc(OC)cc42)C3=O)c(C(F)(F)F)n1]

Example 64

(S)-9-(1-ethyl-3-(trifluoromethyl)-1H-pyrazol-4-yl)-4-(6-methoxychroman-4-yl)-7-((2-methyl-1H-imidazol-1-yl)methyl)-3,4-dihydrobenzo[f][1,4]oxazepin-5(2H)-one The title compound (11.7 mg, 20% yield) was prepared from the procedure described in Example 3, Step J using 2-methyl-1H-imidazole (21 mg, 0.30 mmol, 3.0 equiv.). The reaction mixture was stirred at 50° C. overnight. LCMS: $R_T$=1.461 min, MS (ES) 582.0 $[M+H]^+$; $^1H$ NMR (400 MHz, chloroform-d) δ 7.71 (d, J=2.2 Hz, 1H), 7.46 (s, 1H), 7.07 (d, J=2.0 Hz, 1H), 6.96 (s, 1H), 6.89 (d, J=0.7 Hz, 1H), 6.80-6.73 (m, 2H), 6.68 (d, J=2.5 Hz, 1H), 6.13 (d, J=10.0, 5.4 Hz, 1H), 5.07 (s, 2H), 4.31-4.14 (m, 4H), 4.08-3.97 (m, 2H), 3.72 (s, 3H), 3.35-3.21 (m, 2H), 2.38 (s, 3H), 2.29-2.23 (m, 1H), 2.16-2.05 (m, 1H), 1.55 (t, J=7.3 Hz, 3H); $^{19}F$ NMR (376 MHz, chloroform-d) δ-59.55.

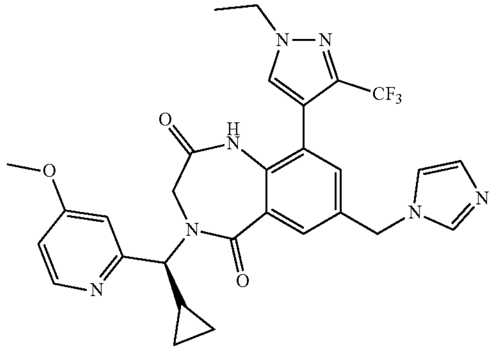 [SMILES: CCn1cc(-c2cc(Cn3ccnc3)cc3c2NC(=O)CN([C@H](c2cc(OC)ccn2)C2CC2)C3=O)c(C(F)(F)F)n1]

Example 65

(S)-7-((1H-imidazol-1-yl)methyl)-4-(cyclopropyl(4-methoxypyridin-2-yl)methyl)-9-(1-ethyl-3-(trifluoromethyl)-1H-pyrazol-4-yl)-3,4-dihydro-1H-benzo[e][1,4]diazepine-2,5-dione Step A. Preparation of methyl 2-amino-3-bromo-5-vinylbenzoate $Pd(dppf)Cl_2$ (70 mg, 0.096 mmol, 0.05 eq.) was added to a mixture of methyl 2-amino-3-bromo-5-iodobenzoate (600 mg, 1.9 mmol, 1.0 eq.), potassium vinyltrifluoroborate (284 mg, 2.1 mmol, 1.1 eg.) and $K_2CO_3$ (800 mg, 5.8 mmol, 3.0 eq.), in 1,4-dioxane/$H_2O$ (3/1, 19 mL) under Ar atmosphere. The resulting mixture was stirred at 95° C. for 2 h, then diluted with water and extracted with EtOAc. The combined organic solution was washed with brine, dried ($MgSO_4$), filtered and concentrated. The residue was purified by flash chromatography (Combi-flash Rf, Hex/EtOAc=0-30% gradient) to afford the title compound (403 mg, 82%). LCMS (ESI): >95%, m/z=255.9 $[M+H]^+$.

Step B. Preparation of methyl 2-amino-3-(1-ethyl-3-(trifluoromethyl)-1H-pyrazol-4-yl)-5-vinylbenzoate The title compound (215 mg, 40% yield) was prepared from the procedure described in Example 65, Step A using methyl 2-amino-3-bromo-5-vinylbenzoate (401 mg, 1.57 mmol, 1.0 eq.) and 1-ethyl-3-(trifluoromethyl)pyrazole-4-boronic acid (425 mg, 2.04 mmol, 1.3 equiv.). LCMS (ESI): >95%, m/z=340.1 $[M+H]^+$.

Step C. Preparation of 2-amino-3-(1-ethyl-3-(trifluoromethyl)-1H-pyrazol-4-yl)-5-vinylbenzoic acid 2 M LiOH (aq. sol. 0.95 mL) was added dropwise to a solution of 2-amino-3-(1-ethyl-3-(trifluoromethyl)-1H-pyrazol-4-yl)-5-vinylbenzoate (210 mg, 0.62 mmol) in THE (2.0 mL). The reaction mixture was stirred at room temperature overnight then diluted with water and washed with EtOAc. The aqueous layer was acidified to pH~2 using 1 M HCl then extracted with EtOAc (3×). The combined organic solution was washed with brine, dried ($MgSO_4$), filtered and concentrated to give the crude title compound (165 mg, 82% yield), which was used in subsequent reaction without further purification.

Step D. Preparation of (S)-2-amino-N-(cyclopropyl(4-methoxypyridin-2-yl)methyl)-3-(1-ethyl-3-(trifluoromethyl)-1H-pyrazol-4-yl)-5-vinylbenzamide 2-amino-3-(1-ethyl-3-(trifluoromethyl)-1H-pyrazol-4-yl)-5-vinylbenzoic acid (165 mgm 0.51 mmol, 1.0 eq.) was dissolved in DMF (2.0 mL) and TBTU (163 mg, 0.51 mmol, 1.0 eq.) and DIPEA (0.18 mL, 1.0 mmol, 2.0 eq.) were added, and the resulting mixture was stirred at room temperature for 10 minutes. (S)-cyclopropyl(4-methoxypyridin-2-yl)methanamine 2HCl salt (127 mg, 0.51 mmol, 1.0 eq.) was added to the reaction mixture at room temperature then stirred overnight. The reaction was diluted with water and extracted with EtOAc. The combined organic solution was washed with brine, dried ($MgSO_4$), filtered and concentrated. The residue was purified by flash chromatography (Combi-flash Rf, Hex/EtOAc=0-30% gradient) to afford the title compound (51 mg, 21% yield). LCMS (ESI): >95%, m/z=487.2 $[M+H]^+$.

Step E. Preparation of (S)-4-(cyclopropyl(4-methoxypyridin-2-yl)methyl)-9-(1-ethyl-3-(trifluoromethyl)-1H-pyrazol-4-yl)-7-vinyl-3,4-dihydro-1H-benzo[e][1,4]diazepine-2,5-dione To a solution of (S)-2-amino-N-(cyclopropyl(4-methoxypyridin-2-yl)methyl)-3-(1-ethyl-3-(trifluoromethyl)-1H-pyrazol-4-yl)-5-vinylbenzamide (51 mg, 0.11 mmol, 1.0 eq.) in DCM (0.5 mL) was added DIPEA (0.037 mL, 2 eq.) followed by chloroacetyl chloride (0.010 mL, 0.13 mmol, 1.2 eq) at 0° C. The reaction mixture was warmed to room temperature and stirred for 30 min. The reaction was quenched by addition of water and extracted with DCM. The combined organic solution was washed with brine, dried ($MgSO_4$), filtered and concentrated. The residue was then dissolved in DMF (0.5 mL) and NaH (3.8 mg, 0.16 mmol, 1.5 eq.) was added. After stirring at room temperature for 2 h, the reaction was quenched with sat. $NH_4Cl$ and extracted with EtOAc. The combined organic solution was washed with brine, dried ($MgSO_4$), filtered and concentrated. The residue was purified by flash chromatography (Combi-flash Rf, DCM/MeOH=0-10% gradient) to afford the title compound (51 mg, 92% yield). LCMS (ESI): >95%, m/z=526.2 $[M+H]^+$.

Step F. Preparation of (S)-4-(cyclopropyl(4-methoxypyridin-2-yl)methyl)-9-(1-ethyl-3-(trifluoromethyl)-1H-pyrazol-4-yl)-2,5-dioxo-2,3,4,5-tetrahydro-1H-benzo[e][1,4]diazepine-7-carbaldehyde To a solution of (S)-4-(cyclopropyl(4-methoxypyridin-2-yl)methyl)-9-(1-ethyl-3-(trifluoromethyl)-1H-pyrazol-4-yl)-7-vinyl-3,4-dihydro-1H-benzo[e][1,4]diazepine-2,5-dione (51 mg, 0.11 mmol, 1.0 eq.) in DCM (1.5 mL) at −78° C., ozone was bubbled for 30 min then purged with air for 5 minutes. Dimethyl sulfide (0.025 mL, 0.35 mmol, 3.0 eq.) was added. The reaction was slowly warmed to room temperature and stirred overnight then concentrated. The residue was purified by flash chromatography (Combi-flash Rf, Hex/EtOAc=50-100% gradient) to afford the title compound (15 mg, 29% yield). LCMS (ESI): >95%, m/z=528.2 $[M+H]^+$.

Step G. Preparation of (S)-4-(cyclopropyl(4-methoxypyridin-2-yl)methyl)-9-(1-ethyl-3-(trifluoromethyl)-1H-pyrazol-4-yl)-7-(hydroxymethyl)-3,4-dihydro-1H-benzo[e][1,4]diazepine-2,5-dione To a solution of (S)-4-(cyclopropyl(4-methoxypyridin-2-yl)methyl)-9-(1-ethyl-3-(trifluoromethyl)-1H-pyrazol-4-yl)-2,5-dioxo-2,3,4,5-tetrahydro-1H-benzo[e][1,4]diazepine-7-carbaldehyde (15 mg, 0.028 mmol) in MeOH (0.2 mL) was added $NaBH_4$ (1.0 mg, 0.028 mmol) was added at room temperature. The reaction was stirred at room temperature for 30 min concentrated. The residue was dissolved in EtOAc, and the solution was washed with brine, dried ($MgSO_4$), filtered and concentrated. The residue was purified by flash chromatography (Combi-flash Rf, DCM/MeOH=0-5% gradient) to afford the title compound (15 mg, 99% yield). LCMS (ESI): >95%, m/z=530.2 $[M+H]^+$.

Step H. Preparation of (S)-7-(bromomethyl)-4-(cyclopropyl(4-methoxypyridin-2-yl)methyl)-9-(1-ethyl-3-(trifluoromethyl)-1H-pyrazol-4-yl)-3,4-dihydro-1H-benzo[e][1,4]diazepine-2,5-dione The title compound (8.7 mg, 52% yield) was prepared from the procedure described in Example 14, Step F using (S)-4-(cyclopropyl(4-methoxypyridin-2-yl)methyl)-9-(1-ethyl-3-(trifluoromethyl)-1H-pyrazol-4-yl)-7-(hydroxymethyl)-3,4-dihydro-1H-benzo[e][1,4]diazepine-2,5-dione (15 mg, 0.028 mmol, 1.0 eq.) and $PBr_3$ (23 mg, 0.085 mmol, 3.0 equiv.). LCMS (ESI): >95%, m/z=592.1 $[M+H]^+$.

Step I. Preparation of (S)-7-((1H-imidazol-1-yl)methyl)-4-(cyclopropyl(4-methoxypyridin-2-yl)methyl)-9-(1-ethyl-3-(trifluoromethyl)-1H-pyrazol-4-yl)-3,4-dihydro-1H-benzo[e][1,4]diazepine-2,5-dione The title compound (3.6 mg, 45% yield) was prepared from the procedure described in Example 3, Step J using (S)-7-(bromomethyl)-4-(cyclopropyl(4-methoxypyridin-2-yl)methyl)-9-(1-ethyl-3-(trifluoromethyl)-1H-pyrazol-4-yl)-3,4-dihydro-1H-benzo[e][1,4]diazepine-2,5-dione (8.1 mg, 0.013 mmol) and imidazole (3.0 mg, 0.40 mmol, 3.0 equiv.). The reaction mixture was stirred at 50° C. for 2 h. LCMS (ESI): >95%, m/z=580.1 $[M+H]^+$.

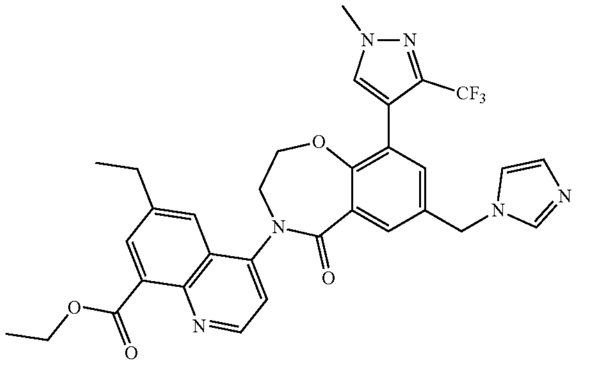 [SMILES: CCOC(=O)c1cc(CC)cc2c(N3CCOc4c(cc(Cn5ccnc5)cc4-c4cn(C)nc4C(F)(F)F)C3=O)ccnc12]

Example 66

Ethyl 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylate Step A. Preparation of methyl 3-bromo-2-(2-((tert-butoxycarbonyl)amino)ethoxy)-5-(hydroxymethyl)benzoate To a stirring solution of methyl 3-bromo-2-hydroxy-5-(hydroxymethyl)benzoate (4.83 g, 18.5 mmol, 1.0 eq.) in anhydrous DMF (25 mL) under Ar atmosphere, potassium carbonate (5.11 g, 37.0 mmol, 2.00 eq.) and tert-butyl (2-bromoethyl)carbamate (5.18 g, 23.1 mmol, 1.25 eq.) were added and the mixture was stirred at 70° C. for 1 h. The reaction mixture was cooled to room temperature, 50 mL of ice-cold water was added and the product was extracted with EtOAc (35 mL×2). The combined organic phases was washed with water and brine, dried over sodium sulfate, and concentrated in vacuo. The residue was purified by flash chromatography (Combi-flash Rf, Hex/EtOAc=0-100% gradient) to afford the title compound (5.50 g, 73.5%) as a white solid. LCMS (ESI): >95%, m/z=404.8 $[M+H]^+$.

Step B. Preparation of methyl 2-(2-((tert-butoxycarbonyl)amino)ethoxy)-5-(hydroxymethyl)-3-(1-methyl-3-(trifluoromethyl)-1H-pyrazol-4-yl)benzoate Methyl 3-bromo-2-(2-((tert-butoxycarbonyl)amino)ethoxy)-5-(hydroxymethyl)benzoate (2.02 g, 5.0 mmol, 1 eq.), (1-methyl-3-(trifluoromethyl)-1H-pyrazol-4-yl)boronic acid (1.45 g, 7.5 mmol, 1.5 eq.), $PdCl_2(dppf).CH_2Cl_2$ (204 mg, 250 μmol, 0.05 eq.) and potassium carbonate (691 mg, 5.0 mmol, 1 eq.) were suspended in 1,4-Dioxane (16 mL) and Water (4 mL). The mixture was purged with Ar twice and stirred under argon atmosphere at 80° C. for 7 h. The reaction mixture was cooled to room temperature, 50 mL of ice-cold water was added and the product was extracted with EtOAc (35 mL×2). The combined organic phases was washed with water and brine, dried over sodium sulfate, and concentrated in vacuo. The residue was purified by flash chromatography (Combi-flash Rf, Hex/EtOAc=0-100% gradient) to afford the title compound (2.25 g, 95.0%) as a brown sticky solid. LCMS (ESI): >95%, m/z=474.9 $[M+H]^+$.

Step C. Preparation of 7-(hydroxymethyl)-9-(1-methyl-3-(trifluoromethyl)-1H-pyrazol-4-yl)-3,4-dihydrobenzo[f][1,4]oxazepin-5(2H)-one To a stirring solution of methyl 2-(2-((tert-butoxycarbonyl)amino)ethoxy)-5-(hydroxymethyl)-3-(1-methyl-3-(trifluoromethyl)-1H-pyrazol-4-yl)benzoate (2.01 g, 4.25 mmol, 1.0 eq.) in DCM (20 mL), 2,2,2-trifluoroacetic acid (7.27 g, 4.91 mL, 63.8 mmol, 15 eq.) was added and the mixture was stirred at 25° C. for 1 h then concentrated in vacuo. The residue was then dissolved in 1,4-Dioxane (40 mL), and N-ethyl-N-isopropylpropan-2-amine (2.75 g, 3.8 mL, 5 Eq, 21.3 mmol) was slowly added. The reaction mixture was stirred at 112° C. for 12 h then concentrated. completion of lacamization. The residue was purified by flash chromatography (Combi-flash Rf, Hex/EtOAc=0-100% gradient) to afford the title compound (0.95 g, 65.5%) as a colorless sticky solid. LCMS (ESI): >95%, m/z=341.8 $[M+H]^+$.

Step D. Preparation of 7-((1H-imidazol-1-yl)methyl)-9-(1-methyl-3-(trifluoromethyl)-1H-pyrazol-4-yl)-3,4-dihydrobenzo[f][1,4]oxazepin-5(2H)-one The title compound was prepared from the sequence of procedures described in Example 65, Step H and I. LCMS (ESI): >95%, m/z=392.1 [M+H]+.

Step E. Preparation of ethyl 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylate To a solution of 7-((1H-imidazol-1-yl)methyl)-9-(1-methyl-3-(trifluoromethyl)-1H-pyrazol-4-yl)-3,4-dihydrobenzo[f][1,4]oxazepin-5(2H)-one (30.9 mg, 79 μmol, 1 eq.) in 1,4-dioxane (0.4 mL) at room temperature were added ethyl 4-bromo-6-ethylquinoline-8-carboxylate (48.7 mg, 158 μmol, 2 eq.), xantphos (9.14 mg, 15.8 μmol, 0.2 eq.), $Pd_2(dba)_3$ (7.23 mg, 7.9 μmol, 0.1 eq.), and $Cs_2CO_3$ (56.6 mg, 174 μmol, 2.2 eq.). The resulting mixture was degassed and back filled with Ar for three times, and then heated in a sealed tube at 105° C. for 24 h. Brine/water was added and the mixture was extracted with EtOAc. The combined organic phase was dried ($Na_2SO_4$), filtered, and concentrated. The residue was purified by reverse phase HPLC (Phenomenex Gemini C18, $H_2O/CH_3CN$ gradient from 5-55% $CH_3CN$, 0.1% TFA) to yield the title compound (26.3 mg, 42.5 μmol, 54% yield). $^1H$ NMR (400 MHz, Chloroform-d) δ 8.05 (d, J=4.8 Hz, 1H), 7.90 (d, J=2.0 Hz, 1H), 7.81 (d, J=1.6 Hz, 1H), 7.78 (d, J=2.4 Hz, 1H), 7.59 (s, 1H), 7.54 (s, 1H), 7.37 (d, J=4.8 Hz, 1H), 7.29 (d, J=2.0 Hz, 1H), 7.12 (s, 1H), 6.98 (s, 1H), 5.16 (s, 2H), 4.54 (q, J=7.2 Hz, 2H), 4.31 (m, 2H), 4.03 (s, 3H), 3.95 (m, 2H), 2.86 (q, J=7.6 Hz, 2H), 1.46 (t, J=7.2 Hz, 3H), 1.33 (t, J=7.6 Hz, 3H); LCMS (ESI): >95%, m/z=619.2 $[M+H]^+$.

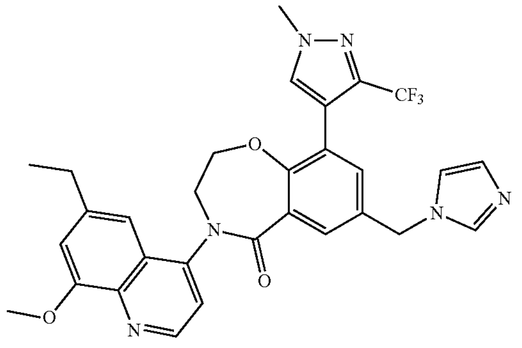 [SMILES: CCc1cc(OC)c2nccc(N3CCOc4c(cc(Cn5ccnc5)cc4-c4cn(C)nc4C(F)(F)F)C3=O)c2c1]

Example 67

7-((1H-imidazol-1-yl)methyl)-4-(6-ethyl-8-methoxyquinolin-4-yl)-9-(1-methyl-3-(trifluoromethyl)-1H-pyrazol-4-yl)-3,4-dihydrobenzo[f][1,4]oxazepin-5(2H)-one The title compound (13.6 mg, 23.6 μmol, 23% yield) was prepared following the procedure described for Example 66 Step E, using 7-((1H-imidazol-1-yl)methyl)-9-(1-methyl-3-(trifluoromethyl)-1H-pyrazol-4-yl)-3,4-dihydrobenzo[f][1,4]oxazepin-5(2H)-one (40 mg, 100 μmol, 1 eq.) and 4-bromo-6-ethyl-8-methoxyquinoline (46 mg, 170 μmol, 1.7 eq.). $^1H$ NMR (400 MHz, Chloroform-d) δ 8.95 (d, J=4.8 Hz, 1H), 7.90 (d, J=2.4 Hz, 1H), 7.59 (s, 1H), 7.54 (s, 1H), 7.37 (d, J=4.4 Hz, 1H), 7.26 (m, 2H), 7.12 (s, 1H), 6.97 (m, 2H), 5.16 (s, 2H), 4.33 (m, 2H), 4.11 (s, 3H), 4.02 (s, 3H), 3.94 (m, 2H), 2.81 (q, J=7.6 Hz, 2H), 1.32 (t, J=7.6 Hz, 3H); LCMS (ESI): >95%, m/z=577.2 $[M+H]^+$.

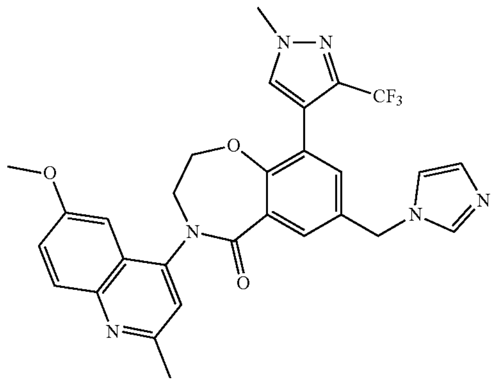 [SMILES: COc1ccc2nc(C)cc(N3CCOc4c(cc(Cn5ccnc5)cc4-c4cn(C)nc4C(F)(F)F)C3=O)c2c1]

Example 68

7-((1H-imidazol-1-yl)methyl)-4-(6-methoxy-2-methylquinolin-4-yl)-9-(1-methyl-3-(trifluoromethyl)-1H-pyrazol-4-yl)-3,4-dihydrobenzo[f][1,4]oxazepin-5(2H)-one The title compound (40.0 mg, 71 μmol, 90% yield) was prepared following the procedure described for Example 66 Step E, using 7-((1H-imidazol-1-yl)methyl)-9-(1-methyl-3-(trifluoromethyl)-1H-pyrazol-4-yl)-3,4-dihydrobenzo[f][1,4]oxazepin-5(2H)-one (31.0 mg, 79 μmol, 1 eq.) and 4-bromo-6-methoxy-2-methylquinoline (39.8 mg, 158 μmol, 2 eq.). $^1$H NMR (400 MHz, Chloroform-d) δ 8.00 (d, J=9.2 Hz, 1H), 7.76 (d, J=2.4 Hz, 1H), 7.59 (s, 1H), 7.52 (s, 1H), 7.39 (dd, J=2.8, 9.2 Hz, 1H), 7.26 (m, 1H), 7.23 (s, 1H), 7.16 (d, J=2.8 Hz, 1H), 7.12 (s, 1H), 6.98 (s, 1H), 5.16 (s, 2H), 4.38 (m, 1H), 4.25 (m, 1H), 4.02 (s, 3H), 3.97 (m, 1H), 3.89 (m, 1H), 3.87 (s, 3H), 2.74 (s, 3H); LCMS (ESI): >95%, m/z=563.2 [M+H]$^+$.

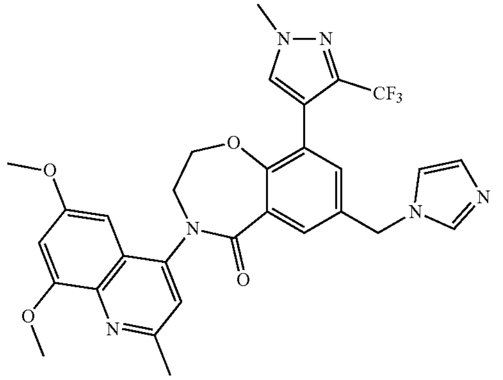 [SMILES: COc1cc(OC)c2nc(C)cc(N3CCOc4c(cc(Cn5ccnc5)cc4-c4cn(C)nc4C(F)(F)F)C3=O)c2c1]

Example 69

7-((1H-imidazol-1-yl)methyl)-4-(6,8-dimethoxy-2-methylquinolin-4-yl)-9-(1-methyl-3-(trifluoromethyl)-1H-pyrazol-4-yl)-3,4-dihydrobenzo[f][1,4]oxazepin-5(2H)-one The title compound (26.9 mg, 45.4 μmol, 57% yield) was prepared following the procedure described for Example 66 Step E, using 7-((1H-imidazol-1-yl)methyl)-9-(1-methyl-3-(trifluoromethyl)-1H-pyrazol-4-yl)-3,4-dihydrobenzo[f][1,4]oxazepin-5(2H)-one (31.0 mg, 79 μmol, 1 eq.) and 4-bromo-6,8-dimethoxy-2-methylquinoline (44.6 mg, 158 μmol, 2 eq.). $^1$H NMR (400 MHz, Chloroform-d) δ 7.76 (d, J=2.4 Hz, 1H), 7.58 (s, 1H), 7.51 (s, 1H), 7.26 (m, 2H), 7.12 (s, 1H), 6.98 (s, 1H), 6.74 (s, 2H), 5.16 (s, 2H), 4.37 (m, 1H), 4.26 (m, 1H), 4.06 (s, 3H), 4.02 (s, 3H), 3.97 (m, 1H), 3.88 (m, 1H), 3.85 (s, 3H), 2.78 (s, 3H); LCMS (ESI): >95%, m/z=593.4 [M+H]$^+$.

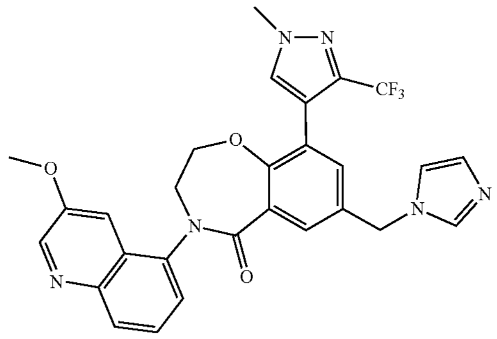 [SMILES: COc1cnc2cccc(N3CCOc4c(cc(Cn5ccnc5)cc4-c4cn(C)nc4C(F)(F)F)C3=O)c2c1]

Example 70

7-((1H-imidazol-1-yl)methyl)-4-(3-methoxyquinolin-5-yl)-9-(1-methyl-3-(trifluoromethyl)-1H-pyrazol-4-yl)-3,4-dihydrobenzo[f][1,4]oxazepin-5(2H)-one The title compound (19.9 mg, 36.3 μmol, 45% yield) was prepared following the procedure described for Example 66 Step E, using 7-((1H-imidazol-1-yl)methyl)-9-(1-methyl-3-(trifluoromethyl)-1H-pyrazol-4-yl)-3,4-dihydrobenzo[f][1,4]oxazepin-5(2H)-one (31.0 mg, 79 μmol, 1 eq.) and 5-bromo-3-methoxyquinoline (37.7 mg, 158 μmol, 2 eq.). $^1$H NMR (400 MHz, Chloroform-d) δ 8.72 (d, J=2.8 Hz, 1H), 8.11 (d, J=8.4 Hz, 1H), 7.76 (d, J=2.4 Hz, 1H), 7.60 (m, 2H), 7.49 (m, 3H), 7.26 (m, 1H), 7.12 (s, 1H), 6.98 (s, 1H), 5.17 (s, 2H), 4.38 (m, 1H), 4.21 (m, 1H), 4.07 (m, 1H), 4.03 (s, 3H), 3.91 (s, 3H), 3.85 (m, 1H); LCMS (ESI): >95%, m/z=549.2 [M+H]$^+$.

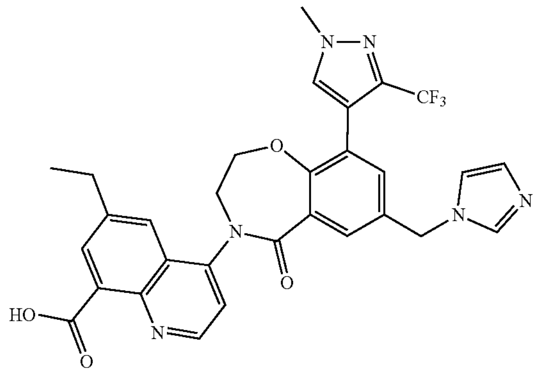 [SMILES: CCc1cc(C(=O)O)c2nccc(N3CCOc4c(cc(Cn5ccnc5)cc4-c4cn(C)nc4C(F)(F)F)C3=O)c2c1]

Example 71

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylic acid To a solution of ethyl 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylate (152.5 mg, 246 μmol, 1 eq.) in a mixture of THF (2.5 mL) and water (0.8 mL) was added $LiOH \cdot H_2O$ (31.0 mg, 0.74 mmol, 3 eq.). The mixture was stirred at room temperature for 16 h, and then neutralized with saturated aqueous $NH_4Cl$. To the mixture was added EtOAc and the resulting mixture was filtered. The filtered off white solid was washed with small amount of water and dried under vacuum to provide the title compound (68.0 mg, 115 μmol, 46% yield). The filtrate was extracted with EtOAc. The combined organic layer was dried ($Na_2SO_4$), filtered, and concentrated to provide the additional title compound (63.0 mg, 107 μmol, 43% yield). $^1$H NMR (400 MHz, DMSO-d6) δ 8.79 (d, J=4.8 Hz, 1H), 8.09 (s, 1H), 7.79 (s, 1H), 7.71 (d, J=2.4 Hz, 1H), 7.64 (s, 1H), 7.55 (s, 1H), 7.46 (d, J=4.4 Hz, 1H), 7.41 (d, J=2.4 Hz, 1H), 7.24 (s, 1H), 6.91 (s, 1H), 5.27 (s, 2H), 4.30 (m, 2H), 3.94 (s, 3H), 3.93 (m, 2H), 2.72 (q, J=7. Hz, 2H), 1.21 (t, J=7.6 Hz, 3H); LCMS (ESI): >95%, m/z=591.2 $[M+H]^+$.

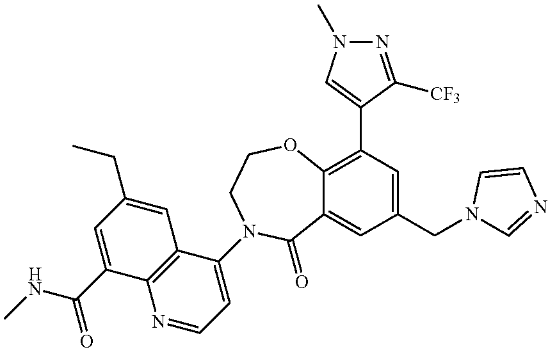 [SMILES: CCc1cc(C(=O)NC)c2nccc(N3CCOc4c(cc(Cn5ccnc5)cc4-c4cn(C)nc4C(F)(F)F)C3=O)c2c1]

Example 72

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethyl-N-methylquinoline-8-carboxamide 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylic acid (27.4 mg, 46.4 μmol, 1 eq.) in 1,4-dioxane (0.5 mL) was added HATU (29 mg, 75 μmol, 1.6 equiv) and N,N-diisopropylethylamine (48.5 μL, 278 μmol, 6 eq.). After stirring at room temperature for 10 min methylamine hydrochloride (5.95 mg, 88.2 μmol, 1.9 eq.) was added then stirred for additional 14 h at room temperature. The reaction mixture was diluted with EtOAc (5 mL) and washed with 1 M HCl (5 mL), sat. $NaHCO_3$ (5 mL), water (5 mL), and brine (5 mL). The organic layer was then dried ($MgSO_4$), filtered and concentrated. The residue was purified by reverse phase HPLC (Phenomenex Gemini C18, $H_2O/CH_3CN$ gradient from 15-80% $CH_3CN$, 0.1% TFA) followed by neutralization with sat. aq. $NaHCO_3$ to yield the title compound (23.0 mg, 38 μmol, 82% yield). $^1$H NMR (400 MHz, Chloroform-d) δ 11.01 (m, 1H), 8.95 (d, J=4.4 Hz, 1H), 8.82 (d, J=2.0 Hz, 1H), 7.84 (d, J=1.6 Hz, 1H), 7.77 (d, J=2.4 Hz, 1H), 7.59 (s, 1H), 7.55 (s, 1H), 7.42 (d, J=4.8 Hz, 1H), 7.30 (d, J=2.0 Hz, 1H), 7.12 (s, 1H), 6.98 (s, 1H), 5.17 (s, 2H), 4.33 (m, 2H), 4.03 (s, 3H), 3.98 (t, J=5.2 Hz, 2H), 3.16 (d, J=4.8 Hz, 3H), 2.89 (q, J=7.6 Hz, 2H), 1.34 (t, J=7.6 Hz, 3H); LCMS (ESI): >95%, m/z=604.2 $[M+H]^+$.

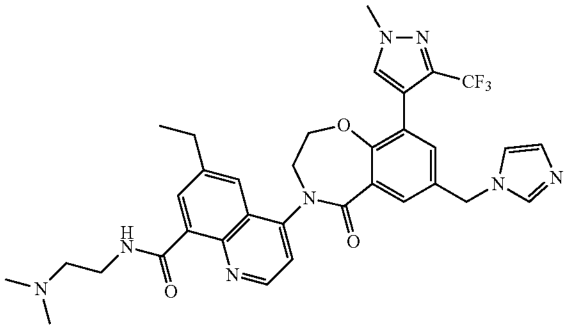 [SMILES: CCc1cc(C(=O)NCCN(C)C)c2nccc(N3CCOc4c(cc(Cn5ccnc5)cc4-c4cn(C)nc4C(F)(F)F)C3=O)c2c1]

Example 73

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-N-(2-(dimethylamino)ethyl)-6-ethylquinoline-8-carboxamide The title compound (25.0 mg, 38 μmol, 82% yield) was prepared following the procedure described for Example 72, using 4-(7-((1H-imidazol-1-yl)methyl)-9-(1-methyl-3-(trifluoromethyl)-1H-pyrazol-4-yl)-5-oxo-2,3-dihydrobenzo[1,4]oxazepin-4(5H)-yl)-6-ethylquinoline-8-carboxylic acid (27.1 mg, 45.9 μmol, 1 eq.), N,N-dimethylethane-1,2-diamine (7.5 μL, 68.8 μmol, 1.5 eq.). $^1$H NMR (400 MHz, Chloroform-d) δ 11.21 (m, 1H), 8.95 (d, J=4.8 Hz, 1H), 8.80 (d, J=2.0 Hz, 1H), 7.83 (s, 1H), 7.78 (d, J=2.4 Hz, 1H), 7.59 (s, 1H), 7.55 (s, 1H), 7.41 (d, J=4.4 Hz, 1H), 7.30 (s, 1H), 7.12 (s, 1H), 6.98 (s, 1H), 5.17 (s, 2H), 4.32 (m, 2H), 4.03 (s, 3H), 3.98 (m, 2H), 3.73 (q, J=6.4 Hz, 2H), 2.88 (q, J=7.6 Hz, 2H), 2.66 (t, J=6.4 Hz, 2H), 2.37 (s, 6H), 1.33 (t, J=7.6 Hz, 3H); LCMS (ESI): >95%, m/z=661.2 $[M+H]^+$.

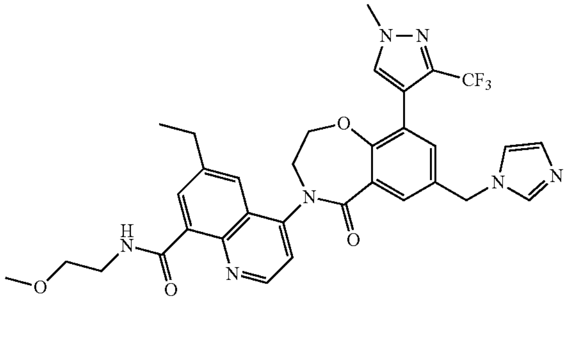 [SMILES: CCc1cc(C(=O)NCCOC)c2nccc(N3CCOc4c(cc(Cn5ccnc5)cc4-c4cn(C)nc4C(F)(F)F)C3=O)c2c1]

Example 74

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethyl-N-(2-methoxyethyl)quinoline-8-carboxamide To a suspension of 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylic acid (27.4 mg, 46.4 μmol, 1 eq.) in DCM at room temperature was added oxalyl chloride (16 μL, 186 μmol, 4 eq.) and stirred for 10 min. DIPEA (48.5 μL, 278 μmol, 6 eq.) was added to the reaction mixture and stirred until LCMS indicated the completion of the reaction. 2-Methoxyethan-1-amine (20 μL, 232 μmol, 5 equiv) was added to the mixture and stirred for another 20 min. The reaction was quenched with sat. aq. $NaHCO_3$ and extracted with EtOAc. The combined organic layer was dried ($Na_2SO_4$), filtered, and concentrated. The residue was purified by chromatography (0-10% MeOH in dichloromethane). The residue was purified by reverse phase HPLC (Phenomenex Gemini C18, $H_2O/CH_3CN$ gradient from 5-50% $CH_3CN$, 0.1% TFA) to yield the title compound (15 mg, 23 μmol, 50% yield). $^1H$ NMR (400 MHz, Chloroform-d) δ 11.34 (m, 1H), 8.97 (d, J=4.4 Hz, 1H), 8.81 (d, J=2.4 Hz, 1H), 7.85 (s, 1H), 7.78 (d, J=2.4 Hz, 1H), 7.59, (s, 1H), 7.55 (s, 1H), 7.42 (d, J=4.8 Hz, 1H), 7.30 (s, 1H), 7.12 (s, 1H), 6.98 (s, 1H), 5.17 (s, 2H), 4.33 (m, 2H), 4.03 (s, 3H), 3.97 (t, J=4.8 Hz, 2H), 3.82 (m, 2H), 3.68 (m, 2H), 3.45 (s, 3H), 2.89 (q, J=7.6 Hz, 2H), 1.36 (t, J=7.6 Hz, 3H); LCMS (ESI): >95%, m/z=648.4 $[M+H]^+$.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, PA) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Delaware Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizawa, 2007) and 10% of all acute leukemia cases (Marschalek, 2011). MLL leukemia patients have a poor prognosis with overall 5-year survival ratio around 35% (Dimartino, 1999; Pui, 2003; Tomizawa, 2007).

MLL is composited of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila* trithorax (Trx) (Thachuk, 1992). Wild type MLL binds to regulatory regions of homeox (HOX) genes (Milne, 2005) through the amino terminal fragment while the catalytic C-terminal domain catalyzes the Histone 3 lysine 4 (H3K4) methylation via interaction with WDR5 and up regulates target genes transcription (Nakamura, 2002; Yokoyama, 2004; Milne, 2002). Wild type MLL in conjunction with WDR5 is required for maintenance HOX genes expression and is widely expressed not only during embryo development but also in adult tissues including myeloid and lymphoid cells (Butler, 1997; Yu, 1998). Reciprocal translocations of MLL gene result in-frame fusion of 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005). The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct dysregulated target gene expression patterns and downstream events (Slany, 2009). Clinical studies reveal that MLL of different chromosomal translocations are associated with different prognosis and are treated differently under current protocols (Tamai, 2010; Balgobind, 2011; Pigazzi, 2011).

Intrinsic HMT activity of MLL1 is extremely low and requires a complex assembly of WDR5, RbBP5, ASH2L, and DPY30 protein partners for effective H3K4 trimethylation, so called WRAD complex. The binding of MLL1 to WDR5 (WD40 repeat protein 5) is particularly critical for HMT activity and occurs through a conserved arginine containing motif on MLL1 called the "Win" or WDR5 interaction motif Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, et al. Molecular Cell, 2014, 53, 247-261.) In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. The molecules described herein will target this interaction and could provide an attractive therapeutic approach to develop novel drugs for leukemias with translocations of MLL gene and other leukemias with upregulation of target genes. It also appreciated that WDR5 has been implicated in other cancer types and may utilize the WIN-site for other chromatin regulatory complexes outside and/or overlapping with WRAD complex. As such the WIN-site inhibitors described herein may have utility in multiple cancer types through mechanisms of action involving both direct competitive WIN-site antagonism, or through allosteric inhibition of higher complexes wherein WDR5 is dependent for their proliferative activity and tumor formation. Examples include breast cancer (Dai, X. et al. PLoS One, 2015), MYC-driven tumor types (Thomas, et al. Molecular Cell, 2015), bladder cancer (Chen, X. et al. Nature, Scientific Reports, 2015), neuroblastoma (Sun, Y. et al. Cancer Research, 2015), and pancreatic cancer (Carugo, A. et al. Cell Reports, 2016).

The disclosed compounds and compositions may be used in methods for treatment of MLL related cancers. The methods of treatment may comprise administering to a subject in need of such treatment a composition comprising a therapeutically effective amount of the compound of formula (I).

In one aspect, disclosed is a method of treating cancer, the method comprising administration of a therapeutically effective amount of a compound of formula (I), or a pharmaceutically acceptable salt thereof to a subject in need thereof.

In certain embodiments, the cancer being treated is associated with dysfunction of MLL.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MLL1, the method comprising administration of a therapeutically effective amount of a compound of formula (I), or a pharmaceutically acceptable salt thereof to a subject in need thereof.

The compositions can be administered to a subject in need thereof to bind WDR5 and modulate MLL, to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL1.

The compositions may be useful for treating certain cancers in humans and animals related to MLL dysfunction. Treatment of such cancers can be effected by modulating MLL1 in a subject, by administering a compound or composition of the invention, either alone or in combination with another active agent as part of a therapeutic regimen to a subject in need thereof.

Disruption of the interaction between WDR5 and its binding partners (such as MLL1) can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof can mediate reduction, clearance or prevention of additional growth of tumor cells by disrupting the ability of MLL1, another transcription factor, or chromatin to associate with WDR5, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of different anti-cancer drugs such as chemotherapeutics, anti-tumor agents, and anti-proliferative agents.

Further, the compound of formula (I) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, vitamin D3 analogs, γ-radiation, DOT1L inhibitors, agents targeting epigenetic mechanisms, or an additional chemotherapeutic agent such as N-Ac-Sar-Gly-Val-D-alloIle-Thr-Nva-Ile-Arg-Pro-NHCH2CH3 or a salt thereof, actinomycin D, AG13736, 17-allylamino-17-demethoxygeldanamycin, 9-aminocamptothecin, N-(4-(3-amino-1H-indazol-4-yl)phenyl}-N-(2-fluoro-5-methylphenyl)urea or a salt thereof, N-(4-(4-aminothieno[2,3-d]pyrimidin-5-yl)phenyl}-N-(2-fluoro-5-(trifluoromethyl)phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino}-3-pyridinyl}-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phyenylpyridinium, MG132, mitomycin, mitoxantrone, MLN518, MLN4924, MS-275, mycophenolic acid, mitomycin C, nitrosoureas, oprelvekin, oxaliplatin, paclitaxel, PARP inhibitors (e.g., rucaparib, niraparib, olaparib, iniparib, talazoparib, and veliparib), PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

The in vitro modulation of WDR5 protein was determined as follows.

MLL Peptide Binding Assay

General

Provided compounds of the present invention can be demonstrated to compete for binding with fluorescently labeled peptides derived from relevant MLL protein.

Time Resolved-Fluorescence Energy Transfer Competition Assay

A Time-Resolved Fluorescence Resonance Energy Transfer (TR-FRET) assay that measures the displacement of the 10 mer-Thr-FAM probe in response to compound treatment was performed for compounds wherein the $IC_{50}$ from FPA assay using 10mer-Thr-FAM was below the lower assay $IC_{50}$ limit~1 nM. Excess 10mer-Thr-FAM probe was utilized with His-tagged WDR5 in conjunction with a commercial anti-His antibody containing a Terbium label. The LanthaScreen™ Elite Tb-anti-HIS Antibody from ThermoFisher Scientific was used for this purpose. This Tb-anti-HIS has an excitation/emission of 340 nm and 490 nm, respectively. The 10mer-Thr-FAM probe when bound to WDR5 will undergo a FRET interaction with the Tb-anti-HIS and emit at 520 nm. The ratio of the 520 and 495 signals are then utilized to generate a dose-response curve to calculate an $IC_{50}$ value. By virtue of FRET there is little to no background fluorescence interference from 10mer-Thr-FAM probe allowing an excess of the probe to be used permitting an increase in the lower limit of the calculated $K_i$ when testing against highly potent inhibitors with $K_i$<<1 nM. WDR5-His Tag (Δ23, residues 24-334) is expressed and purified in our lab in sufficient quantities for screening. 10mer-Thr-FAM peptide is used at 150 nM. WDR5-His tag protein is used at 2 nM. A source plate is prepared using an Echo Liquid Handler, which distributes the compounds to the assay plate (white, flat-bottom; OptiPlate) in a 10-point, 5-fold dilution schemes with a top concentration of 5 M, in a final volume of 20 μL. A final target (WDR5)/Tb-Ab concentration of 2 nM/1 nM is dispensed from appropriate stock solutions, respectively. The final DMSO concentration in each well of the assay plate is 1% or lower. The plate is covered, shielded from light, and incubated for 60 minutes at room temperature with rocking. 10mer-Thr-FAM and Anti-His terbium antibody fluorescence is then measured on a Biotek Cytation 3 at excitation wavelength of 340 nm, and emission wavelengths of 495 nm and 520 nm. Working buffer conditions contain 1× Phosphate Buffered Saline, 300 mM NaCl, 0.5 mM TCEP, 0.1% CHAPS, at pH 7.2. TR-FRET signal is plotted and $IC_{50}$ and $K_i$ values are calculated according to the formula of Wang Z. FEBS Lett (1996) 3, 245.

$$K_i=[I]_{50}/([L]_{50}/K_d+[P]_0/K_d+1)$$

where $[I]_{50}$ is the concentration of the free inhibitor at 50% inhibition, $[L]_{50}$ is the concentration of the free labeled ligand at 50% inhibition, $[P]_0$ is the concentration of the free protein at 0% inhibition, $K_d$ represents the dissociation constant of the FITC-MLL or 10mer-Thr-FAM probe for WDR5. Total fluorescence is also measured, to rule out compounds that are inherently fluorescent or able to act as quenchers in the assay.

TR-FRET Binding Assay

TABLE 2

$K_i$ for Exemplified Compounds for Inhibition of WDR5 by TR-FRET assay

| Example | $K_i$ (nM) | Example | $K_i$ (nM) | Example | $K_i$ (nM) |
|---|---|---|---|---|---|
| 1 | <0.05 | 26 | <0.05 | 51 | <0.05 |
| 2 | >33 | 27 | <0.05 | 52 | <0.05 |
| 3 | <0.05 | 28 | 0.071 | 53 | <0.05 |
| 4 | >33 | 29 | 0.055 | 54 | <0.05 |
| 5 | >33 | 30 | 0.16 | 55 | 0.12 |
| 6 | <0.05 | 31 | <0.05 | 56 | <0.05 |

TABLE 2-continued $K_i$ for Exemplified Compounds for Inhibition of WDR5 by TR-FRET assay

| Example | $K_i$ (nM) | Example | $K_i$ (nM) | Example | $K_i$ (nM) |
|---|---|---|---|---|---|
| 7 | >33 | 32 | 0.11 | 57 | 0.062 |
| 8 | 2.3 | 33 | <0.05 | 58 | 0.063 |
| 9 | 0.12 | 34 | <0.05 | 59 | <0.05 |
| 10 | >33 | 35 | <0.05 | 60 | <0.05 |
| 11 | <0.05 | 36 | 0.074 | 61 | <0.05 |
| 12 | <0.05 | 37 | 0.15 | 62 | 0.056 |
| 13 | <0.05 | 38 | <0.05 | 63 | <0.05 |
| 14 | 0.14 | 39 | 0.18 | 64 | <0.05 |
| 15 | <0.05 | 40 | 0.12 | 65 | <0.05 |
| 16 | <0.05 | 41 | <0.05 | 66 | 0.050 |
| 17 | <0.05 | 42 | 0.18 | 67 | <0.05 |
| 18 | 0.40 | 43 | 0.23 | 68 | <0.05 |
| 19 | 2.8 | 44 | 0.2 | 69 | <0.05 |
| 20 | <0.05 | 45 | 0.076 | 70 | <0.05 |
| 21 | 0.067 | 46 | 0.24 | 72 | 0.064 |
| 22 | <0.05 | 47 | <0.05 | 73 | <0.05 |
| 23 | <0.05 | 48 | <0.05 | 74 | 0.053 |
| 24 | 0.61 | 49 | <0.05 | | |
| 25 | 0.081 | 50 | <0.05 | | |

Among other things, these data demonstrate the utility of representative compounds as selective inhibitors of the activity of WDR5 protein to bind peptides from relevant MLL domain.

Cellular Viability of Human Tumor Cell Lines

Anti-Proliferative Activity Using MLL-Harboring Cell Lines.

MV-4-11 and K562 cells are grown in IMDM media supplemented with 10% FBS and 100 penicillin/streptomycin, Molm-13 cells are cultured in RPMI-1640 media supplemented with 10% FBS and 1% o penicillin/streptomycin. Viability assays are performed by dispensing 200 cells at 7200 cells/mL into each well of an opaque 384-well plate and adding compounds at the indicated concentrations in a final volume of 32 μL and a final concentration of DMSO of 0.3% for all samples. A certain range of compound concentrations is made through a series of 2-fold dilutions starting 30 μM at the highest, total 22 dilutions. After a set incubation period, 5 day protocol, the viability of cells in each well is assessed using the CellTiter-Glo assay (Promega), read on a 96 Microplane Luminometer (Cytation 3, BioTek). Serial dilutions of each cell type are performed in all assays to generate standard curves and the final densities of cells are determined within the dynamic range of the instrument. $GI_{50}$ values are calculated based on XLfit software (IDBS, Guildford, UK) with Sigmoidal Dose-Response Model. Each compound is tested in minimum of two replicates. Data are expressed as mean.

TABLE 3

$GI_{50}$ (in nM) for representative compounds on cellular proliferation of MV4:11 human cancer cell lines

| Example | $GI_{50}$ (nM) | Example | $GI_{50}$ (nM) | Example | $GI_{50}$ (nM) |
|---|---|---|---|---|---|
| 1 | 150 | 26 | 135 | 51 | 79 |
| 2 | >940 | 27 | 192 | 52 | 63 |
| 3 | 19 | 28 | 232 | 53 | 67 |
| 4 | >940 | 29 | 38 | 54 | 9.0 |
| 5 | >940 | 30 | 190 | 55 | 570 |
| 6 | 86 | 31 | 231 | 56 | 37 |
| 7 | >940 | 32 | 775 | 57 | 29 |
| 8 | 355 | 33 | 130 | 58 | 77 |
| 9 | 259 | 34 | 1469 | 59 | 108 |
| 10 | >940 | 35 | 306 | 60 | 111 |

TABLE 3-continued $GI_{50}$ (in nM) for representative compounds on cellular proliferation of MV4:11 human cancer cell lines

| Example | $GI_{50}$ (nM) | Example | $GI_{50}$ (nM) | Example | $GI_{50}$ (nM) |
|---|---|---|---|---|---|
| 11 | 11 | 36 | 2426 | 61 | 158 |
| 12 | 3.5 | 37 | 1079 | 62 | 1379 |
| 13 | 12 | 38 | 262 | 63 | 70 |
| 14 | 167 | 39 | 730 | 64 | 39 |
| 15 | 101 | 40 | 529 | 65 | 290 |
| 16 | 79 | 41 | 985 | 66 | 772 |
| 17 | 22 | 42 | 282 | 67 | 321 |
| 18 | 672 | 43 | 159 | 68 | 100 |
| 19 | 7976 | 44 | 548 | 69 | 39 |
| 20 | 630 | 45 | 157 | 70 | 306 |
| 21 | 194 | 46 | 703 | 72 | 494 |
| 22 | 173 | 47 | 31 | 73 | 255 |
| 23 | 92 | 48 | 95 | 74 | 458 |
| 24 | 9008 | 49 | 45 | | |
| 25 | 300 | 50 | 50 | | |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A compound of formula (I)

(I)

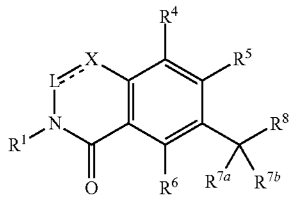

or a pharmaceutically acceptable salt thereof, wherein:

$R^1$ is $G^1$ or —$(CR^aR^b)_p$-$G^1$;

p is 1, 2, or 3;

$G^1$ is a 6- to 12-membered aryl, a 5- to 12-membered heteroaryl, a 4- to 12-membered heterocyclyl, or a $C_{3-10}$carbocycle optionally fused to a phenyl or to a 5- to 6-membered heteroaryl, wherein $G^1$ is optionally substituted with 1-5 substituents independently selected from the group consisting of halogen, $C_{1-6}$alkyl, $C_{1-6}$haloalkyl, oxo, —$OR^{1a}$, —$N(R^{1a})$, —$SR^{1a}$, cyano, —$C(O)OR^{1a}$, —$C(O)N(R^{1a})_2$, —$C(O)R^{1a}$, —$SOR^{1b}$, —$SO_2R^{1b}$, —$SO_2N(R^{1a})_2$, —$NR^{1a}C(O)R^{1a}$, —$NR^{1a}C(O)OR^{1b}$, —$NR^{1a}C(O)N(R^{1a})_2$, —$NR^{1a}S(O)_2R^{1b}$, —$NR^{1a}S(O)_2N(R^{1a})_2$, and -$L^1$-$G^{1a}$;

L is —$(CR^{2a}R^{2b})_n$—, wherein ------ is a single bond and X is O, $NR^3$, or S; or L is —$C(R^{2c})$, wherein ------ is a double bond and X is N;

n is 1, 2, or 3;

$R^{1a}$, at each occurrence, is independently hydrogen, $C_{1-6}$alkyl, $C_{1-6}$haloalkyl, —$C_{2-4}$alkylene-Y, $G^{1a}$, or —$C_{1-6}$alkylene-$G^{1a}$, wherein two $R^{1a}$, together with a common nitrogen atom to which the $R^{1a}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

Y, at each occurrence, is independently —OH, —$OC_{1-4}$alkyl, —$NH_2$, —$NHC_{1-4}$alkyl, or —$N(C_{1-4}$ alkyl$)_2$, $R^{1b}$, at each occurrence, is independently $C_{1-6}$alkyl, $C_{1-6}$haloalkyl, $G^{1a}$, or —$C_{1-6}$alkylene-$G^{1a}$;

$L^1$ is a bond or $C_{1-3}$alkylene;

$G^{1a}$, at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, —$OR^{1c}$, —$N(R^{1c})_2$, —$SR^{1c}$, cyano, —$C(O)OR^{1c}$, —$C(O)N(R^{1c})_2$, —$C(O)R^{1c}$, —$SOR^{1d}$, —$SO_2R^{1d}$, —$SO_2N(R^{1c})_2$, —$NR^{1c}C(O)R^{1c}$, —$NR^{1c}C(O)OR^{1d}$, —$NR^{1c}C(O)N(R^{1c})_2$, —$NR^{1c}S(O)_2R^{1d}$, and —$NR^{1c}S(O)_2N(R^{1d})_2$;

$R^a$, at each occurrence, is independently hydrogen, $C_{1-4}$alkyl, $C_{1-4}$haloalkyl, —$C_{1-6}$alkylene-$R^{aa}$, $G^{1b}$, or —$C_{1-6}$alkylene-$G^{1b}$, wherein each $C_{1-6}$alkylene is optionally substituted with 1-4 halogen;

$R^{aa}$, at each occurrence, is independently —$OR^{1e}$, —$N(R^{1e})_2$, —$SR^{1e}$, cyano, —$C(O)OR^{1e}$, —$C(O)N(R^{1e})_2$, —$C(O)R^{1e}$, —$SOR^{1f}$, —$SO_2R^{1f}$, —$SO_2N(R^{1e})_2$, —$NR^{1e}C(O)R^{1e}$, —$NR^{1e}C(O)OR^{1f}$, —$NR^{1e}C(O)N(R^{1e})_2$, —$NR^{1e}S(O)_2R^{1f}$, or —$NR^{1e}S(O)_2N(R^{1e})_2$;

$G^{1b}$, at each occurrence, is independently a $C_{3-6}$carbocycle or a 4- to 10-membered heterocyclyl, wherein the $C_{3-6}$carbocycle and 4- to 10-membered heterocyclyl are optionally substituted with 1-4 substituents independently selected from the group consisting of halogen, $C_{1-4}$alkyl, $C_{1-4}$haloalkyl, oxo, —$OR^{1e}$, —$N(R^{1e})_2$, —$SR^{1e}$, cyano, —$C(O)OR^{1e}$, —$C(O)N(R^{1e})_2$, —$C(O)R^{1e}$, —$SOR^{1f}$, —$SO_2R^{1f}$, —$SO_2N(R^{1e})_2$, —$NR^{1e}C(O)R^{1e}$, —$NR^{1e}C(O)OR^{1f}$, —$NR^{1e}C(O)N(R^{1e})_2$, —$NR^{1e}S(O)_2R^{1f}$, and —$NR^{1e}S(O)_2N(R^{1e})_2$, $R^b$ is hydrogen or $C_{1-4}$alkyl;

or alternatively one $R^a$ and one $R^b$ together with the carbon atom to which they are attached form a 3-8 membered saturated or partially unsaturated carbocyclic or heterocyclic ring;

or alternatively one $R^a$ and one $R^b$ are taken together to form an oxo group;

$R^{2a}$ and $R^{2b}$, at each occurrence, are independently hydrogen, halogen, $C_{1-4}$alkyl, $C_{1-4}$haloalkyl, $C_{3-6}$cycloalkyl, or —$C_{1-3}$alkylene-$C_{3-6}$cycloalkyl; or alternatively one $R^{2a}$ and one $R^{2b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$ haloalkyl, and —$OC_{1-4}$alkyl; or alternatively one $R^{2a}$ and one $R^{2b}$ are taken together to form an oxo group;

$R^{2c}$ is hydrogen, $C_{1-4}$alkyl, $C_{1-4}$haloalkyl, $C_{3-6}$cycloalkyl, or —$C_{1-3}$alkylene-$C_{3-6}$cycloalkyl;

$R^3$ is hydrogen or $C_{1-6}$alkyl;

$R^4$ is halogen, $C_{1-6}$haloalkyl, $C_{1-6}$haloalkenyl, —$OR^{4a}$, —$SR^{4a}$, —$N(R^{4a})_2$, —$S(O)R^{4b}$, —$S(O)_2R^{4b}$, —$S(O)_2N(R^{4a})_2$, —$C(O)N(R^{4a})_2$, —$C(O)R^{4a}$, —$NR^{4a}C(O)R^{4a}$—$NR^{4a}C(O)OR^{4b}$, —$NR^{4a}C(O)N(R^{4a})_2$, —$NR^{4a}S(O)_2R^{4b}$, $NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or —$C_{1-3}$ alkylene-$G^2$;

$R^{4b}$ is $C_{1-6}$alkyl, $C_{1-6}$haloalkyl, $G^2$, or —$C_{1-3}$alkylene-$G^2$;

$G^2$, at each occurrence, is independently a $C_{3-10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of halogen, $C_{1-6}$alkyl, $C_{1-6}$haloalkyl, oxo, —$OR^{4c}$, —$N(R^{4c})_2$, —$SR^{4c}$, cyano, —$C(O)OR^{4c}$, —$C(O)N(R^{4c})_2$, —$C(O)R^{4c}$, —$SOR^{4d}$, —$SO_2R^{4d}$, —$SO_2N(R^{4c})_2$, —$NR^{4c}C(O)R^4$, —$NR^{4c}C(O)OR^{4d}$, —$NR^{4c}C(O)N(R^{4c})_2$, —$NR^{4c}S(O)_2R^{4d}$, —$NR^{4c}S(O)_2N(R^{4c})_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^{1c}$, $R^{1e}$, and $R^{4c}$, at each occurrence, are independently hydrogen, $C_{1-6}$alkyl, $C_{1-6}$haloalkyl, $C_{3-8}$ cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$ alkyl and halogen, wherein alternatively two $R^{1c}$, two $R^{1e}$, and/or two $R^{4c}$, together with a common nitrogen atom to which the $R^{1c}$, $R^{1e}$, and/or $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{1d}$, $R^{1f}$ and $R^{4d}$, at each occurrence, are independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or —$OC_{1-4}$alkyl;

$R^{7a}$ and $R^{7b}$ are independently selected from the group consisting of hydrogen, halogen, $C_{1-4}$ alkyl, and $C_{1-4}$haloalkyl, or $R^{7a}$ and $R^{7b}$ are taken together to form an oxo group;

$R^8$ is

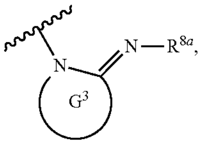, 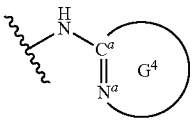, indolyl, pyrrolopyridinyl, or imidazolyl, wherein the indolyl, pyrrolopyridinyl, and imidazolyl are optionally substituted with 1-3 substituents independently selected from the group consisting of $C_{1-4}$alkyl, $C_{1-4}$haloalkyl, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$ haloalkyl, OH, and —$OC_{1-4}$alkyl;

$G^3$ is a 5- to 12-membered heterocyclic ring system containing a first nitrogen at the point of attachment and optionally 1-4 additional heteroatoms selected from the group consisting of oxygen, nitrogen, and sulfur, $G^3$ having the imine substituent =$NR^{8a}$ adjacent to the first nitrogen and being optionally substituted with 1-4 substituents independently selected from the group consisting of halogen, oxo, $C_{1-6}$alkyl, $C_{1-6}$haloalkyl, $G^{3a}$ and —$C_{1-3}$alkylene-$G^{3a}$;

$G^4$ is a 5- to 7-membered heterocyclic or 5- to 6-membered heteroaryl ring system, $G^4$ being attached at a first carbon atom $C^a$ and containing a first nitrogen Na double bonded to $C^a$, $G^4$ being optionally substituted with 1-4 substituents independently selected from the group consisting of halogen, oxo, $C_{1-6}$alkyl, $C_{1-6}$haloalkyl, and $C_{3-6}$cycloalkyl;

$R^{8a}$ is hydrogen, $C_{1-4}$alkyl, $C_{3-6}$cycloalkyl, $C(O)C_{1-4}$alkyl, or $C(O)OC_{1-4}$alkyl; and $G^{3a}$ is $C_{3-10}$carbocycle or a 6- to 12 membered aryl, wherein $G^{3a}$ is optionally substituted with 1-4 substituents independently selected from the group consisting of halogen, $C_{1-4}$alkyl, $C_{1-4}$ haloalkyl, OH, and —$OC_{1-4}$ alkyl.

Clause 2. The compound of clause 1, or a pharmaceutically acceptable salt thereof, wherein $R^8$ is

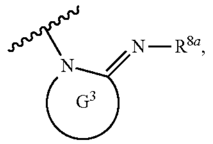

which is selected from the group consisting of

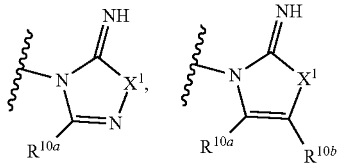, and

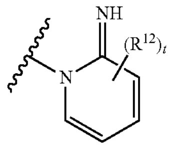;

$X^1$ is $NR^{13}$, O, or S;

$R^{10a}$ and $R^{10b}$ are independently hydrogen, halogen, $C_{1-4}$alkyl, $C_{1-4}$haloalkyl, $C_{3-8}$cycloalkyl, or —$C_{1-3}$alkylene-$C_{3-8}$cycloalkyl;

$R^{12}$, at each occurrence, is independently halogen, $C_{1-4}$alkyl, $C_{1-4}$haloalkyl, $C_{3-8}$cycloalkyl, or —$C_{1-3}$alkylene-$C_{3-8}$cycloalkyl;

$R^{13}$ is hydrogen, $C_{1-4}$alkyl, $C_{1-4}$haloalkyl, $C_{3-8}$cycloalkyl, or —$C_{1-3}$alkylene-$C_{3-8}$cycloalkyl; wherein each cycloalkyl in $R^{10a}$, $R^{10b}$, $R^{12}$, and $R^{13}$ is further optionally substituted with 1-4 substituents independently selected from the group consisting of halogen, $C_{1-4}$alkyl, $C_{1-4}$ haloalkyl, OH, and —$OC_{1-4}$alkyl; and t is 0, 1, 2, 3, or 4.

Clause 3. The compound of clause 2, or a pharmaceutically acceptable salt thereof, wherein $R^8$ is

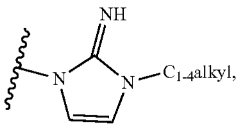, 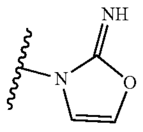,

-continued

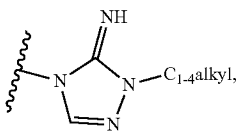

or

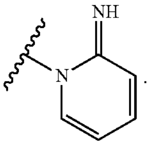

Clause 4. The compound of clause 1, or a pharmaceutically acceptable salt thereof, wherein $R^8$ is the imidazolyl, indolyl, or pyrrolopyridinyl, which are selected from the group consisting of

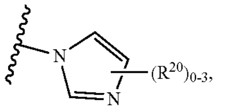

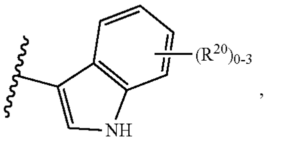

,

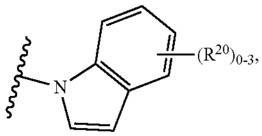

and

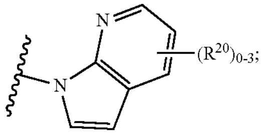

and $R^{20}$, at each occurrence, is independently $C_{1-4}$alkyl, $C_{1-4}$haloalkyl, $C_{3-8}$cycloalkyl, or $—C_{1-3}$ alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$ haloalkyl, OH, and $—OC_{1-4}$alkyl.

Clause 5. The compound of clause 4, or a pharmaceutically acceptable salt thereof, wherein $R^8$ is

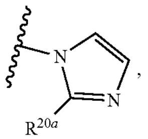

,

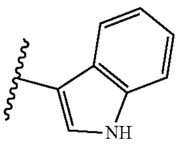

,

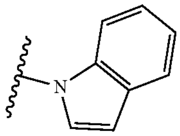

, or

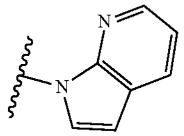

;

and $R^{20a}$ is hydrogen, $C_{1-4}$alkyl, or $C_{3-8}$cycloalkyl.

Clause 6. The compound of clause 5, or a pharmaceutically acceptable salt thereof, wherein $R^8$ is

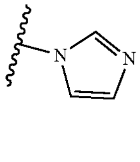

or

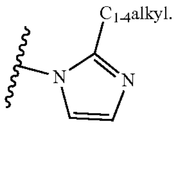

Clause 7. The compound of clause 1, or a pharmaceutically acceptable salt thereof, wherein $R^8$ is

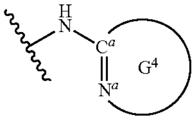

, which is selected from the group consisting of

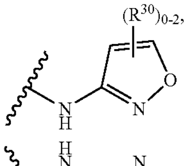

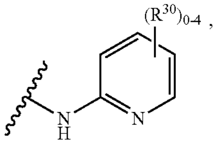

and

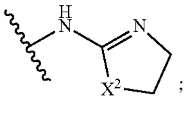

;

$R^{30}$, at each occurrence, is independently halogen, $C_{1-4}$alkyl, $C_{1-4}$haloalkyl, or $C_{3-6}$cycloalkyl; and $X^2$ is $CH_2$, O, or NH.

Clause 8. The compound of any of clauses 1-7, or a pharmaceutically acceptable salt thereof, wherein $R^1$ is $—(CR^aR^b)_p$-$G^1$.

Clause 9. The compound of clause 8, or a pharmaceutically acceptable salt thereof, wherein p is 1.

Clause 10. The compound of clause 8 or 9, or a pharmaceutically acceptable salt thereof, wherein $G^1$ is a phenyl or a 5- to 6-membered heteroaryl, wherein $G^1$ is optionally substituted as defined in clause 1.

Clause 11. The compound of clause 10, wherein the 5- to 6-membered heteroaryl of $G^1$ contains 1-3 nitrogen atoms.

Clause 12. The compound of claim 11, wherein $G^1$ is a phenyl or pyridinyl, and $G^1$ is optionally substituted as defined in clause 1.

Clause 13. The compound of any of clauses 1-7, or a pharmaceutically acceptable salt thereof, wherein $R^1$ is $G^1$.

Clause 14. The compound of clause 13, or a pharmaceutically acceptable salt thereof, wherein $G^1$ is a 6- to 12-membered aryl, an 8- to 10-membered heteroaryl, an 8- to 11-membered heterocycle, or a $C_{5-7}$carbocycle fused to a phenyl or to a 5- to 6-membered heteroaryl, wherein the 8- to 11-membered heterocycle is a 5- to 7-membered monocyclic heterocycle fused to a phenyl or to a 5- to 6-membered heteroaryl, and wherein $G^1$ is optionally substituted as defined in clause 1.

Clause 15. The compound of clause 14, or a pharmaceutically acceptable salt thereof, wherein $G^1$ is a phenyl substituted with $G^{1a}$.

Clause 16. The compound of clause 15, or a pharmaceutically acceptable salt thereof, wherein $G^{1a}$ is phenyl.

Clause 17. The compound of clause 14, or a pharmaceutically acceptable salt thereof, wherein $G^1$ is a quinolin-4-yl, 1,2,3,4-tetrahydronaphthalen-1-yl, or chroman-4-yl, wherein $G^1$ is optionally substituted as defined in clause 1.

Clause 18. The compound of any of clauses 1-17, wherein $G^1$ is optionally substituted with 1-3 substituents independently selected from the group consisting of halogen, $C_{1-6}$alkyl, $C_{1-6}$haloalkyl, $—OR^{1a}$, $—N(R^{1a})_2$, $—SR^{1a}$, cyano, $—C(O)OR^{1a}$, $—C(O)N(R^{1a})_2$, $—C(O)R^{1a}$, $—SO_2R^{1b}$, $—NR^{1a}C(O)R^{1a}$, $C_{3-8}$cycloalkyl, and $—C_{1-3}$alkylene-$C_{3-8}$ cycloalkyl, wherein each $C_{3-8}$cycloalkyl is optionally substituted with 1-4 substituents independently selected from the group consisting of $C_{1-4}$alkyl and halogen.

Clause 19. The compound of any of clauses 8-12, or a pharmaceutically acceptable salt thereof, wherein $G^1$ is

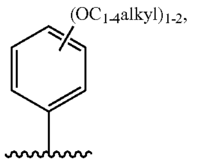

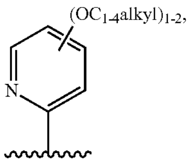

or

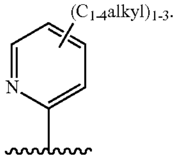

Clause 20. The compound of clause 19, or a pharmaceutically acceptable salt thereof, wherein $G^1$ is

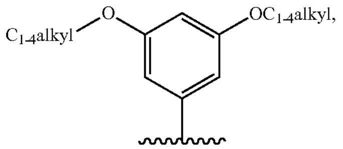

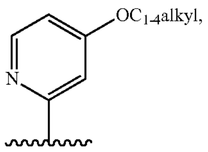

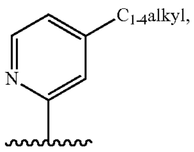

or

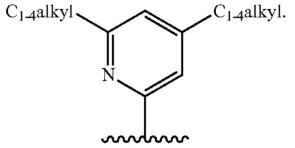

Clause 21. The compound of clause 20, or a pharmaceutically acceptable salt thereof, wherein $G^1$ is

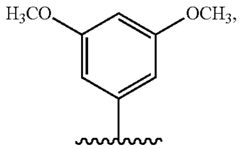

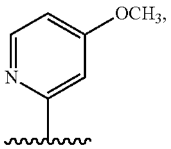

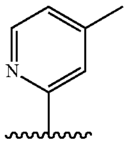

, or

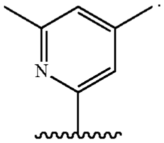

.

Clause 22. The compound of any of clauses 1-12 or 18-21, or a pharmaceutically acceptable salt thereof, wherein $R^a$ is hydrogen, $C_{1-4}$alkyl, or $C_{3-6}$carbocycle.

Clause 23. The compound of any of clauses 1-12 or 18-22, or a pharmaceutically acceptable salt thereof, wherein $R^b$ is hydrogen.

Clause 24. The compound of clause 13, or a pharmaceutically acceptable salt thereof, wherein $G^1$ is

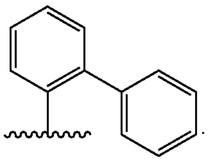

Clause 25. The compound of clause 13, or a pharmaceutically acceptable salt thereof, wherein $G^1$ is

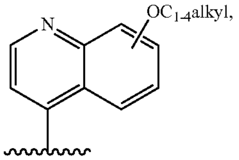

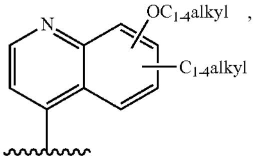

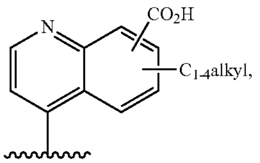

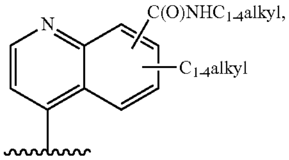

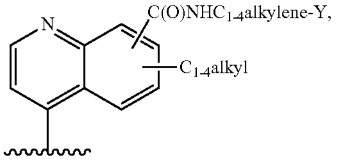

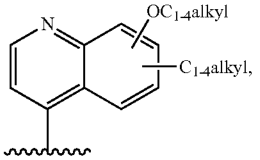

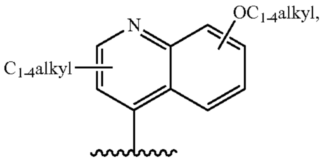

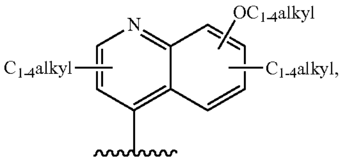

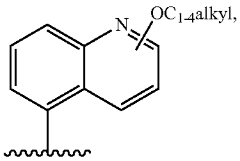

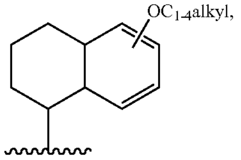

or

-continued
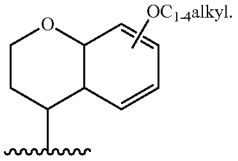
Clause 26. The compound of clause 13, or a pharmaceutically acceptable salt thereof, wherein $G^1$ is
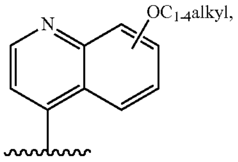
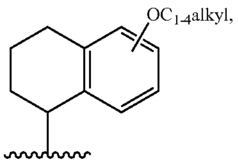
or
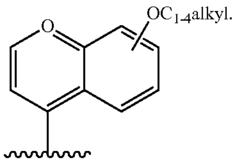
Clause 27. The compound of clause 13, or a pharmaceutically acceptable salt thereof, wherein $G^1$ is
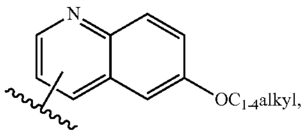
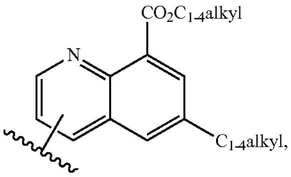
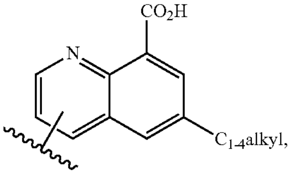
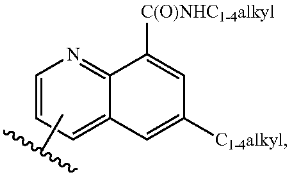
-continued
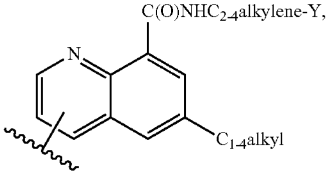
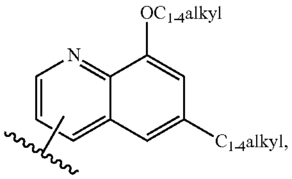
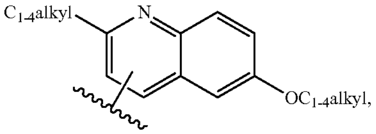
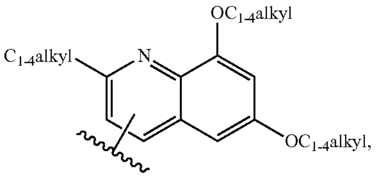
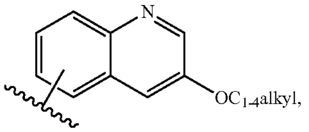
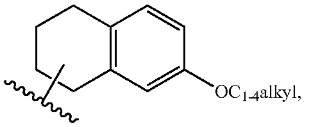
or
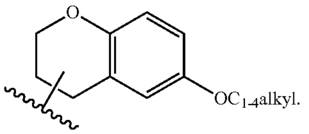
Clause 28. The compound of clause 13, or a pharmaceutically acceptable salt thereof, wherein $G^1$ is
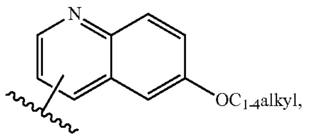
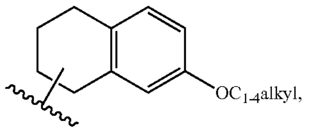
or
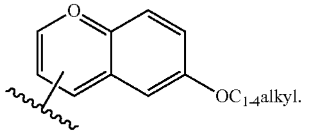

Clause 29. The compound of clause 13, or a pharmaceutically acceptable salt thereof, wherein $G^1$ is
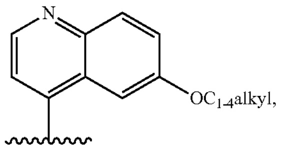
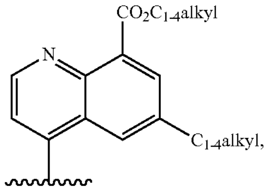
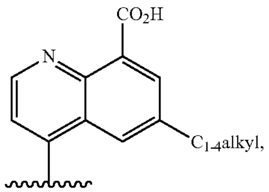
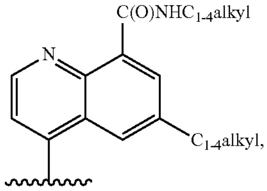
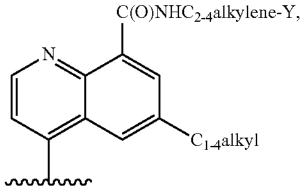
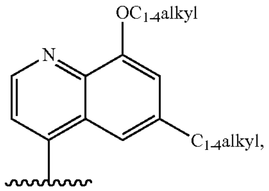
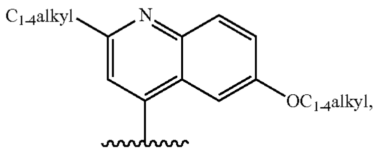
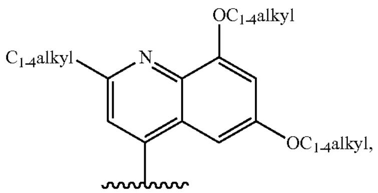
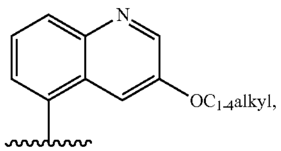
-continued
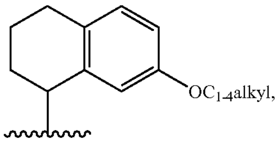
or
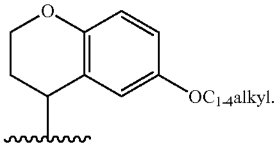
Clause 30. The compound of clause 13, or a pharmaceutically acceptable salt thereof, wherein $G^1$ is
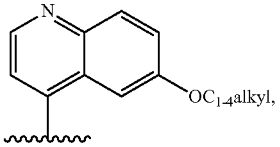
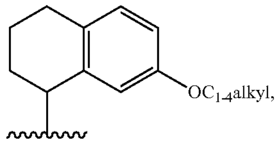
or
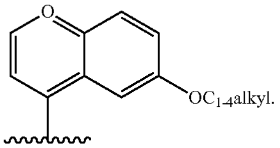
Clause 31. The compound of clause 13, or a pharmaceutically acceptable salt thereof, wherein $G^1$ is
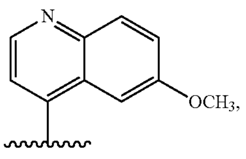
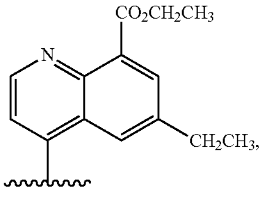
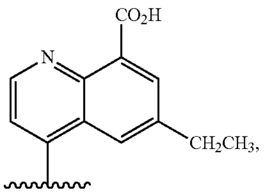
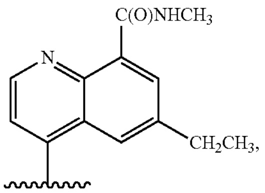

-continued

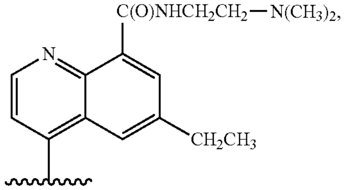

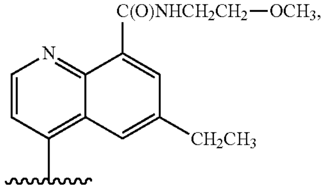

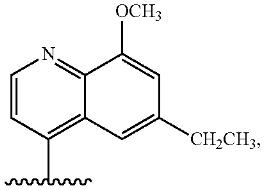

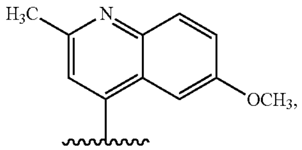

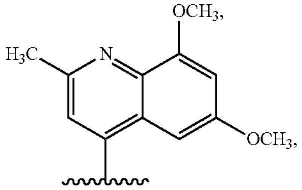

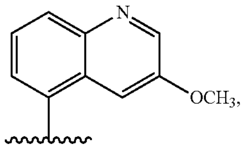

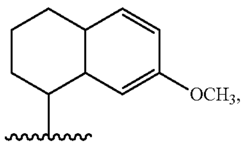

or

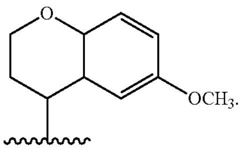

Clause 32. The compound of clause 13, or a pharmaceutically acceptable salt thereof, wherein $G^1$ is

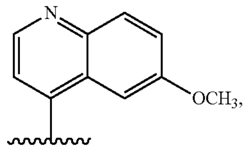

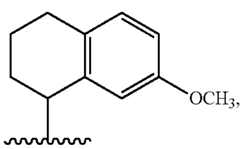

or

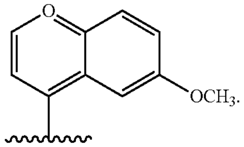

Clause 33. The compound of any of clauses 1-32, or a pharmaceutically acceptable salt thereof, wherein $R^4$ is $G^2$.

Clause 34. The compound of any of clauses 1-33, or a pharmaceutically acceptable salt thereof, wherein $G^2$ is a 6- to 12-membered aryl or a 5- to 12-membered heteroaryl, and optionally substituted as defined in clause 1.

Clause 35. The compound of clause 34, or a pharmaceutically acceptable salt thereof, wherein $G^2$ is a phenyl or a 5- to 6-membered heteroaryl, and optionally substituted as defined in clause 1.

Clause 36. The compound of clause 35, or a pharmaceutically acceptable salt thereof, wherein the 5- to 6-membered heteroaryl of $G^2$ contains 1-3 heteroatoms independently selected from the group consisting of sulfur and nitrogen.

Clause 37. The compound of any of clauses 1-33, or a pharmaceutically acceptable salt thereof, wherein $G^2$ is phenyl, pyridinyl, pyrazolyl, or thiazolyl, and $G^2$ is optionally substituted as defined in clause 1.

Clause 38. The compound of any of clauses 1-37, or a pharmaceutically acceptable salt thereof, wherein $G^2$ is optionally substituted with 1-4 substituents independently selected from the group consisting of halogen, $C_{1-6}$alkyl, and $C_{1-6}$haloalkyl.

Clause 39. The compound of any of clauses 1-33, or a pharmaceutically acceptable salt thereof, wherein, $G^2$ is

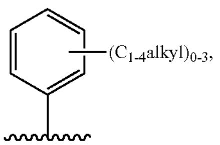

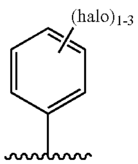

,

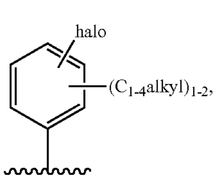

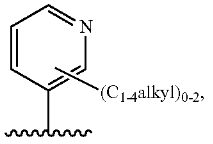

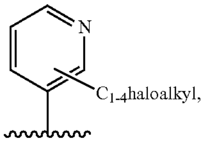

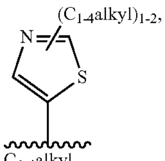

or

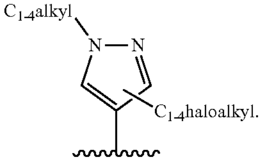

Clause 40. The compound of any of clauses 1-33, or a pharmaceutically acceptable salt thereof, wherein, $G^2$ is

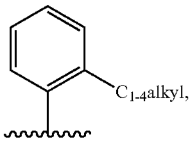
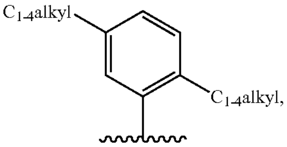
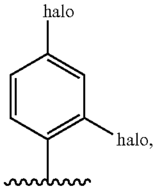
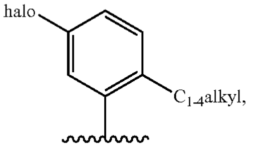
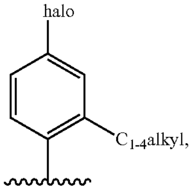
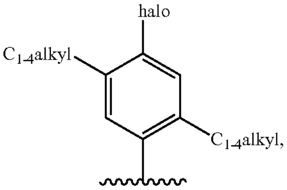
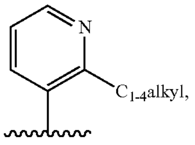
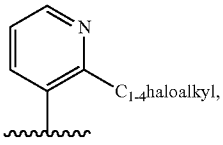
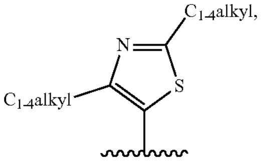
, or
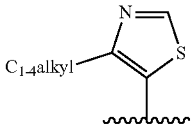
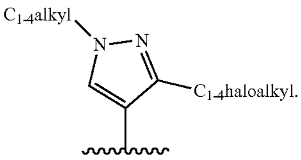

Clause 41. The compound of any of clauses 1-33, or a pharmaceutically acceptable salt thereof, wherein, $G^2$ is

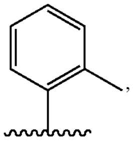
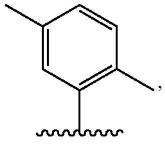
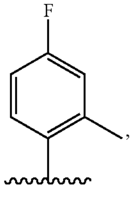
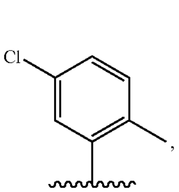
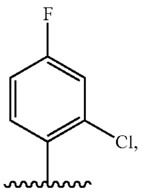
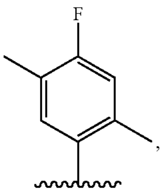

-continued

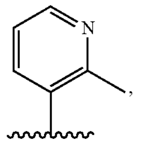
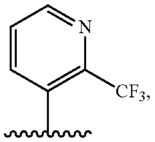
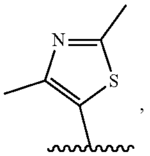
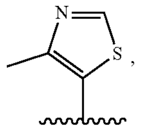
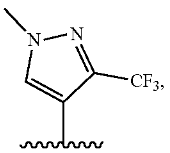
or
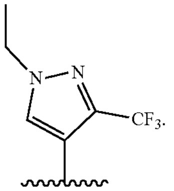

Clause 42. The compound of any of clauses 1-41, or a pharmaceutically acceptable salt thereof, wherein n is 1.

Clause 43. The compound of any of clauses 1-41, or a pharmaceutically acceptable salt thereof, wherein n is 2.

Clause 44. The compound of any of clauses 1-41, or a pharmaceutically acceptable salt thereof, of formula (I-A)

(I-A)

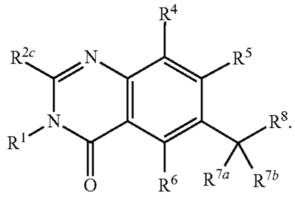

Clause 45. The compound of any of clauses 1-41, or a pharmaceutically acceptable salt thereof, of formula (I-B)

(I-B)

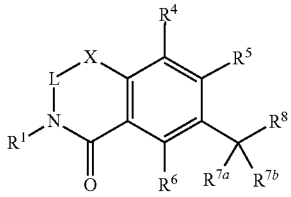

wherein L is $—(CR^{2a}R^{2b})_n—$.

Clause 46. The compound of any of clauses 1-43 or 45, or a pharmaceutically acceptable salt thereof, wherein L is $—CH_2—$ and X is NH.

Clause 47. The compound of any of clauses 1-43 or 45, or a pharmaceutically acceptable salt thereof, of formula (I-B1)

(I-B1)

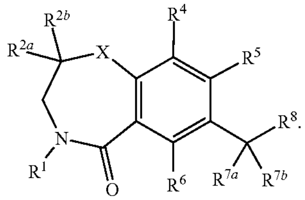

Clause 48. The compound of clause 47, or a pharmaceutically acceptable salt thereof, wherein $R^{2a}$ and $R^{2b}$ are independently hydrogen or $C_{1-4}$alkyl.

Clause 49. The compound of clause 47, or a pharmaceutically acceptable salt thereof, wherein $R^{2a}$ and $R^{2b}$ together form an oxo group.

Clause 50. The compound of any of clauses 1-43 or 47-49, wherein X is O.

Clause 51. The compound of any of clauses 1-43 or 47-49, wherein X is NH.

Clause 52. The compound of any of clauses 1-51, or a pharmaceutically acceptable salt thereof, wherein $R^5$ is hydrogen.

Clause 53. The compound of any of clauses 1-52, or a pharmaceutically acceptable salt thereof, wherein $R^6$ is hydrogen.

Clause 54. The compound of any of clauses 1-53, or a pharmaceutically acceptable salt thereof, wherein $R^{7a}$ and $R^{7b}$ are each hydrogen.

Clause 55. The compound of clause 1, selected from the group consisting of 3-(3,5-Dimethoxybenzyl)-8-(4-fluoro-2-methylphenyl)-6-((2-imino-3-methyl-2,3-dihydro-1H-imidazol-1-yl)methyl)quinazolin-4(3H)-one;

6-((1H-Indol-3-yl)methyl)-3-(3,5-dimethoxybenzyl)-8-(4-fluoro-2-methylphenyl)quinazolin-4(3H)-one;

4-(3,5-Dimethoxybenzyl)-9-(4-fluoro-2-methylphenyl)-7-((2-imino-3-methyl-2,3-dihydro-1H-imidazol-1-yl)methyl)-3,4-dihydrobenzo[f][1,4]oxazepin-5(2H)-one;

6-((1H-Indol-1-yl)methyl)-3-(3,5-dimethoxybenzyl)-8-(4-fluoro-2-methylphenyl)quinazolin-4(3H)-one;

6-((1H-Pyrrolo[2,3-b]pyridin-1-yl)methyl)-3-(3,5-dimethoxybenzyl)-8-(4-fluoro-2-methylphenyl)quinazolin-4(3H)-one;

4-(3,5-Dimethoxybenzyl)-9-(4-fluoro-2-methylphenyl)-7-((5-imino-1-methyl-1,5-dihydro-4H-1,2,4-triazol-4-yl)methyl)-3,4-dihydrobenzo[f][1,4]oxazepin-5(2H)-one;

4-(3,5-Dimethoxybenzyl)-9-(4-fluoro-2-methylphenyl)-7-(((4-methylisoxazol-3-yl)amino)methyl)-3,4-dihydrobenzo[f][1,4]oxazepin-5(2H)-one;

4-(3,5-Dimethoxybenzyl)-9-(4-fluoro-2-methylphenyl)-7-((2-iminopyridin-1(2H)-yl)methyl)-3,4-dihydrobenzo[f][1,4]oxazepin-5(2H)-one;

4-(3,5-Dimethoxybenzyl)-9-(4-fluoro-2-methylphenyl)-7-((2-iminooxazol-3(2H)-yl)methyl)-3,4-dihydrobenzo[f][1,4]oxazepin-5(2H)-one;

4-(3,5-Dimethoxybenzyl)-9-(4-fluoro-2-methylphenyl)-7-((pyridin-2-ylamino)methyl)-3,4-dihydrobenzo[f][1,4]oxazepin-5(2H)-one;

9-(4-Fluoro-2-methylphenyl)-7-((2-imino-3-methyl-2,3-dihydro-1H-imidazol-1-yl)methyl)-4-((4-methylpyridin-2-yl)methyl)-3,4-dihydrobenzo[f][1,4]oxazepin-5(2H)-one;

4-((4,6-Dimethylpyridin-2-yl)methyl)-9-(4-fluoro-2-methylphenyl)-7-((2-imino-3-methyl-2,3-dihydro-1H-imidazol-1-yl)methyl)-3,4-dihydrobenzo[f][1,4]oxazepin-5(2H)-one;

9-(4-Fluoro-2-methylphenyl)-7-((2-imino-3-methyl-2,3-dihydro-1H-imidazol-1-yl)methyl)-4-((4-methoxypyridin-2-yl)methyl)-3,4-dihydrobenzo[f][1,4]oxazepin-5(2H)-one;

4-(3,5-Dimethoxybenzyl)-9-(4-fluoro-2-methylphenyl)-7-((2-imino-3-methyl-2,3-dihydro-1H-imidazol-1-yl)methyl)-3,4-dihydro-1H-benzo[e][1,4]diazepine-2,5-dione;

4-(3,5-Dimethoxybenzyl)-7-((5-imino-1-methyl-1,5-dihydro-4H-1,2,4-triazol-4-yl)methyl)-9-(1-methyl-3-(trifluoromethyl)-1H-pyrazol-4-yl)-3,4-dihydrobenzo[f][1,4]oxazepin-5(2H)-one;

4-(3,5-Dimethoxybenzyl)-7-((2-imino-3-methyl-2,3-dihydro-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

4-(3,5-Dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one;

3-(3,5-Dimethoxybenzyl)-8-(4-fluoro-2-methylphenyl)-6-((5-imino-1-methyl-1,5-dihydro-4H-1,2,4-triazol-4-yl)methyl)quinazolin-4(3H)-one;

3-(3,5-Dimethoxybenzyl)-8-(4-fluoro-2-methylphenyl)-6-((2-iminooxazol-3(2H)-yl)methyl)quinazolin-4(3H)-one;

3-(3,5-Dimethoxybenzyl)-6-((2-imino-3-methyl-2,3-dihydro-1H-imidazol-1-yl)methyl)-8-(1-methyl-3-(trifluoromethyl)-1H-pyrazol-4-yl)quinazolin-4(3H)-one;

6-(((4,5-Dihydro-1H-imidazol-2-yl)amino)methyl)-3-(3,5-dimethoxybenzyl)-8-(4-fluoro-2-methylphenyl)-2-methylquinazolin-4(3H)-one;

4-((4,6-Dimethylpyridin-2-yl)methyl)-7-((2-imino-3-methyl-2,3-dihydro-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

3-(3,5-Dimethoxybenzyl)-8-(4-fluoro-2-methylphenyl)-6-((2-imino-3-methyl-2,3-dihydro-1H-imidazol-1-yl)methyl)-2,3-dihydroquinazolin-4(1H)-one;

3-([1,1'-Biphenyl]-2-yl)-6-((2-imino-3-methyl-2,3-dihydro-1H-imidazol-1-yl)methyl)-8-(1-methyl-3-(trifluoromethyl)-1H-pyrazol-4-yl)quinazolin-4(3H)-one;

9-(4-Fluoro-2-methylphenyl)-7-((2-methyl-1H-imidazol-1-yl)methyl)-4-((4-methylpyridin-2-yl)methyl)-3,4-dihydrobenzo[f][1,4]oxazepin-5(2H)-one;

4-((4,6-Dimethylpyridin-2-yl)methyl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

7-((2-Methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one;

4-(3,5-Dimethoxybenzyl)-9-(4-fluoro-2-methylphenyl)-7-((2-methyl-1H-imidazol-1-yl)methyl)-3,4-dihydro-1H-benzo[e][1,4]diazepine-2,5-dione;

4-(3,5-Dimethoxybenzyl)-9-(4-fluoro-2-methylphenyl)-7-((2-imino-3-methyl-2,3-dihydro-1H-imidazol-1-yl)methyl)-1,2,3,4-tetrahydro-5H-benzo[e][1,4]diazepin-5-one;

4-(3,5-Dimethoxybenzyl)-9-(4-fluoro-2-methylphenyl)-7-((2-iminooxazol-3(2H)-yl)methyl)-3,4-dihydro-1H-benzo[e][1,4]diazepine-2,5-dione;

4-((4,6-dimethylpyridin-2-yl)methyl)-7-((5-imino-1-methyl-1,5-dihydro-4H-1,2,4-triazol-4-yl)methyl)-9-(1-methyl-3-(trifluoromethyl)-1H-pyrazol-4-yl)-3,4-dihydrobenzo[f][1,4]oxazepin-5(2H)-one;

7-((5-imino-1-methyl-1,5-dihydro-4H-1,2,4-triazol-4-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one;

(R)-4-(3,5-Dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one;

(R)-4-(3,5-Dimethoxybenzyl)-9-(4-fluoro-2-methylphenyl)-2-methyl-7-((2-methyl-1H-imidazol-1-yl)methyl)-3,4-dihydrobenzo[f][1,4]oxazepin-5(2H)-one;

(S)-4-(3,5-Dimethoxybenzyl)-9-(4-fluoro-2-methylphenyl)-7-((2-imino-3-methyl-2,3-dihydro-1H-imidazol-1-yl)methyl)-2-methyl-3,4-dihydrobenzo[f][1,4]oxazepin-5(2H)-one;

(S)-4-(3,5-Dimethoxybenzyl)-9-(4-fluoro-2-methylphenyl)-2-methyl-7-((2-methyl-1H-imidazol-1-yl)methyl)-3,4-dihydrobenzo[f][1,4]oxazepin-5(2H)-one;

7-((2-Ethyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one;

4-((4,6-Dimethylpyridin-2-yl)methyl)-7-((2-ethyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

(S)-2-Methyl-7-((2-methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one;

(R)-2-Methyl-7-((2-methyl-1H-imidazol-1-yl)methyl)-9-(1-methyl-3-(trifluoromethyl)-1H-pyrazol-4-yl)-4-((4-methylpyridin-2-yl)methyl)-3,4-dihydrobenzo[f][1,4]oxazepin-5(2H)-one;

4-((4,6-Dimethylpyridin-2-yl)methyl)-9-(4-fluoro-2-methylphenyl)-7-((2-methyl-1H-imidazol-1-yl)methyl)-3,4-dihydrobenzo[f][1,4]oxazepin-5(2H)-one;

4-((4,6-Dimethylpyridin-2-yl)methyl)-7-((2-methyl-1H-imidazol-1-yl)methyl)-9-(2-(trifluoromethyl)pyridin-3-yl)-3,4-dihydrobenzo[f][1,4]oxazepin-5(2H)-one;

4-((4,6-Dimethylpyridin-2-yl)methyl)-9-(2,4-dimethylthiazol-5-yl)-7-((2-methyl-1H-imidazol-1-yl)methyl)-3,4-dihydrobenzo[f][1,4]oxazepin-5(2H)-one;

4-((4,6-Dimethylpyridin-2-yl)methyl)-7-((2-methyl-1H-imidazol-1-yl)methyl)-9-(2-methylpyridin-3-yl)-3,4-dihydrobenzo[f][1,4]oxazepin-5(2H)-one;

4-((4,6-Dimethylpyridin-2-yl)methyl)-7-((2-methyl-1H-imidazol-1-yl)methyl)-9-(o-tolyl)-3,4-dihydrobenzo[f][1,4]oxazepin-5(2H)-one;

4-((4,6-Dimethylpyridin-2-yl)methyl)-7-((2-methyl-1H-imidazol-1-yl)methyl)-9-(4-methylthiazol-5-yl)-3,4-dihydrobenzo[f][1,4]oxazepin-5(2H)-one;

(S)-4-(1-(4-Methoxypyridin-2-yl)ethyl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

9-(2-Chloro-4-fluorophenyl)-4-((4,6-dimethylpyridin-2-yl)methyl)-7-((2-methyl-1H-imidazol-1-yl)methyl)-3,4-dihydrobenzo[f][1,4]oxazepin-5(2H)-one;

9-(2,5-Dimethylphenyl)-4-((4,6-dimethylpyridin-2-yl)methyl)-7-((2-methyl-1H-imidazol-1-yl)methyl)-3,4-dihydrobenzo[f][1,4]oxazepin-5(2H)-one;

(S)-9-(4-Fluoro-2-methylphenyl)-4-(1-(4-methoxypyridin-2-yl)ethyl)-7-((2-methyl-1H-imidazol-1-yl)methyl)-3,4-dihydrobenzo[f][1,4]oxazepin-5(2H)-one;

4-((4,6-Dimethylpyridin-2-yl)methyl)-9-(4-fluoro-2,5-dimethylphenyl)-7-((2-methyl-1H-imidazol-1-yl)methyl)-3,4-dihydrobenzo[f][1,4]oxazepin-5(2H)-one;

9-(5-Chloro-2-methylphenyl)-4-((4,6-dimethylpyridin-2-yl)methyl)-7-((2-methyl-1H-imidazol-1-yl)methyl)-3,4-dihydrobenzo[f][1,4]oxazepin-5(2H)-one;

(S)-7-((5-Imino-1-methyl-1,5-dihydro-4H-1,2,4-triazol-4-yl)methyl)-4-(1-(4-methoxypyridin-2-yl)ethyl)-9-(1-methyl-3-(trifluoromethyl)-1H-pyrazol-4-yl)-3,4-dihydrobenzo[f][1,4]oxazepin-5(2H)-one;

(S)-9-(2-Chloro-4-fluorophenyl)-7-((5-imino-1-methyl-1,5-dihydro-4H-1,2,4-triazol-4-yl)methyl)-4-(1-(4-methoxypyridin-2-yl)ethyl)-3,4-dihydrobenzo[f][1,4]oxazepin-5(2H)-one;

3-((4-Methoxypyridin-2-yl)methyl)-6-((2-methyl-1H-imidazol-1-yl)methyl)-8-(1-methyl-3-(trifluoromethyl)-1H-pyrazol-4-yl)quinazolin-4(3H)-one;

(S)-9-(2,5-Dimethylphenyl)-4-(1-(4-methoxypyridin-2-yl)ethyl)-7-((2-methyl-1H-imidazol-1-yl)methyl)-3,4-dihydrobenzo[f][1,4]oxazepin-5(2H)-one;

4-(7-Methoxy-1,2,3,4-tetrahydronaphthalen-1-yl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

4-(6-Methoxyquinolin-4-yl)-7-((2-methyl-1H-imidazol-1-yl)methyl)-9-(1-methyl-3-(trifluoromethyl)-1H-pyrazol-4-yl)-3,4-dihydrobenzo[f][1,4]oxazepin-5(2H)-one;

(S)-7-((1H-Imidazol-1-yl)methyl)-4-(cyclopropyl(4-methoxypyridin-2-yl)methyl)-9-(1-ethyl-3-(trifluoromethyl)-1H-pyrazol-4-yl)-3,4-dihydrobenzo[f][1,4]oxazepin-5(2H)-one;

(S)-4-(Cyclopropyl(4-methoxypyridin-2-yl)methyl)-9-(1-ethyl-3-(trifluoromethyl)-1H-pyrazol-4-yl)-7-((2-methyl-1H-imidazol-1-yl)methyl)-3,4-dihydrobenzo[f][1,4]oxazepin-5(2H)-one;

(S)-4-(Cyclopropyl(4-methoxypyridin-2-yl)methyl)-7-((2-ethyl-1H-imidazol-1-yl)methyl)-9-(1-ethyl-3-(trifluoromethyl)-1H-pyrazol-4-yl)-3,4-dihydrobenzo[f][1,4]oxazepin-5(2H)-one;

(S)-6-((1H-imidazol-1-yl)methyl)-3-(cyclopropyl(4-methoxypyridin-2-yl)methyl)-8-(1-ethyl-3-(trifluoromethyl)-1H-pyrazol-4-yl)quinazolin-4(3H)-one;

(S)-7-((1H-imidazol-1-yl)methyl)-9-(1-ethyl-3-(trifluoromethyl)-1H-pyrazol-4-yl)-4-(6-methoxychroman-4-yl)-3,4-dihydrobenzo[f][1,4]oxazepin-5(2H)-one;

(S)-9-(1-ethyl-3-(trifluoromethyl)-1H-pyrazol-4-yl)-4-(6-methoxychroman-4-yl)-7-((2-methyl-1H-imidazol-1-yl)methyl)-3,4-dihydrobenzo[f][1,4]oxazepin-5(2H)-one;

(S)-7-((1H-imidazol-1-yl)methyl)-4-(cyclopropyl(4-methoxypyridin-2-yl)methyl)-9-(1-ethyl-3-(trifluoromethyl)-1H-pyrazol-4-yl)-3,4-dihydro-1H-benzo[e][1,4]diazepine-2,5-dione;

Ethyl 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylate;

7-((1H-imidazol-1-yl)methyl)-4-(6-ethyl-8-methoxyquinolin-4-yl)-9-(1-methyl-3-(trifluoromethyl)-1H-pyrazol-4-yl)-3,4-dihydrobenzo[f][1,4]oxazepin-5(2H)-one;

7-((1H-imidazol-1-yl)methyl)-4-(6-methoxy-2-methylquinolin-4-yl)-9-(1-methyl-3-(trifluoromethyl)-1H-pyrazol-4-yl)-3,4-dihydrobenzo[f][1,4]oxazepin-5(2H)-one;

7-((1H-imidazol-1-yl)methyl)-4-(6,8-dimethoxy-2-methylquinolin-4-yl)-9-(1-methyl-3-(trifluoromethyl)-1H-pyrazol-4-yl)-3,4-dihydrobenzo[f][1,4]oxazepin-5(2H)-one;

7-((1H-imidazol-1-yl)methyl)-4-(3-methoxyquinolin-5-yl)-9-(1-methyl-3-(trifluoromethyl)-1H-pyrazol-4-yl)-3,4-dihydrobenzo[f][1,4]oxazepin-5(2H)-one;

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethylquinoline-8-carboxylic acid;

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethyl-N-methylquinoline-8-carboxamide;

4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-N-(2-(dimethylamino)ethyl)-6-ethylquinoline-8-carboxamide; and 4-(7-((1H-imidazol-1-yl)methyl)-9-(1-methyl-3-(trifluoromethyl)-1H-pyrazol-4-yl)-5-oxo-2,3-dihydrobenzo[f][1,4]oxazepin-4(5H)-yl)-6-ethyl-N-(2-methoxyethyl)quinoline-8-carboxamide;

or a pharmaceutically acceptable salt thereof.

Clause 56. The compound of any of clauses 1-55, or a pharmaceutically acceptable salt thereof, wherein the compound is isotopically labeled.

Clause 57. A pharmaceutical composition comprising the compound of any of clauses 1-56, or a pharmaceutically acceptable salt thereof, and a pharmaceutically acceptable carrier.

Clause 58. A method of treating cancer comprising administering to a subject in need thereof, a therapeutically effective amount of the compound of any of clauses 1-56, or a pharmaceutically acceptable salt thereof, or the pharmaceutical composition of clause 57.

Clause 59. A method of inhibiting cancer cell proliferation, comprising administering to a subject in need thereof, the compound of any of clauses 1-56, or a pharmaceutically acceptable salt thereof, or the pharmaceutical composition of clause 57, in an amount effective to inhibit the cancer cell proliferation.

Clause 60. Use of the compound of any of clauses 1-56, or a pharmaceutically acceptable salt thereof, or the pharmaceutical composition of clause 57, in the manufacture of a medicament for the treatment of cancer.

Clause 61. Use of the compound of any of clauses 1-56, or a pharmaceutically acceptable salt thereof, or the pharmaceutical composition of clause 57, in the manufacture of a medicament for the inhibition of cancer cell proliferation.

Clause 62. The compound of any of clauses 1-56, or a pharmaceutically acceptable salt thereof, or the pharmaceutical composition of clause 57, for use in the treatment of cancer.

Clause 63. The compound of any of clauses 1-56, or a pharmaceutically acceptable salt thereof, or the pharmaceutical composition of clause 57, for use in the inhibition of cancer cell proliferation.

What is claimed is:

1. A compound of formula (I)

(I)

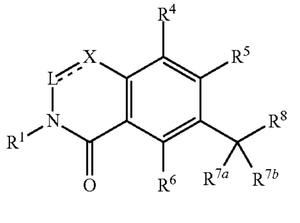

or a pharmaceutically acceptable salt thereof, wherein:

$R^1$ is $G^1$ or $-(CR^aR^b)_p-G^1$;

p is 1, 2, or 3;

$G^1$ is a 6- to 12-membered aryl, a 5- to 12-membered heteroaryl, a 4- to 12-membered heterocyclyl, or a $C_{3-10}$carbocycle optionally fused to a phenyl or to a 5- to 6-membered heteroaryl, wherein $G^1$ is optionally substituted with 1-5 substituents independently selected from the group consisting of halogen, $C_{1-6}$alkyl, $C_{1-6}$haloalkyl, oxo, $-OR^{1a}$, $-N(R^{1a})_2$, $-SR^{1a}$, cyano, $-C(O)OR^{1a}$, $-C(O)N(R^{1a})_2$, $-C(O)R^{1a}$, $-SOR^{1b}$, $-SO_2R^{1b}$, $-SO_2N(R^{1a})_2$, $-NR^{1a}C(O)R^{1a}$, $-NR^{1a}C(O)OR^{1b}$, $-NR^{1a}C(O)N(R^{1a})_2$, $-NR^{1a}S(O)_2R^{1b}$, $-NR^{1a}S(O)_2N(R^{1a})_2$, and $-L^1-G^{1a}$;

L is $-(CR^{2a}R^{2b})_n-$, wherein ------ is a single bond and X is O, $NR^3$, or S; or L is $-C(R^{2c})$: wherein ------ is a double bond and X is N;

n is 1, 2, or 3;

$R^{1a}$, at each occurrence, is independently hydrogen, $C_{1-6}$alkyl, $C_{1-6}$haloalkyl, $-C_{2-4}$alkylene-Y, $G^{1a}$, or $-C_{1-6}$alkylene-$G^{1a}$, wherein two $R^{1a}$, together with a common nitrogen atom to which the $R^{1a}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, $-OH$, and $-OC_{1-4}$alkyl;

Y, at each occurrence, is independently $-OH$, $-OC_{1-4}$alkyl, $-NH_2$, $-NHC_{1-4}$alkyl, or $-N(C_{1-4}alkyl)_2$, $R^{1b}$, at each occurrence, is independently $C_{1-6}$alkyl, $C_{1-6}$haloalkyl, $G^{1a}$, or $-C_{1-6}$alkylene-$G^{1a}$;

$L^1$ is a bond or $C_{1-3}$alkylene;

$G^{1a}$, at each occurrence, is independently $C_{3-8}$cycloalkyl, 6- to 10-membered aryl, 5- to 10-membered heteroaryl, or 4- to 10-membered heterocyclyl, wherein $G^{1a}$ is optionally substituted with 1-4 substituents independently selected from the group consisting of halogen, $C_{1-4}$alkyl, $C_{1-4}$haloalkyl, oxo, $-OR^{1c}$, $-N(R^{1c})_2$, $-SR^{1c}$, cyano, $-C(O)OR^{1c}$, $-C(O)N(R^{1c})_2$, $-C(O)R^{1c}$, $-SOR^{1d}$, $-SO_2R^{1d}$, $-SO_2N(R^{1c})_2$, $-NR^{1c}C(O)R^{1c}$, $-NR^{1c}C(O)OR^{1d}$, $-NR^{1c}C(O)N(R^{1c})_2$, $-NR^{1c}S(O)_2R^{1d}$, and $-NR^{1c}S(O)_2N(R^{1d})_2$;

$R^a$, at each occurrence, is independently hydrogen, $C_{1-4}$alkyl, $C_{1-4}$haloalkyl, $-C_{1-6}$alkylene-$R^{aa}$, $G^{1b}$, or $-C_{1-6}$alkylene-$G^{1b}$, wherein each $C_{1-6}$alkylene is optionally substituted with 1-4 halogen;

$R^{aa}$, at each occurrence, is independently $-OR^{1e}$, $-N(R^{1e})_2$, $-SR^{1e}$, cyano, $-C(O)OR^{1e}$, $-C(O)N(R^{1e})_2$, $-C(O)R^{1e}$, $-SOR^{1f}$, $-SO_2R^{1f}$, $-SO_2N(R^{1e})_2$, $-NR^{1e}C(O)R^{1e}$, $-NR^{1e}C(O)OR^{1f}$, $-NR^{1e}C(O)N(R^{1e})_2$, $-NR^{1e}S(O)_2R^{1f}$, or $-NR^{1e}S(O)_2N(R^{1e})_2$;

$G^{1b}$, at each occurrence, is independently a $C_{3-6}$carbocycle or a 4- to 10-membered heterocyclyl, wherein the $C_{3-6}$carbocycle and 4- to 10-membered heterocyclyl are optionally substituted with 1-4 substituents independently selected from the group consisting of halogen, $C_{1-4}$alkyl, $C_{1-4}$haloalkyl, oxo, $-OR^{1e}$, $-N(R^{1e})_2$, $-SR^{1e}$, cyano, $-C(O)OR^{1e}$, $-C(O)N(R^{1e})_2$, $-C(O)R^{1e}$, $-SOR^{1f}$, $-SO_2R^{1f}$, $-SO_2N(R^{1e})_2$, $-NR^{1e}C(O)R^{1e}$, $-NR^{1e}C(O)OR^{1f}$, $-NR^{1e}C(O)N(R^{1e})_2$, $-NR^{1e}S(O)_2R^{1f}$, and $-NR^{1e}S(O)_2N(R^{1e})_2$;

$R^b$ is hydrogen or $C_{1-4}$alkyl;

or alternatively one $R^a$ and one $R^b$ together with the carbon atom to which they are attached form a 3-8 membered saturated or partially unsaturated carbocyclic or heterocyclic ring;

or alternatively one $R^a$ and one $R^b$ are taken together to form an oxo group;

$R^{2a}$ and $R^{2b}$, at each occurrence, are independently hydrogen, halogen, $C_{1-4}$alkyl, $C_{1-4}$haloalkyl, $C_{3-6}$cycloalkyl, or $-C_{1-3}$alkylene-$C_{3-6}$cycloalkyl; or alternatively one $R^{2a}$ and one $R^{2b}$ are taken together with the atom or atoms to which they attach to form a 3-8 membered saturated or partially unsaturated carbocyclic or heterocyclic ring that is optionally substituted with 1-4 substituents independently selected from the group consisting of halogen, $C_{1-4}$alkyl, $C_{1-4}$haloalkyl, and $-OC_{1-4}$alkyl; or alternatively one $R^{2a}$ and one $R^{2b}$ are taken together to form an oxo group;

$R^{2c}$ is hydrogen, $C_{1-4}$alkyl, $C_{1-4}$haloalkyl, $C_{3-6}$cycloalkyl, or $-C_{1-3}$alkylene-$C_{3-6}$cycloalkyl;

$R^3$ is hydrogen or $C_{1-6}$alkyl;

$R^4$ is halogen, $C_{1-6}$haloalkyl, $C_{1-6}$haloalkenyl, —$OR^{4a}$, —$SR^{4a}$, —$N(R^{4a})_2$, —$S(O)R^{4b}$, —$S(O)_2R^{4b}$, —$S(O)_2N(R^{4a})_2$, —$C(O)N(R^{4a})_2$, —$C(O)R^{4a}$, —$NR^{4a}C(O)$ $R^{4a}$, —$NR^{4a}C(O)OR^{4b}$, —$NR^{4a}C(O)N(R^{4a})_2$, —$NR^{4a}S(O)_2R^{4b}$, —$NR^{4a}S(O)_2N(R^{4a})_2$, or $G^2$;

$R^{4a}$ at each occurrence, is independently hydrogen, $C_{1-6}$alkyl, $C_{1-6}$haloalkyl, $G^2$, or —$C_{1-3}$alkylene-$G^2$;

$R^{4b}$ is $C_{1-6}$alkyl, $C_{1-6}$haloalkyl, $G^2$, or —$C_{1-3}$alkylene-$G^2$;

$G^2$, at each occurrence, is independently a $C_{3-10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of halogen, $C_{1-6}$alkyl, $C_{1-6}$haloalkyl, oxo, —$OR^{4c}$, —$N(R^{4c})_2$, —$SR^{4c}$, cyano, —$C(O)OR^{4c}$, —$C(O)N(R^{4c})_2$, —$C(O)R^{4c}$, —$SOR^{4d}$, —$SO_2R^{4d}$, —$SO_2N(R^{4c})_2$, —$NR^{4c}C(O)R^{4c}$, —$NR^{4c}C(O)OR^{4d}$, —$NR^{4c}C(O)N(R^{4c})_2$, —$NR^{4c}S(O)_2R^{4d}$, —$NR^{4c}S(O)_2N(R^{4c})_2$, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^{1c}$, $R^{1e}$, and $R^{4c}$, at each occurrence, are independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen, wherein alternatively two $R^{1c}$, two $R^{1e}$, and/or two $R^{4c}$, together with a common nitrogen atom to which the $R^{1c}$, $R^{1e}$, and/or $R^{4c}$ attach form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{1d}$, $R^{1f}$, and $R^{4c}$, at each occurrence, are independently $C_{1-6}$alkyl, $C_{1-6}$haloalkyl, $C_{3-8}$cycloalkyl, or —$C_{1-6}$alkylene-$C_{3-8}$cycloalkyl, wherein each $C_{3-8}$cycloalkyl is optionally substituted with 1-4 substituents independently selected from the group consisting of $C_{1-4}$alkyl and halogen;

$R^5$ and $R^6$ are each independently hydrogen, halogen, $C_{1-4}$alkyl, $C_{1-4}$haloalkyl, or —$OC_{1-4}$alkyl;

$R^{7a}$ and $R^{7b}$ are independently selected from the group consisting of hydrogen, halogen, $C_{1-4}$alkyl, and $C_{1-4}$haloalkyl, or $R^{7a}$ and $R^{7b}$ are taken together to form an oxo group;

$R^8$ is

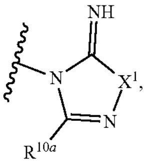
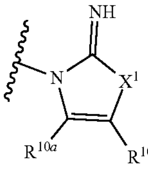
,
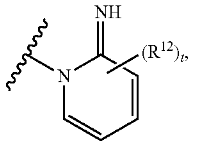
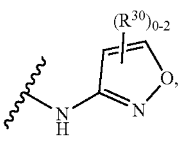
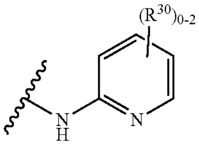
,
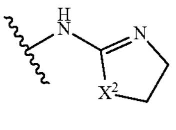

indolyl, pyrrolopyridinyl, or imidazolyl, wherein the indolyl, pyrrolopyridinyl, and imidazolyl are optionally substituted with 1-3 substituents independently selected from the group consisting of $C_{1-4}$alkyl, $C_{1-4}$haloalkyl, $C_{3-8}$cycloalkyl, and —$C_{1-3}$alkylene-$C_{3-8}$cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl;

wherein $X^1$ is $NR^{13}$, O, or S;

$R^{10a}$ and $R^{10b}$ are independently hydrogen, halogen, $C_{1-4}$alkyl, $C_{1-4}$haloalkyl, $C_{3-8}$cycloalkyl, or —$C_{1-3}$alkylene-$C_{3-8}$cycloalkyl;

$R^{12}$, at each occurrence, is independently halogen, $C_{1-4}$alkyl, $C_{1-4}$haloalkyl, $C_{3-8}$cycloalkyl, or —$C_{1-3}$alkylene-$C_{3-8}$cycloalkyl;

$R^{13}$ is hydrogen, $C_{1-4}$alkyl, $C_{1-4}$haloalkyl, $C_{3-8}$cycloalkyl, or —$C_{1-3}$alkylene-$C_{3-8}$cycloalkyl;

wherein each cycloalkyl in $R^{10a}$, $R^{10b}$, $R^{12}$, and $R^{13}$ is further optionally substituted with 1-4 substituents independently selected from the group consisting of halogen, $C_{1-4}$alkyl, $C_{1-4}$haloalkyl, OH, and —$OC_{1-4}$ alkyl; and t is 0, 1, 2, 3, or 4;

wherein $R^{30}$, at each occurrence, is independently halogen, $C_{1-4}$alkyl, $C_{1-4}$haloalkyl, or $C_{3-6}$cycloalkyl; and $X^2$ is $CH_2$, O, or NH.

2. The compound of claim 1, or a pharmaceutically acceptable salt thereof, wherein $R^8$ is the imidazolyl, indolyl, or pyrrolopyridinyl, which are selected from the group consisting of

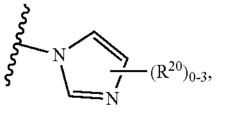
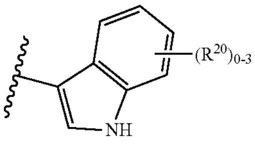
,
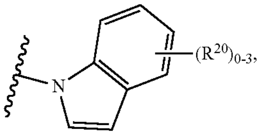
and
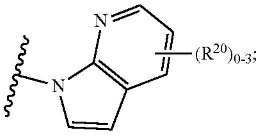

and $R^{20}$, at each occurrence, is independently $C_{1-4}$alkyl, $C_{1-4}$haloalkyl, $C_{3-8}$cycloalkyl, or —$C_{1-3}$alkylene-$C_{3-8}$ cycloalkyl, wherein each $C_{3-8}$cycloalkyl is optionally substituted with 1-4 substituents independently selected from the group consisting of halogen, $C_{1-4}$alkyl, $C_{1-4}$haloalkyl, OH, and —$OC_{1-4}$alkyl.

3. The compound of claim 2, or a pharmaceutically acceptable salt thereof, wherein $R^8$ is

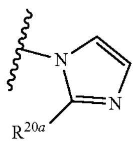
,
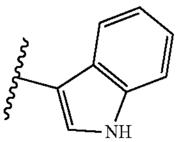
,
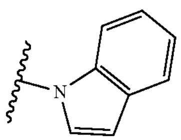
, or

-continued

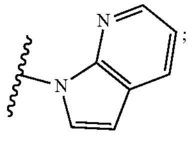

and $R^{20a}$ is hydrogen, $C_{1-4}$alkyl, or $C_{3-4}$cycloalkyl.

4. The compound of claim 3, or a pharmaceutically acceptable salt thereof, wherein $R^8$ is

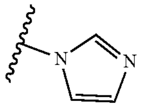

or

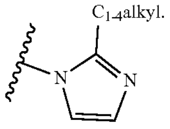

5. The compound of claim 1, or a pharmaceutically acceptable salt thereof, wherein:

$R^1$ is $G^1$; and $G^1$ is a 6- to 12-membered aryl, an 8- to 10-membered heteroaryl, an 8- to 11-membered heterocycle, or a $C_{5-7}$carbocycle fused to a phenyl or to a 5- to 6-membered heteroaryl, wherein the 8- to 11-membered heterocycle is a 5- to 7-membered monocyclic heterocycle fused to a phenyl or to a 5- to 6-membered heteroaryl, and wherein $G^1$ is optionally substituted as defined in claim 1.

6. The compound of claim 5, or a pharmaceutically acceptable salt thereof, wherein $R^1$ is

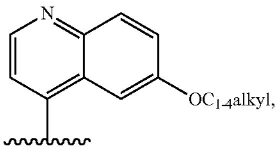

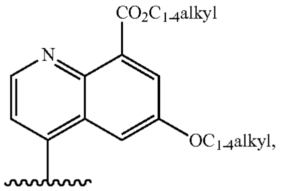

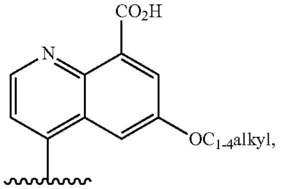

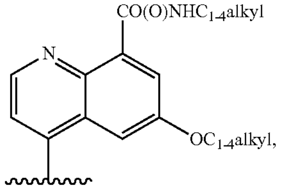

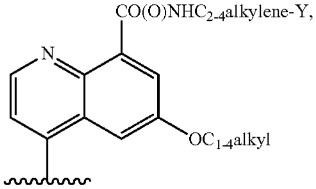

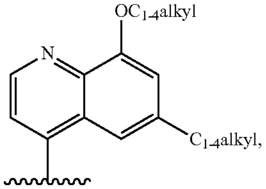

-continued

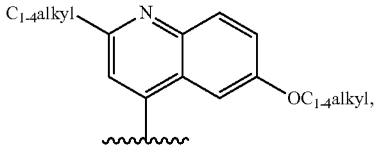

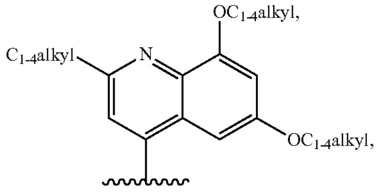

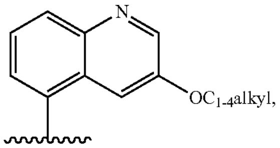

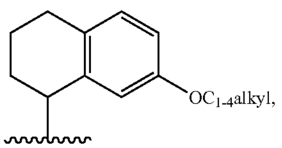

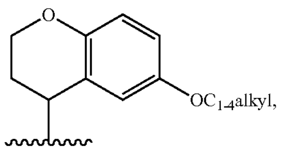

or

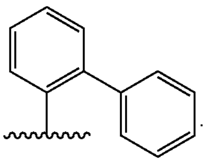 [SMILES: *c1ccccc1-c1ccccc1]

7. The compound of claim 1, or a pharmaceutically acceptable salt thereof, wherein $R^1$ is $-(CR^aR^b)_p-G^1$;

p is 1; and $G^1$ is a phenyl or a 5- to 6-membered heteroaryl, wherein $G^1$ is optionally substituted as defined in claim 1.

8. The compound of claim 7, or a pharmaceutically acceptable salt thereof, wherein $G^1$ is

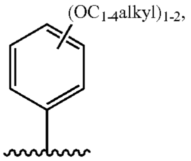

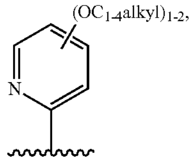

or

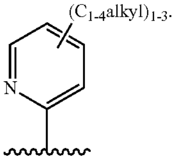

9. The compound of claim 1, or a pharmaceutically acceptable salt thereof, wherein $R^4$ is $G^2$; and $G^2$ is a phenyl or a 5- to 6-membered heteroaryl, and optionally substituted as defined in claim 1.

10. The compound of claim 9, or a pharmaceutically acceptable salt thereof, wherein $G^2$ is phenyl, pyridinyl, pyrazolyl, or thiazolyl, and $G^2$ is optionally substituted with 1-4 substituents independently selected from the group consisting of halogen, $C_{1-6}$alkyl, and $C_{1-6}$haloalkyl.

11. The compound of claim 10, or a pharmaceutically acceptable salt thereof, wherein $G^2$ is

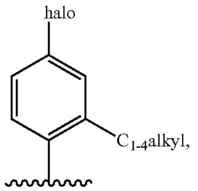

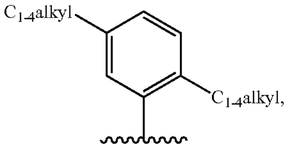

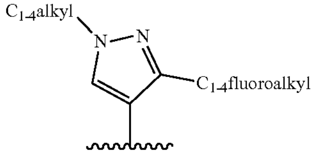

,

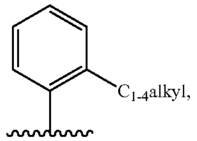

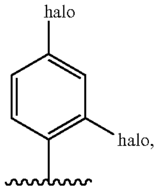

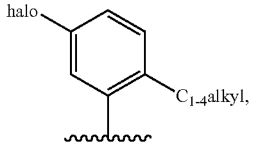

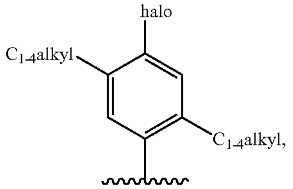

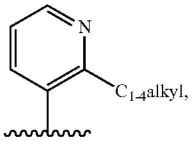

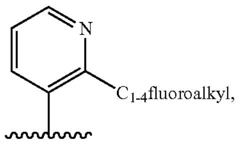

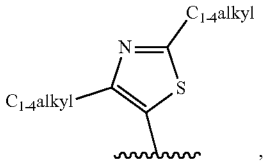

, or

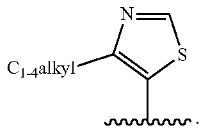

12. The compound of claim 1, or a pharmaceutically acceptable salt thereof, wherein the compound is a compound of formula (II-A)

(II-A)

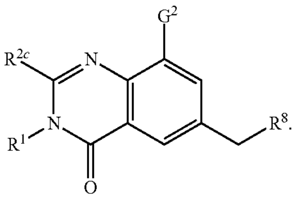

13. The compound of claim 1, or a pharmaceutically acceptable salt thereof, wherein the compound is a compound of formula (II-B1)

(II-B1)

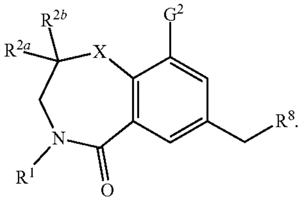

14. The compound of claim 13, or a pharmaceutically acceptable salt thereof, wherein $R^{2a}$ and $R^{2b}$ are independently hydrogen or $C_{1-4}$alkyl.

15. The compound of claim 13, or a pharmaceutically acceptable salt thereof, wherein $R^{2a}$ and $R^{2b}$ form an oxo.

16. A pharmaceutical composition comprising the compound of claim 1, or a pharmaceutically acceptable salt thereof, and a pharmaceutically acceptable carrier.

17. A method of treating cancer comprising administering to a subject in need thereof, a therapeutically effective amount of the compound of claim 1, or a pharmaceutically acceptable salt thereof.

18. A method of inhibiting cancer cell proliferation, comprising administering to a subject in need thereof, the compound of claim 1, or a pharmaceutically acceptable salt thereof, in an amount effective to inhibit the cancer cell proliferation.

* * * * *